US011633563B2

(12) United States Patent
Scheiner et al.

(10) Patent No.: US 11,633,563 B2
(45) Date of Patent: Apr. 25, 2023

(54) PATIENT INTERFACE HAVING SEAL-FORMING STRUCTURE WITH VARYING CONSTRUCTION

(71) Applicant: RESMED PTY LTD, Bella Vista (AU)

(72) Inventors: Rupert Christian Scheiner, Sydney (AU); Memduh Guney, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/631,347

(22) PCT Filed: Apr. 8, 2020

(86) PCT No.: PCT/IB2020/053347
§ 371 (c)(1),
(2) Date: Jan. 28, 2022

(87) PCT Pub. No.: WO2021/019312
PCT Pub. Date: Feb. 4, 2021

(65) Prior Publication Data
US 2022/0280740 A1    Sep. 8, 2022

(30) Foreign Application Priority Data

Jul. 31, 2019   (AU) ............................... 2019902729
Aug. 30, 2019  (AU) ............................... 2019903201
Oct. 16, 2019   (WO) .................. PCT/IB2019/058832

(51) Int. Cl.
*A61M 16/06*     (2006.01)
*A61M 16/08*     (2006.01)
*A61M 16/20*     (2006.01)

(52) U.S. Cl.
CPC .... *A61M 16/0622* (2014.02); *A61M 16/0694* (2014.02); *A61M 16/0825* (2014.02);
(Continued)

(58) Field of Classification Search
CPC .......... A61M 16/0057; A61M 16/0066; A61M 16/06; A61M 16/0605; A61M 16/0616;
(Continued)

(56) References Cited

U.S. PATENT DOCUMENTS

| 4,782,832 A | 11/1988 | Trimble et al. |
| 4,944,310 A | 7/1990 | Sullivan |

(Continued)

FOREIGN PATENT DOCUMENTS

| CN | 109172977 A | 1/2019 |
| WO | WO 98/004310 A1 | 2/1998 |

(Continued)

OTHER PUBLICATIONS

"*Respiratory Physiology*", by John B. West, Lippincott Williams & Wilkins, $9^{th}$ edition published 2012 (8 pages).
(Continued)

*Primary Examiner* — Annette Dixon
(74) *Attorney, Agent, or Firm* — Nixon & Vanderhye P.C.

(57) ABSTRACT

A patient interface comprises a seal-forming structure including a textile membrane and a support structure to support the textile membrane. The seal-forming structure may have a varying construction in order to accommodate different regions and the varying contours of the patients face to ensure a robust and comfortable seal. An air impermeable layer of the textile membrane may have a thickness that varies in different portions of the textile membrane and/or different regions of the cushion assembly. Further, the seal-forming structure may include an underlying cushion, and an arrangement of the textile membrane and the underlying cushion and/or the configuration of the underlying cushion may vary in different regions of the cushion assembly to optimize patient comfort and the effectiveness of the seal in different regions of the patients face.

23 Claims, 99 Drawing Sheets

(52) U.S. Cl.
CPC ............... *A61M 16/208* (2013.01); *A61M 2016/0661* (2013.01); *A61M 2202/0225* (2013.01); *A61M 2205/0216* (2013.01); *A61M 2205/0222* (2013.01); *A61M 2207/10* (2013.01)

(58) Field of Classification Search
CPC .......... A61M 16/0622; A61M 16/0633; A61M 16/0666; A61M 16/0683; A61M 16/0694; A61M 16/0816; A61M 16/0825; A61M 16/0875; A61M 16/1055; A61M 16/107; A61M 16/1075; A61M 16/16; A61M 16/161; A61M 16/208; A61M 16/22; A61M 2016/0027; A61M 2016/0036; A61M 2016/0661; A61M 2205/3368; A61M 2206/14; A61M 2210/0618; A62B 18/084; Y10T 24/1959; Y10T 24/32
See application file for complete search history.

(56) References Cited

U.S. PATENT DOCUMENTS

| | | | |
|---|---|---|---|
| 5,687,715 A | 11/1997 | Landis | |
| 6,532,959 B1 | 3/2003 | Berthon-Jones | |
| 6,581,594 B1 | 6/2003 | Drew et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 2003/0196658 A1* | 10/2003 | Ging | A61M 16/0666 128/201.22 |
| 2007/0119458 A1* | 5/2007 | Ging | A61M 16/0816 128/206.26 |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2015/0359986 A1 | 12/2015 | Skipper et al. | |
| 2017/0049983 A1 | 4/2017 | Ellis | |
| 2017/0128689 A1 | 5/2017 | Law et al. | |
| 2017/0326320 A1* | 11/2017 | Baigent | A61M 16/0683 |
| 2019/0009045 A1 | 1/2019 | Bernard | |
| 2022/0134039 A1* | 5/2022 | Hartono | A61M 16/0622 128/206.24 |

FOREIGN PATENT DOCUMENTS

| | | |
|---|---|---|
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2008/011683 A1 | 1/2008 |
| WO | WO 2009/052560 A1 | 4/2009 |
| WO | WO 2010/135785 A1 | 12/2010 |
| WO | WO 2011/003128 A1 | 1/2011 |
| WO | WO 2012/171072 A1 | 12/2012 |
| WO | WO 2013/006913 A1 | 1/2013 |
| WO | WO 2013/020167 A1 | 2/2013 |
| WO | WO 2016/082001 A1 | 6/2016 |
| WO | WO 2017/049359 A1 | 3/2017 |
| WO | WO 2017/049361 A1 | 3/2017 |
| WO | WO 2017/158471 A1 | 9/2017 |
| WO | WO 2018/124889 A1 | 7/2018 |
| WO | WO 2018/160077 A1 | 9/2018 |
| WO | WO 2019/183681 A1 | 10/2019 |
| WO | WO 2020/000033 A1 | 1/2020 |
| WO | WO 2020/009589 A1 | 1/2020 |
| WO | WO 2020/079617 A1 | 4/2020 |

OTHER PUBLICATIONS

International Search Report dated Jul. 7, 2020 in corresponding PCT application No. PCT/IB2020/053347 (5 pages).
Written Search Report dated Jul. 7, 2020 PCT in corresponding PCT application No. PCT/IB2020/053347 (7 pages).
International Preliminary Report on Patentability dated Jun. 15, 2021 in corresponding PCT application No. PCT/IB2020/053347 (30 pages).
Supplementary European Search Report dated Sep. 26, 2022 in corresponding EP application 20845968.5 (16 pages).

* cited by examiner

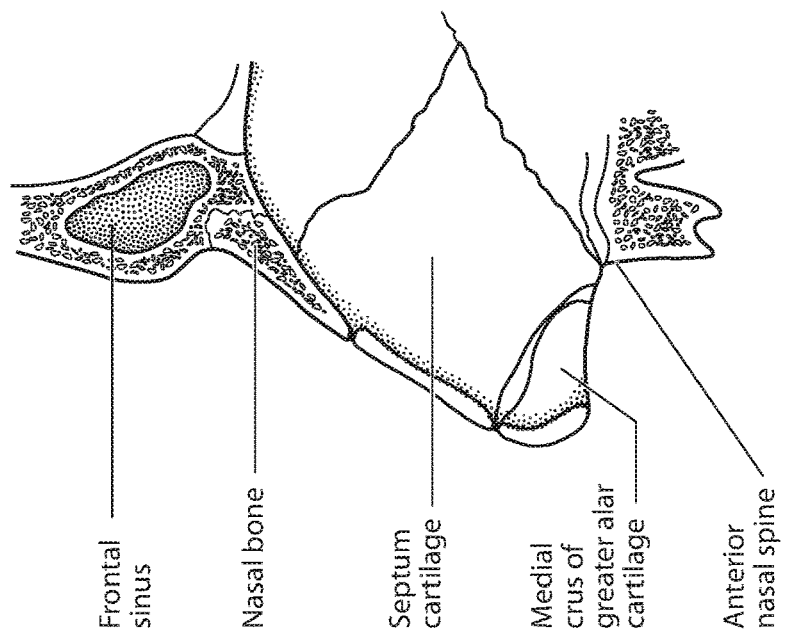
FIG. 2I
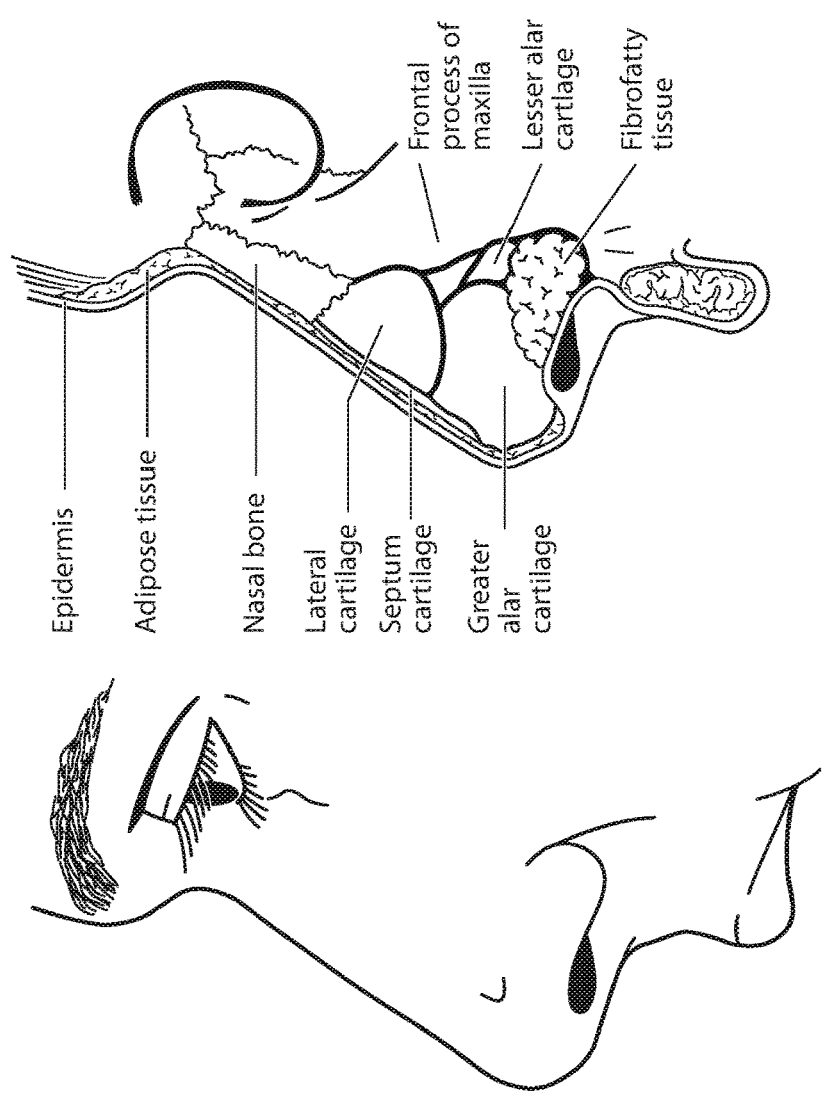
FIG. 2H
FIG. 2G

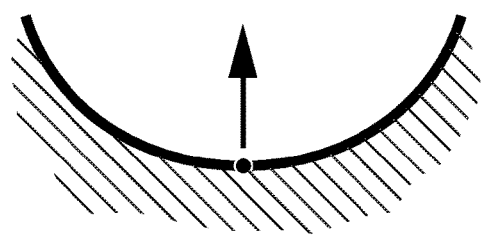
FIG. 3B — Relatively Large Positive Curvature
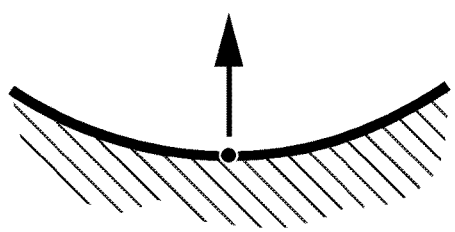
FIG. 3C — Relatively Small Positive Curvature
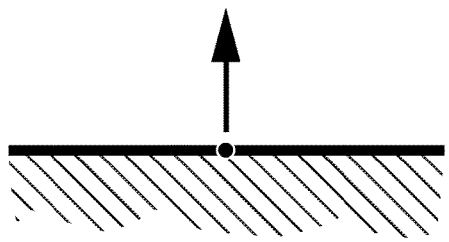
FIG. 3D — Zero Curvature
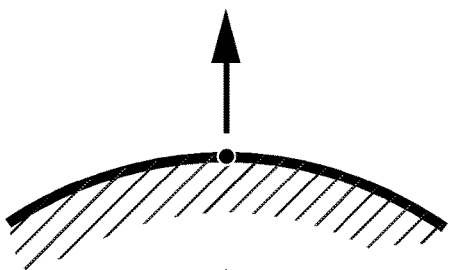
FIG. 3E — Relatively Small Negative Curvature
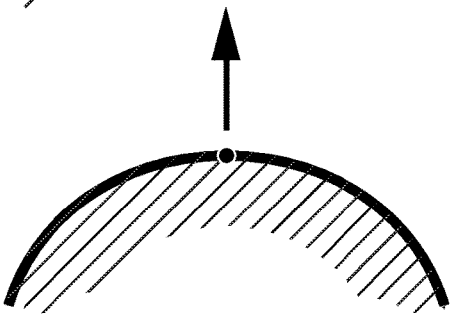
FIG. 3F — Relatively Large Negative Curvature
Copyright 2015 ResMed Limited

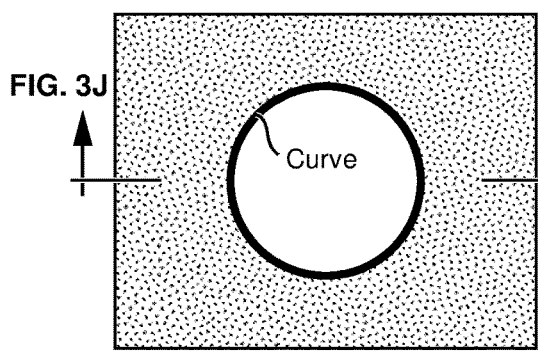
FIG. 3I
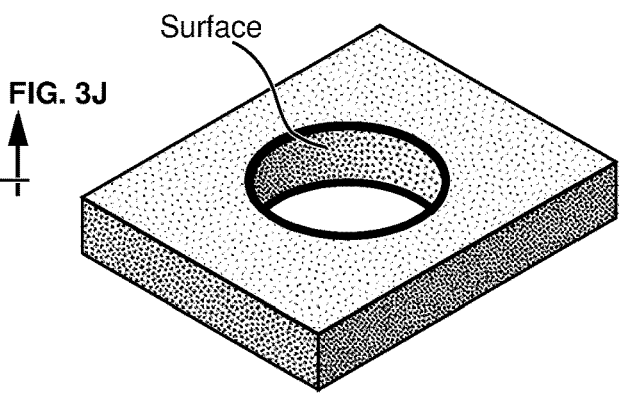
FIG. 3K
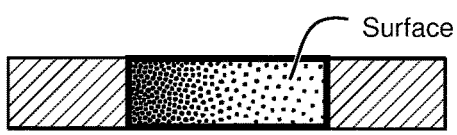
FIG. 3J
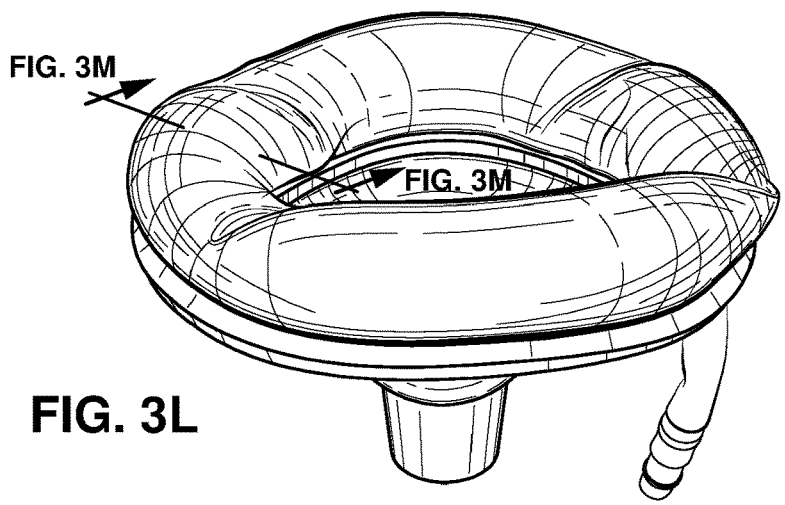
FIG. 3L
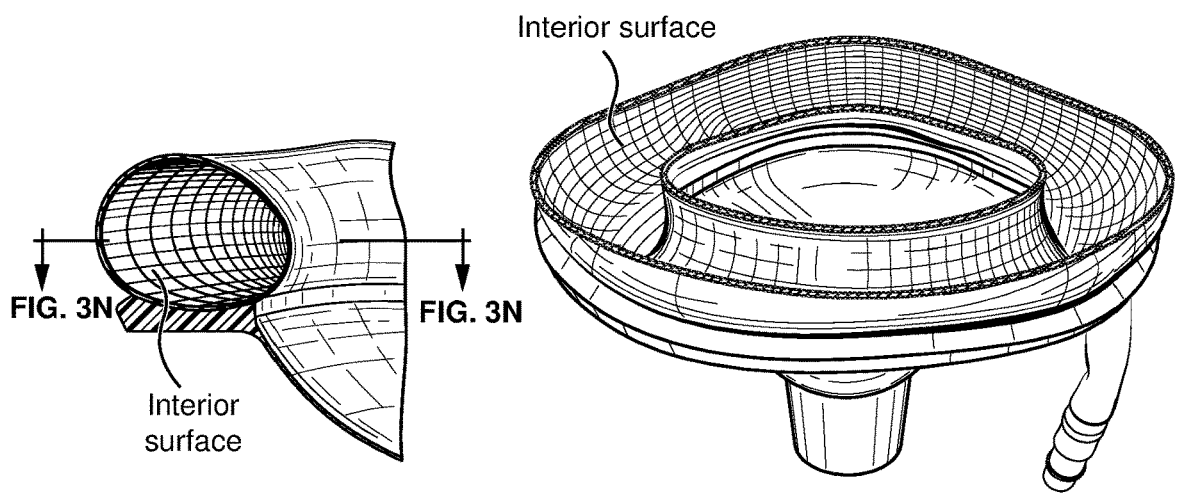
FIG. 3M  FIG. 3N
Copyright 2015 ResMed Limited

Left-hand rule

Right-hand rule

Left ear helix

Right-hand helix
Right-hand positive

Right ear helix

Copyright 2015 ResMed Limited

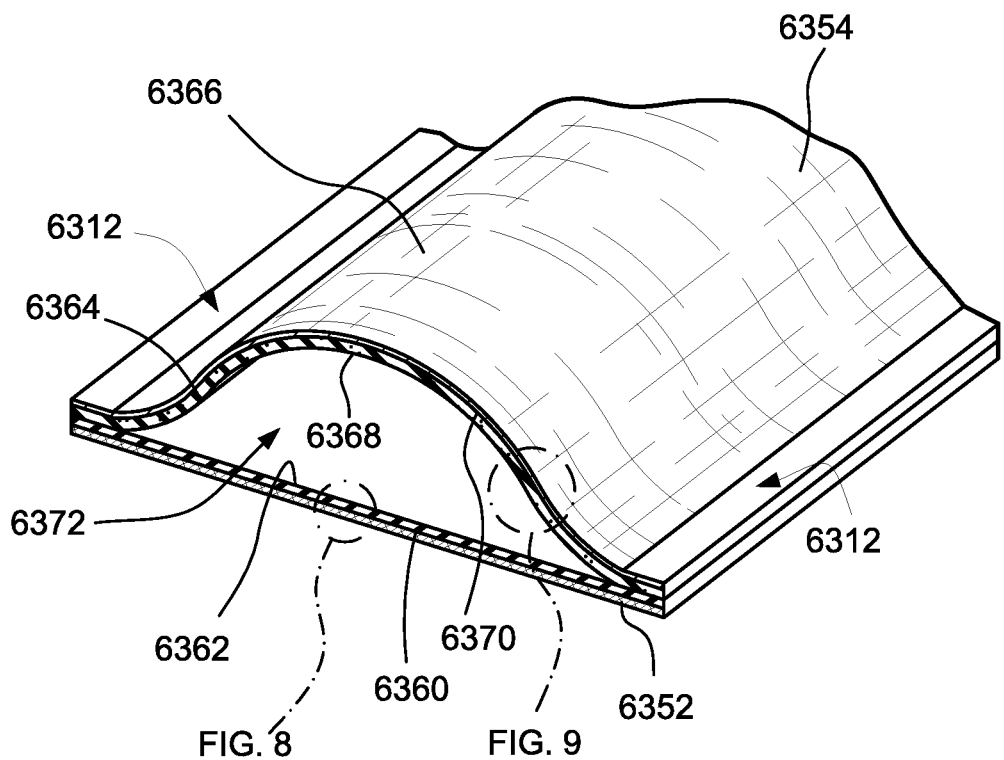
FIG. 7
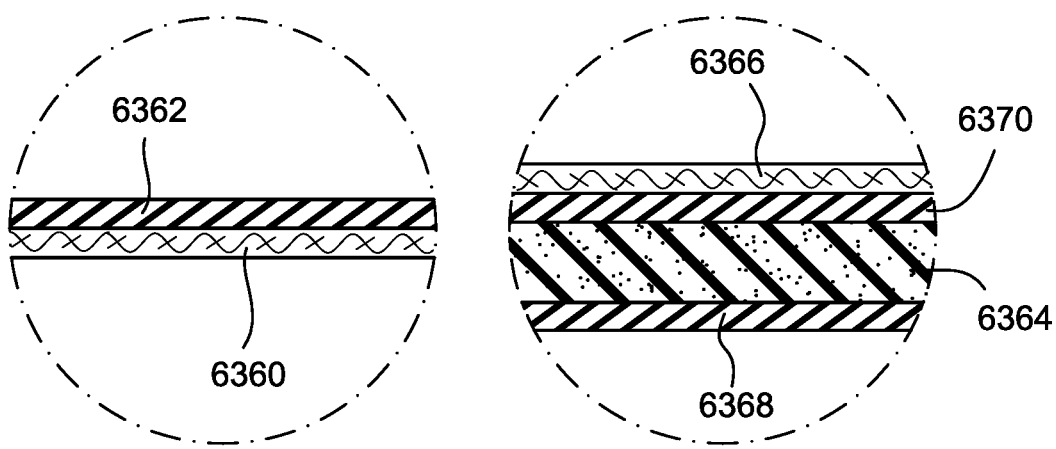
FIG. 8  FIG. 9

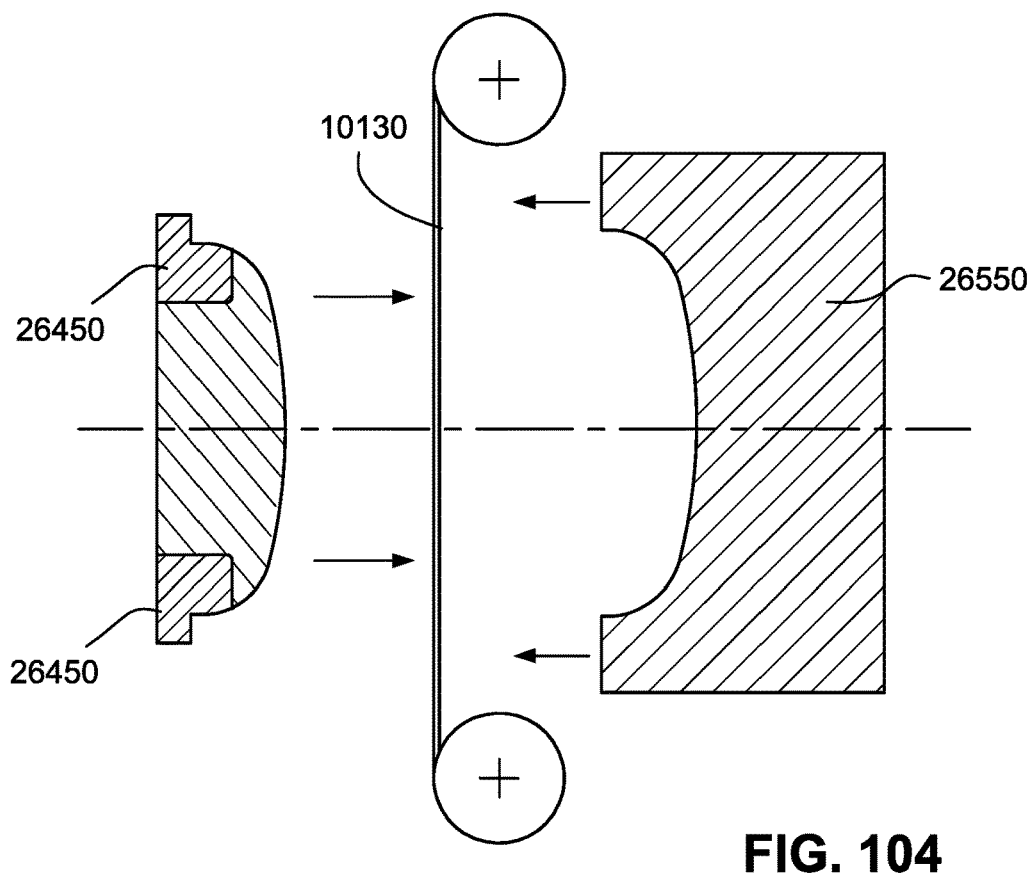
FIG. 104
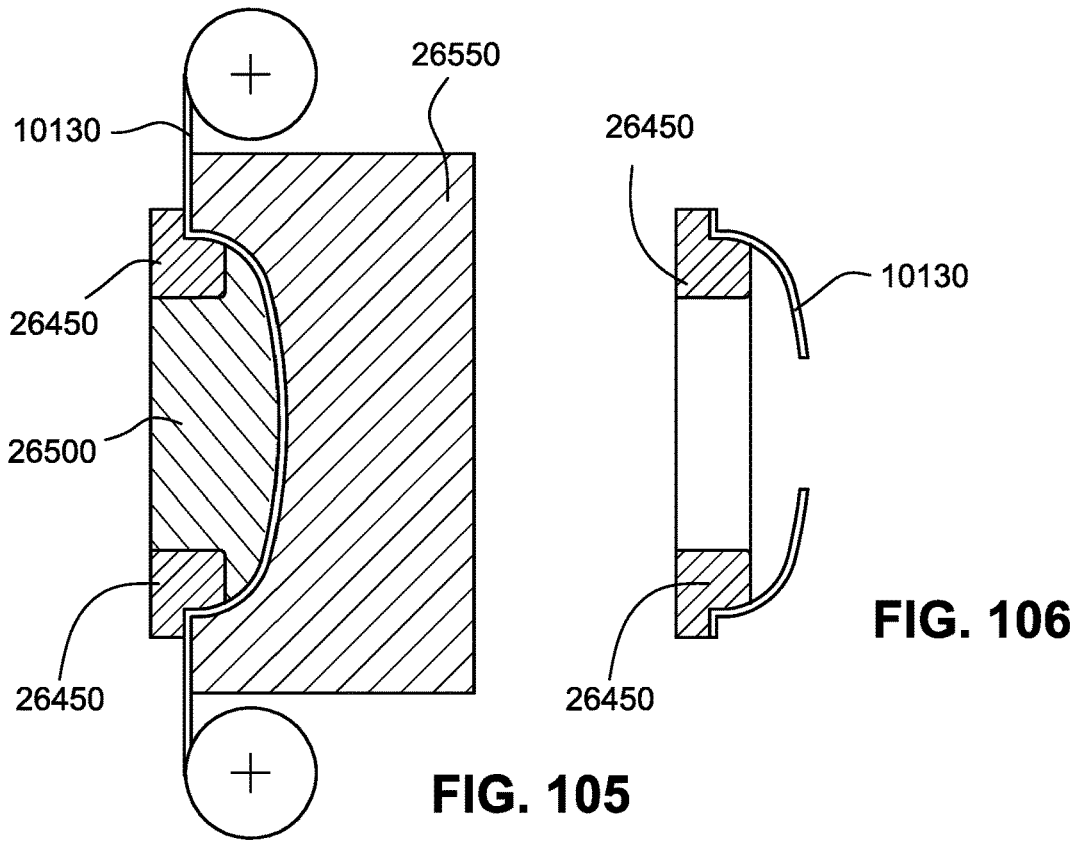
FIG. 105
FIG. 106

PATIENT INTERFACE HAVING SEAL-FORMING STRUCTURE WITH VARYING CONSTRUCTION

1 CROSS-REFERENCE TO RELATED APPLICATIONS

This application is the U.S. national phase of International Application No. PCT/IB2020/053347 filed Apr. 8, 2020 which designated the U.S. and claims priority to International Application No. PCT/IB2019/058832, filed Oct. 16, 2019, and Australian Provisional Application Nos. AU2019903201, filed Aug. 30, 2019, and AU2019902729, filed Jul. 31, 2019, the entire contents of each of which are hereby incorporated by reference.

2 BACKGROUND OF THE TECHNOLOGY

2.1 Field of the Technology

The present technology relates to one or more of the diagnosis, treatment, prevention and amelioration of respiratory-related disorders. The present technology also relates to medical devices or apparatuses, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact on the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity of the regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form. This can lead to patient discomfort.

A seal-forming structure which fits one person may not fit another person. Furthermore, a design which fits a patient at one pressure, or in one position may not be suitable for other pressures or other positions. Some designs may leak when a patient moves, e.g. whilst asleep.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Furthermore, some manufacturing processes result in undesirable folds, creases or buckles in the seal-forming structure even when not in use.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus, a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |

| RPT Device name | A-weighted sound pressure level dB(A) | Year (approx.) |
| --- | --- | --- |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers.

While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules." One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
| --- | --- | --- | --- | --- |
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | pillows | 37 | 29 | 2004 |

-continued

| Mask name | Mask type | A-weighted sound power level dB(A) (uncertainty) | A-weighted sound pressure dB(A) (uncertainty) | Year (approx.) |
|---|---|---|---|---|
| ResMed Mirage Swift™ II | nasal pillows | 28 (3) | 20 (3) | 2005 |
| ResMed Mirage Swift™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculography (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Clinical experts may be able to diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatuses that improve the compliance of patients with respiratory therapy.

Another aspect of the present technology relates to a seal-forming structure of a patient interface, the seal-forming structure including a textile membrane.

In one form, the textile membrane is air impermeable.

Another aspect of the present technology relates to a process of manufacturing a patient interface utilizing a flat textile composite to create a textile membrane having a curved shape.

Another aspect of the present technology relates to a seal-forming structure of a patient interface, the seal-forming structure including a textile membrane where the seal-forming structure has no (or few) buckles or creases.

Another aspect of the present technology is a patient interface comprising a textile membrane including a knitted textile material.

In one form the knitted textile material is warp knitted.

In one form the knitted textile material is weft knitted.

In one form, the textile membrane is stretchy (e.g., equally stretchy) in both vertical and horizontal directions.

In one form, the textile membrane is more stretchy in the horizontal direction than in the vertical direction.

Another aspect of the present technology pertains to a patient interface having a wide fit range.

Another aspect of the present technology relates to a seal-forming structure of a patient interface, the seal-forming structure including a sealing portion (e.g., comprising a textile material) that is held in tension prior to use.

Another aspect of the present technology relates to a seal-forming structure of a patient interface, the seal-forming structure including an untensioned textile membrane that is without creases, folds, wrinkles and/or buckles in an outer surface of the textile membrane Another aspect of the present technology relates to a seal-forming structure of a patient interface, the seal-forming structure including a textile membrane having a bridge portion that is slack and/or buckled with excess material.

Another aspect of the present technology relates to a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH$_2$O to about 30 cmH$_2$O above ambient air pressure in use, throughout a patient's respiratory cycle, while the patient is sleeping, to ameliorate sleep disordered breathing; said patient interface comprising: 1) a plenum chamber at least partially forming a cavity pressurisable to a therapeutic pressure of at least 6 cmH$_2$O above ambient air pressure, said plenum chamber including a plenum chamber inlet port sized and structured to receive a flow of air at the therapeutic pressure for breathing by a patient; and 2) a seal-forming structure having a textile membrane constructed and arranged to form a pressure-assisted seal with a region of the patient's face surrounding an entrance to the patient's airways inferior to a nasal bridge region of the patient's face, said textile membrane having a hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use.

In examples: (a) the seal-forming structure includes a flexible support structure attached to and supporting the textile membrane; (b) the textile membrane comprises a textile material and an air impermeable layer applied to the textile material, the air impermeable layer having a first thickness at a first location on the textile membrane and a second thickness at a second location on the textile membrane that is different than the first thickness; (c) the first thickness of the air impermeable layer is less than the second thickness.

In further examples: (a) stretchability of the textile membrane at the first location is greater than stretchability of the textile membrane at the second location; (b) a rigidity of the textile membrane at the first location is less than a rigidity of the textile membrane at the second location; (c) the first location on the textile membrane is in a nasal bridge region of the seal-forming structure, and the second location on the textile membrane is in a cheek region of the seal-forming structure; (d) the first location on the textile membrane is in a chin region of the seal-forming structure, and the second location on the textile membrane is in a cheek region of the seal-forming structure: (e) a thickness of the air impermeable layer varies in different regions around a perimeter of the seal-forming structure to vary compliance of the textile membrane in the different regions; (f) the thickness of the air impermeable layer in a nasal bridge region of the seal-forming structure is less than a thickness of the air impermeable layer in a cheek region of the seal-forming structure; (g) the thickness of the air impermeable layer in a chin region of the seal-forming structure is less than a thickness of the air impermeable layer in a cheek region of the seal-forming structure; (h) in cross-sectional view, a thickness of the air impermeable layer decreases toward an inner edge of the textile membrane, such that the first location on the textile membrane is more radially inner as compared to the second location on the textile membrane.

In further examples: (a) in cross-sectional view, a thickness of the air impermeable layer decreases toward an inner edge of the textile membrane, such that the first location on the textile membrane is more radially inner as compared to the second location on the textile membrane; (b) the support structure comprises silicone and the textile membrane is molded to an inner edge of the support structure; (c) the textile membrane has a saddle shape in nasal bridge region of the cushion assembly; (d) the textile material is weft knit; (e) the textile material comprises nylon, spandex, or polyester; (f) the air impermeable layer comprises silicone; (g) in use the therapeutic pressure in the cavity urges the textile membrane towards the patient's face.

In further examples: (a) the patient interface further comprises a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; (b) the patient interface further comprises a vent structure to allow a continuous flow of gases exhaled by the patient from an interior of the cavity to ambient, said vent structure being sized and shaped to maintain the therapeutic pressure in the cavity in use; (c) the plenum chamber and seal-forming structure form a full-face cushion assembly; (d) in use, the patient's nose is configured to be received in the cavity.

Another aspect of the present technology relates to a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH$_2$O to about 30 cmH$_2$O above ambient air pressure in use, throughout a patient's respiratory cycle, while the patient is sleeping, to ameliorate sleep disordered breathing; said patient interface comprising: 1) a plenum chamber at least partially forming a cavity pressurisable to a therapeutic pressure of at least 6 cmH$_2$O above ambient air pressure, said plenum chamber including a plenum chamber inlet port sized and structured to receive a flow of air at the therapeutic pressure for breathing by a patient; and 2) a seal-forming structure having a textile membrane constructed and arranged to form a pressure-assisted seal with a region of the patient's face surrounding an entrance to the patient's airways inferior to a nasal bridge region of the patient's face, said textile membrane having a hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use.

In examples: (a) the seal-forming structure includes a flexible support structure attached to and supporting the textile membrane, the support structure including an underlying cushion to support the textile membrane; (b) in a cross-sectional view, a length of the textile membrane that loosely overlays the underlying cushion in a first region of the seal-forming structure is different than a length of the textile membrane that loosely overlays the underlying cushion in a second region of the seal-forming structure; (c) a length of the textile membrane that is bonded to the underlying cushion in the first region of the seal-forming structure is different than a length of the textile membrane that is bonded to the underlying cushion in the second region of the seal-forming structure; (d) the length of the textile membrane that is bonded to the underlying cushion in the first region of the seal-forming structure is shorter than a length of the textile membrane that is bonded to the underlying cushion in the second region of the seal-forming structure; (e) the length of the textile membrane that loosely overlays the underlying cushion in the first region of the seal-forming structure is longer than the length of the textile membrane that loosely overlays the underlying cushion in the second region of the seal-forming structure;

In further examples: (a) in the first region of the seal-forming structure substantially no portion of the textile membrane is bonded to the underlying cushion; (b) in the first region of the seal-forming structure, portions of the textile membrane loosely overlay the underlying cushion and other portions of the textile membrane are bonded to the underlying cushion; (c) in the second region of the seal-forming structure the textile membrane is bonded to at least a portion of an exterior-facing side wall of the underlying cushion; (d) in the second region of the seal-forming structure the textile membrane is bonded to the underlying cushion to at least an upper exterior edge of the underlying cushion; (e) in the second region of the seal-forming structure the textile membrane is bonded to at least a portion of a patient-facing surface of the underlying cushion; (f) in the second region of the seal-forming structure the textile membrane is bonded to the patient-facing surface of the underlying cushion up to an interior edge of the underlying cushion; (g) in the second region of the seal-forming structure, portions of the textile membrane loosely overlay the underlying cushion and other portions of the textile membrane are bonded to the underlying cushion; (h) in the second region of the seal-forming structure substantially no portion of the textile membrane loosely overlays the underlying cushion.

In further examples: (a) the first region of the seal-forming structure is a nasal bridge region of the seal-forming structure; (b) the first region of the seal-forming structure is a chin region of the seal-forming structure; (c) the first region of the seal-forming structure is a side of nose region of the seal-forming structure; (d) the second region of the seal-forming structure is a cheek region of the seal-forming structure; (e) the cheek region is a lower cheek region of the seal-forming structure.

In further examples: (a) a cross-sectional configuration of the underlying cushion varies in different regions around a perimeter of the seal-forming structure; (b) a cross-sectional configuration of the underlying cushion in a side of nose region of the seal-forming structure is different than a cross-sectional configuration of the underlying cushion in a chin region of the seal-forming structure; (c) the underlying cushion has a radially flat region in at least a portion of the seal-forming structure that is inwardly inclined, with respect to a mid-contact plane of the seal-forming structure; (d) the underlying cushion comprises a compressible material; (e) the underlying cushion comprises a foam material; (f) the underlying cushion comprises polyurethane foam.

In further examples: (a) the textile membrane comprises a textile material and an air impermeable layer applied to the textile material; (b) the air impermeable layer has a first thickness at a first location on the textile membrane and a second thickness at a second location on the textile membrane that is different than the first thickness; (c) the support structure comprises silicone and the textile membrane is molded to an inner edge of the support structure; (d) the textile material is weft knit; (e) the textile material comprises nylon, spandex, or polyester; (f) the air impermeable layer comprises silicone; (g) in use the therapeutic pressure in the cavity urges the textile membrane and underlying cushion towards the patient's face.

In further examples: (a) the patient interface further comprises a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; (b) the patient interface further comprises a vent structure to allow a continuous flow of gases exhaled by the patient from an interior of the cavity to ambient, said vent structure being sized and shaped to maintain the therapeutic pressure in the cavity in use; (c) the plenum chamber and seal-forming structure form a full-face cushion assembly; (d) in use, the patient's nose is configured to be received in the cavity.

Another aspect of the present technology relates to a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH$_2$O to about 30 cmH$_2$O above ambient air pressure in use, throughout a patient's respiratory cycle, while the patient is sleeping, to ameliorate sleep disordered breathing; said patient interface comprising: 1) a plenum chamber at least partially forming a cavity pressurisable to a therapeutic pressure of at least 6 cmH$_2$O above ambient air pressure, said plenum chamber being adapted to receive a flow of air at the therapeutic pressure for breathing by a patient; and 2) a seal-forming structure having a textile membrane constructed and arranged to form a seal with a region of the patient's face surrounding an entrance to the patient's airways, said textile membrane having a hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use.

In examples: (a) the seal-forming structure includes a support structure to support the textile membrane, the support structure being configured to connect to the plenum chamber; and (b) the textile membrane is attached to the support structure along an outer perimeter of the textile membrane in a manner that causes the textile membrane to be in tension prior to use.

Another aspect of the present technology relates to a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH$_2$O to about 30 cmH$_2$O above ambient air pressure in use, throughout a patient's respiratory cycle, while the patient is sleeping, to ameliorate sleep disordered breathing; said patient interface comprising: 1) a plenum chamber at least partially forming a cavity pressurisable to a therapeutic pressure of at least 6 cmH$_2$O above ambient air pressure, said plenum chamber including a plenum chamber inlet port sized and structured to receive a flow of air at the therapeutic pressure for breathing by a patient; and 2) a seal-forming structure having a textile membrane constructed and arranged to form a seal with a region of the patient's face surrounding an entrance to the patient's airways, said textile membrane having a hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use. The seal-forming structure may include a flexible support structure to support the textile membrane, the support structure being connected to the plenum chamber, the support structure being stiffer than the textile membrane. In use, the textile membrane may be configured to press against the patient's face such that the patient's nose is not received in the cavity. The textile membrane may be attached to the support structure along an outer perimeter of the textile membrane such that textile membrane extends radially inwardly beyond the support structure.

In examples: (a) the plenum chamber and the support structure comprise silicone and form a one piece structure having a first lateral support section with a first thickness and a second centrally disposed nose base section with a second thickness that is less than the first thickness, and the nose base section is configured to fold or form a pivot point upon engagement of the textile membrane with the patient's face thereby allowing left and right lateral sides of the support structure to deform inwardly to cradle the patient's nose; (b) the support structure includes an underlying cushion; (c) the support structure comprises foam; (d) the support structure comprises silicone and the textile membrane is molded to an inner edge of the support structure; (e) the textile membrane has a dome shape in a corner region of the textile membrane; (f) the textile membrane has a saddle shape in a lower central region of the textile membrane that is configured to seal against the patient's subnasale in use.

In further examples: (a) the textile membrane comprises a membrane layer applied to a textile material to make the textile material substantially air impermeable; (b) the textile membrane has a thickness in the range of 0.3 mm to 0.5 mm; (c) the membrane layer has a thickness in the range of 0.05 mm to 0.1 mm; (d) the textile material is weft knit; (e) the weight of the textile material is in the range of 105 gsm to 120 gsm; (f) the machine gauge of the textile material is in the range of 44GG to 60GG; (g) the textile material has a melange aesthetic; (h) the textile material has a solid color aesthetic; (i) the membrane layer comprises silicone; (j) the textile material comprises nylon, spandex, or polyester; (k) in use, the therapeutic pressure in the cavity urges the textile membrane towards the patient's face; (l) the plenum chamber comprises silicone and is formed in one piece with the support structure.

In further examples: (a) the patient interface further comprises a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; (b) the patient interface further comprises a vent structure to allow a continuous flow of gases exhaled by the patient from an interior of the cavity to ambient, said vent structure being sized and shaped to maintain the therapeutic pressure in the cavity in use; (c) the plenum chamber and seal-forming structure form an oro-nasal cushion assembly; (d) the plenum chamber and seal-forming structure form a nasal cushion.

Another aspect of the present technology relates to a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH$_2$O to about 30 cmH$_2$O above ambient air pressure in use, throughout a patient's respiratory cycle, while the patient is sleeping, to ameliorate sleep disordered breathing; said patient interface comprising: 1) a plenum chamber at least partially forming a cavity pressurisable to a therapeutic pressure of at least 6 cmH$_2$O above ambient air pressure, said plenum chamber including a plenum chamber inlet port sized and structured to receive a flow of air at the therapeutic pressure for breathing by a patient; and 2) a seal-forming structure having a textile membrane constructed and arranged to form a seal with a region of the patient's face surrounding an entrance to the patient's airways, said textile membrane having at least one hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use. The seal-forming structure may include a flexible support structure to support the textile membrane, the support structure being stiffer than the textile membrane, the support structure being connected to the plenum chamber. At a transition portion, the textile membrane may be attached to the support structure along an outer edge of the textile membrane and an inner edge of the support structure such that textile membrane extends radially inwardly beyond the support structure. At the transition portion, both the support structure and the textile membrane may extend along a curve in a direction from an anterior side of the seal-forming structure to a posterior patient-facing side of the seal-forming structure.

In examples: (a) at the transition portion, the support structure and the textile membrane have substantially the same radius of curvature; (b) the textile membrane extends continuously along the curve from the transition portion to the inner edge of the textile membrane; (c) in use, the textile membrane may be configured to press against the patient's face such that the patient's nose is not received in the cavity; (d) the at least one hole in the textile membrane comprises two holes, and a bridge portion is disposed between the two holes in the textile membrane; (e) the support structure comprises silicone and the textile membrane is molded to an inner edge of the support structure; (f) the seal-forming structure has a seamless transition along an outer surface thereof from the support structure to the textile membrane.

In further examples: (a) the textile membrane comprises a textile material and a membrane layer applied thereto to make the textile material substantially air impermeable; (b) the textile membrane has a thickness in the range of 0.3 mm to 0.5 mm; (c) the textile material is weft knit; (d) the membrane layer comprises silicone; (e) the textile material comprises nylon, spandex, or polyester; (f) in use the therapeutic pressure in the cavity urges the textile membrane towards the patient's face; (g) the plenum chamber and seal-forming structure form an oro-nasal cushion assembly; (h) the plenum chamber and seal-forming structure form a nasal cushion.

Another aspect of the present technology relates to a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH$_2$O to about 30 cmH$_2$O above ambient air pressure in use, throughout a patient's respiratory cycle, while the patient is sleeping, to ameliorate sleep disordered breathing; said patient interface comprising: 1) a plenum chamber at least partially forming a cavity pressurisable to a therapeutic pressure of at least 6 cmH$_2$O above ambient air pressure, said plenum chamber including a plenum chamber inlet port sized and structured to receive a flow of air at the therapeutic pressure for breathing by a patient; and 2) a seal-forming structure having a textile membrane constructed and arranged to form a seal with a region of the patient's face surrounding an entrance to the patient's airways, said textile membrane having at least one hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use. The textile membrane may comprise a textile material and a membrane layer applied thereto to make the textile material substantially air impermeable, the textile material may be a weft knit textile. The seal-forming structure may include a flexible support structure to support the textile membrane, the support structure may be connected to the plenum chamber, and the support structure may be stiffer than the textile membrane. The textile membrane may be attached to the support structure along an outer perimeter of the textile membrane such that textile membrane extends radially inwardly beyond the support structure. In use, the textile membrane may be configured to press against the patient's face such that the patient's nose is not received in the cavity. The textile membrane may have a dome shape in a corner region of the textile membrane configured to seal against the patient's subalare, and a saddle shape at a lower central region of the textile membrane configured to seal against the patient's subnasale.

In examples: (a) in use, the therapeutic pressure in the cavity urges the textile membrane towards the patient's face to assist the textile membrane in forming a seal with the patient's face; (b) the at least one hole in the textile membrane comprises two holes, a bridge portion is disposed between the two holes in the textile membrane, and the bridge portion is buckled with excess material to allow the textile membrane to expand to accommodate different size noses; (c) the support structure comprises silicone and the textile membrane is molded to an inner edge of the support structure; (d) the plenum chamber comprises silicone and is formed in one piece with the support structure; (e) the textile membrane is attached to the support structure in a manner that causes the textile membrane to be in tension prior to use; (f) a first region of the textile membrane is in tension prior to use and a second region of the textile membrane is untensioned prior to use.

In further examples: (a) the textile membrane has four-way elasticity; (b) the textile membrane has a first elasticity in lateral left-right direction and a second different elasticity in a superior-inferior direction, wherein the elasticity in the first direction is greater than the elasticity in the second direction; (c) the membrane layer comprises silicone; (d) the textile material comprises nylon, spandex, or polyester; (e) the plenum chamber and seal-forming structure form an oro-nasal cushion assembly; (f) the plenum chamber and seal-forming structure form a nasal cushion.

Another aspect of the present technology relates to a method of forming a cushion assembly for a patient interface, the cushion assembly being configured for sealed delivery of a flow of air at a continuously positive pressure with respect to ambient air pressure to an entrance to a patient's airways including at least entrance of a patient's nares, wherein the cushion assembly is configured to maintain a therapy pressure in a range of about 4 cmH2O to about 30 cmH2O above ambient air pressure in use, throughout a patient's respiratory cycle, while the patient is sleeping, to ameliorate sleep disordered breathing; said method comprising: 1) forming an airtight textile composite by applying an air impermeable material to a textile material, the textile composite having a flat shape; 2) cutting the textile composite to desired dimensions according to a particular cushion assembly type to be used; and 3) overmolding a flexible support structure onto the cut textile composite to form a seal-forming structure having a textile membrane such that the textile membrane is attached to the support structure along an outer edge of the textile membrane and an inner edge of the support structure. In the overmolding step, the textile composite may be held in place by vacuum so as to have a non-flat shape during overmolding thereby imparting a curved non-flat shape to the textile membrane. No wrinkles, creases, folds and/or buckles are formed in the textile membrane.

In examples: (a) the seal-forming structure has a seamless transition along an outer surface thereof from the support structure to the textile membrane; (b) at a transition portion, the textile membrane is attached to the support structure along an outer edge of the textile membrane and an inner edge of the support structure such that textile membrane extends radially inwardly beyond the support structure, and at the transition portion, both the support structure and the textile membrane extend along a curve in a direction from an anterior side of the seal-forming structure to a posterior patient-facing side of the seal-forming structure; (c) two holes are formed in the textile membrane, and a bridge portion is disposed between the two holes in the textile membrane, and the bridge portion is buckled with excess material to allow the textile membrane to expand to accommodate different size noses; (d) the support structure comprises silicone.

Another aspect of the present technology relates to a seal-forming structure of a patient interface, the seal-forming structure including a support structure and a sealing portion, the support structure supporting the sealing portion, wherein the sealing portion is attached to the support structure along an outer perimeter of the sealing portion such that the sealing portion extends radially inwardly beyond the support structure, and wherein, in use, the sealing portion is configured to press against the patient's face such that the patient's nose is not received in the cavity and the sealing portion is in tension due to reactive stress of the support structure and/or a resilient stretch characteristic of the textile which thereby causes the sealing portion to exert a force against the patient's face.

According to a further aspect of the present technology, the sealing portion comprises textile. In a further example, the patient interface comprises a plenum chamber and the support structure is configured to connect to the plenum chamber, the plenum chamber at least partially forming a cavity pressurisable to a therapeutic pressure of at least 6 cmH$_2$O above ambient air pressure, the plenum chamber including a plenum chamber inlet port sized and structured to receive a flow of air at the therapeutic pressure for breathing by a patient. In a further example, the sealing portion is constructed and arranged to form a seal with a region of the patient's face surrounding an entrance to the patient's airways, the sealing portion having a hole formed therein such that the flow of air at the therapeutic pressure is delivered to at least an entrance to the patient's nares, the seal-forming structure being constructed and arranged to maintain the therapeutic pressure in the cavity throughout the patient's respiratory cycle in use. In a further example, the support structure comprise silicone and/or a thermoplastic elastomer.

According to a further aspect of the present technology, a wall structure of the support structure between the sealing portion and the plenum chamber has a first section with a first thickness and a second section with a second thickness that is different than the first thickness.

Another aspect of the present technology relates to a seal-forming structure of a patient interface, the seal-forming structure including a support structure and a sealing portion, the support structure supporting the sealing portion, wherein the sealing portion is attached to the support structure along an outer perimeter of the sealing portion in a manner that causes the sealing portion to be in tension prior to use.

According to a further aspect of the present technology, the sealing portion comprising a textile material. In a further example, the patient interface comprises a plenum chamber and the support structure is configured to connect to the plenum chamber, the plenum chamber at least partially forming a cavity pressurisable to a therapeutic pressure of at least 6 cmH$_2$O above ambient air pressure, the plenum chamber including a plenum chamber inlet port sized and structured to receive a flow of air at the therapeutic pressure for breathing by a patient. In a further example, the sealing portion is constructed and arranged to form a seal with a region of the patient's face surrounding an entrance to the patient's airways, the sealing portion having a hole formed therein such that the flow of air at the therapeutic pressure is delivered to at least an entrance to the patient's nares, the seal-forming structure being constructed and arranged to maintain the therapeutic pressure in the cavity throughout the patient's respiratory cycle in use. In a further example, the support structure comprise silicone and/or a thermoplastic elastomer.

Another aspect of the present technology relates to a seal-forming structure of a patient interface, the seal-forming structure including a support structure and a sealing portion, the support structure supporting the sealing portion, wherein the sealing portion comprises a textile material and is attached to the support structure along an outer perimeter of the sealing portion, wherein the support structure is more rigid than the sealing portion, the support structure having a first section with a first thickness and a second section with a second thickness that is different than the first thickness.

According to a further aspect of the present technology, the support structure comprises silicone and/or a thermoplastic elastomer, the patient interface comprises a plenum chamber and the support structure is configured to connect to the plenum chamber, the plenum chamber at least partially forming a cavity pressurisable to a therapeutic pressure of at least 6 cmH$_2$O above ambient air pressure, the plenum chamber including a plenum chamber inlet port sized and structured to receive a flow of air at the therapeutic pressure for breathing by a patient. In a further example, the sealing portion is constructed and arranged to form a seal with a region of the patient's face surrounding an entrance to the patient's airways, the sealing portion having a hole formed therein such that the flow of air at the therapeutic pressure is delivered to at least an entrance to the patient's nares, the seal-forming structure being constructed and arranged to maintain the therapeutic pressure in the cavity throughout the patient's respiratory cycle in use.

Another aspect of one form of the present technology is a patient interface that is moulded or otherwise constructed with a perimeter shape which is complementary to that of an intended wearer.

An aspect of one form of the present technology is a method of manufacturing the apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

Another aspect of the present technology relates to a treatment system used for treatment of sleep disordered breathing, comprising: 1) the patient interface according to any of the above aspects; 2) a respiratory pressure therapy (RPT) device to supply breathable gas at positive pressure; and 3) an air delivery tube to pass the breathable gas from the RPT device to the patient interface.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 2A:
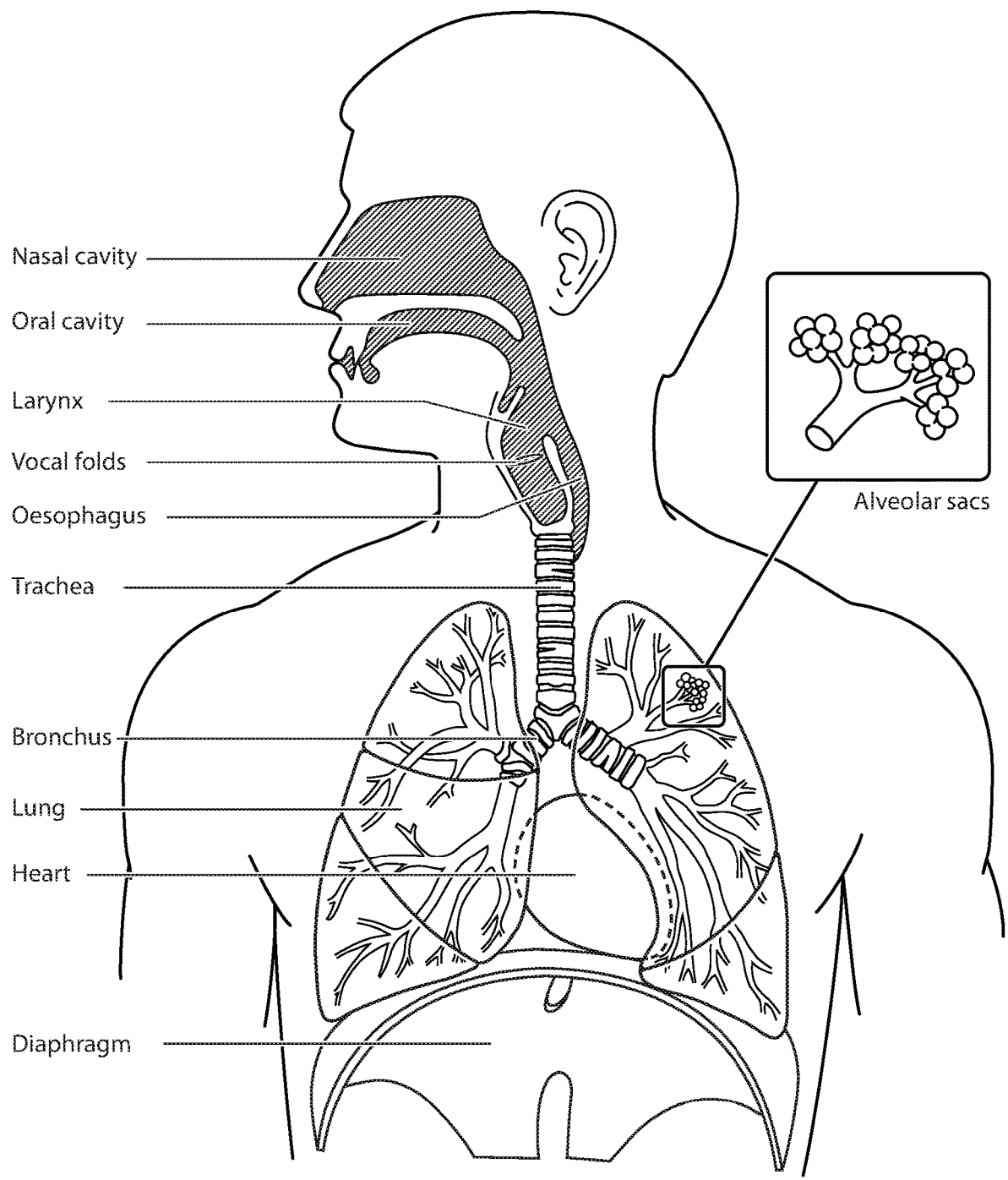
FIG. 2A shows an overview of a human respiratory system including the nasal and oral cavities, the larynx, vocal folds, oesophagus, trachea, bronchus, lung, alveolar sacs, heart and diaphragm.
Figure 2B:
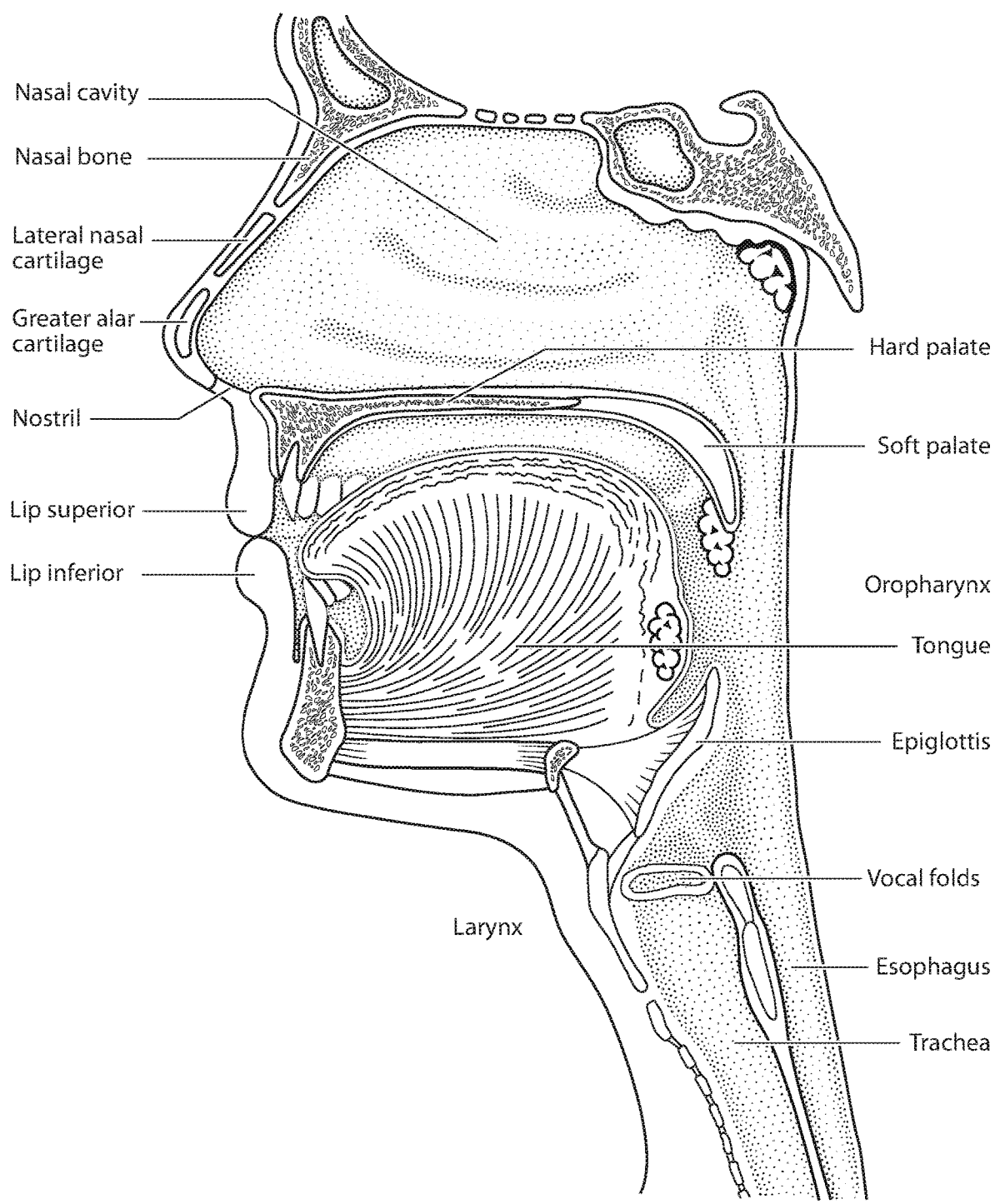
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
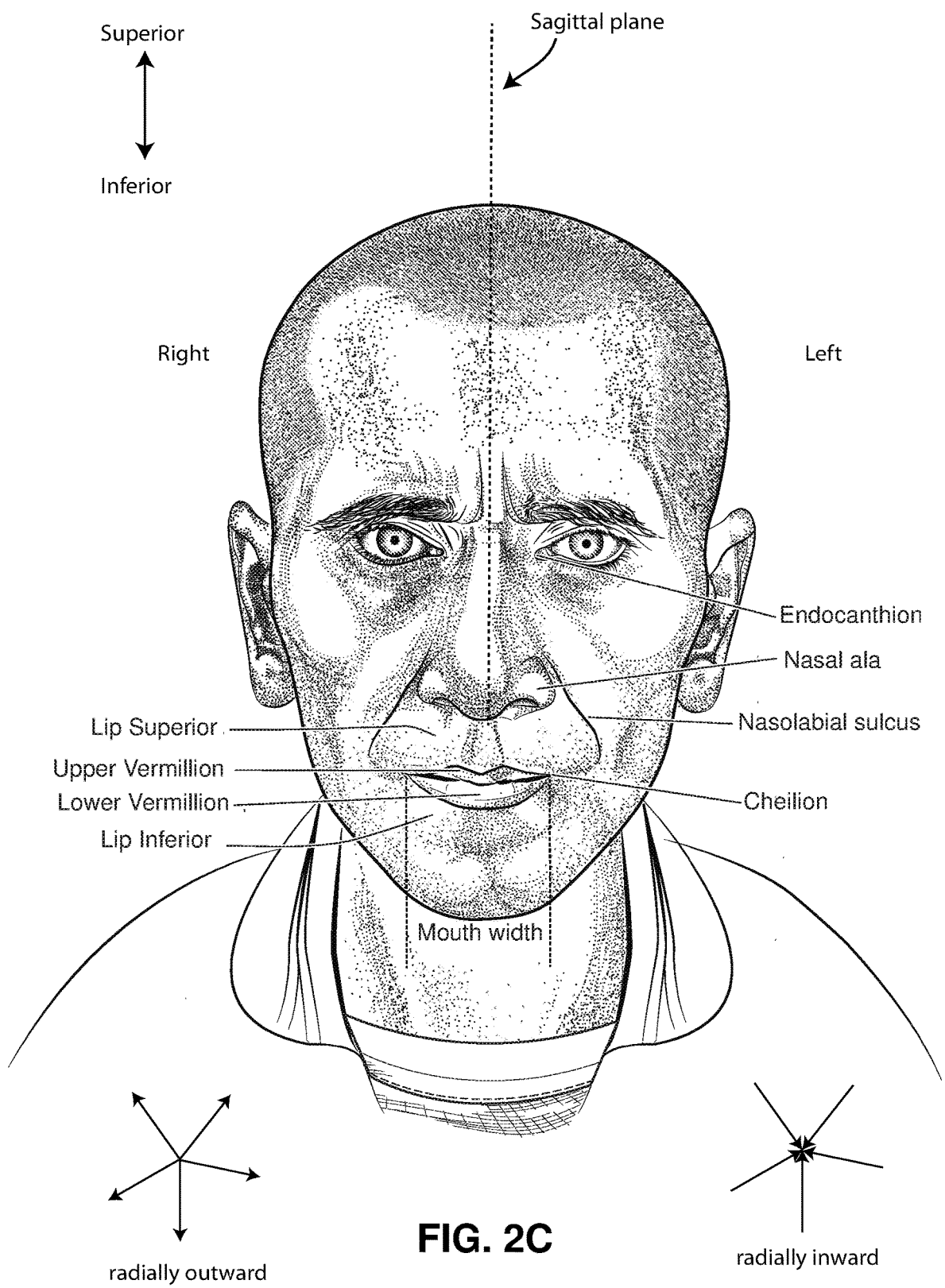
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
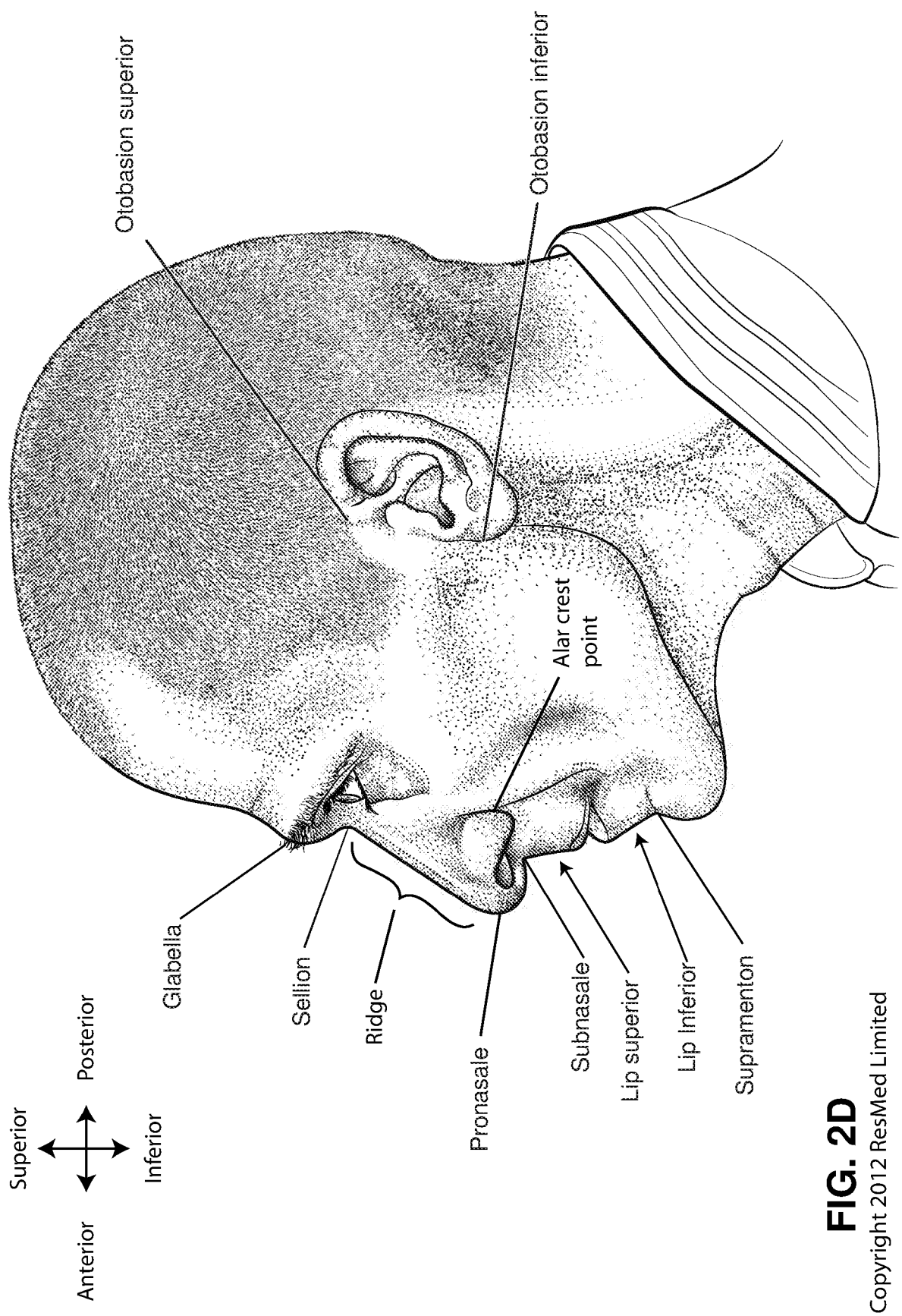
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
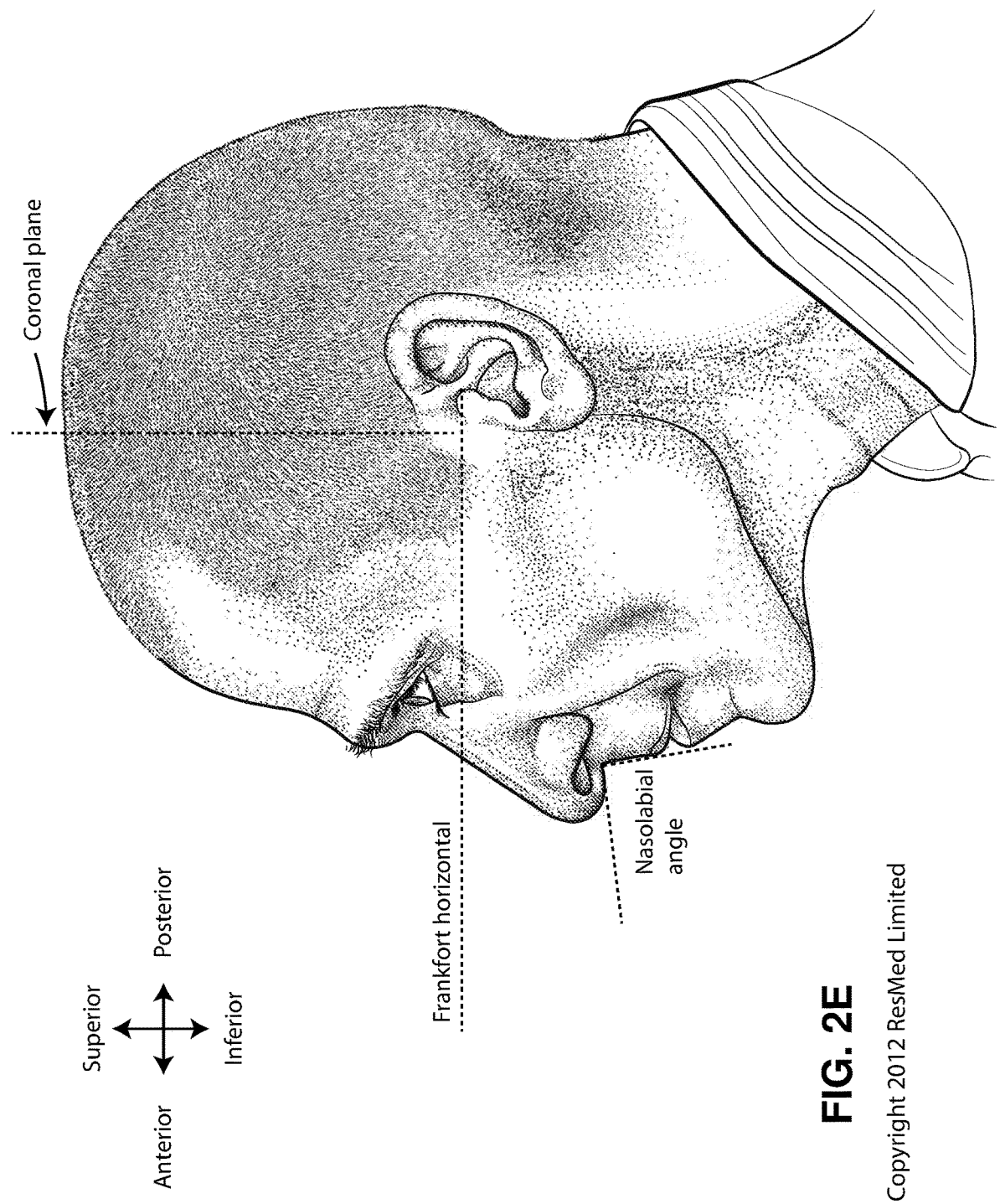

FIG. 2E is a further side view of a head. The approximate locations of the Frankfort horizontal and nasolabial angle are indicated. The coronal plane is also indicated.

Figure 2F:
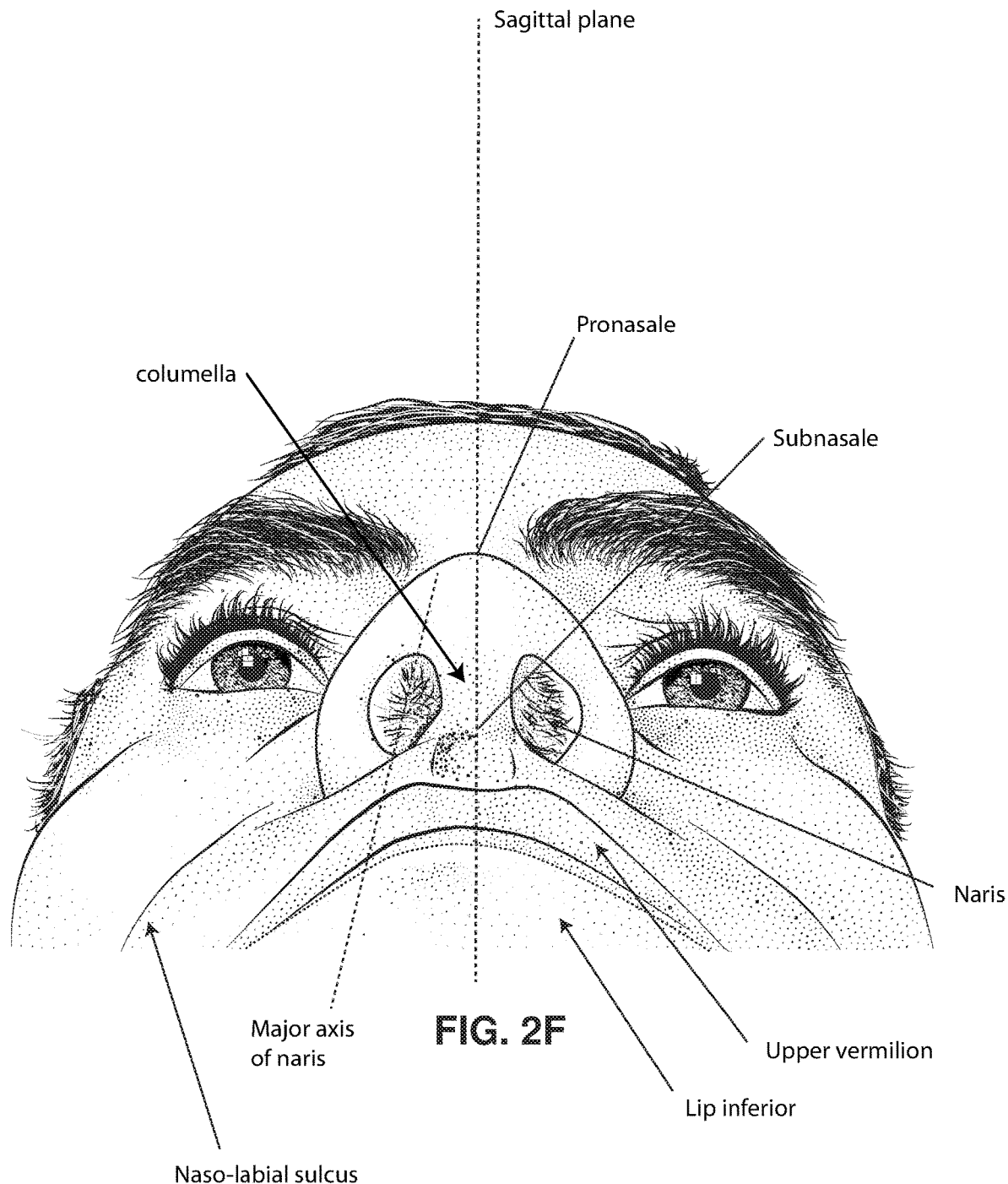

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
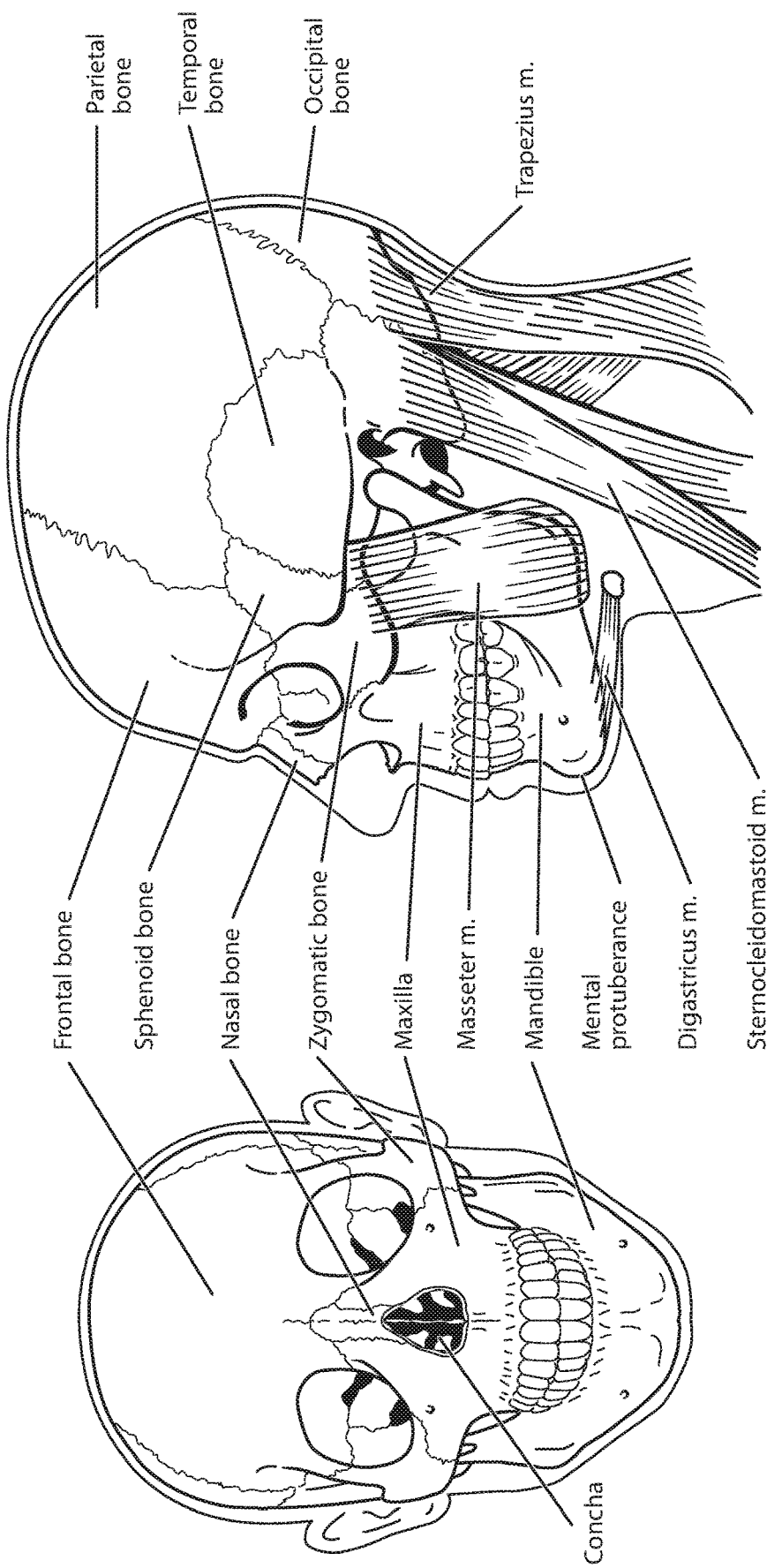

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
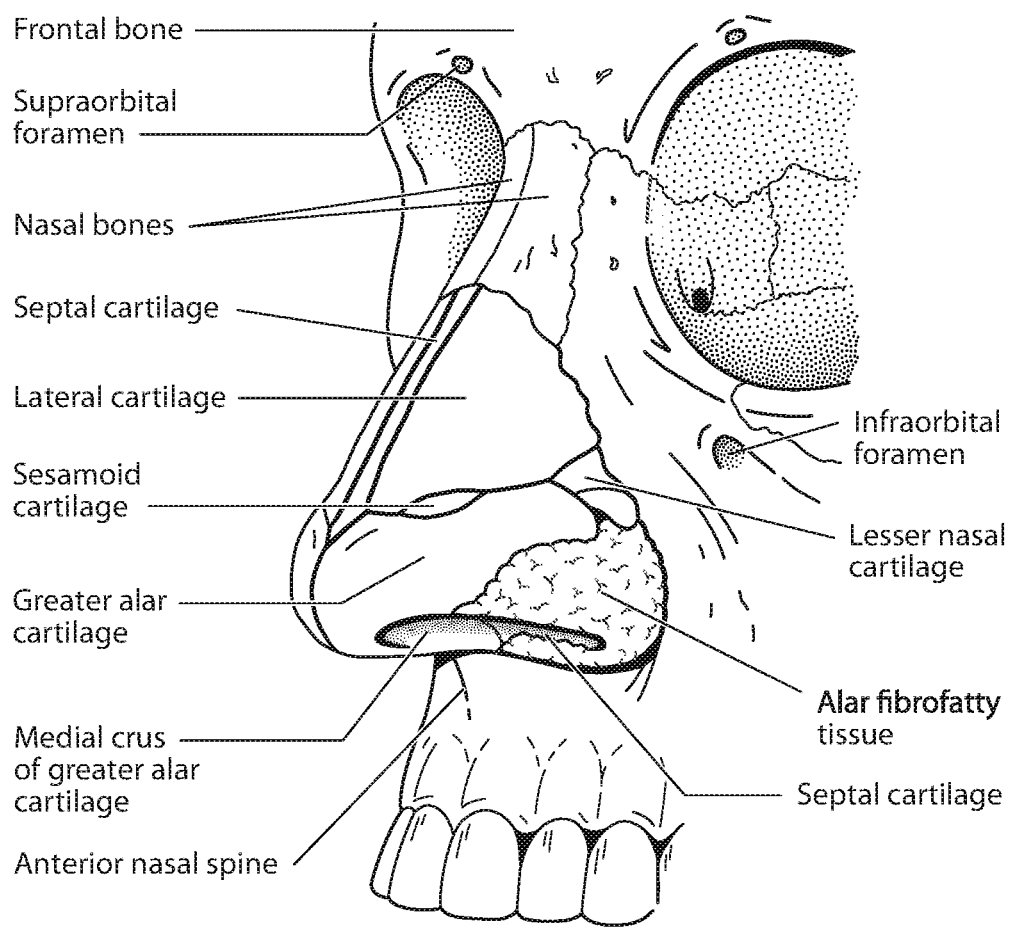

FIG. 2L shows an anterolateral view of a nose.

4.3 Patient Interface

Figure 3A:
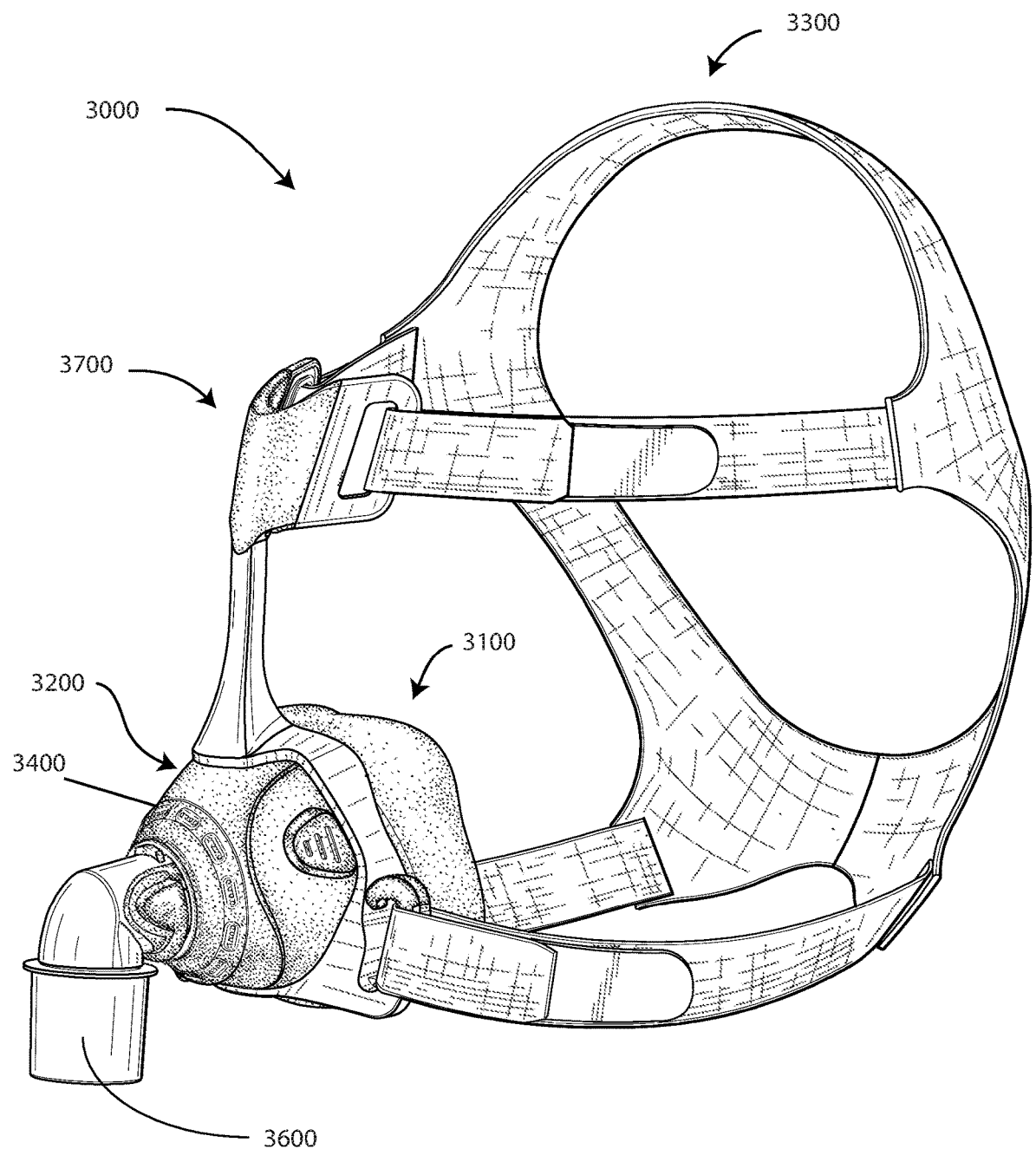

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
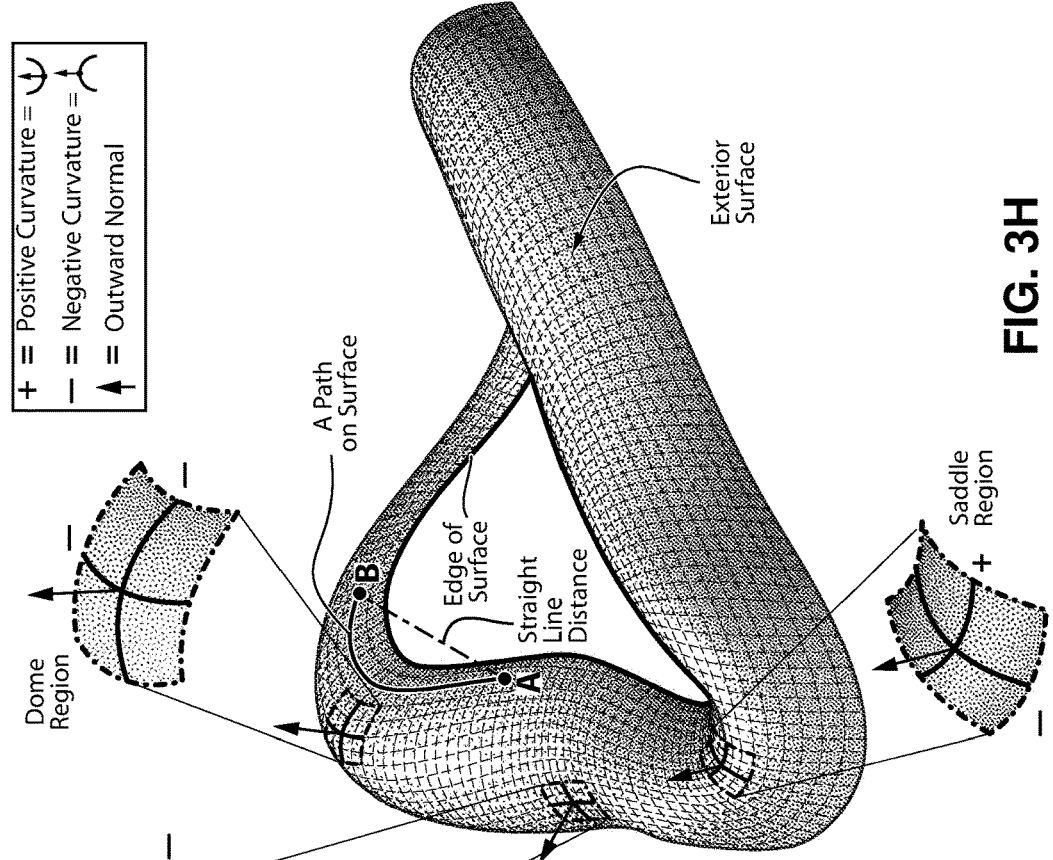
Figure 3G:
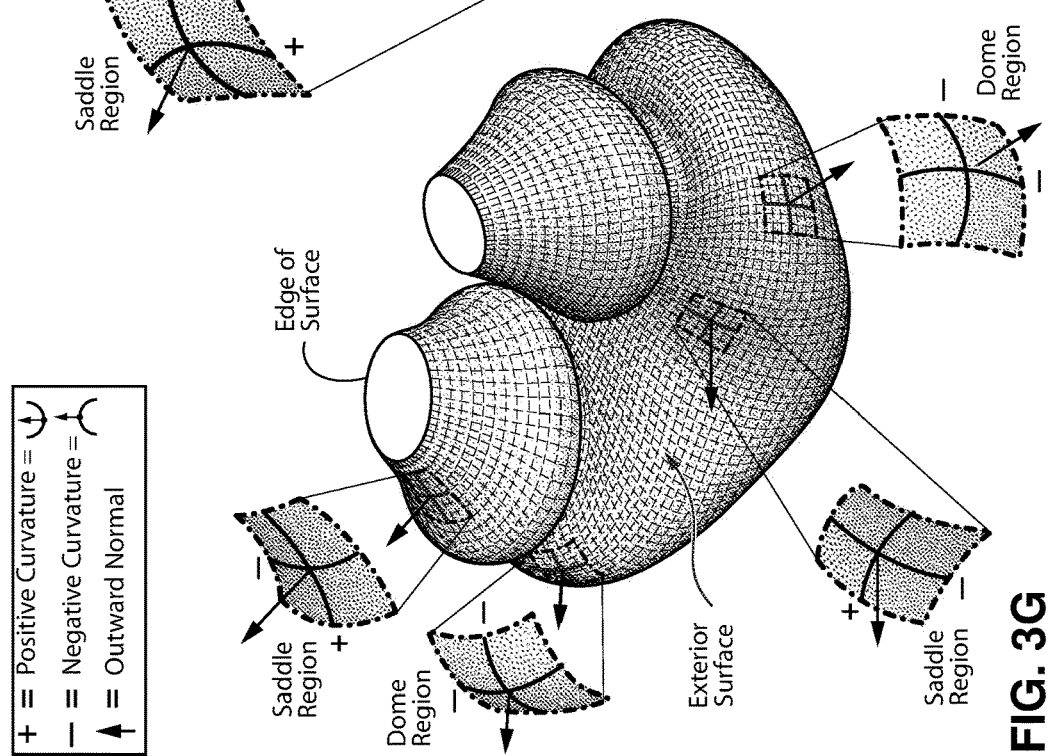

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

Figure 3O:
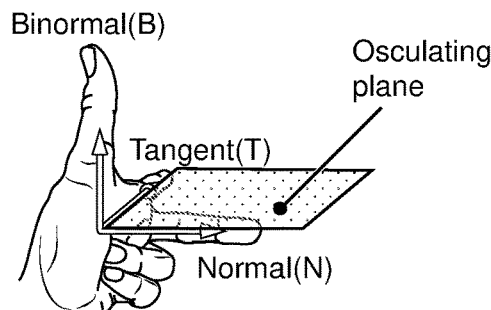

FIG. 3O illustrates a left-hand rule.

Figure 3P:
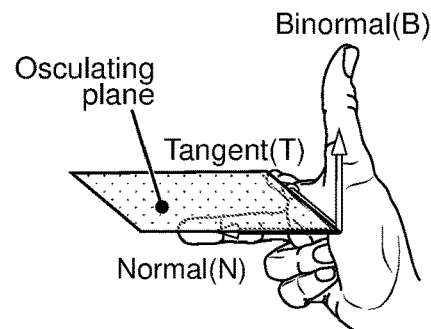

FIG. 3P illustrates a right-hand rule.

Figure 3Q:
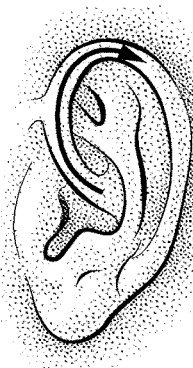

FIG. 3Q shows a left ear, including the left ear helix.

Figure 3S:
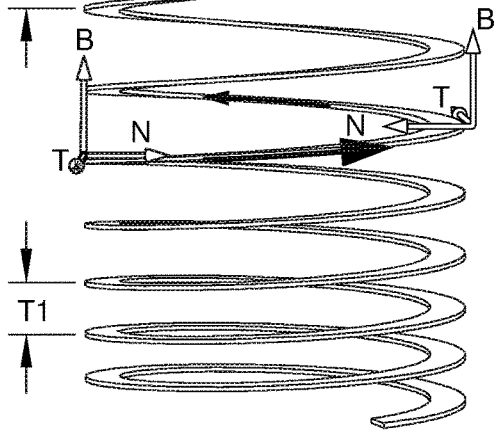
Figure 3R:
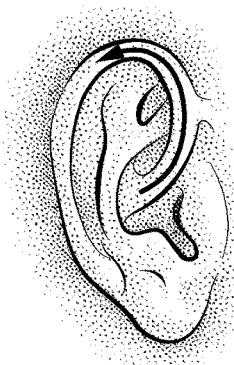

FIG. 3R shows a right ear, including the right ear helix.

FIG. 3S shows a right-hand helix.

Figure 3T:
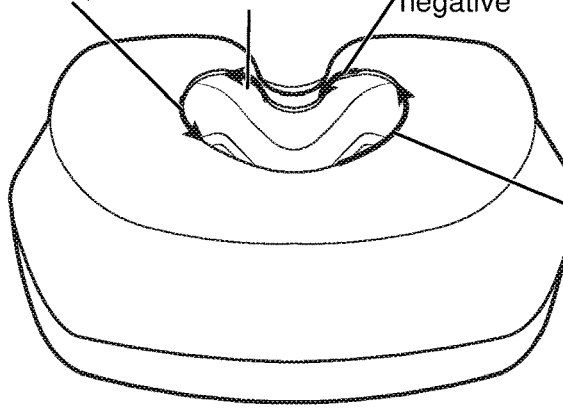

FIG. 3T shows a view of a mask, including the sign of the torsion of the space curve defined by the edge of the sealing membrane in different regions of the mask.

Figure 3U:
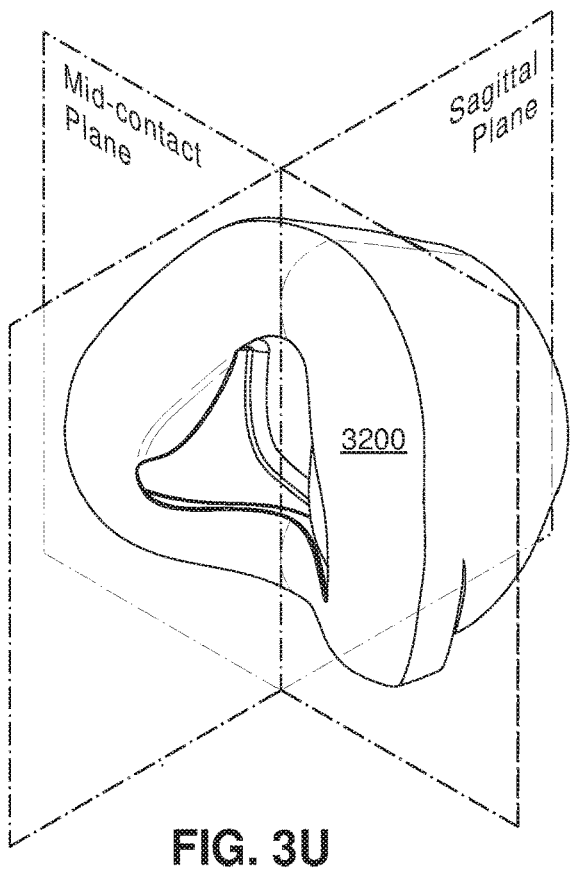

FIG. 3U shows a view of a plenum chamber 3200 showing a sagittal plane and a mid-contact plane.

Figure 3V:
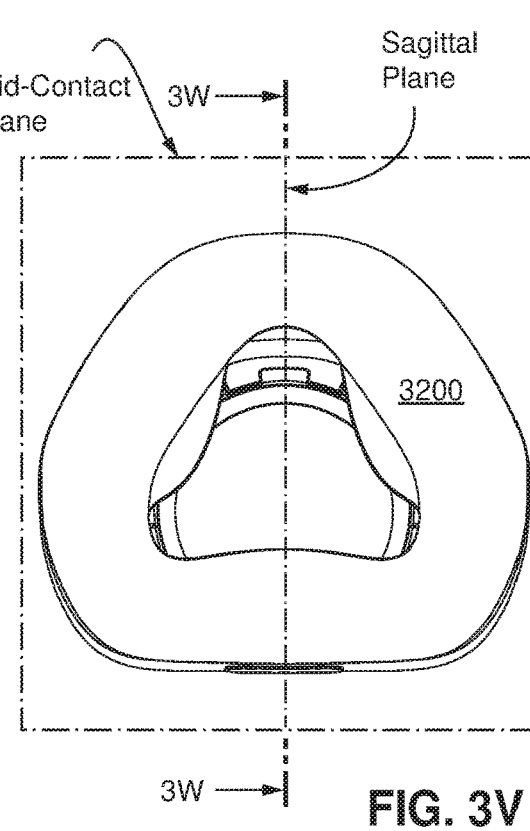

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
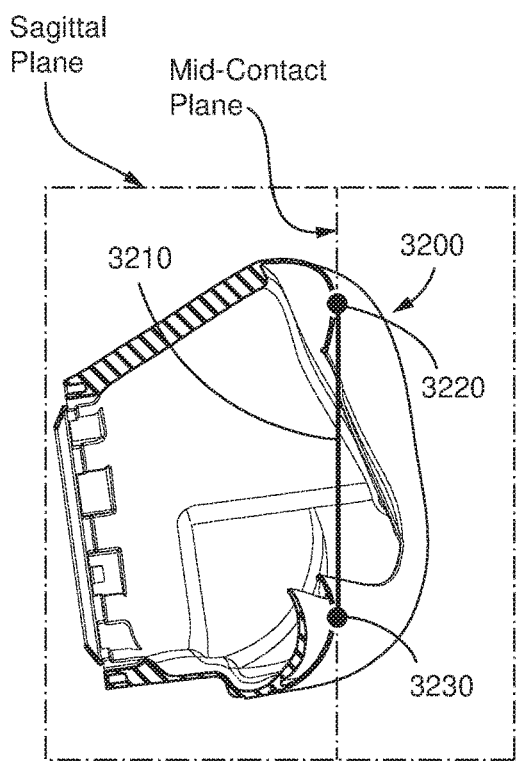

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
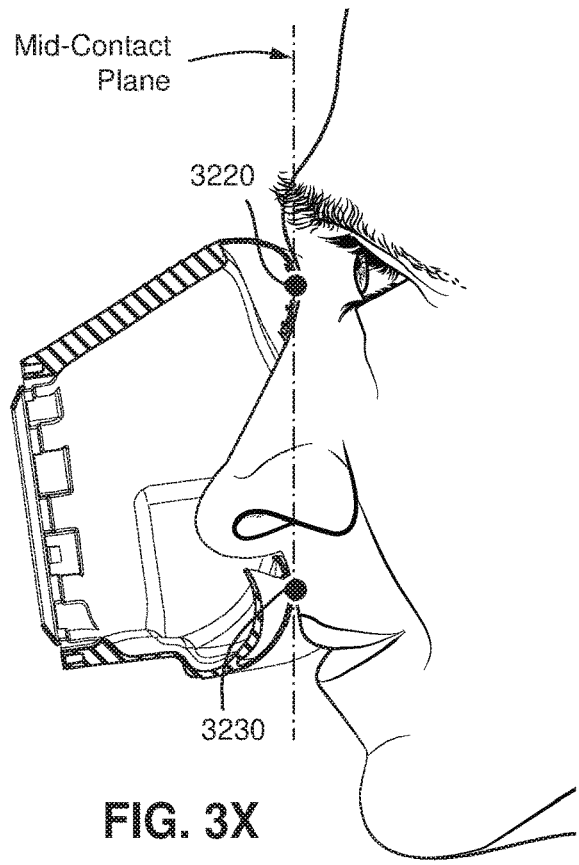

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
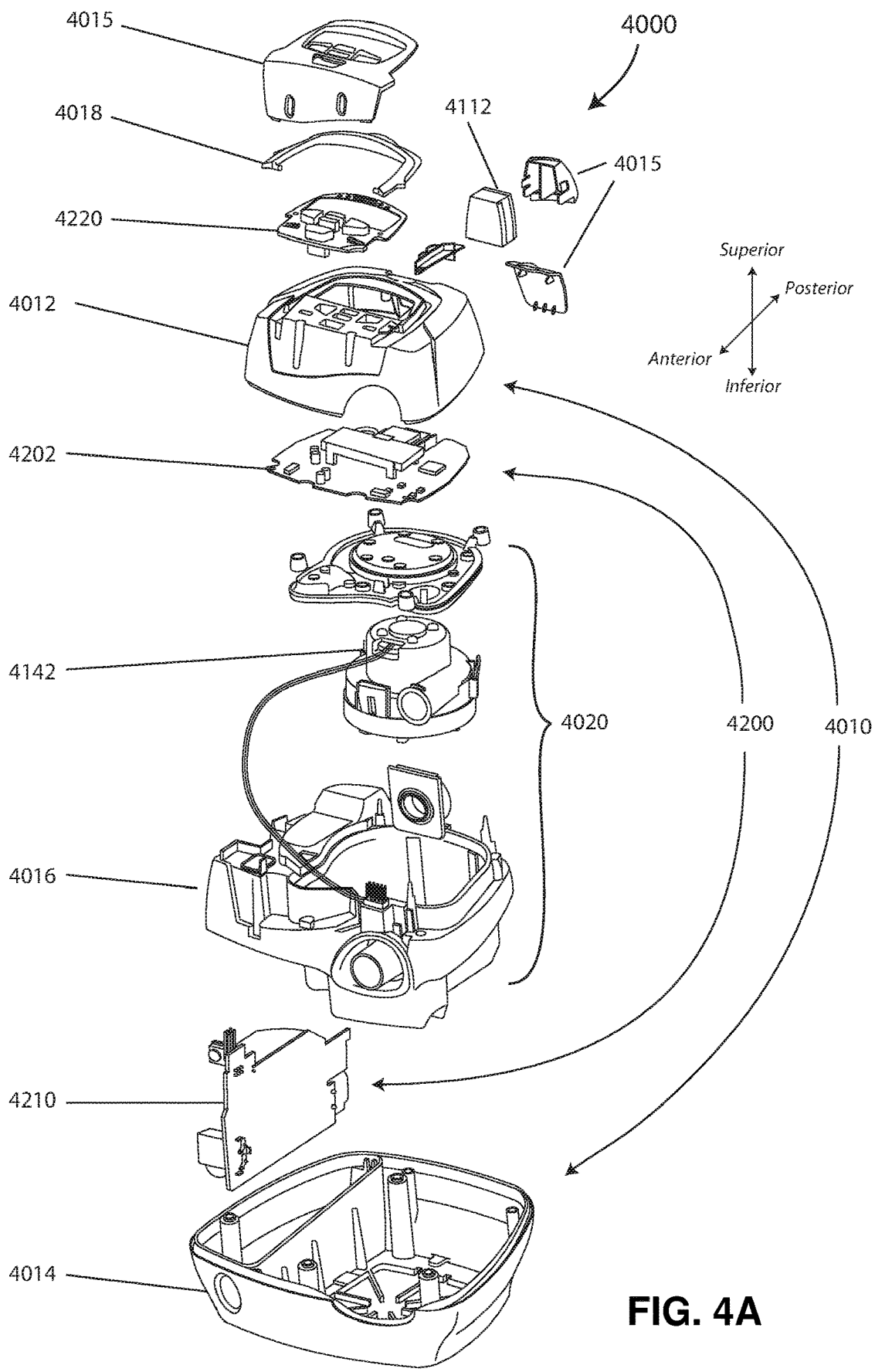

FIG. 4A shows an RPT device in accordance with one form of the present technology.

4.5 Patient Interface According to the Present Technology

Figure 5:
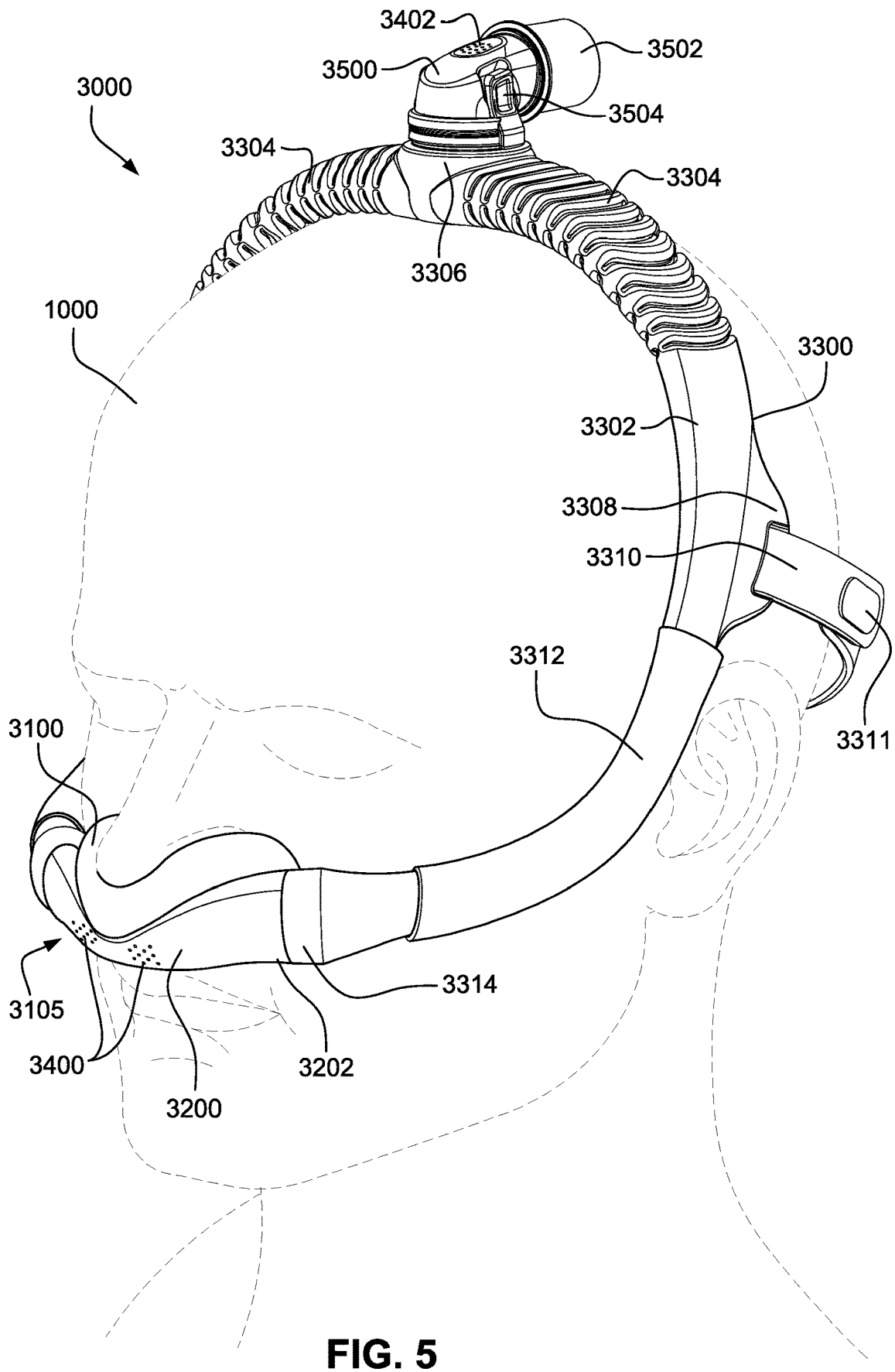

FIG. 5 is a perspective view of a patient interface according to an example of the present technology worn by a patient.

Figure 6:
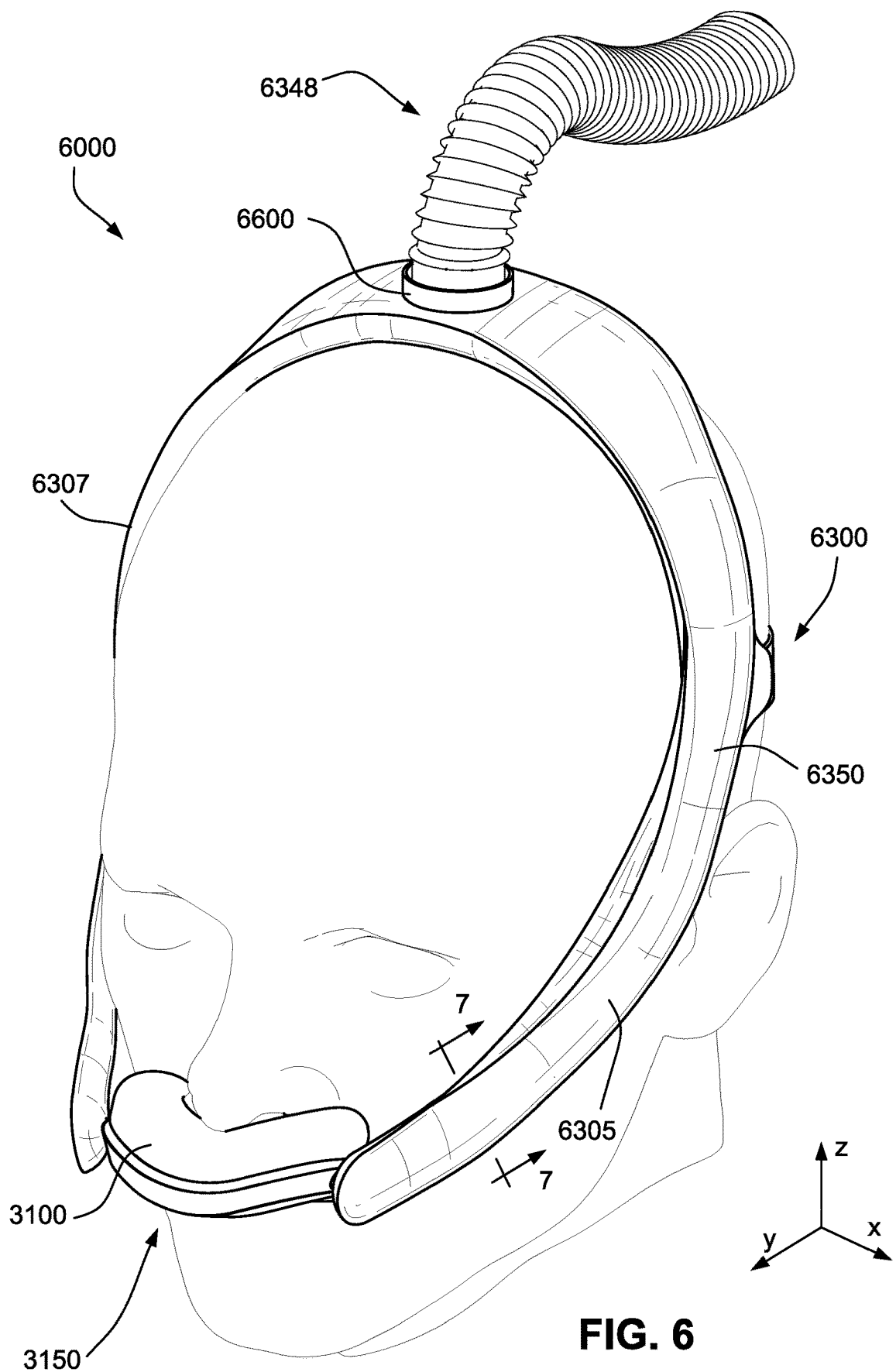

FIG. 6 is a perspective view of a patient interface according to another example of the present technology worn by a patient.

FIG. 7 is a cross-sectional view of the positioning and stabilising structure along the line 7-7 in FIG. 6.

FIG. 8 is an enlarged view of a portion of the positioning and stabilising structure of FIG. 7.

FIG. 9 is an enlarged view of a portion of the positioning and stabilising structure of FIG. 7.

Figure 10:
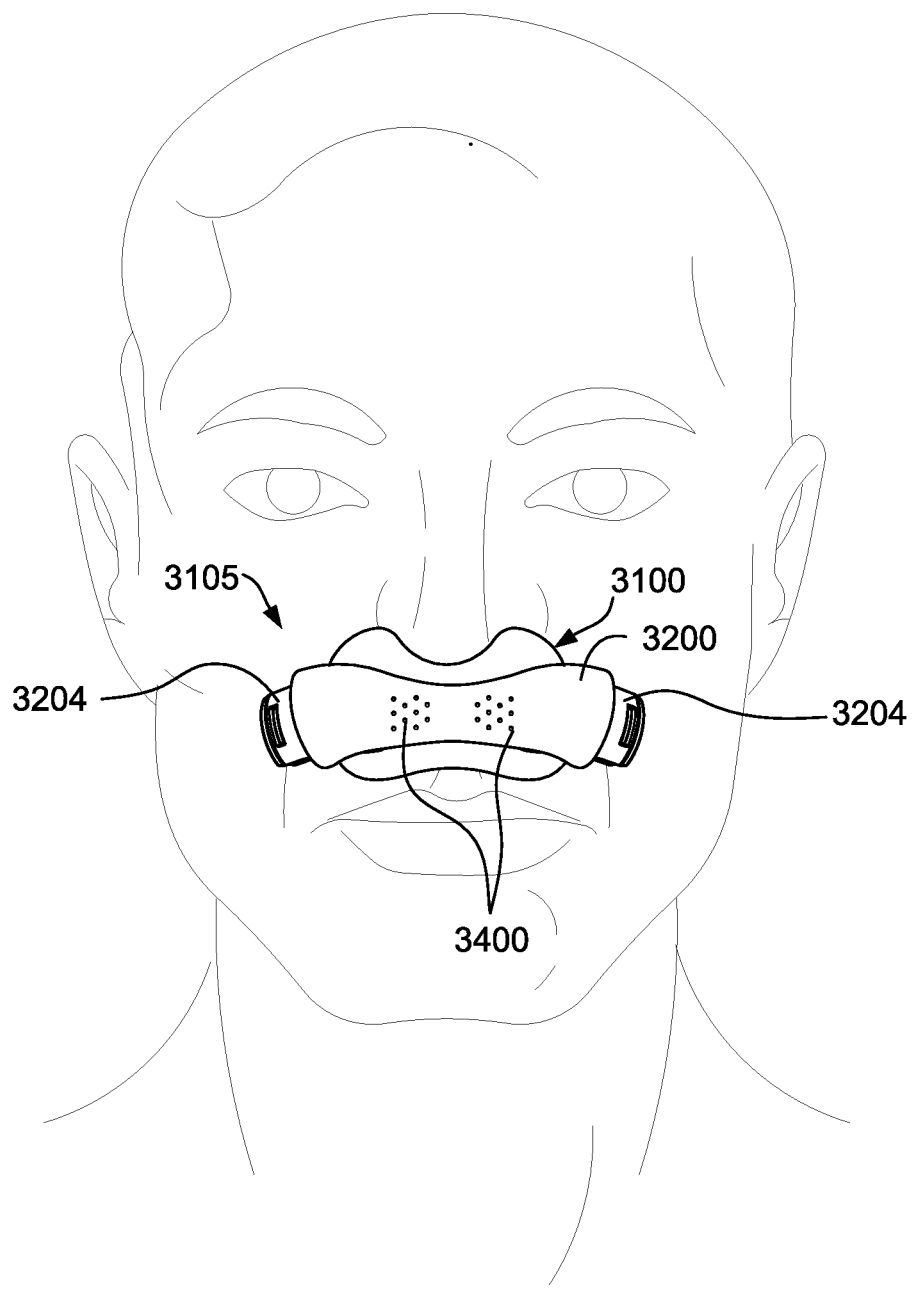

FIG. 10 is a front view of the cushion assembly of FIG. 5 positioned on a patient's face.

Figure 11:
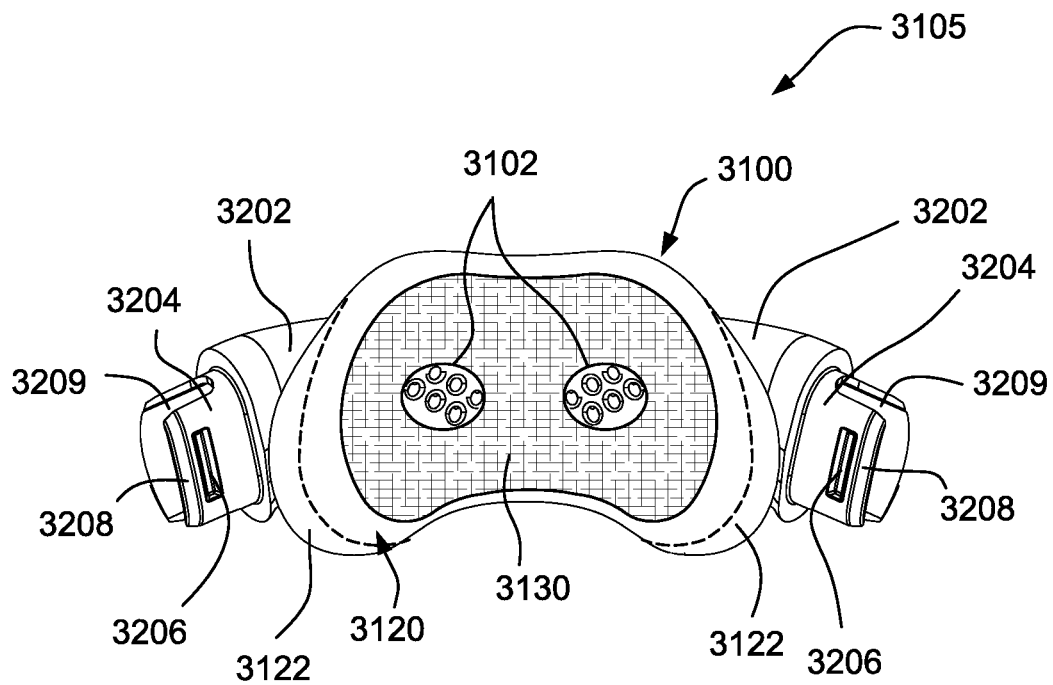

FIG. 11 is a front view of the cushion assembly of FIG. 5.

Figure 12:
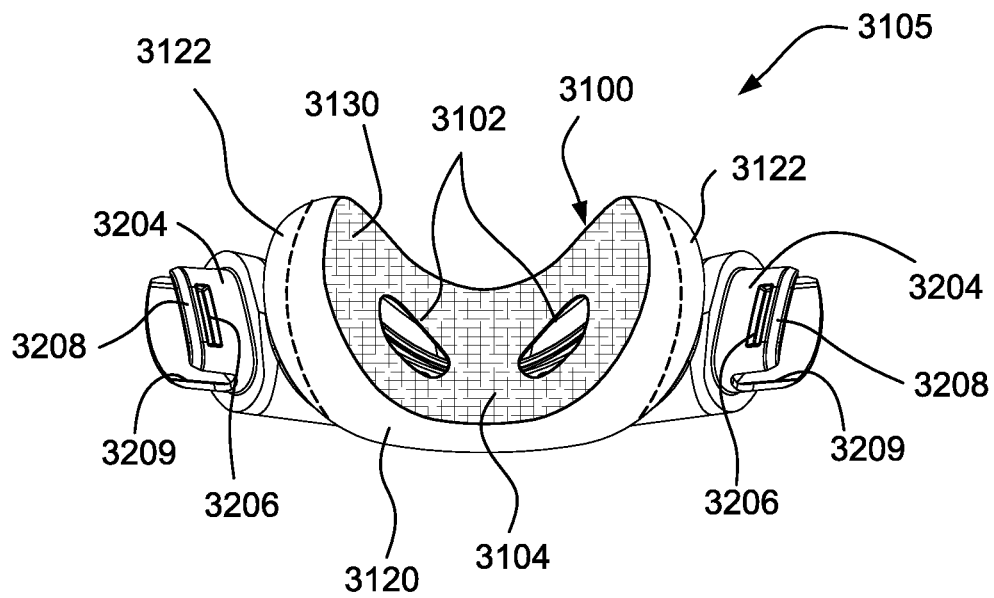

FIG. 12 is a top perspective view of the cushion assembly of FIG. 5.

Figure 13:
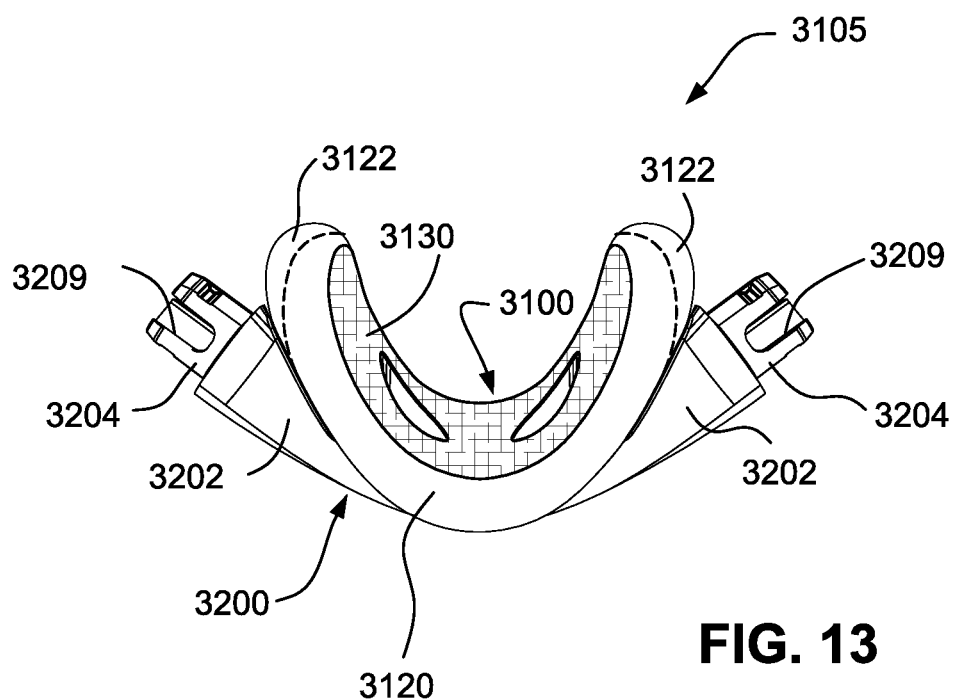

FIG. 13 is a top view of the cushion assembly of FIG. 5.

Figure 14:
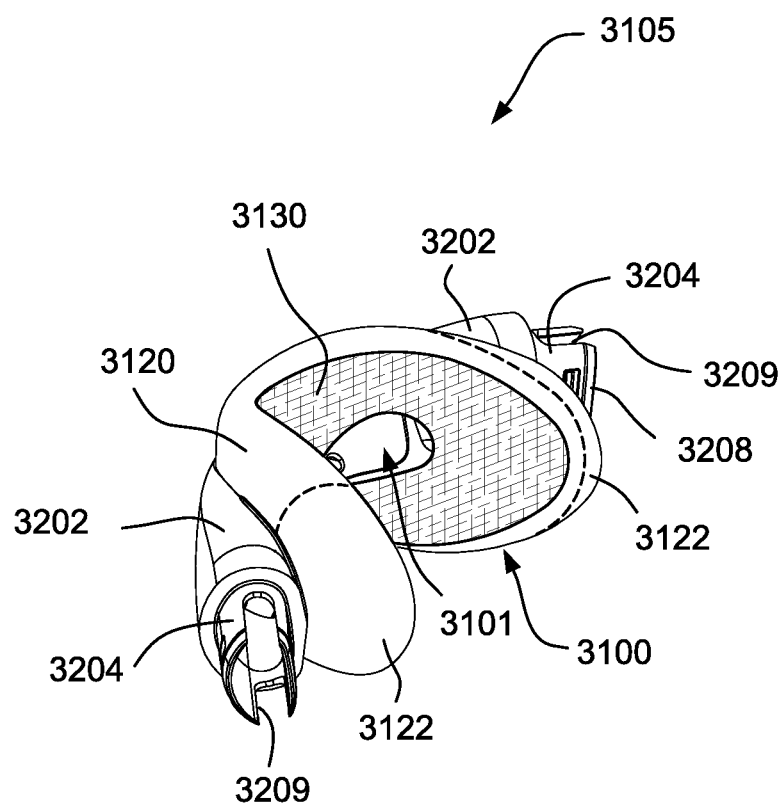

FIG. 14 is a side view of the cushion assembly of FIG. 5.

Figure 15:
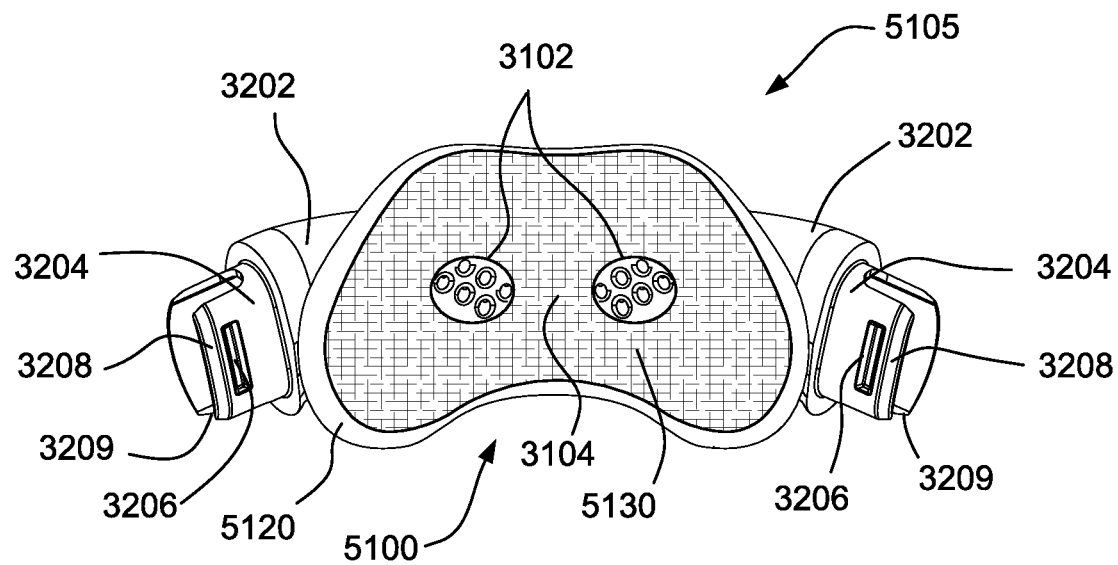

FIG. 15 is a front view of the cushion assembly of FIG. 5.

Figure 16:
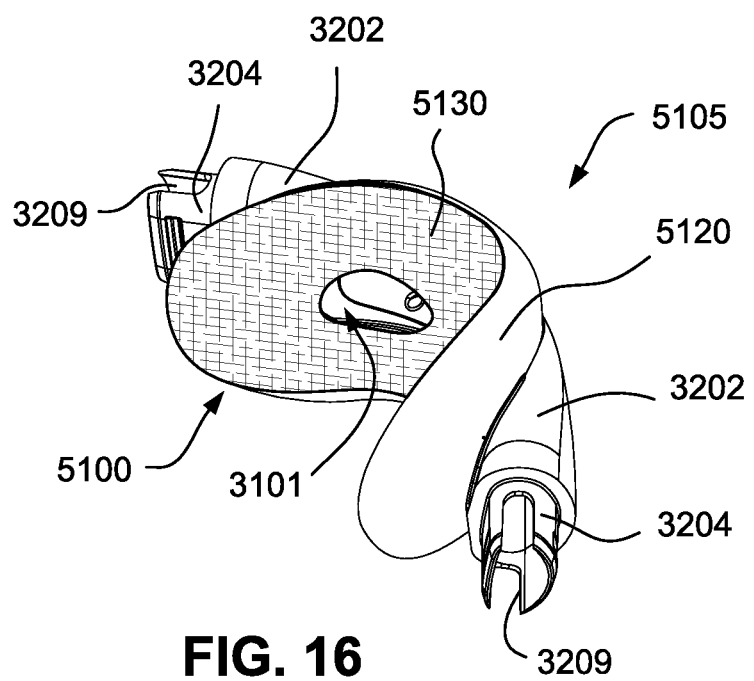

FIG. 16 is a side view of the cushion assembly of FIG. 5.

Figure 17:
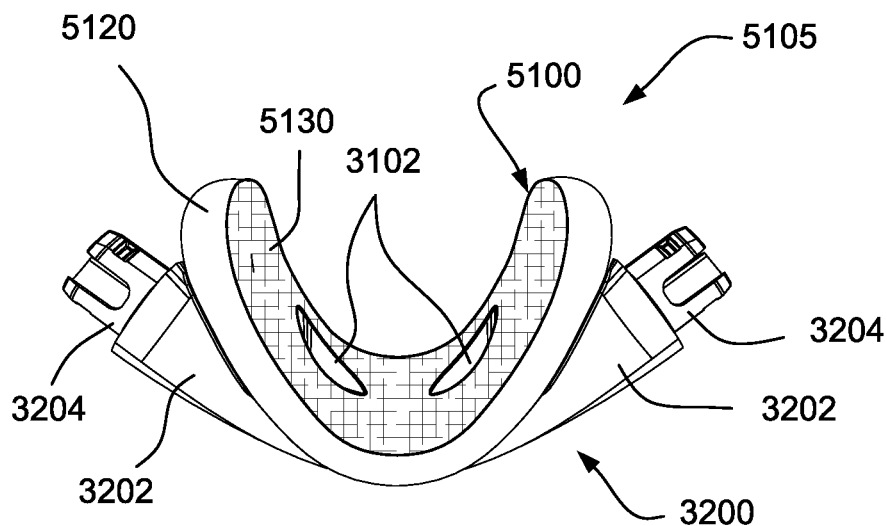

FIG. 17 is a top view of the cushion assembly of FIG. 5.

Figure 18:
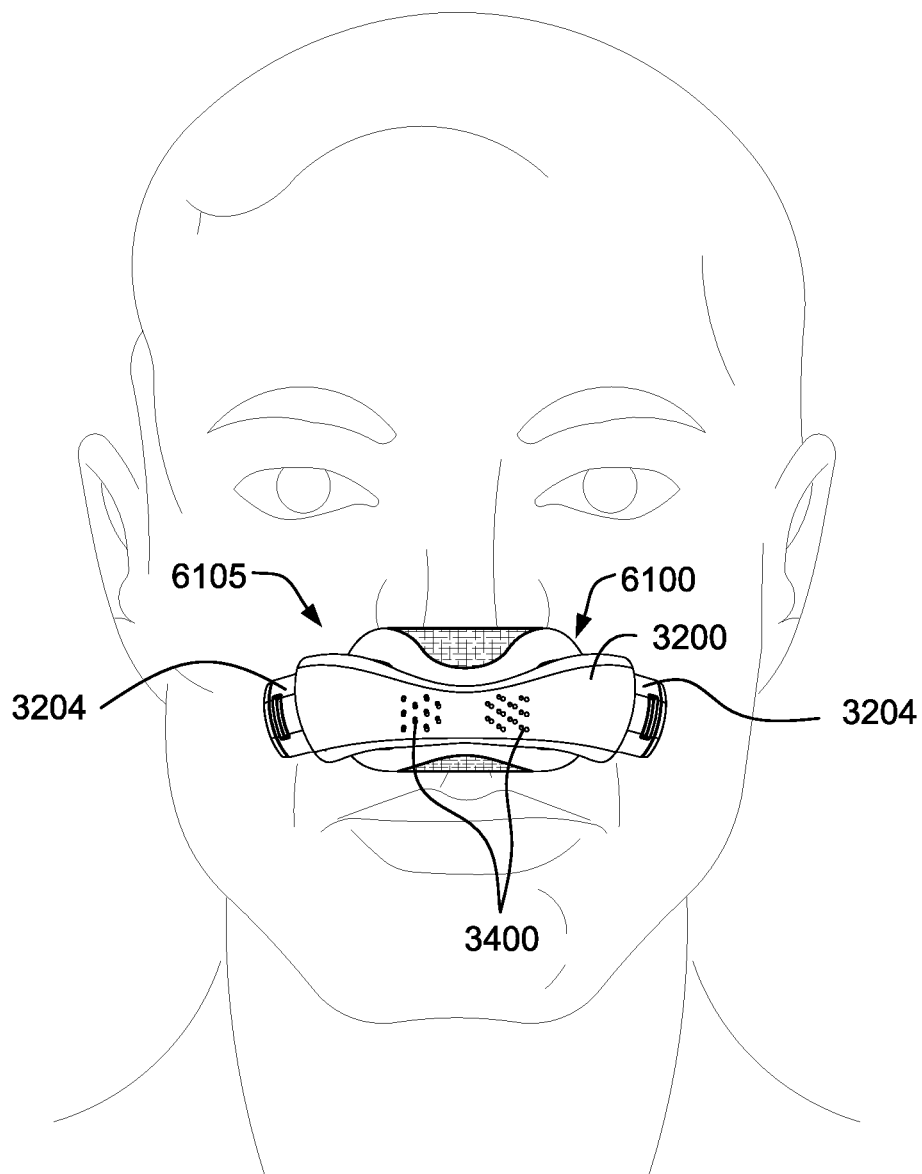

FIG. 18 is a front view of a cushion assembly according to another example of the present technology positioned on a patient's face.

Figure 19:
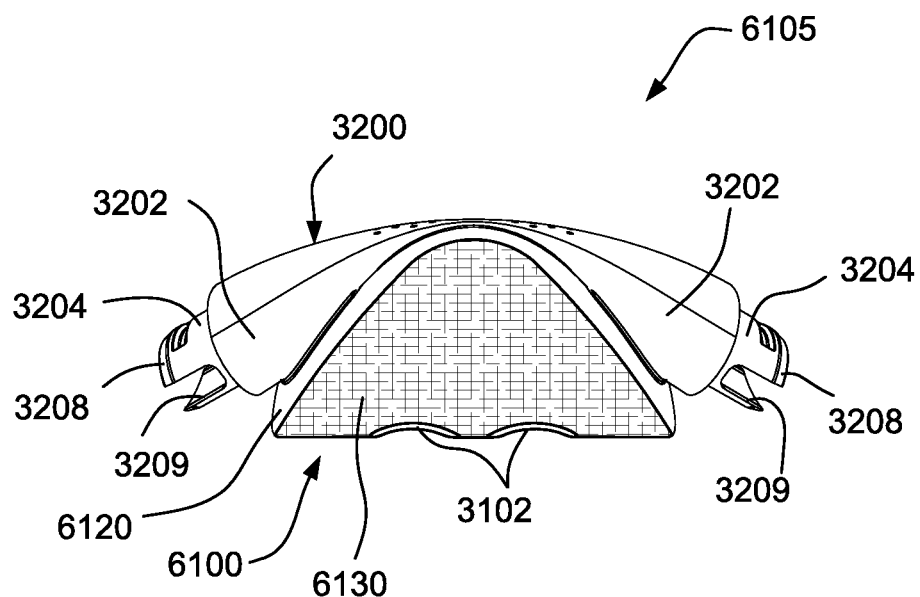

FIG. 19 is a top view of the cushion assembly of FIG. 18.

Figure 20:
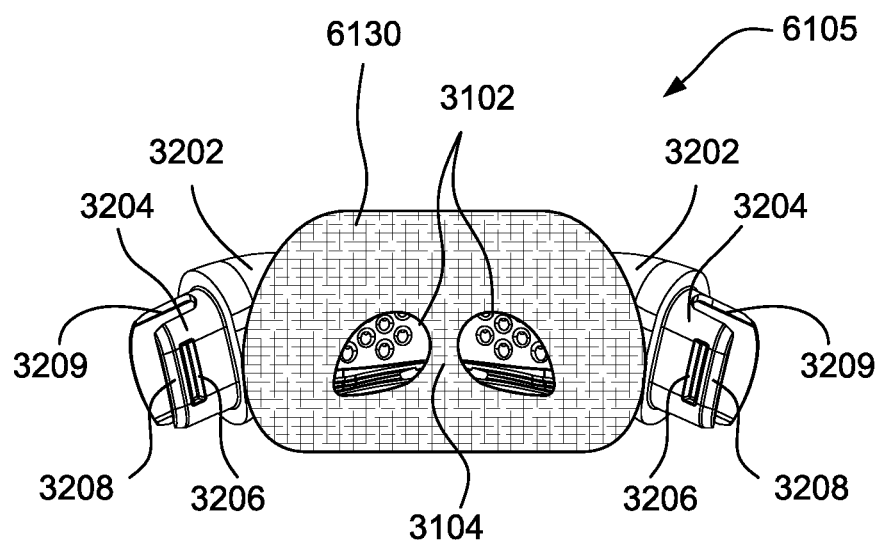

FIG. 20 is a front view of the cushion assembly of FIG. 18.

Figure 21:
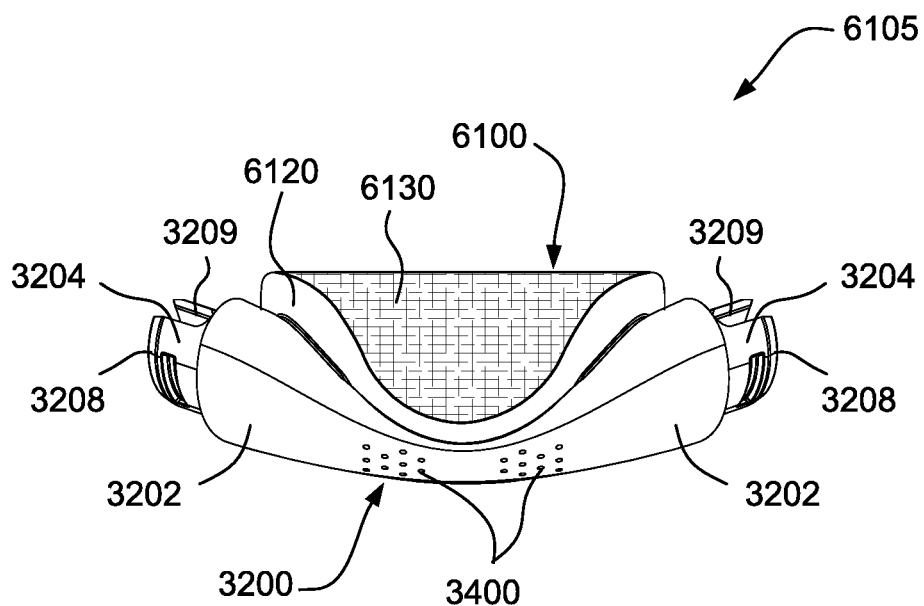

FIG. 21 is a bottom view of the cushion assembly of FIG. 18.

Figure 22:
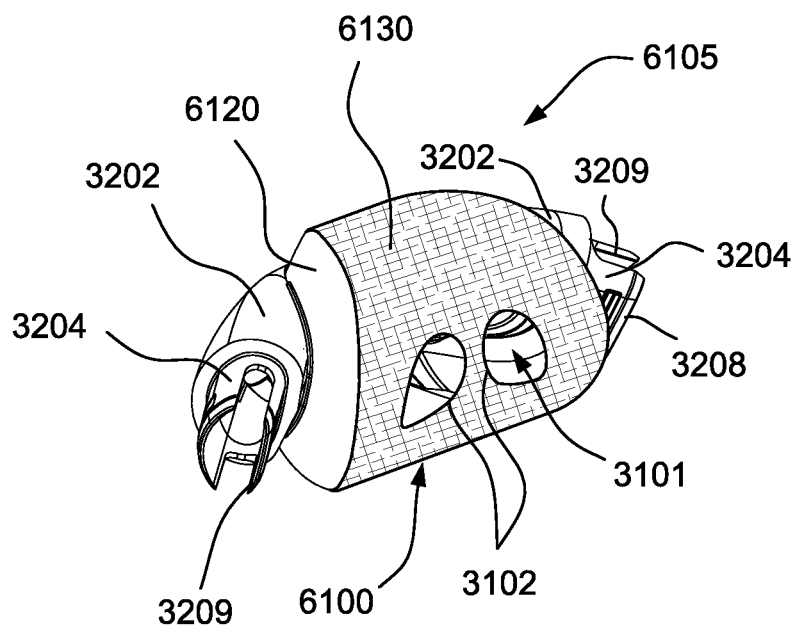

FIG. 22 is a side perspective view of the cushion assembly of FIG. 18.

Figure 23:
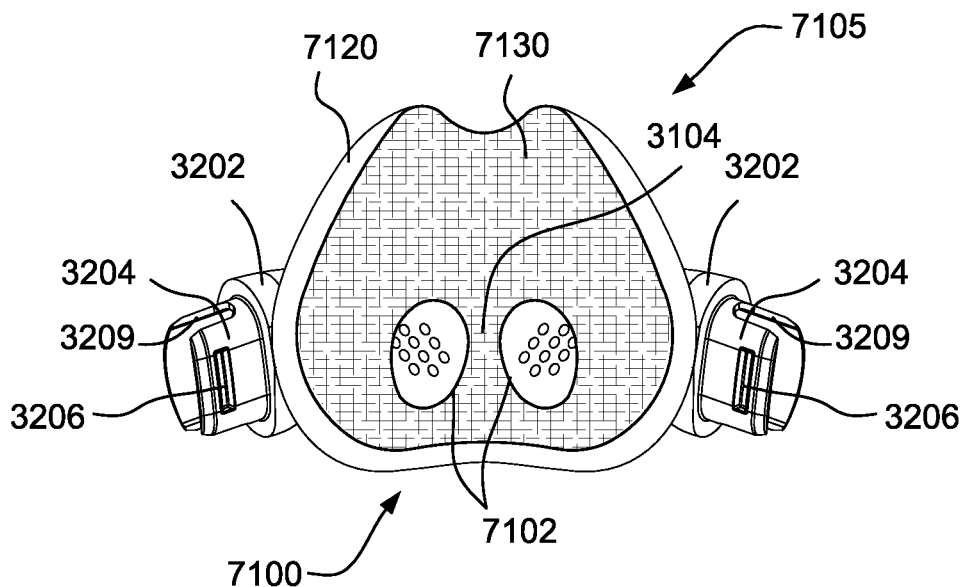

FIG. 23 is a front view of a cushion assembly according to another example of the present technology.

Figure 24:
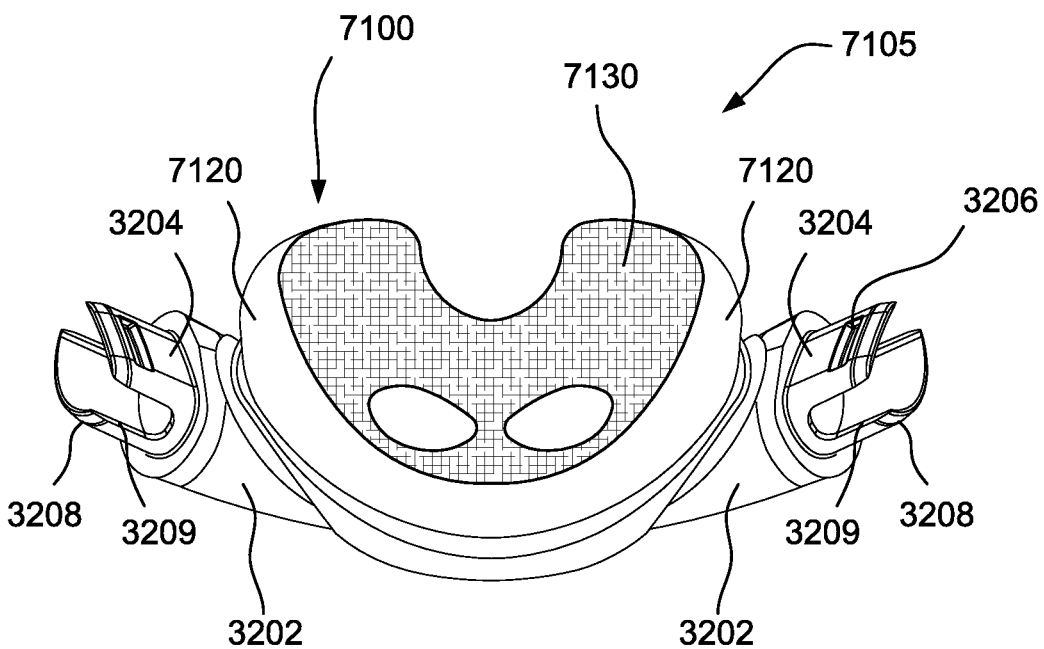

FIG. 24 is a bottom perspective view of the cushion assembly of FIG. 23.

Figure 25:
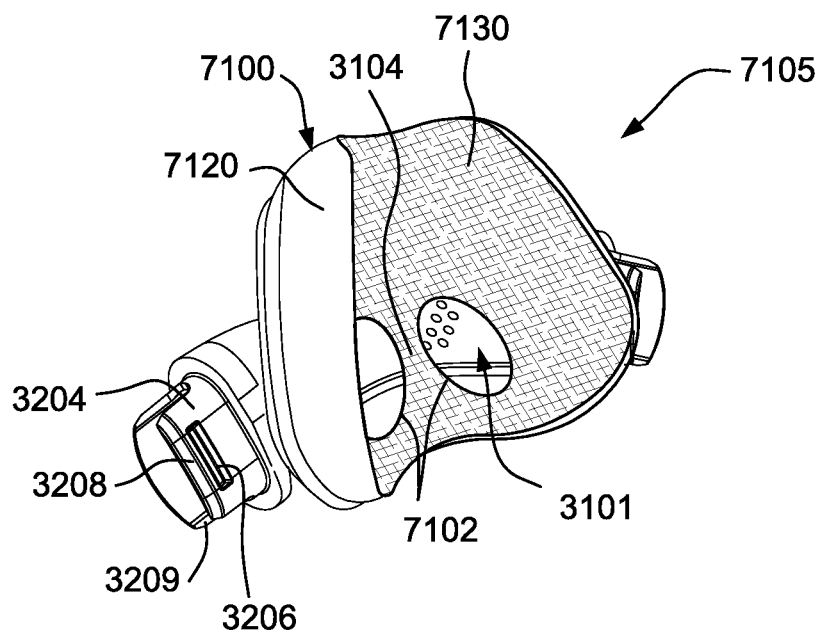

FIG. 25 is a side view of the cushion assembly of FIG. 23.

Figure 26:
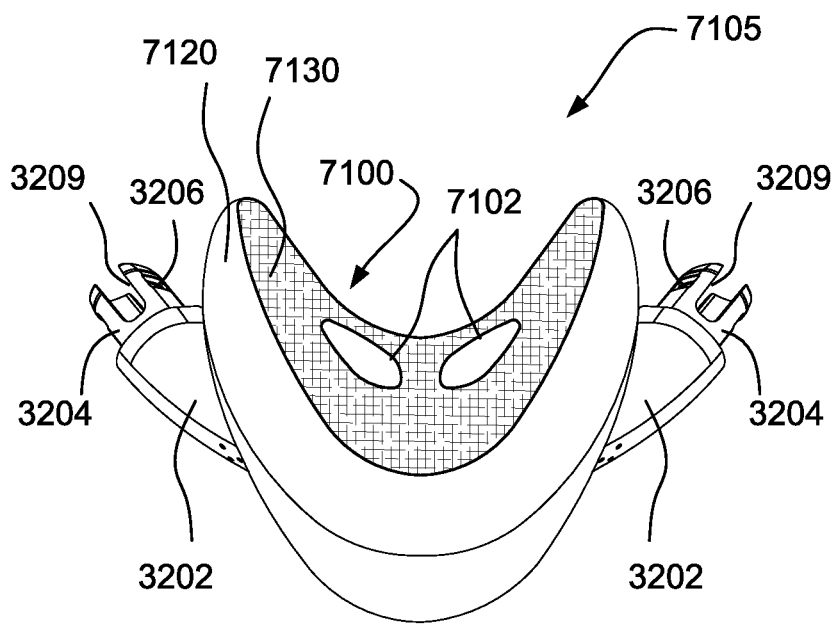

FIG. 26 is a top perspective view of the cushion assembly of FIG. 23.

Figure 27:
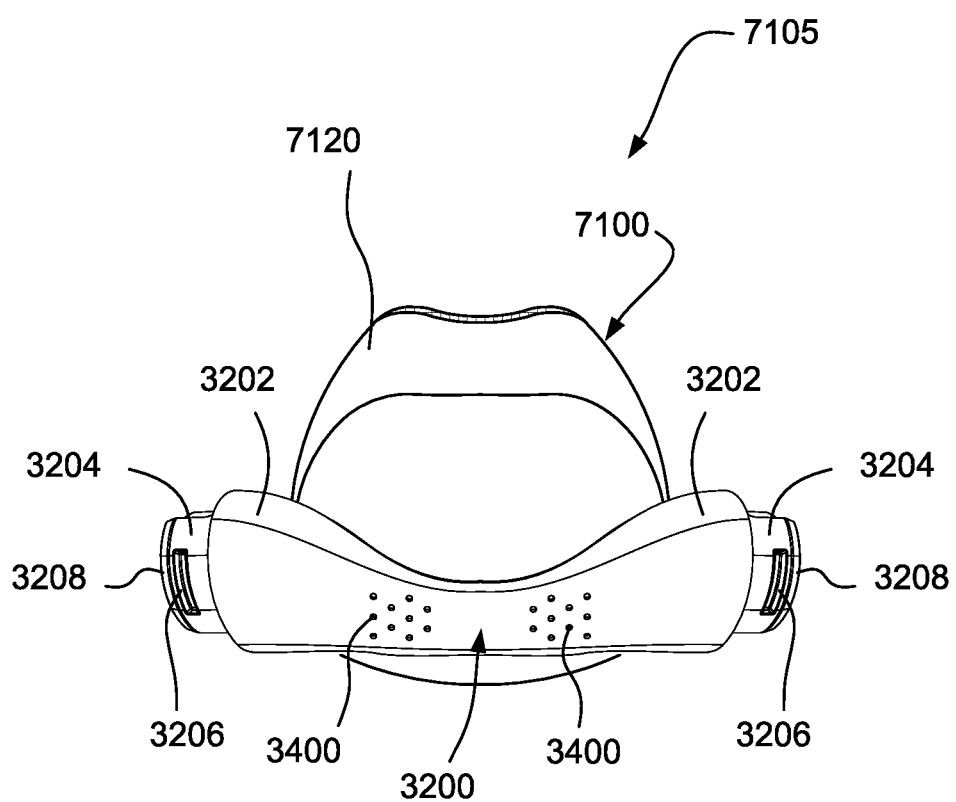

FIG. 27 is a rear perspective view of the cushion assembly of FIG. 23.

Figure 28:
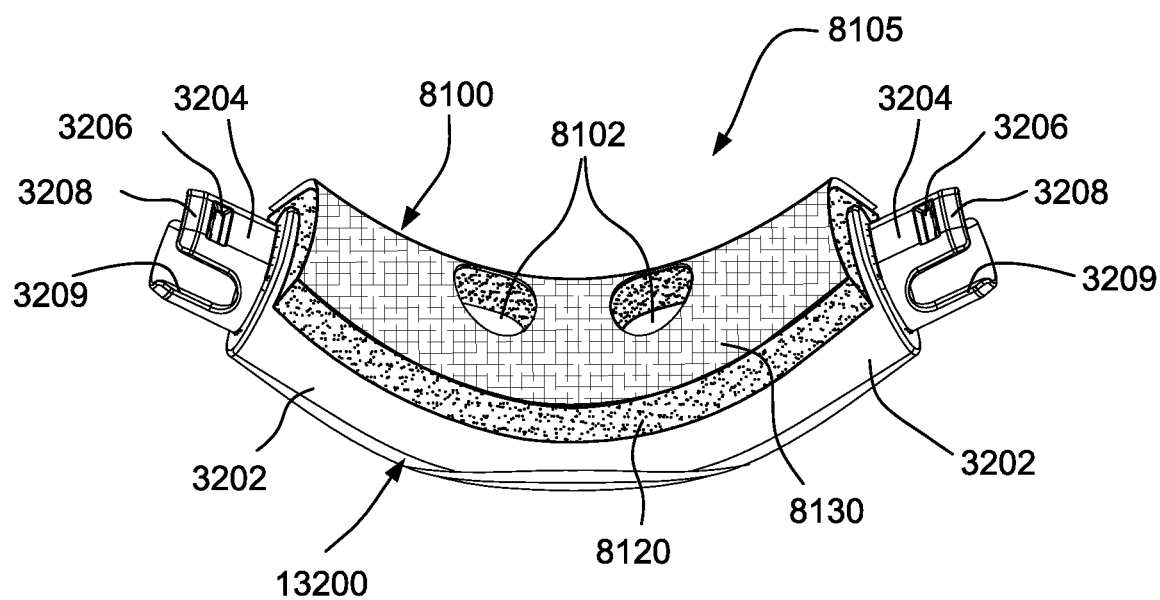

FIG. 28 is a top perspective view of a cushion assembly according to another example of the present technology.

Figure 29:
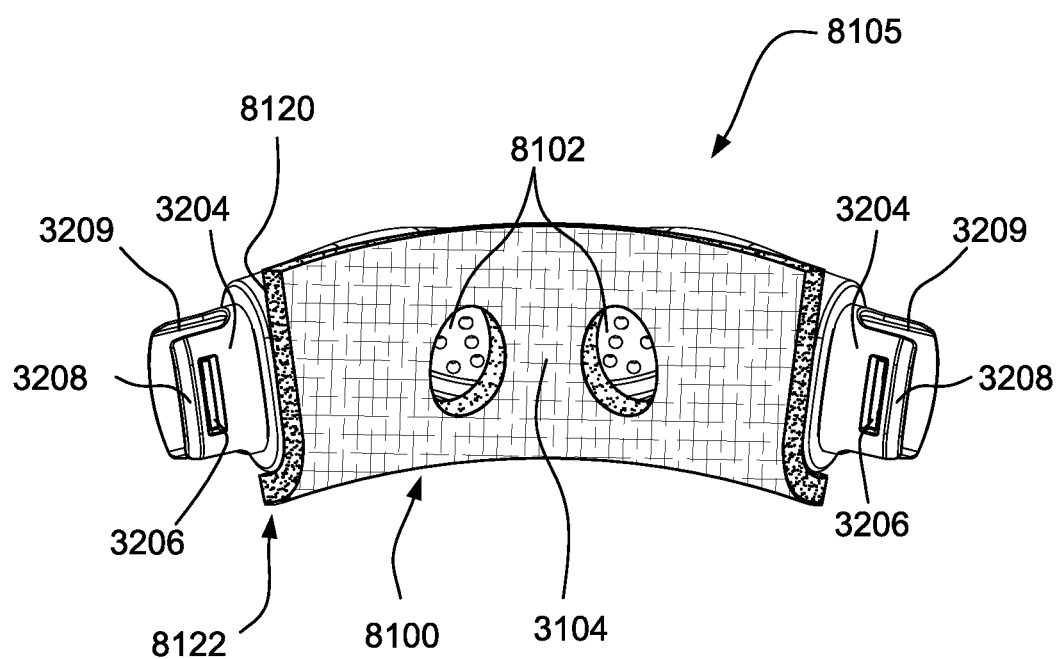
Figure 30:
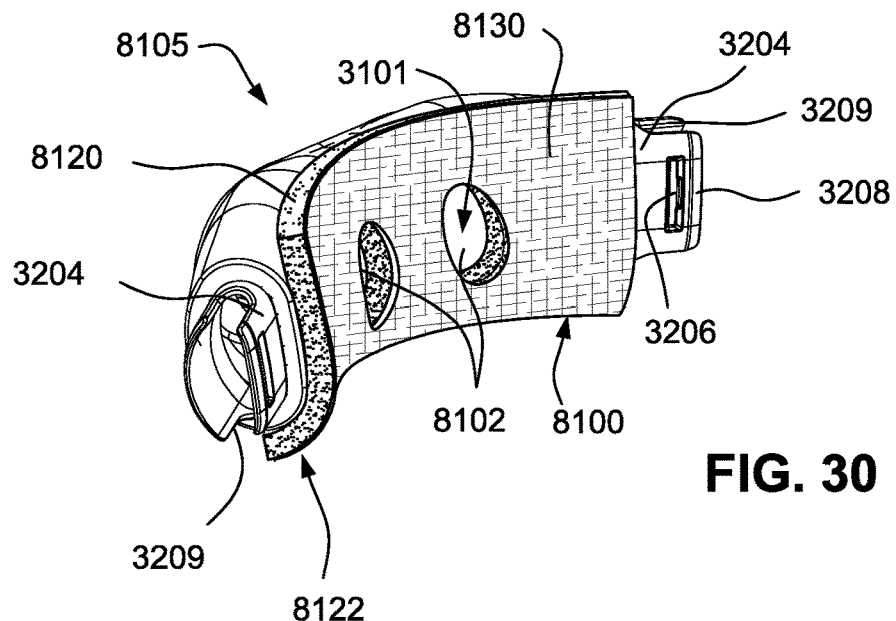

FIG. 29 is a front view of the cushion assembly of FIG. 28.

FIG. 3O is a side perspective view of the cushion assembly of FIG. 28.

Figure 31:
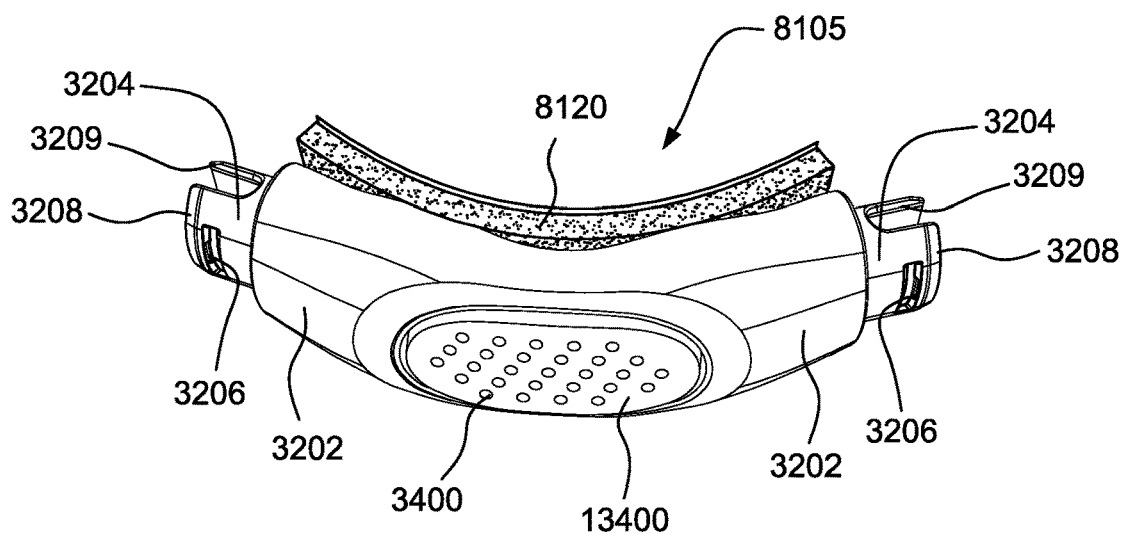

FIG. 31 is a rear perspective view of the cushion assembly of FIG. 28.

Figure 32:
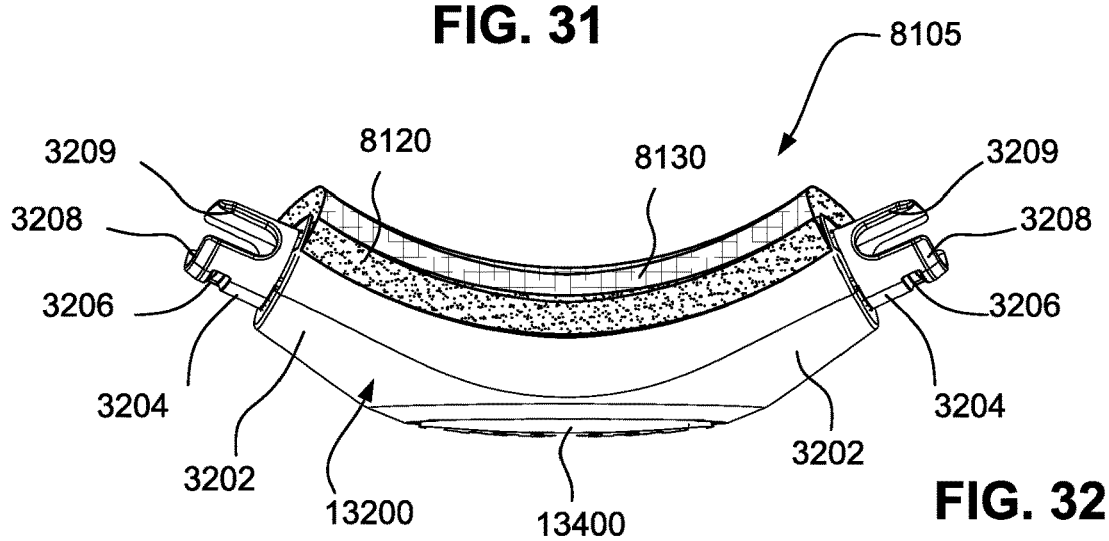

FIG. 32 is a bottom view of the cushion assembly of FIG. 28.

Figure 33:
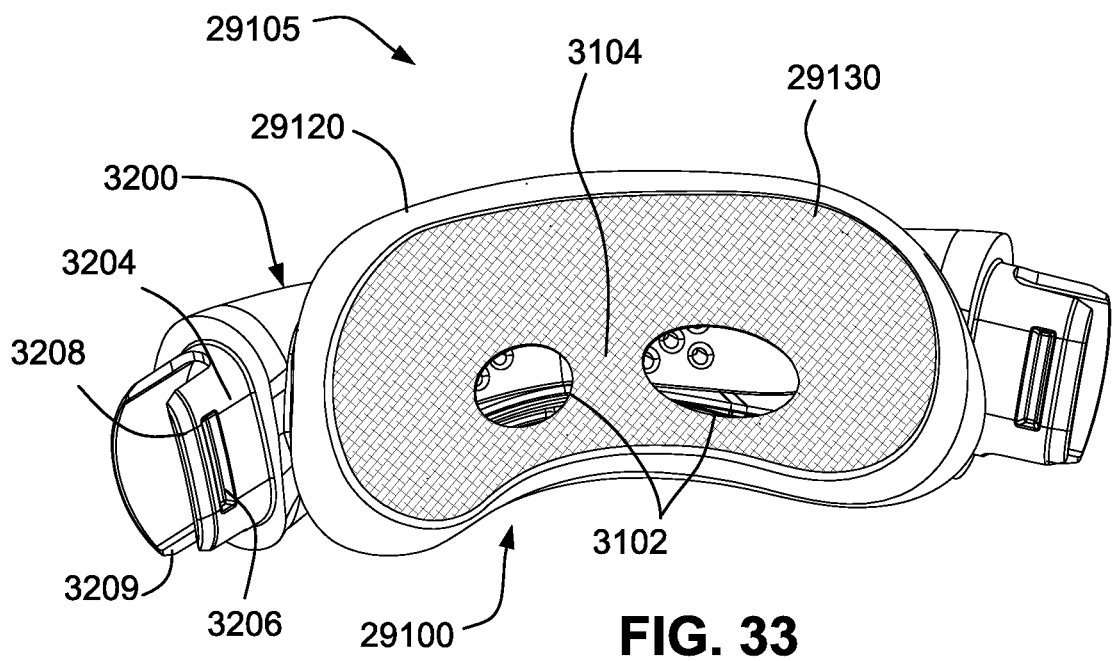

FIG. 33 is a front perspective view of a cushion assembly according to another example of the present technology.

Figures 1, 33:
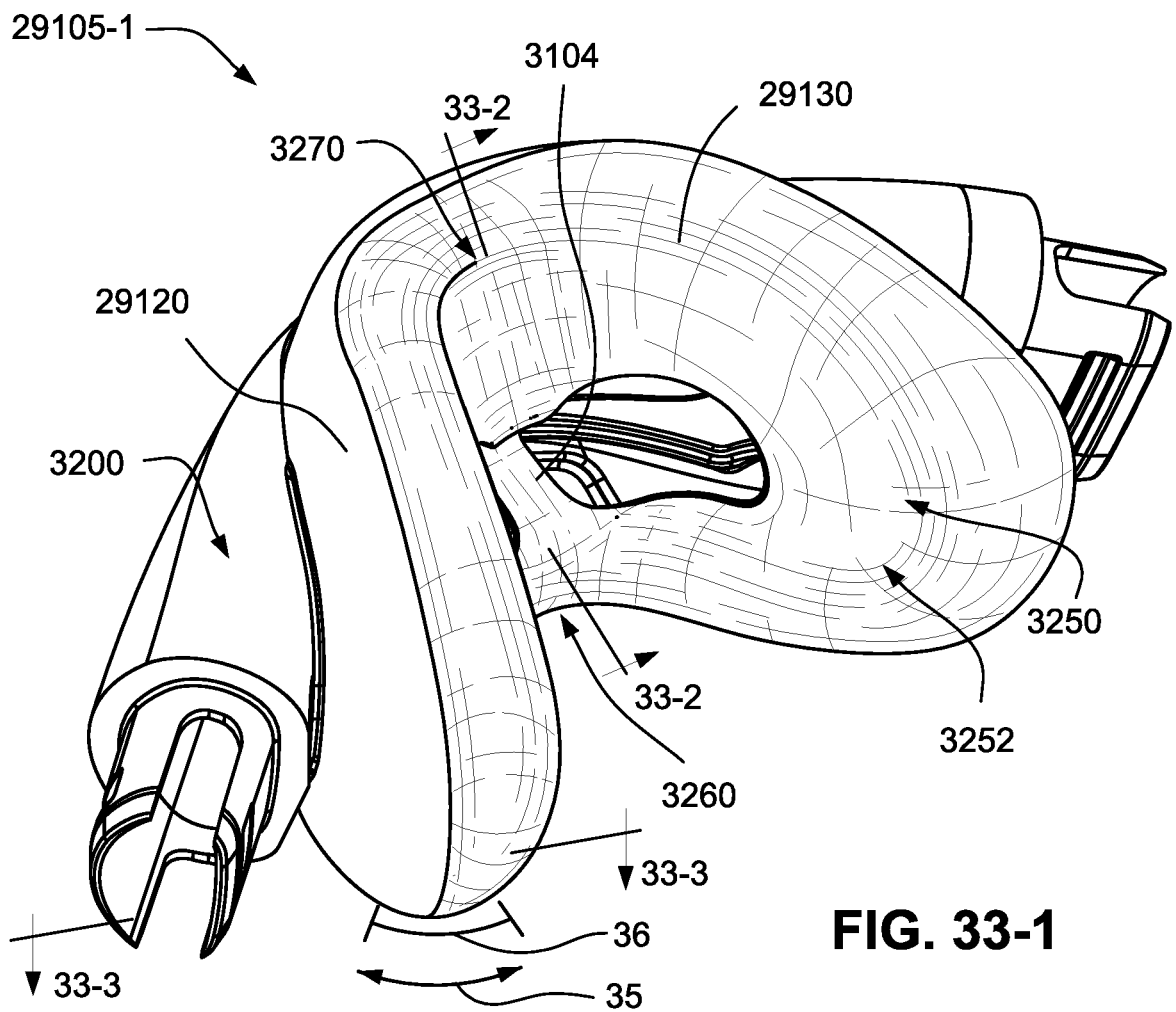

FIG. 33-1 is a front perspective view of a cushion assembly according to another example of the present technology.

Figures 2, 33:
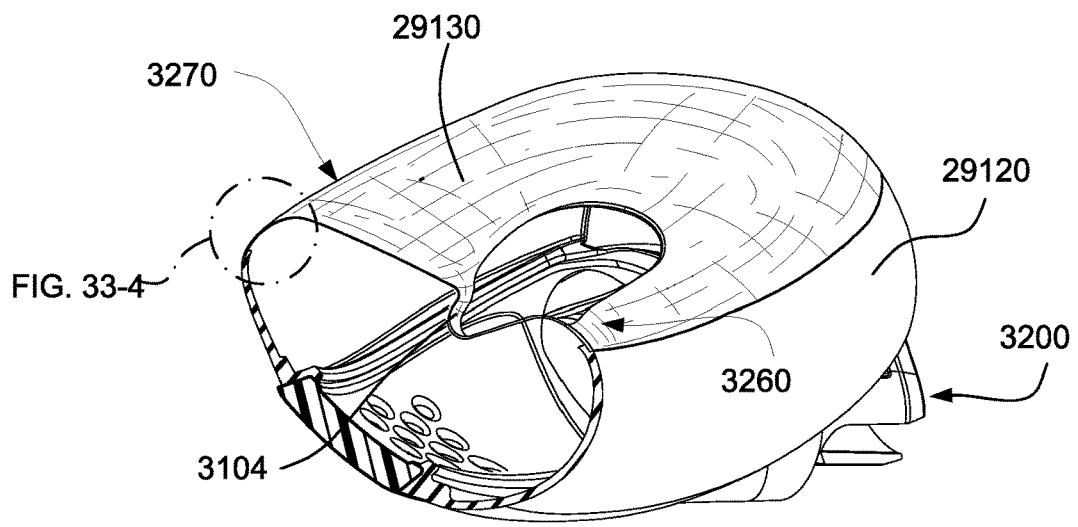

FIG. 33-2 is a cross-sectional view along the line 33-2-33-2 in FIG. 33-1.

Figures 3, 33:
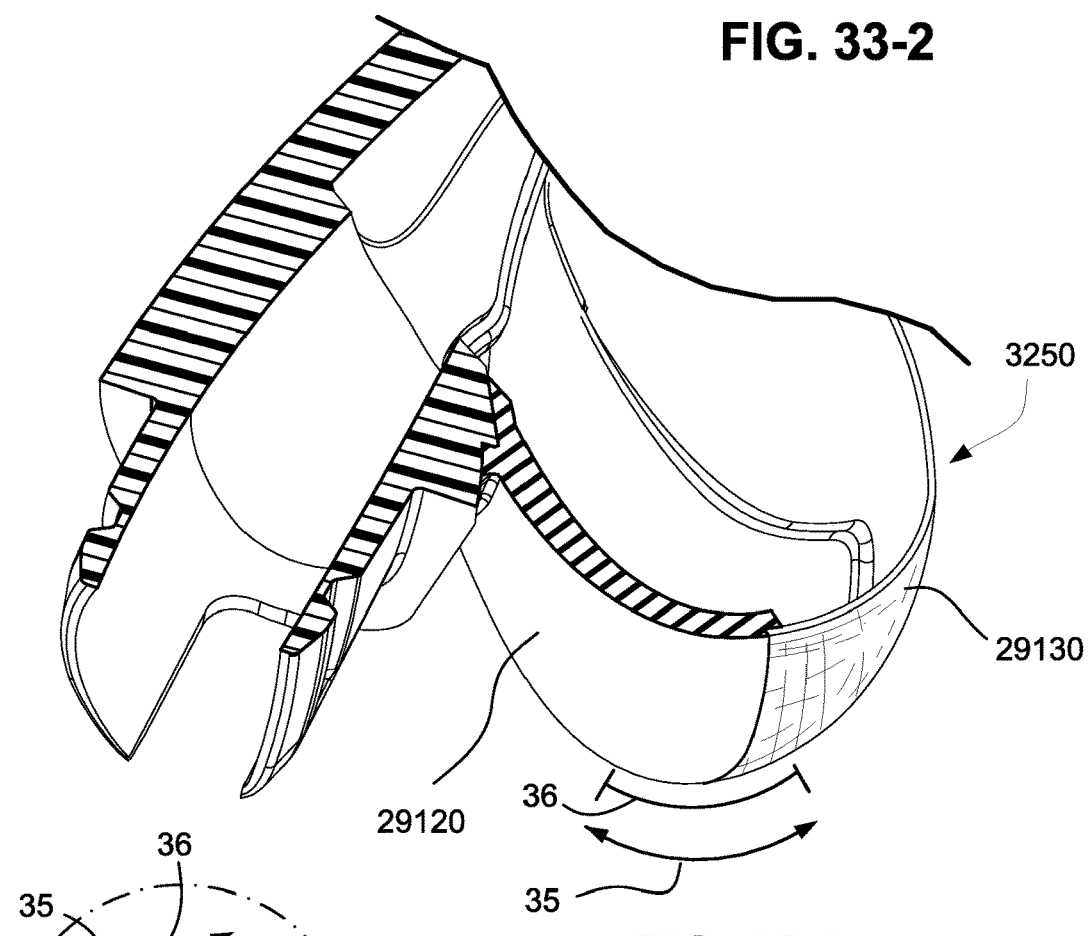

FIG. 33-3 is a cross-sectional view along the line 33-3-33-3 in FIG. 33-1.

Figures 4, 33:
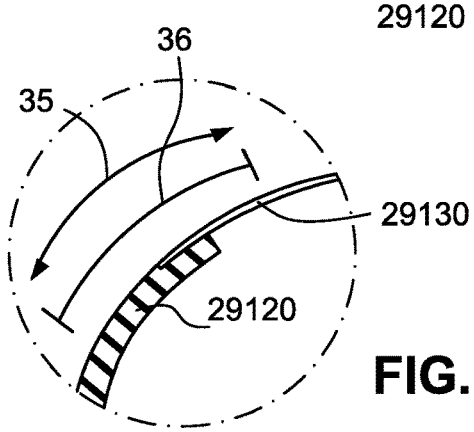

FIG. 33-4 is an enlarged detail taken from FIG. 33-2.

Figure 34:
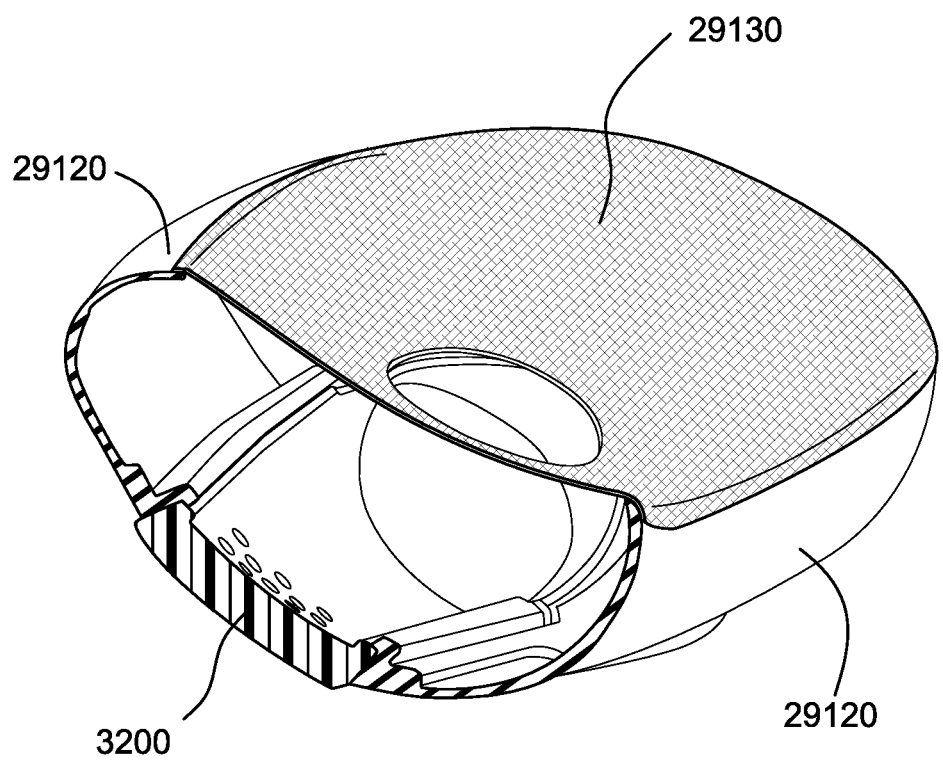
Figure 35:
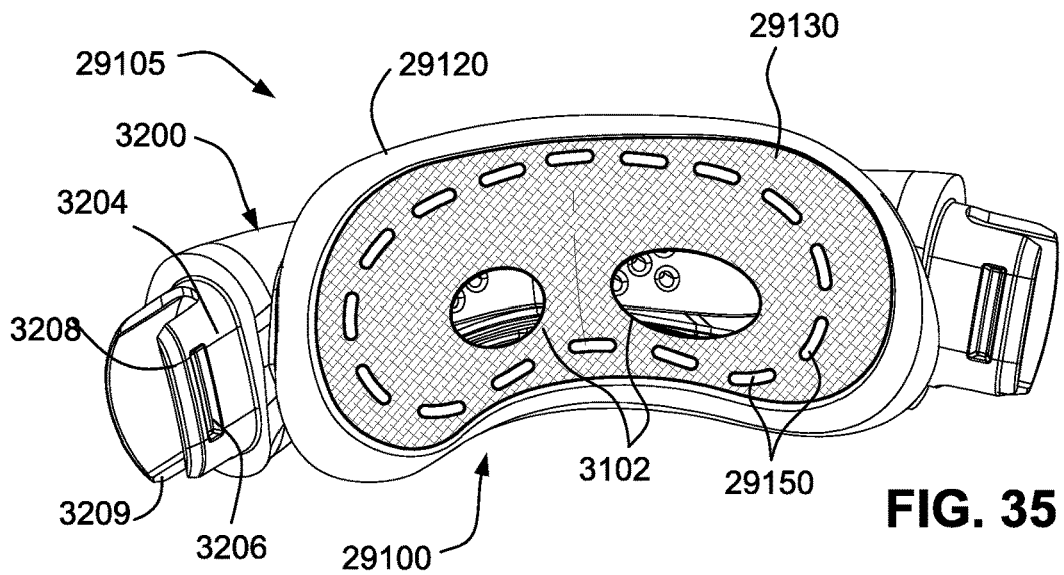
Figure 36:
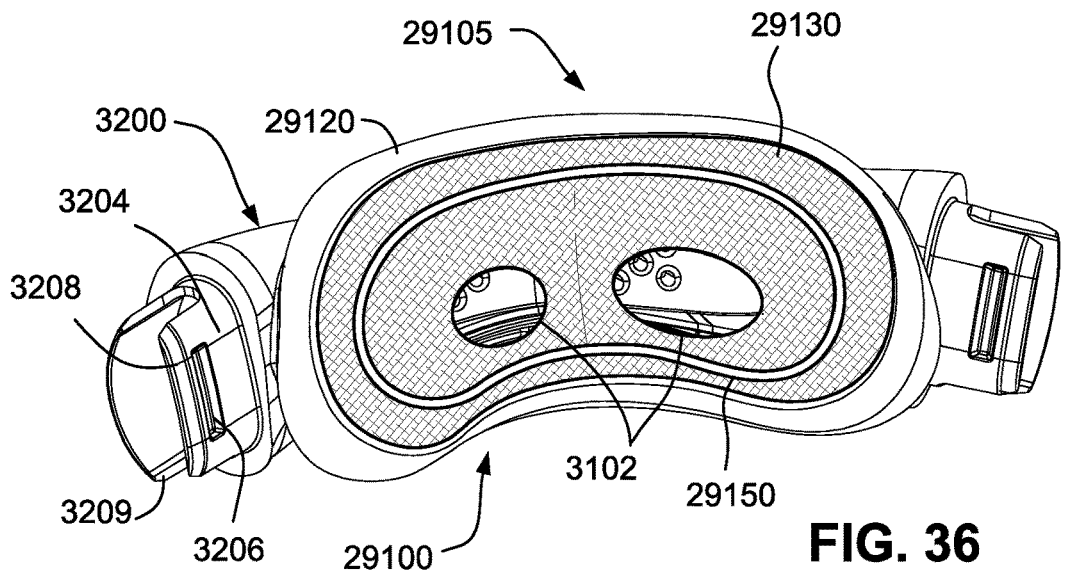
Figure 37:
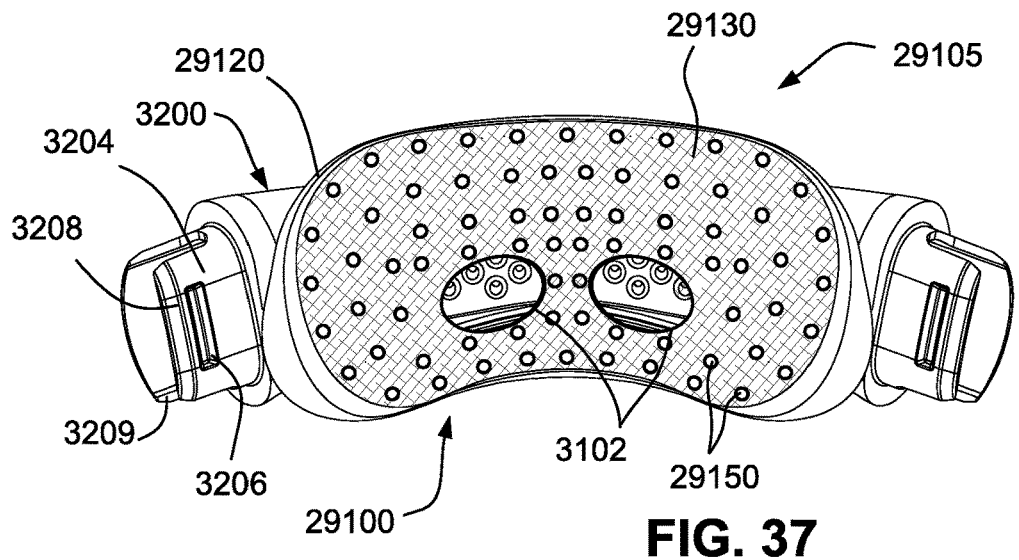

FIG. 34 is a cross-sectional view of the cushion assembly of FIG. 33.

FIGS. 34-37 are front perspective views of cushion assemblies having grip pads disposed on the textile membrane according examples of the present technology.

Figure 38:
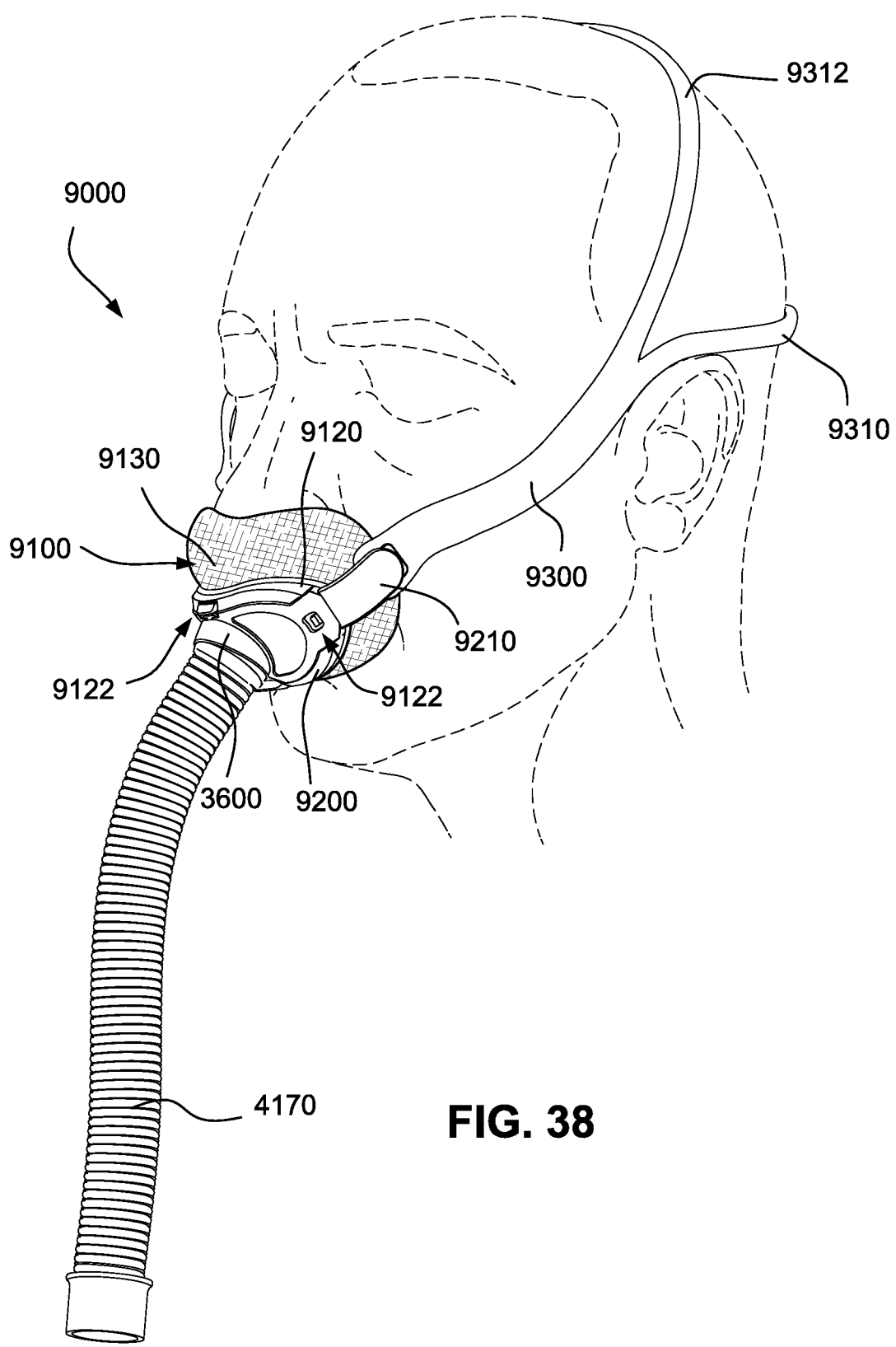

FIG. 38 is a perspective view of a patient interface according to another example of the present technology worn by a patient.

Figure 39:
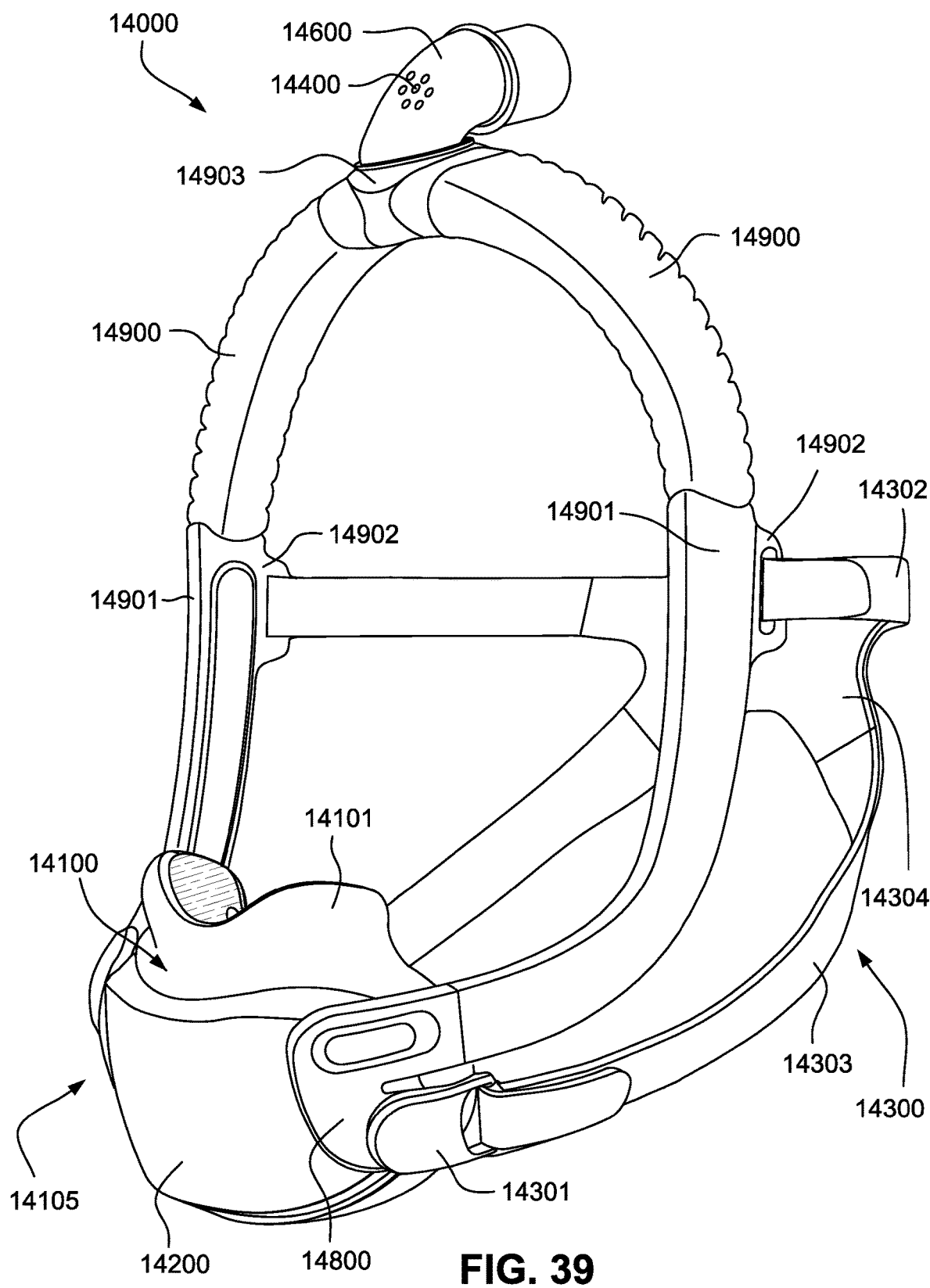

FIG. 39 is a perspective view of a patient interface according to another example of the present technology.

Figure 40:
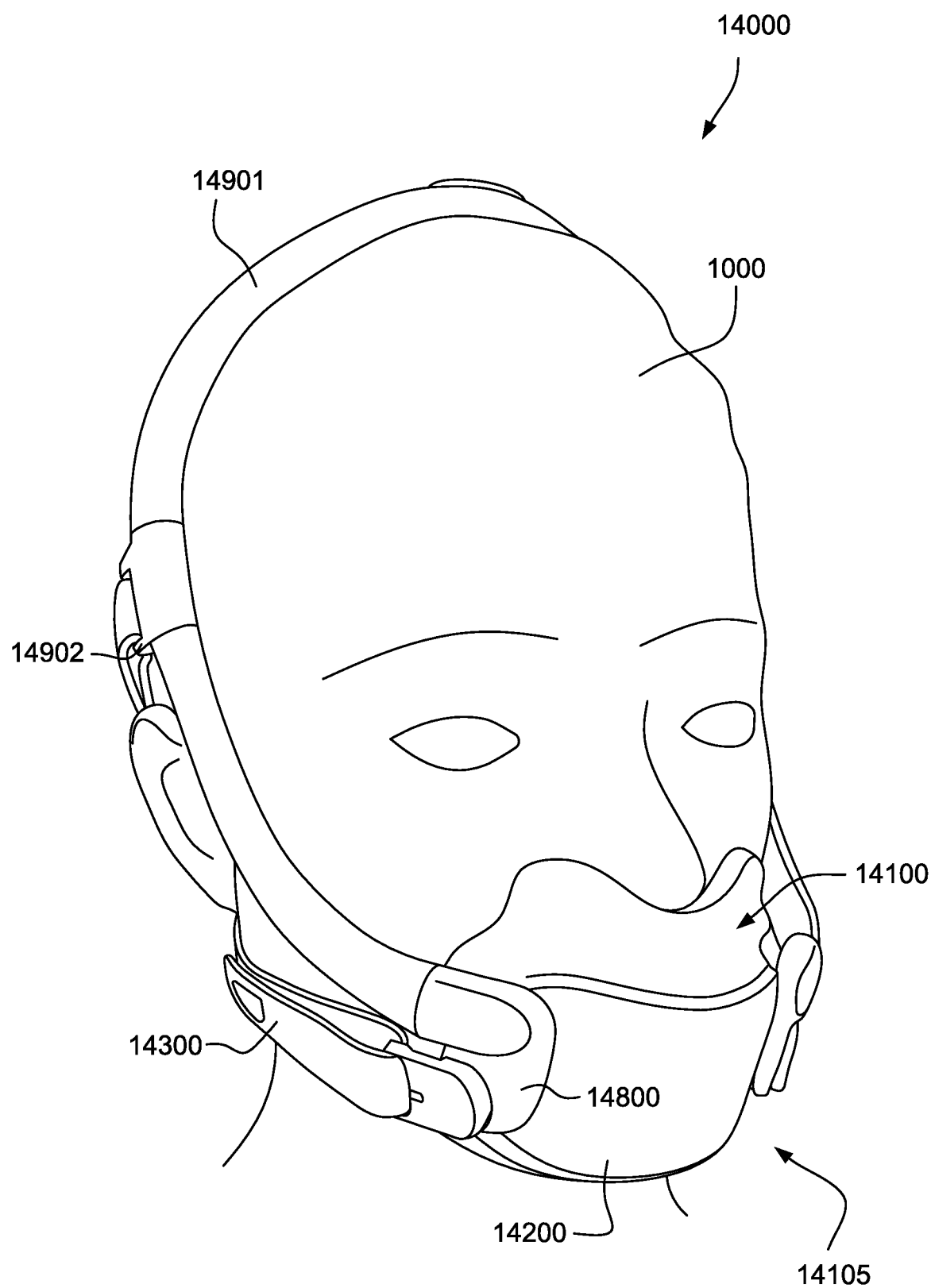

FIG. 40 is a perspective view of the patient interface of FIG. 39 worn by a patient.

Figure 41:
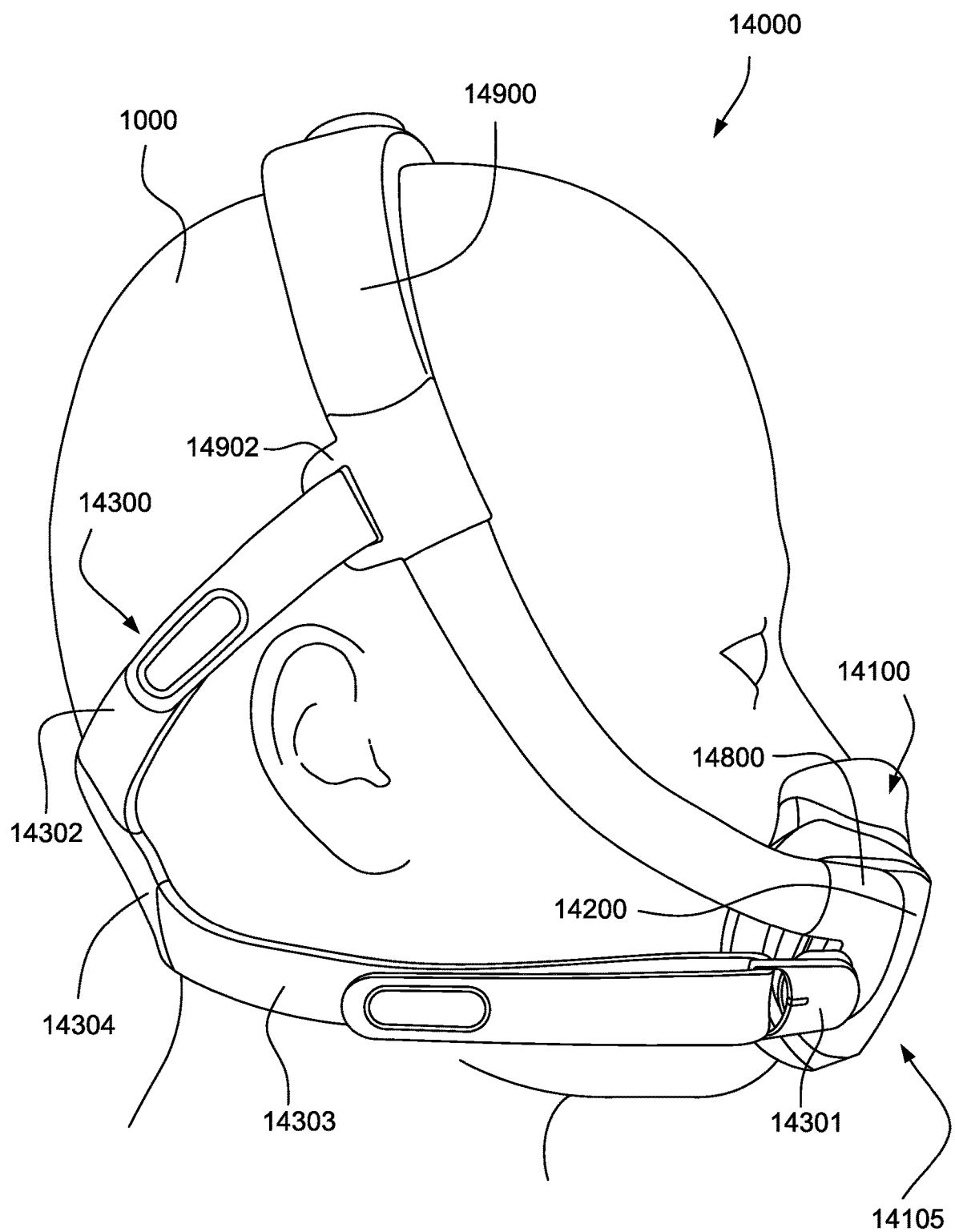

FIG. 41 is a side view of the patient interface of FIG. 40.

Figure 42:
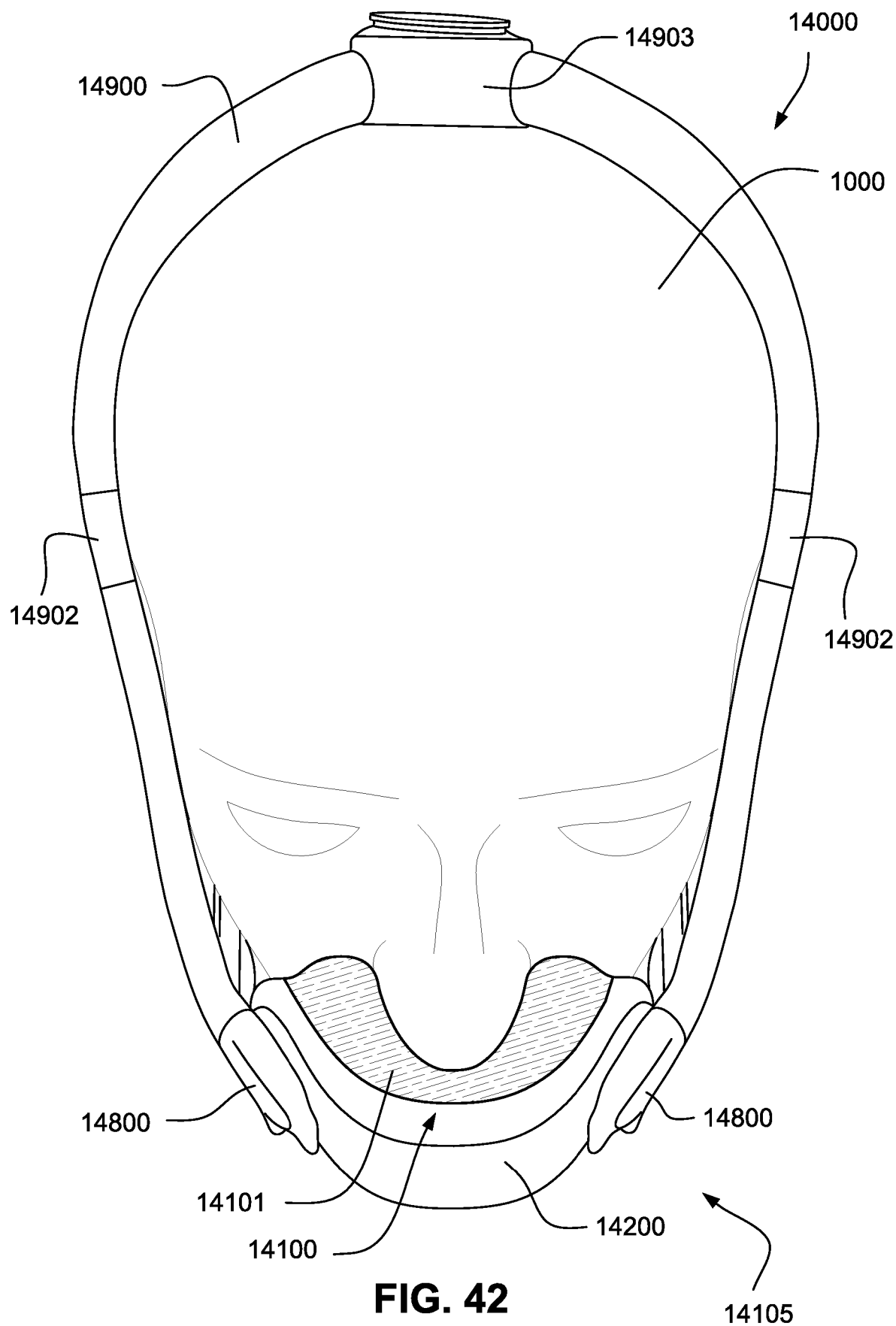

FIG. 42 is a front perspective view of the patient interface of FIG. 40.

Figure 43:
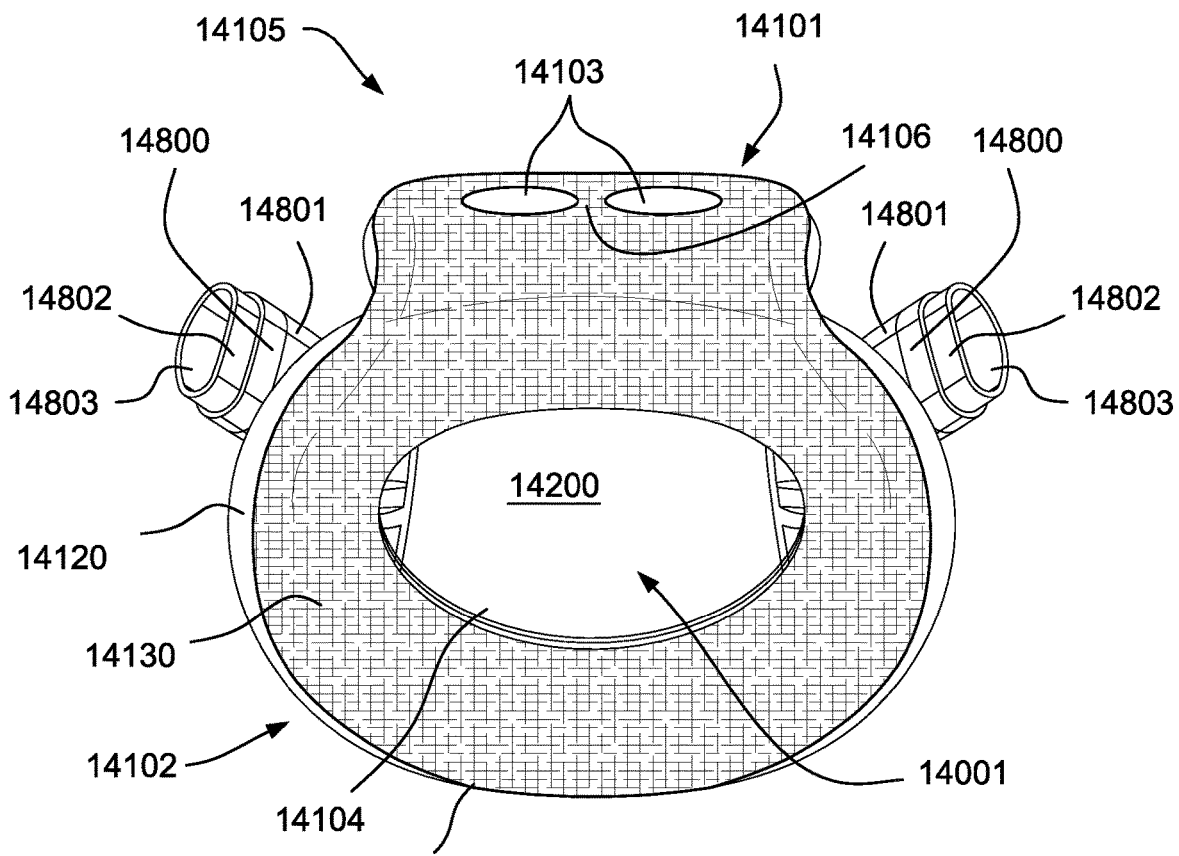

FIG. 43 is a front view of the cushion assembly of the patient interface of FIG. 39.

Figure 44:
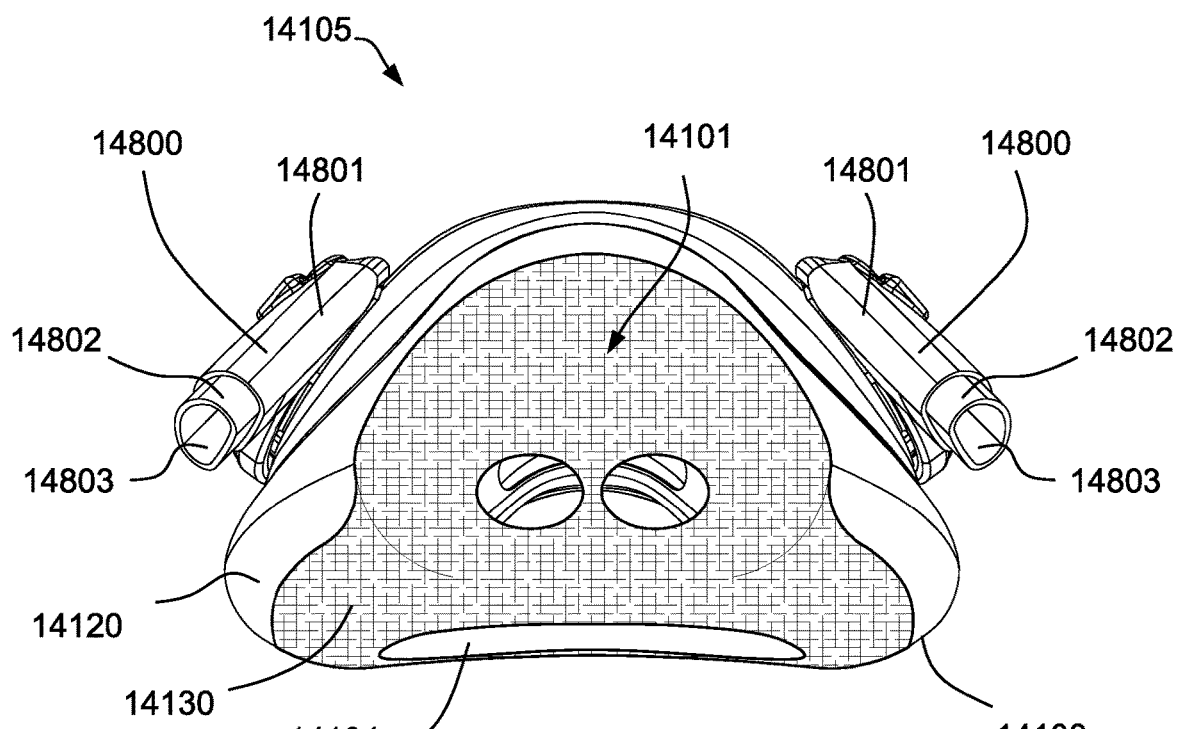

FIG. 44 is a top view of the cushion assembly of FIG. 39.

Figure 45:
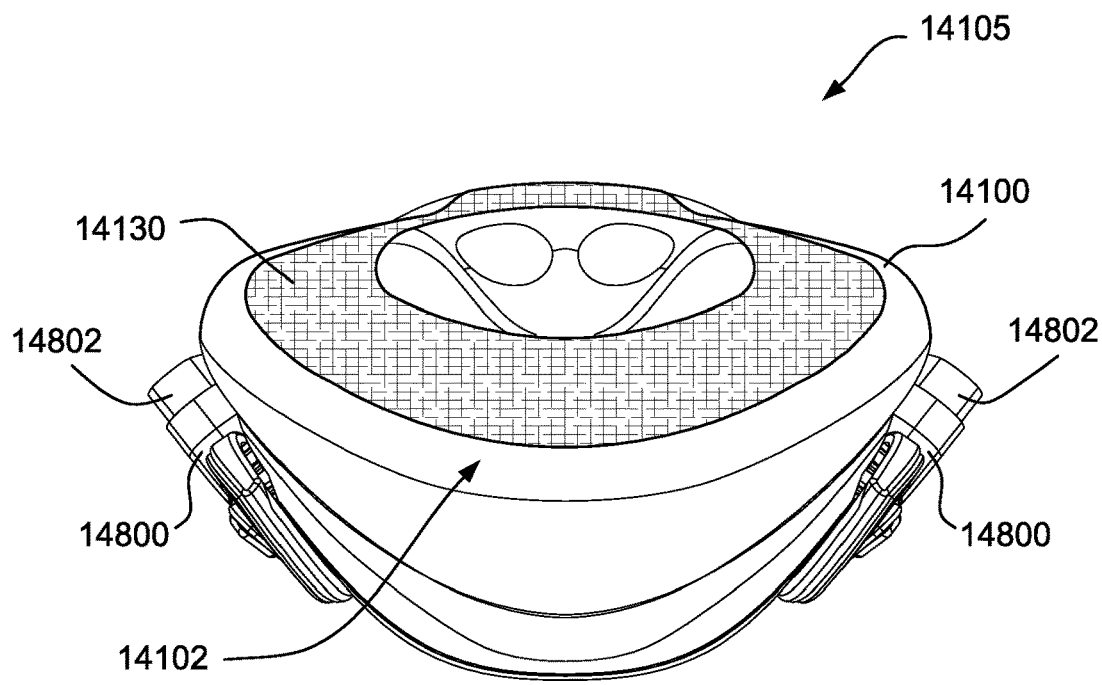

FIG. 45 is a bottom view of the cushion assembly of FIG. 39.

Figure 46:
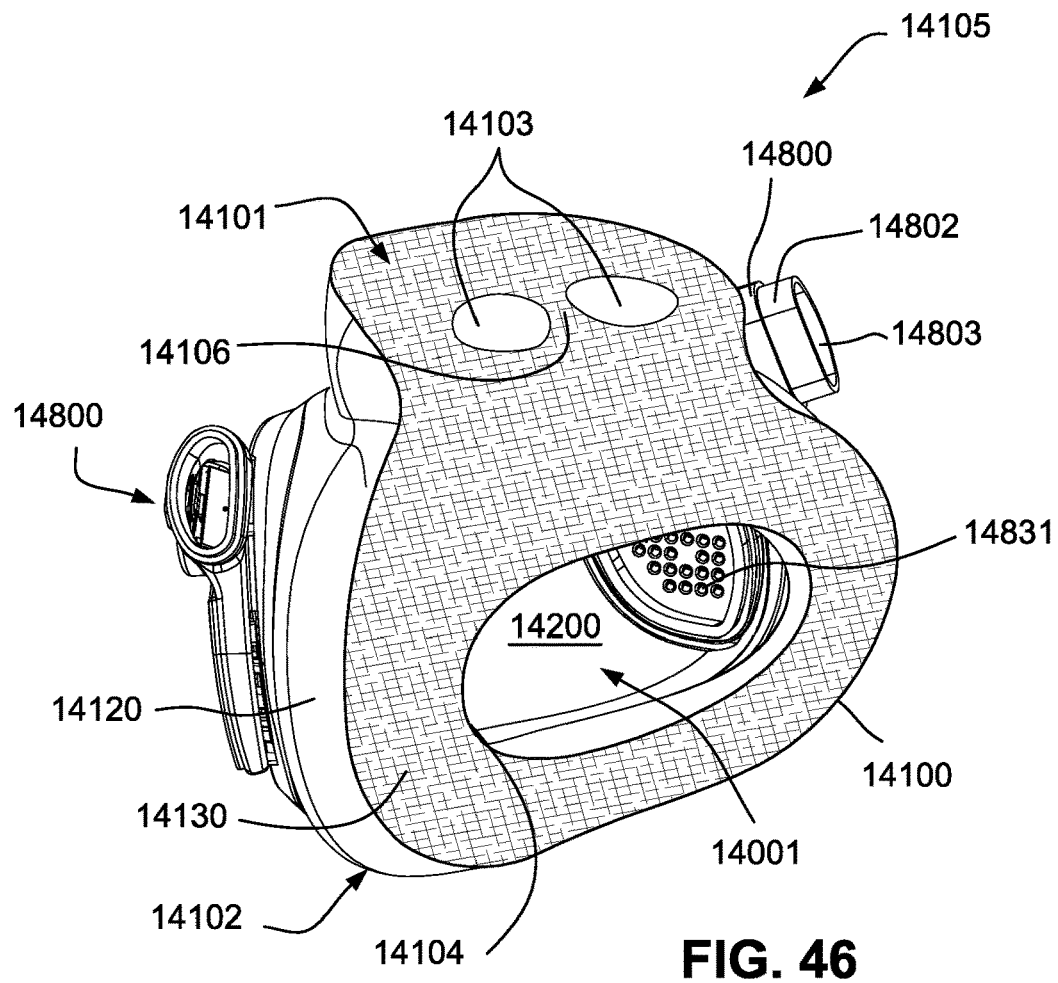

FIG. 46 is a front perspective view of the cushion assembly of FIG. 39.

Figure 47:
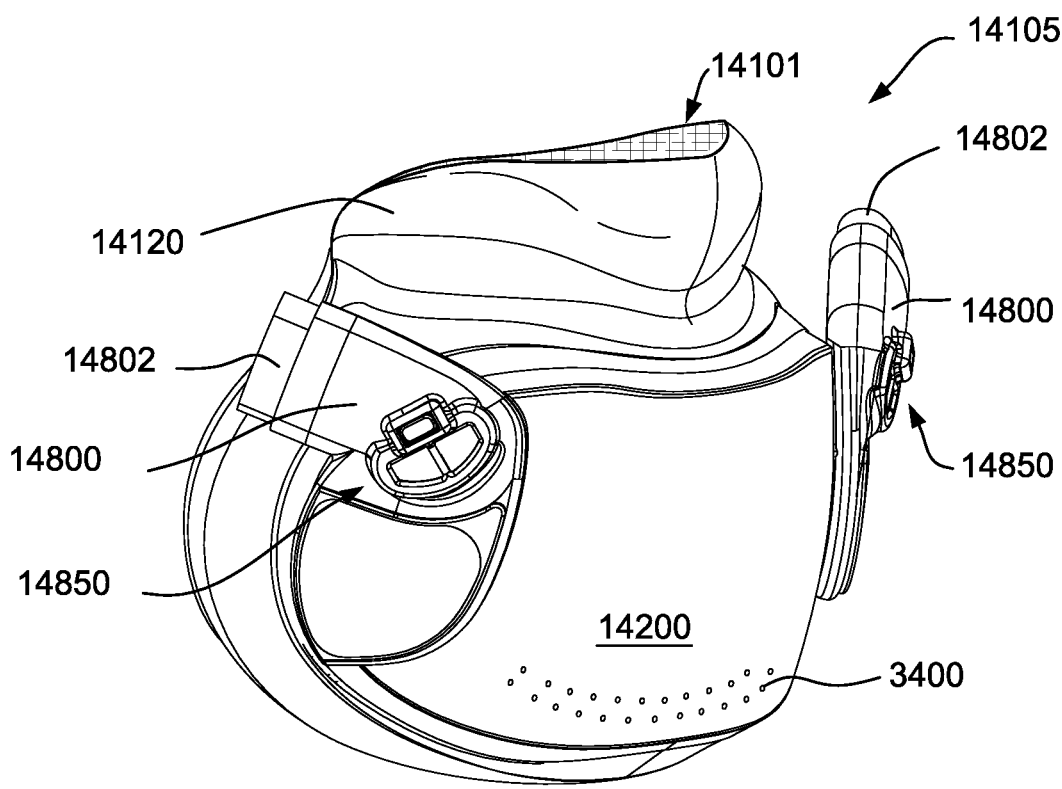

FIG. 47 is a rear perspective view of the cushion assembly of FIG. 39.

Figure 48:
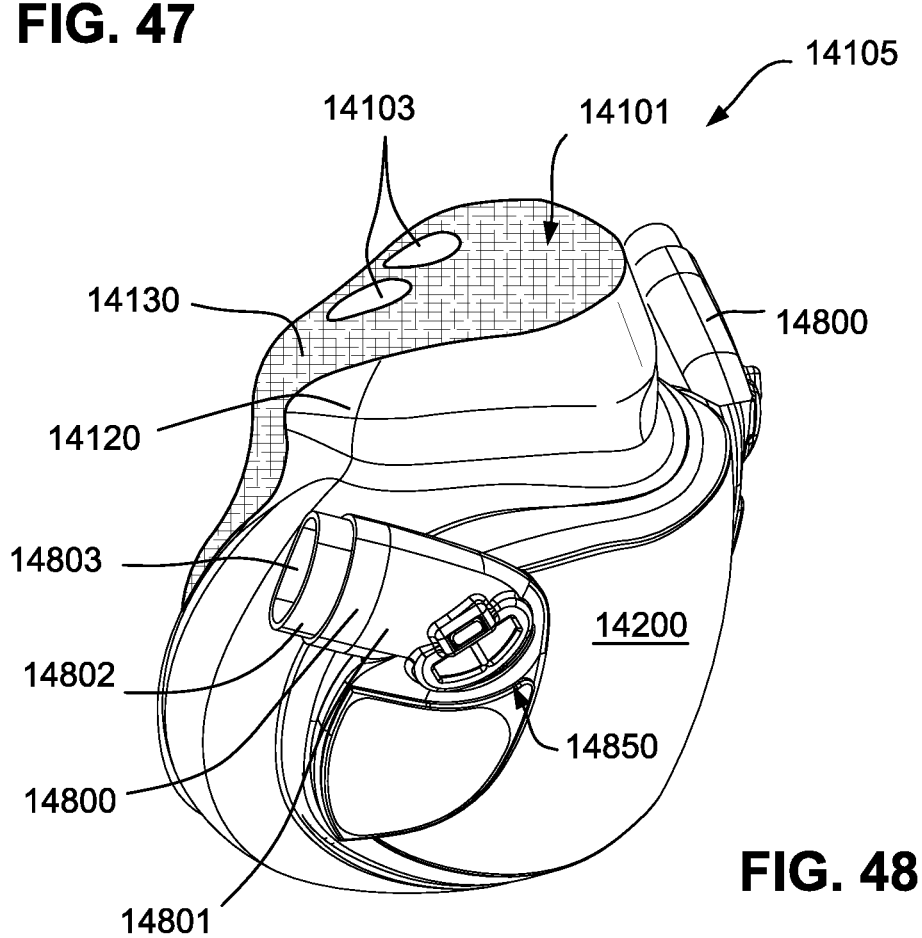

FIG. 48 is a side perspective view of the cushion assembly of FIG. 39.

Figure 49:
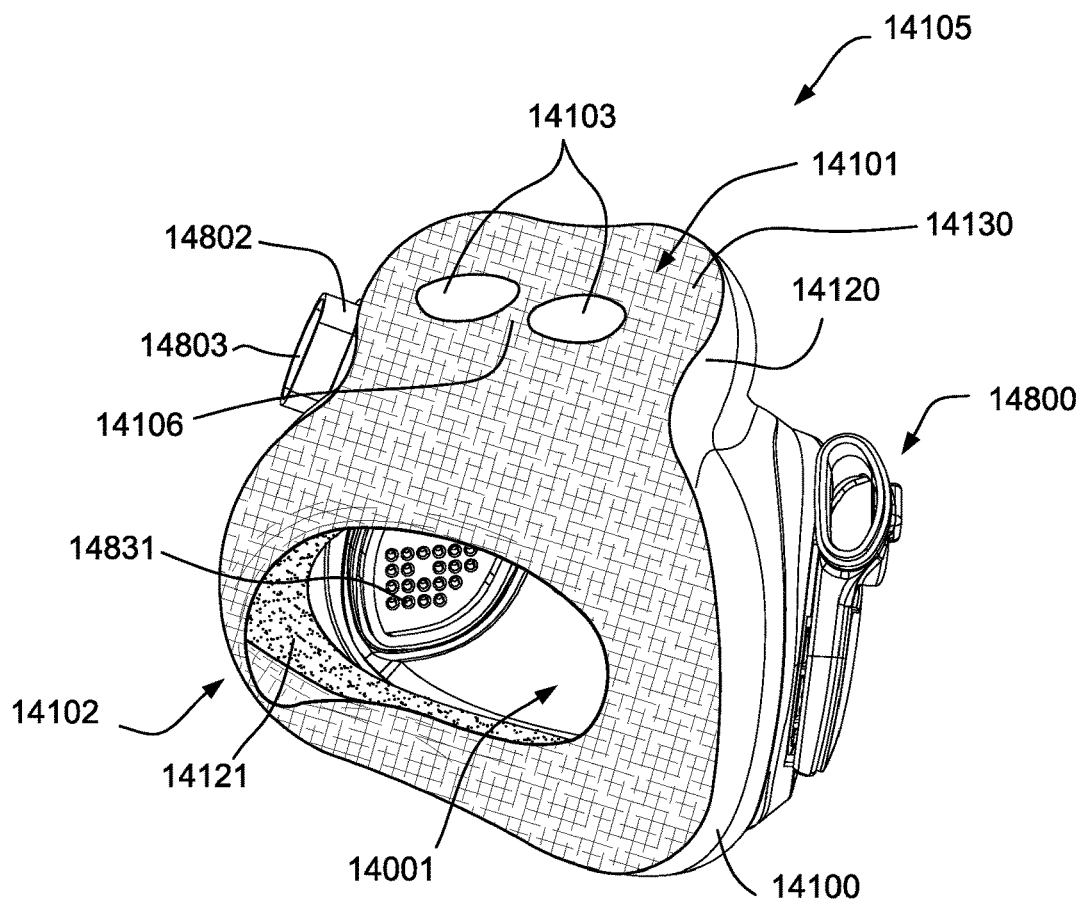

FIG. 49 is a front perspective view of the cushion assembly of FIG. 39 showing an interior portion of the cushion assembly.

Figure 50:
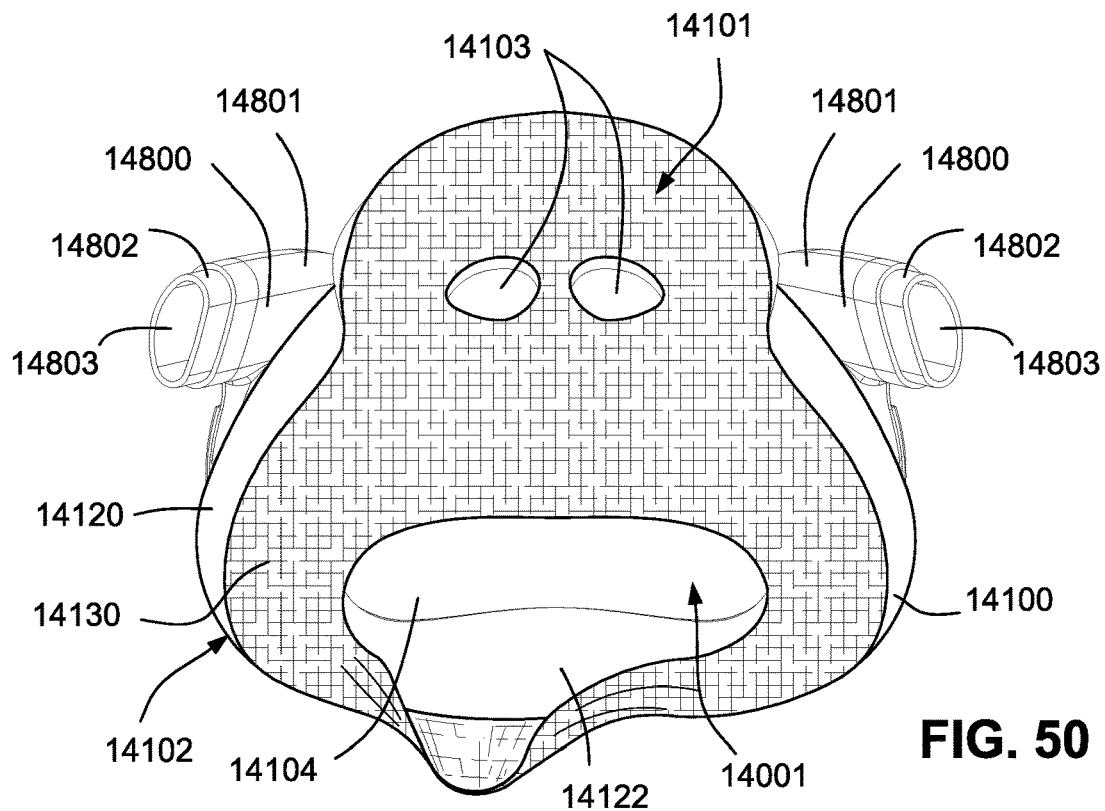

FIG. 50 is a front view of the cushion assembly of FIG. 39 showing an interior portion of the cushion assembly.

Figure 51:
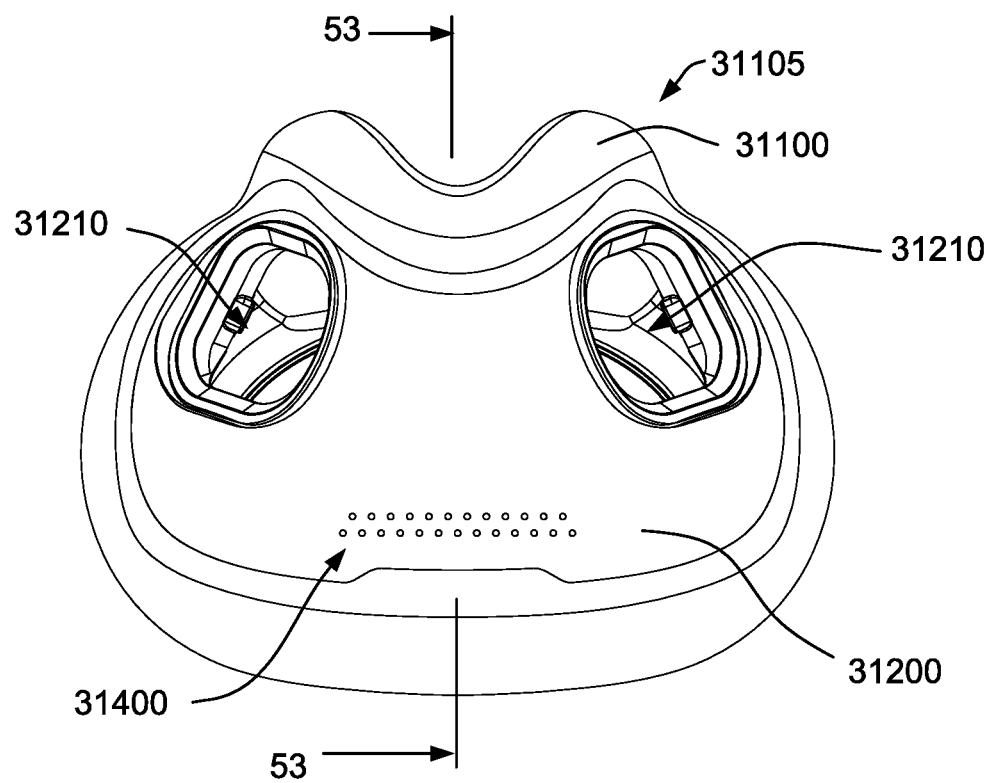

FIG. 51 is a rear view of a cushion assembly according to an example of the present technology.

Figure 52:
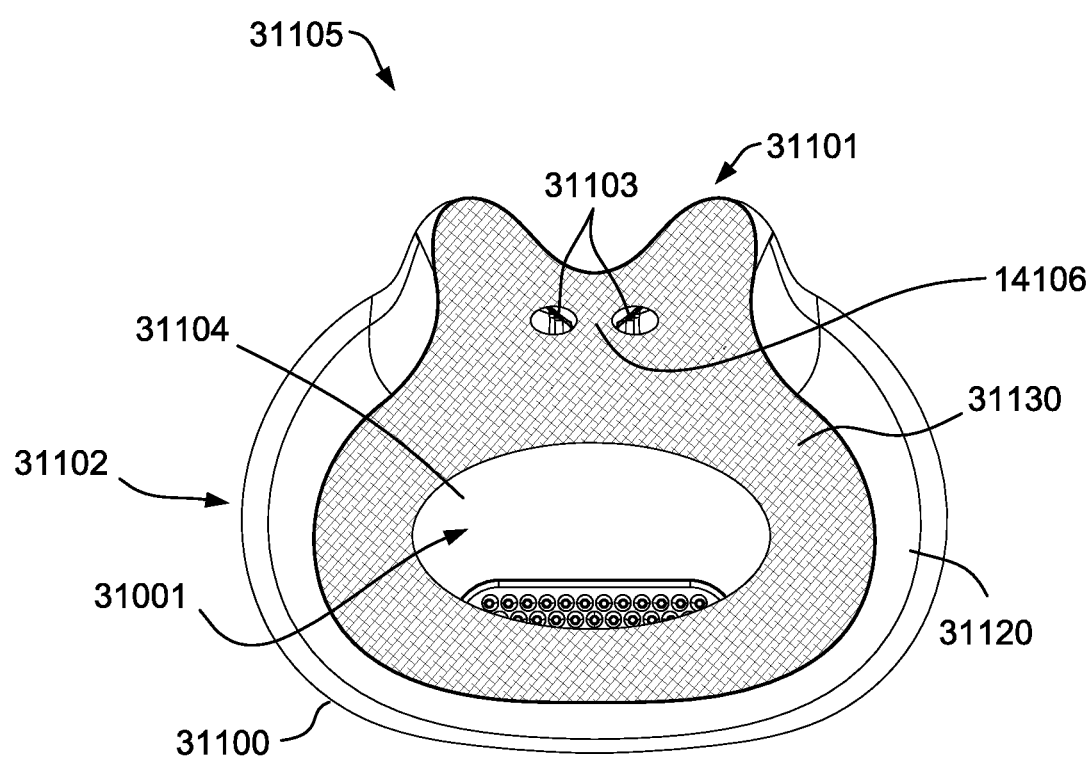

FIG. 52 is a front view of the cushion assembly of FIG. 51.

Figure 53:
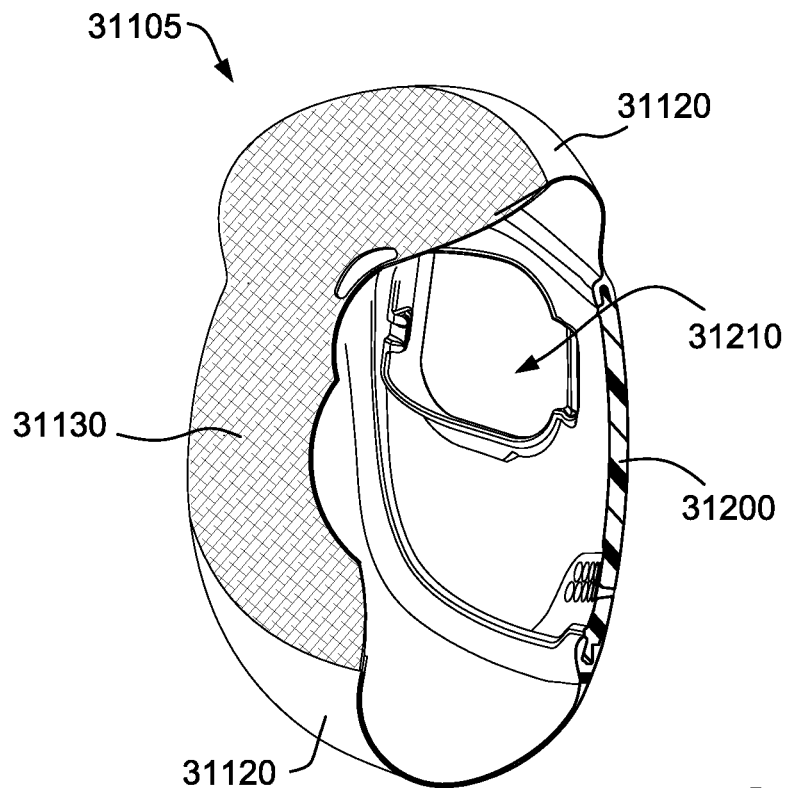

FIG. 53 is a cross-sectional view of the cushion assembly of FIG. 51.

Figure 54:
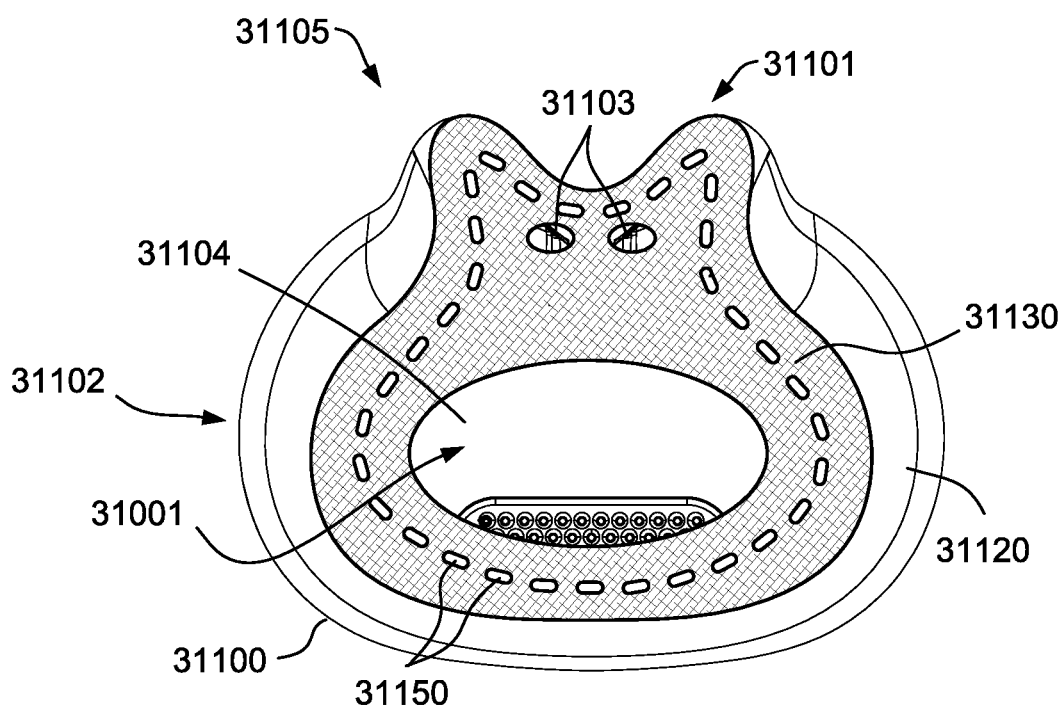
Figure 55:
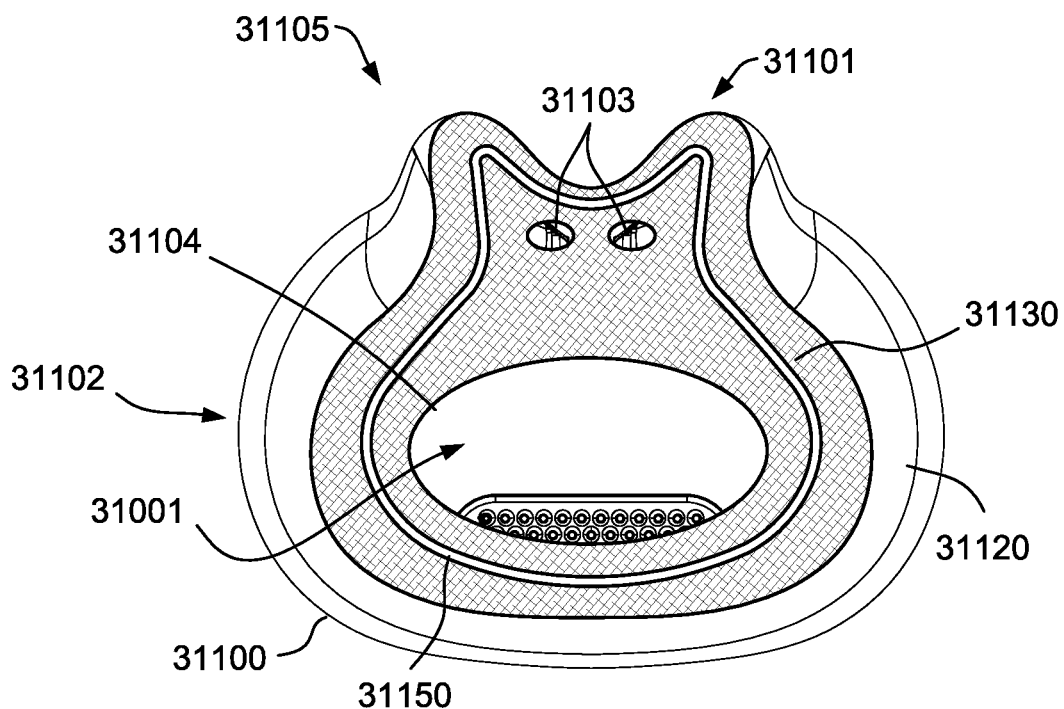
Figure 56:
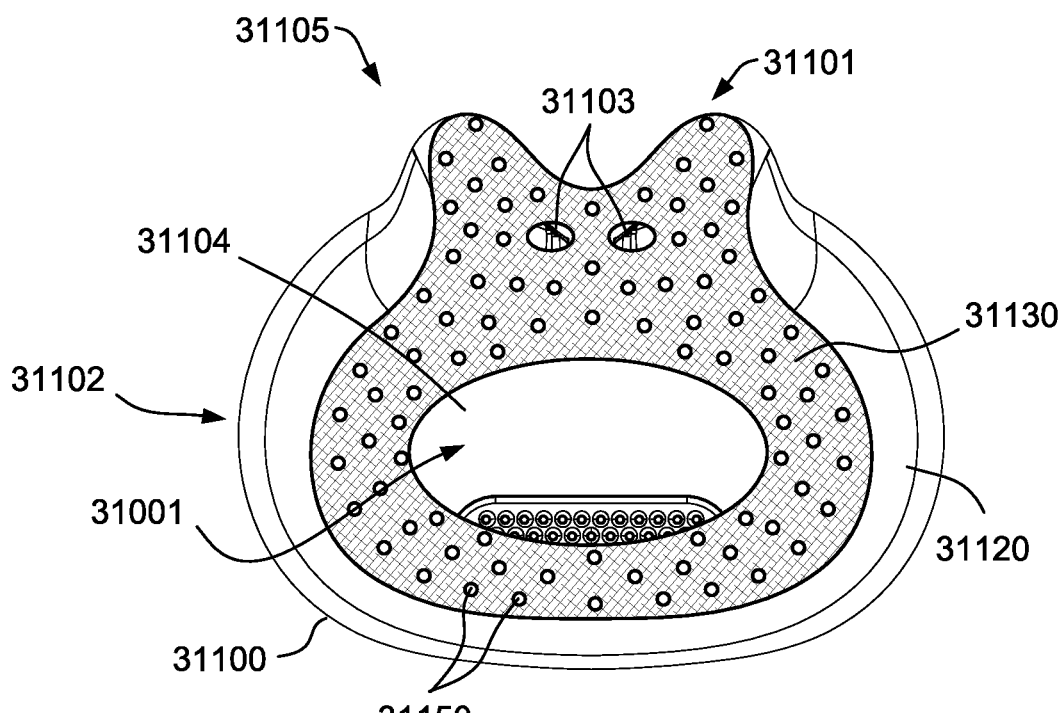

FIGS. 54-56 are front perspective views of cushion assemblies having grip pads disposed on the textile membrane according examples of the present technology.

Figure 57:
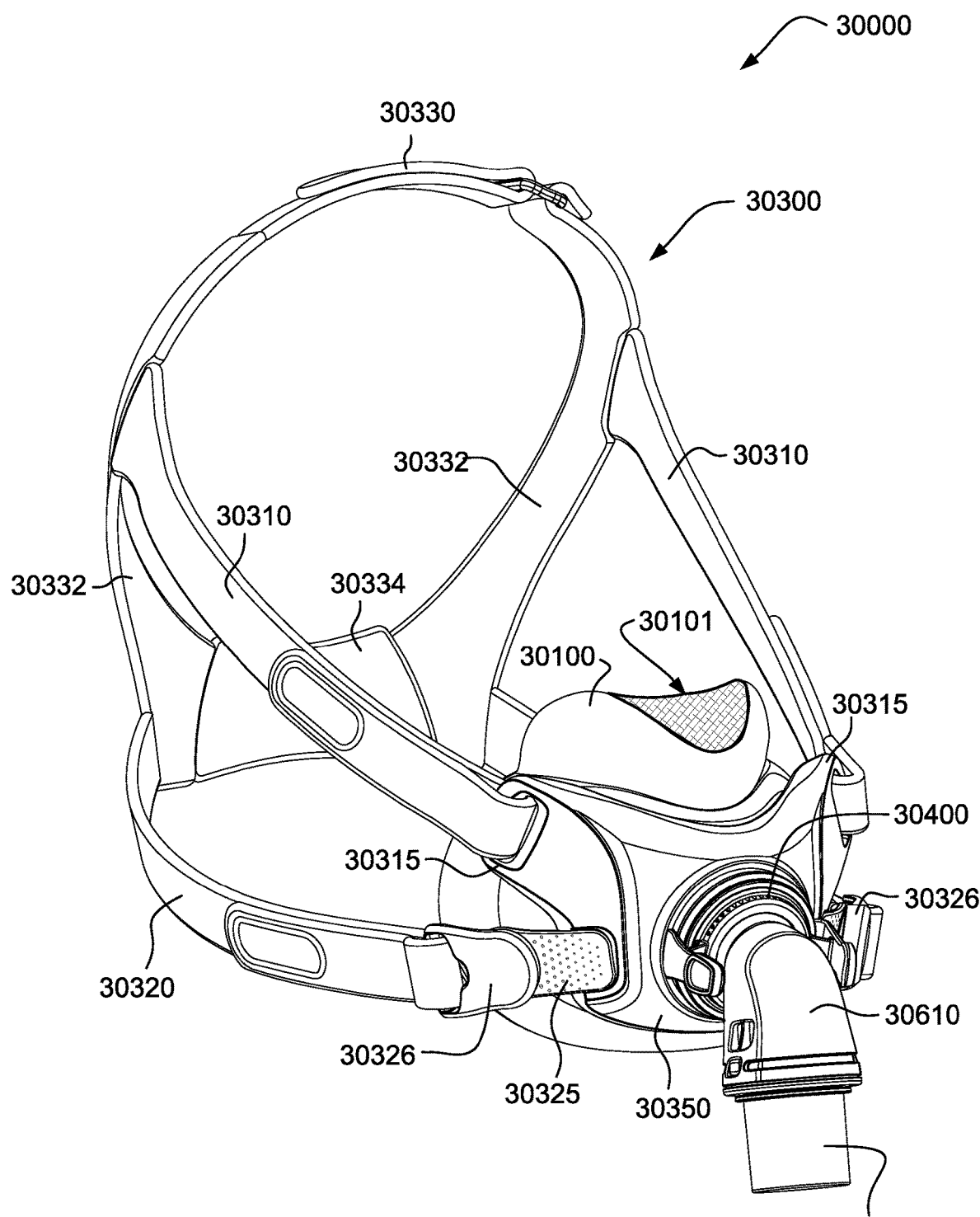

FIG. 57 is a perspective view of a patient interface 30000 according to an example of the present technology.

Figure 58:
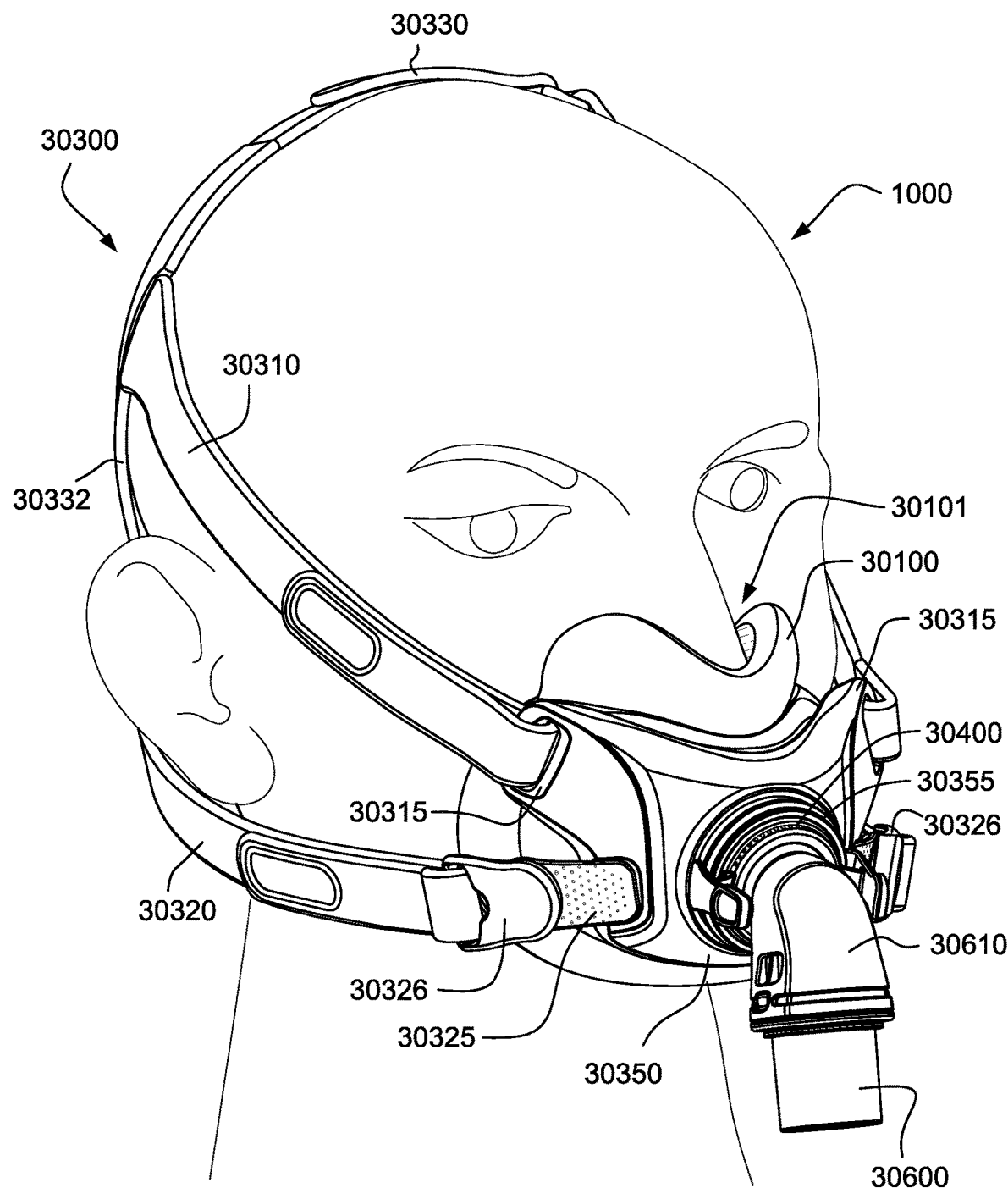

FIG. 58 is a perspective view of the patient interface 30000 of FIG. 57 while worn by a patient.

Figure 59:
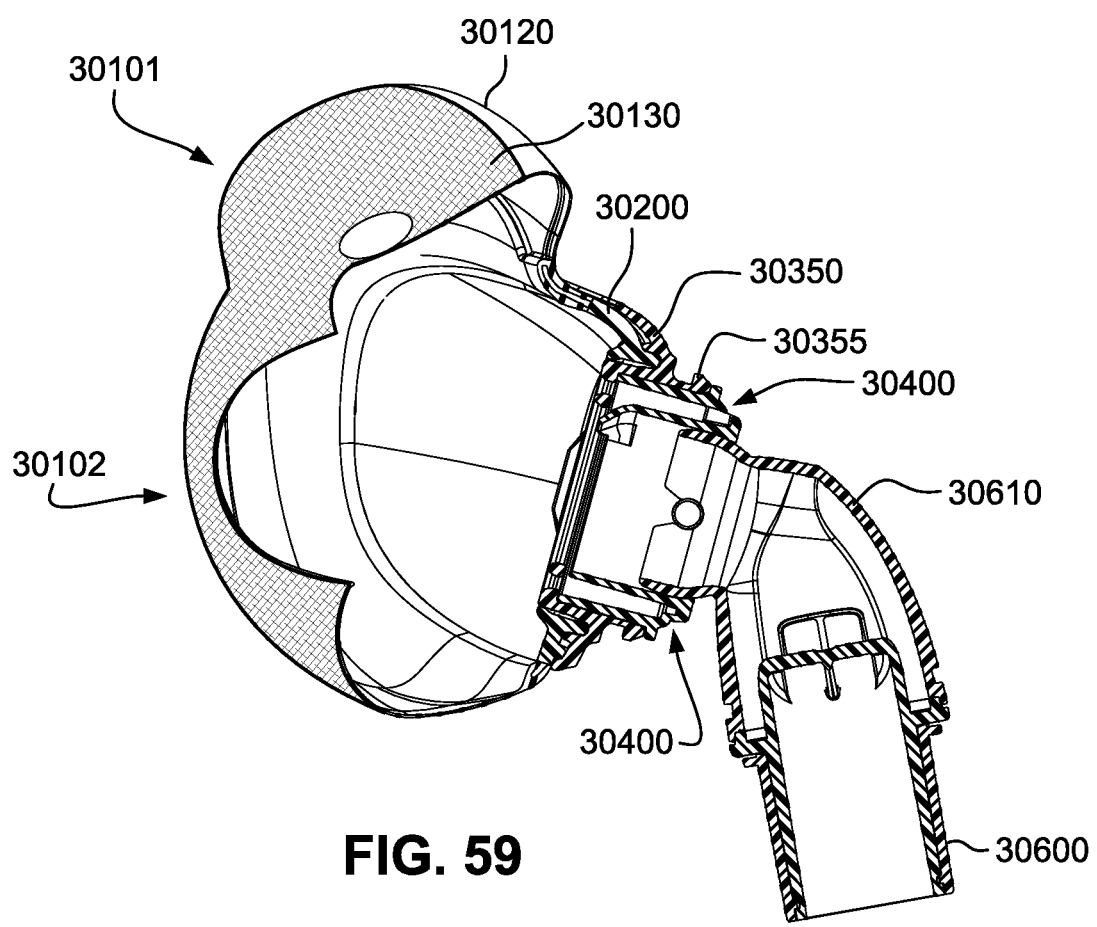

FIG. 59 is a cross section view of the patient interface 30000 shown in FIG. 57.

Figure 60:
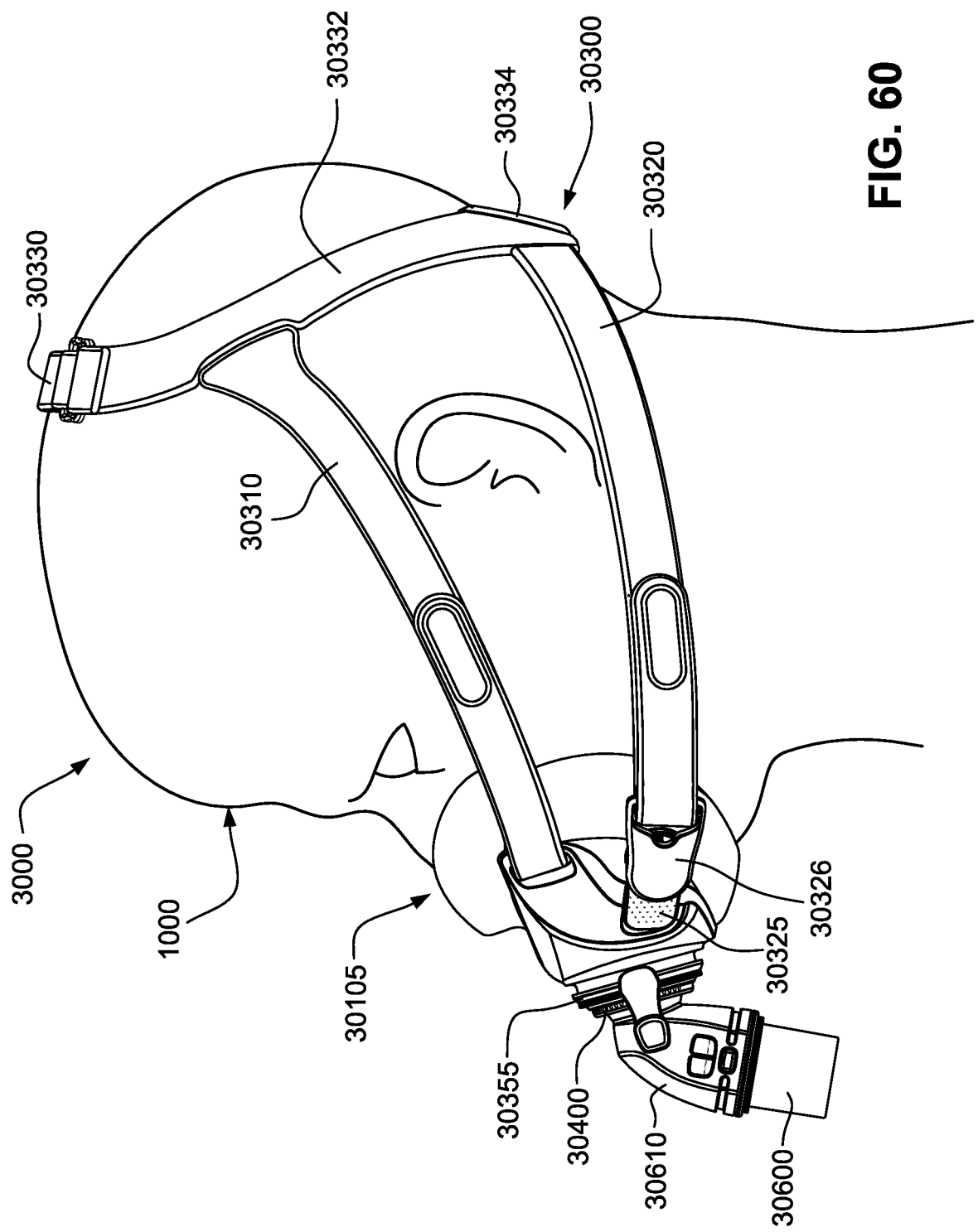

FIG. 60 is a side view of the patient interface 30000 of FIG. 57 while worn by a patient.

Figure 61:
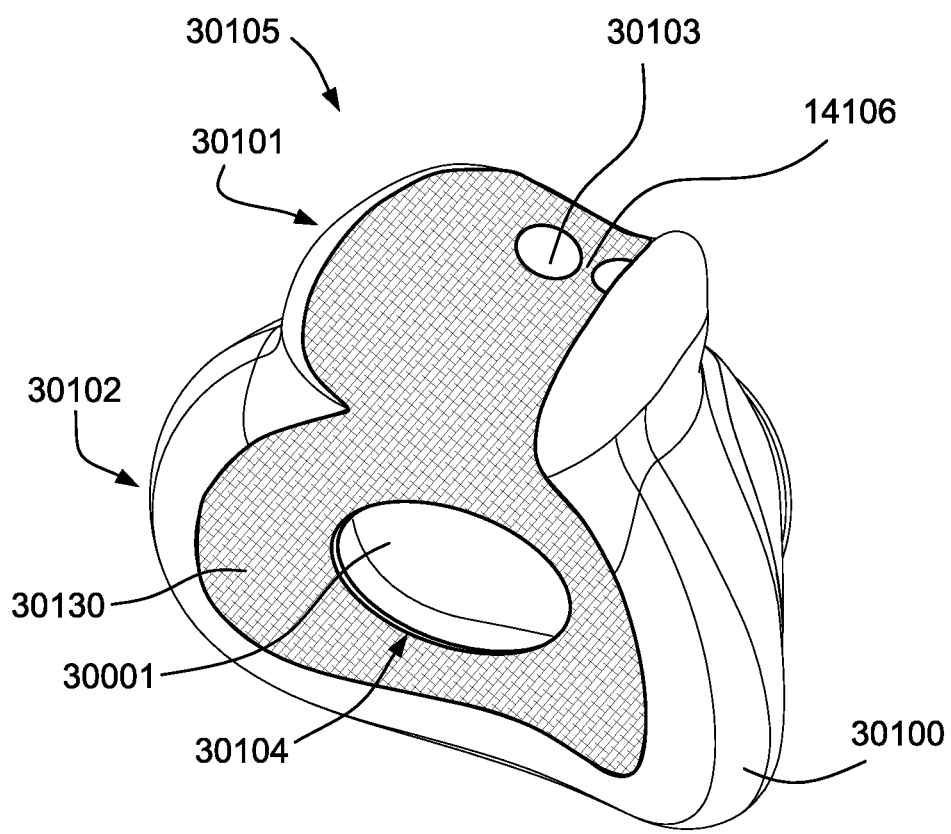

FIG. 61 is a front perspective view of the cushion assembly 30105 of FIG. 57.

Figure 62:
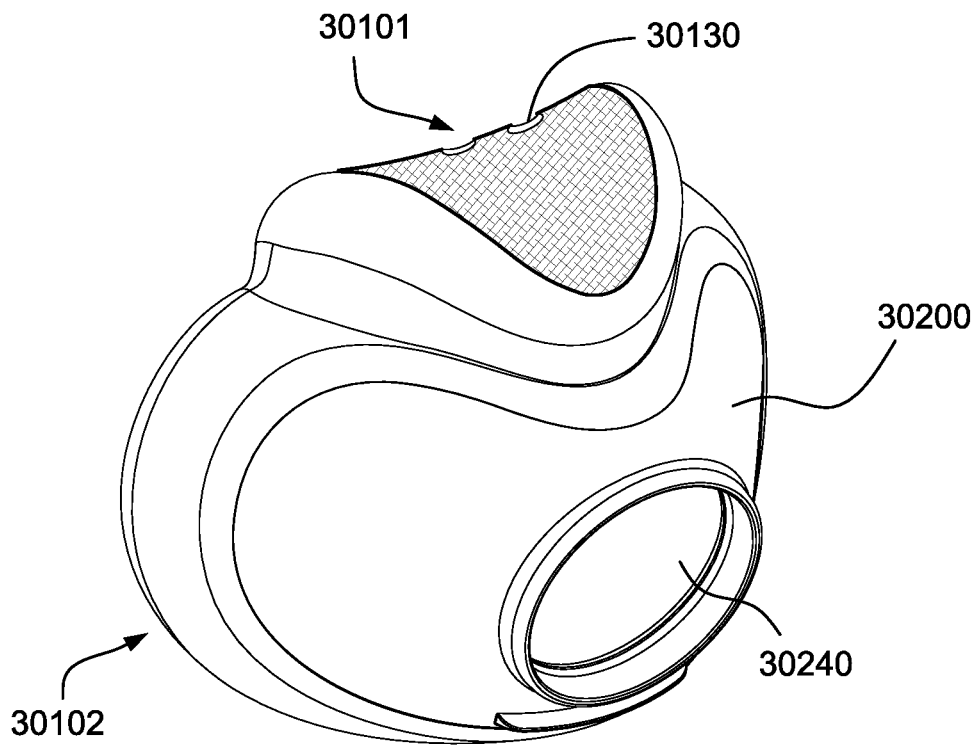

FIG. 62 is a rear perspective view of the cushion assembly 30105 of FIG. 57.

Figure 63:
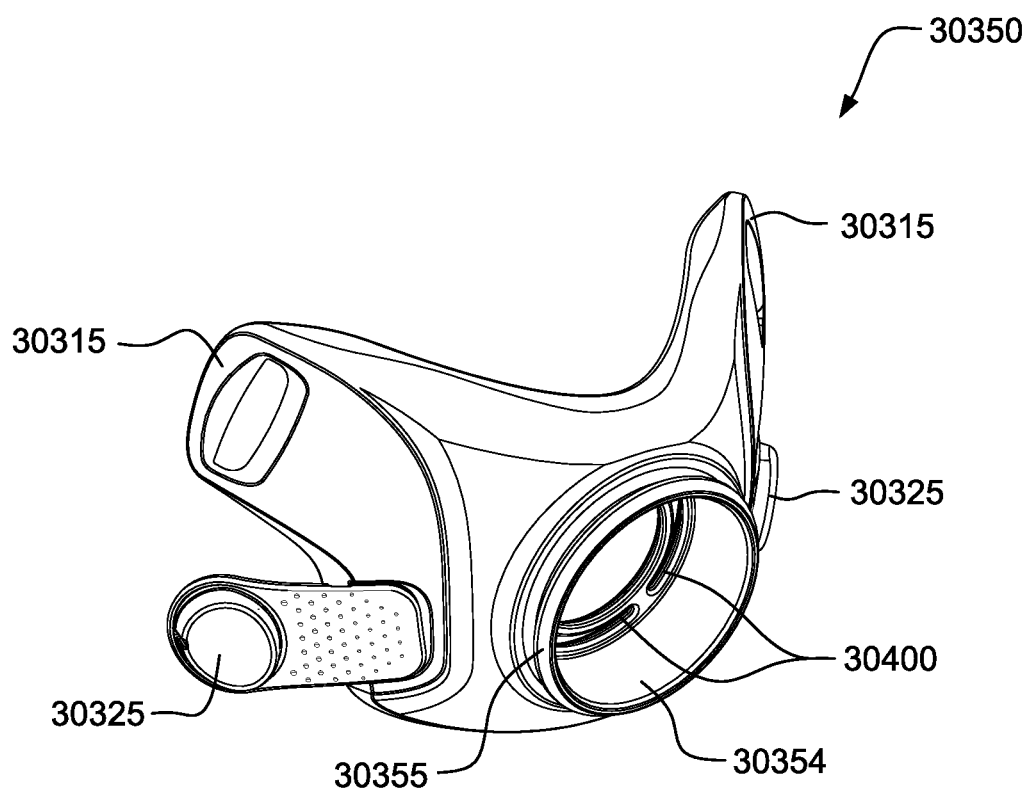

FIG. 63 is a front view of the frame 30350 of FIG. 57.

Figure 64:
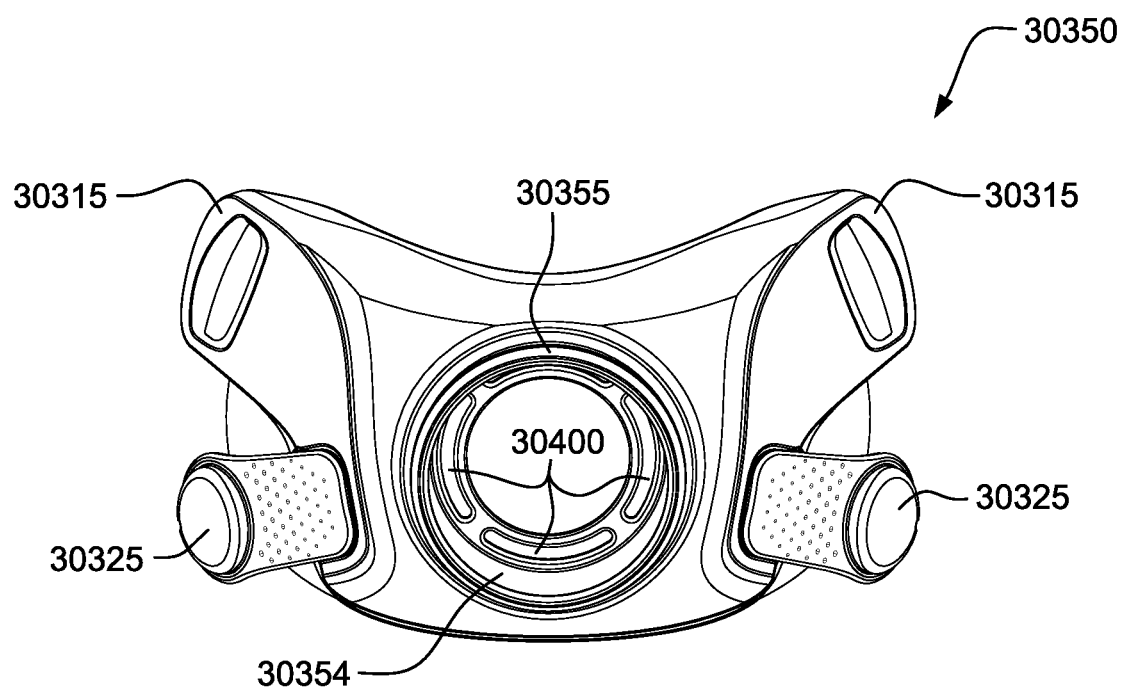

FIG. 64 is a back view of the frame 30350 of FIG. 57.

Figure 65:
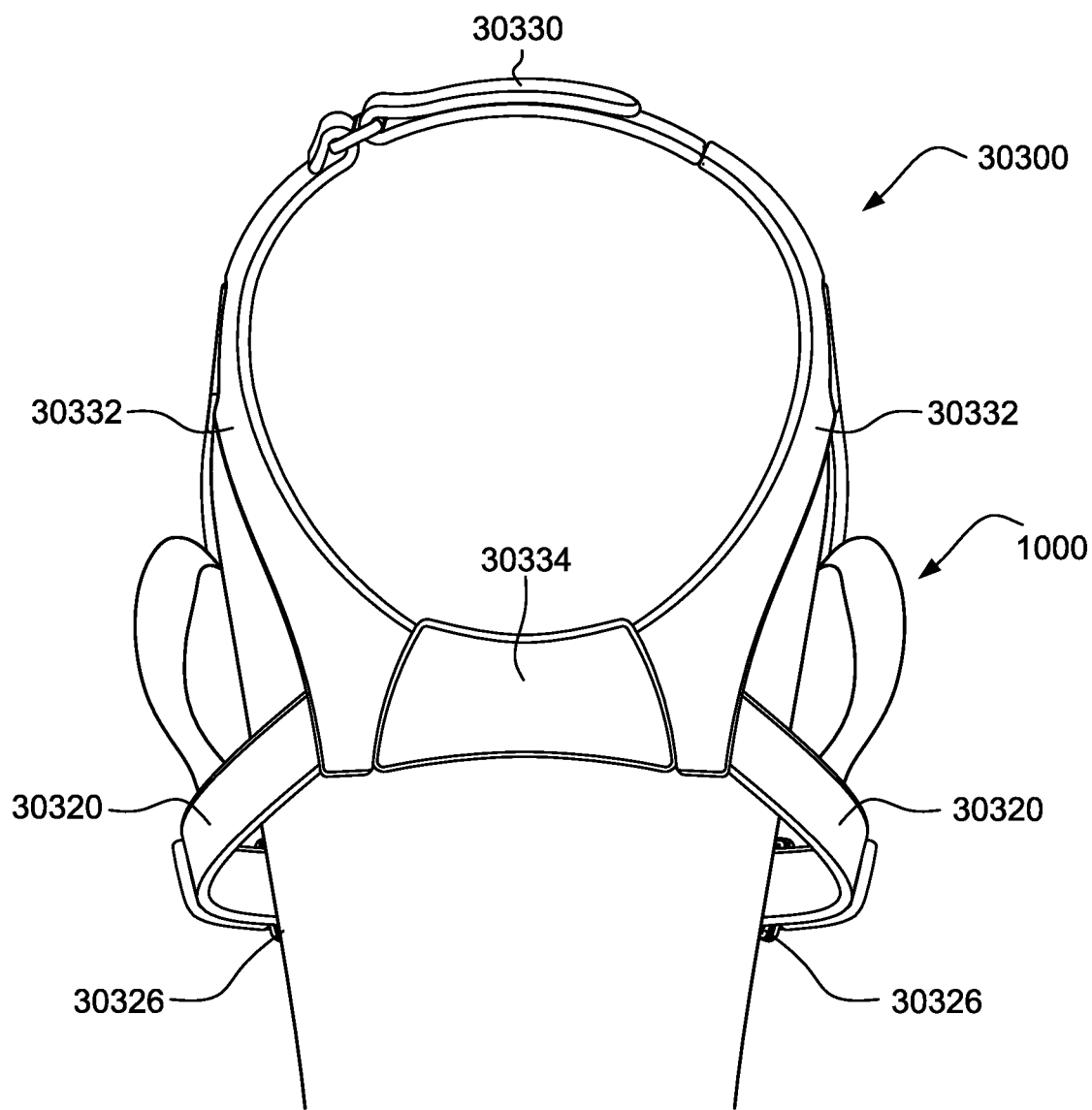

FIG. 65 is a back view of the patient interface 30000 of FIG. 57 while worn by a patient.

Figure 66:
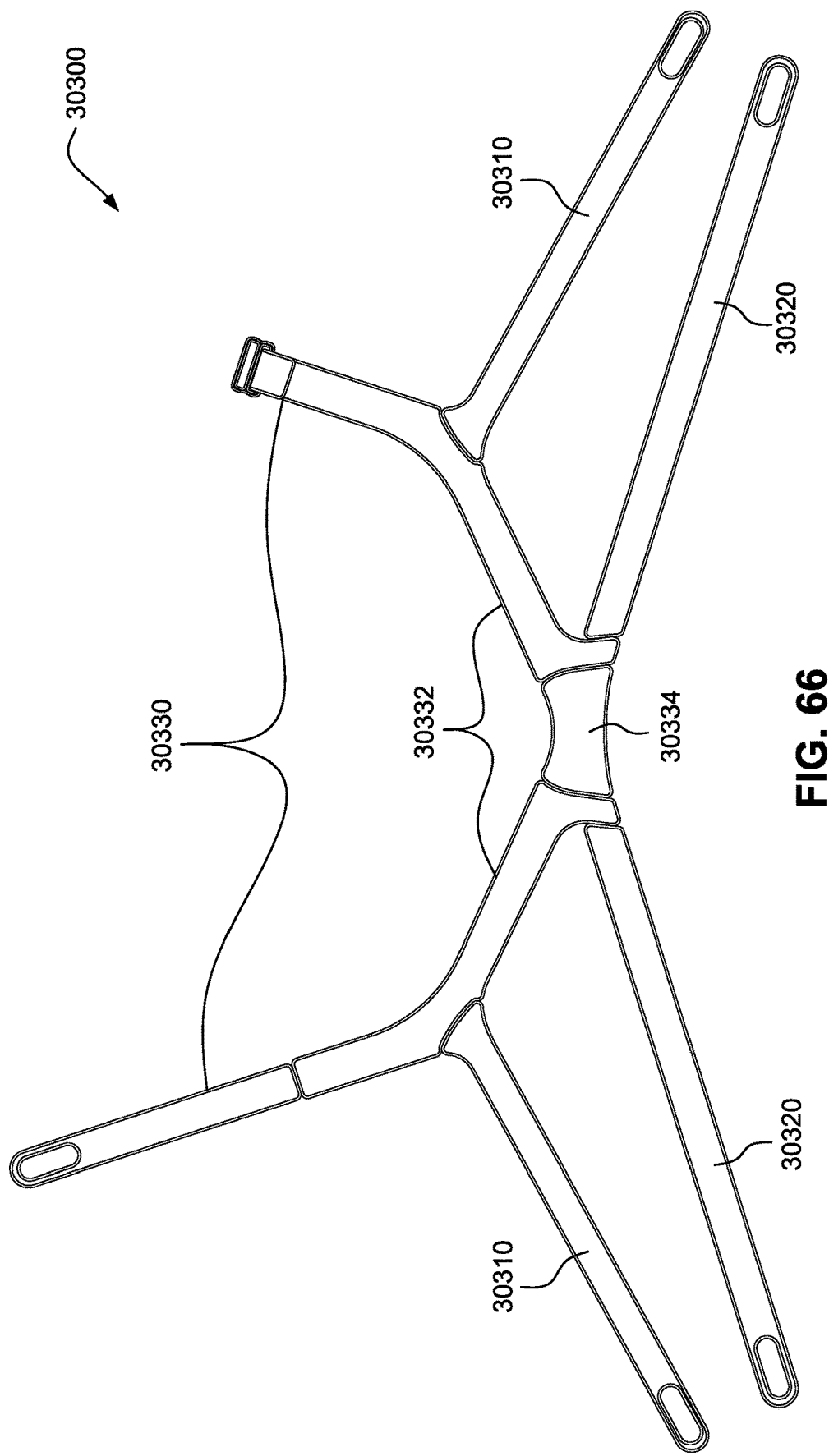

FIG. 66 is view of straps of the positioning and stabilising structure 30300 of the patient interface 30000 of FIG. 57.

Figure 67:
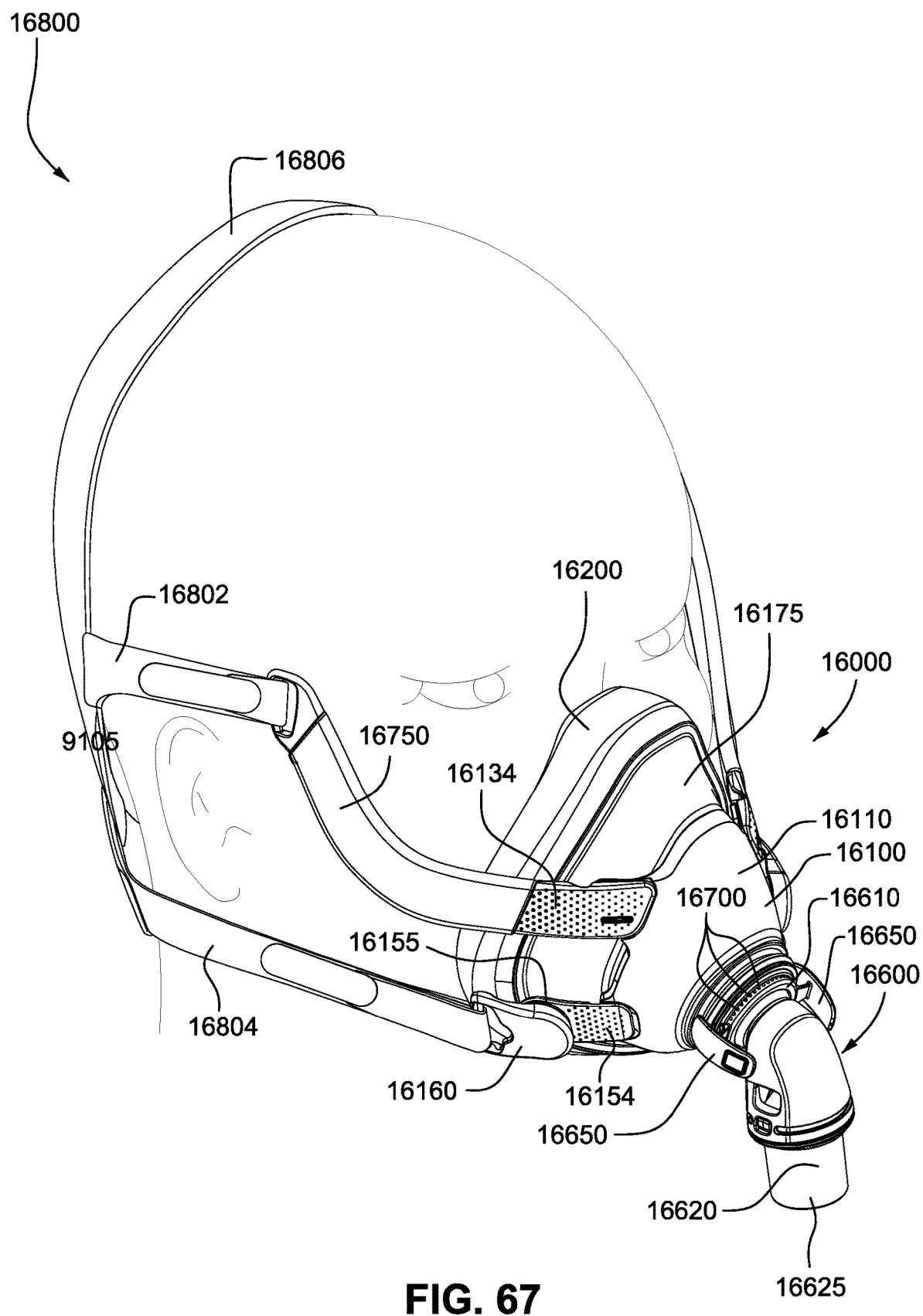

FIG. 67 is a perspective view of a patient interface according to another example of the present technology worn by a patient.

Figure 68:
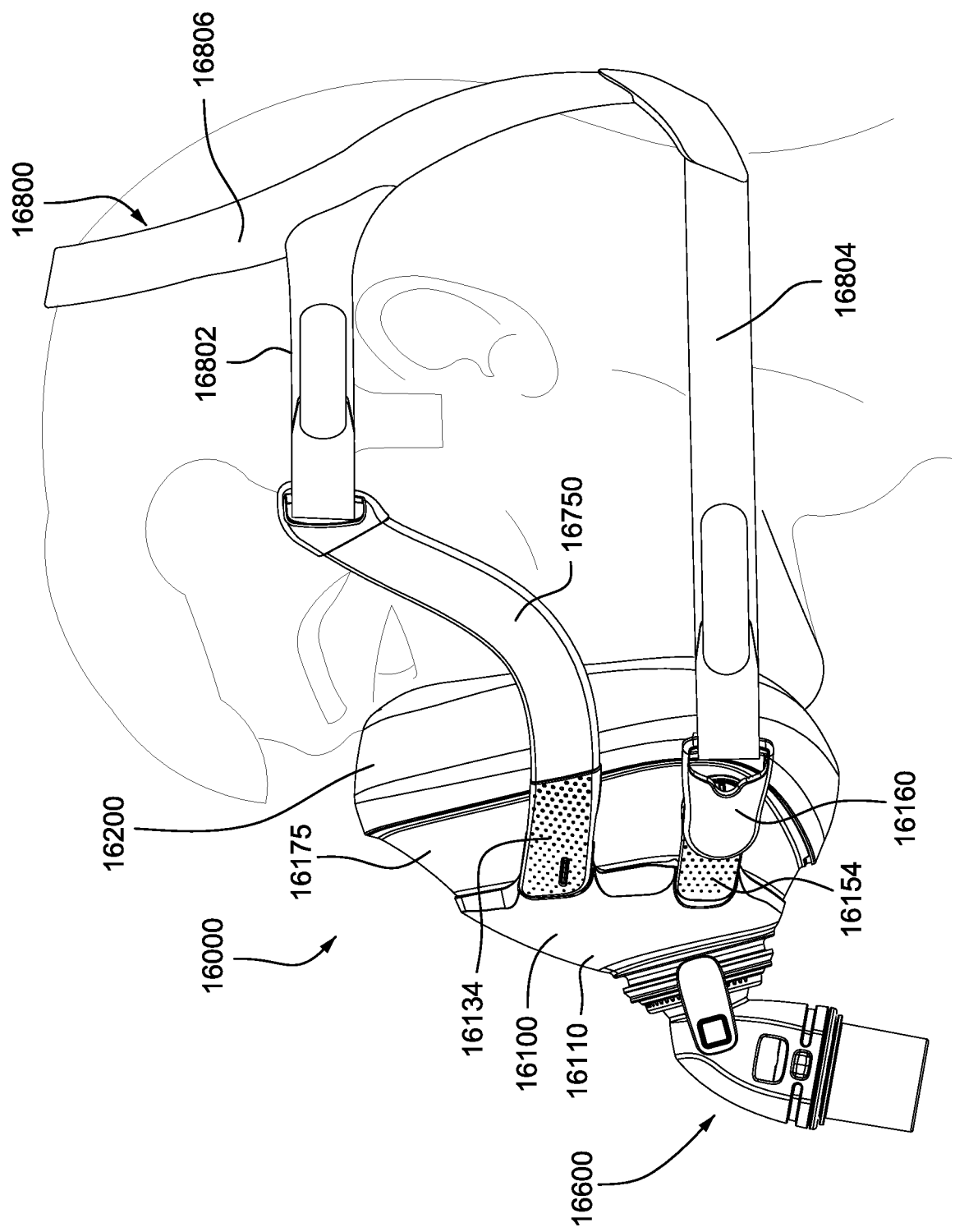

FIG. 68 is a side view of the patient interface of FIG. 67.

Figure 69:
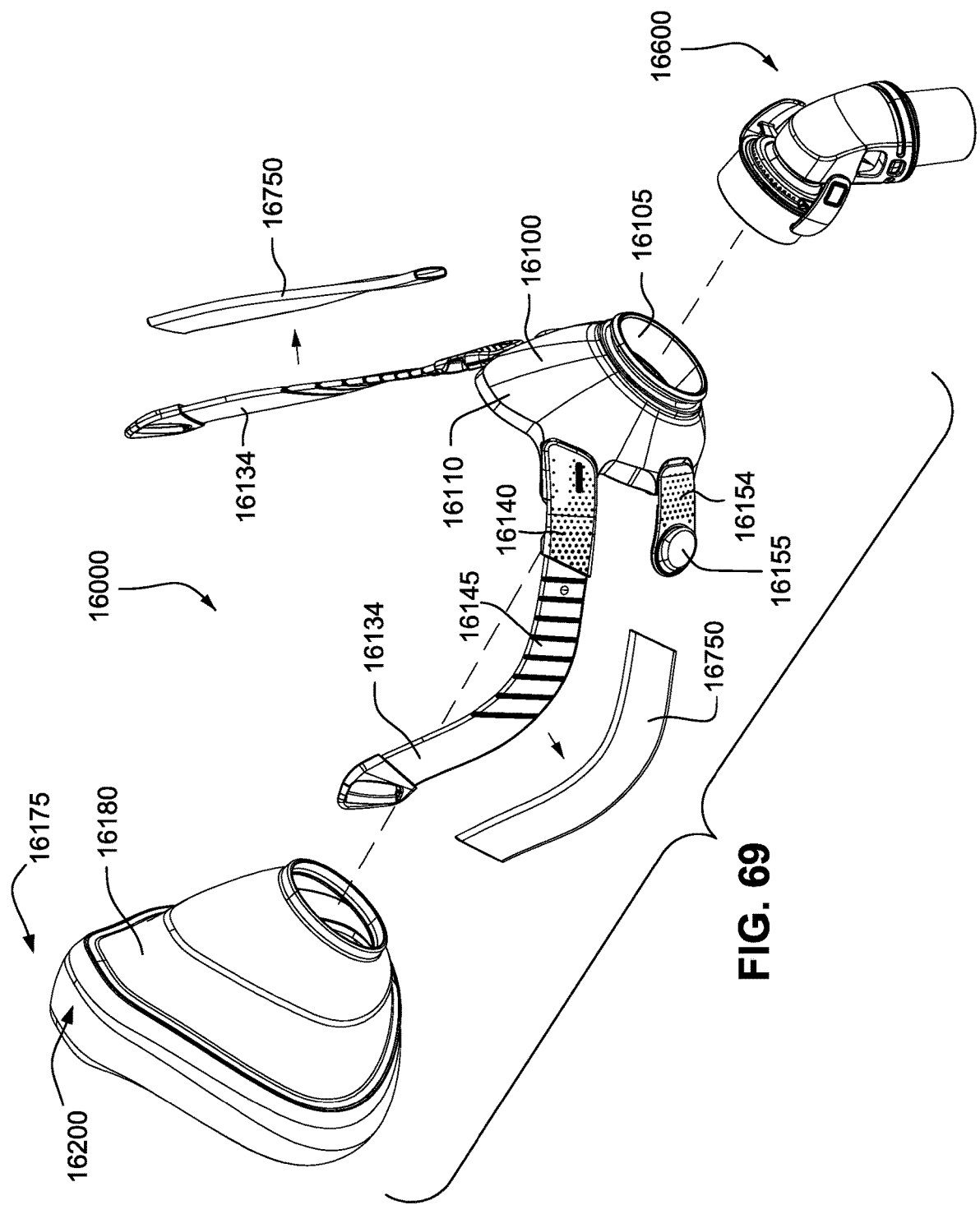
Figure 70:
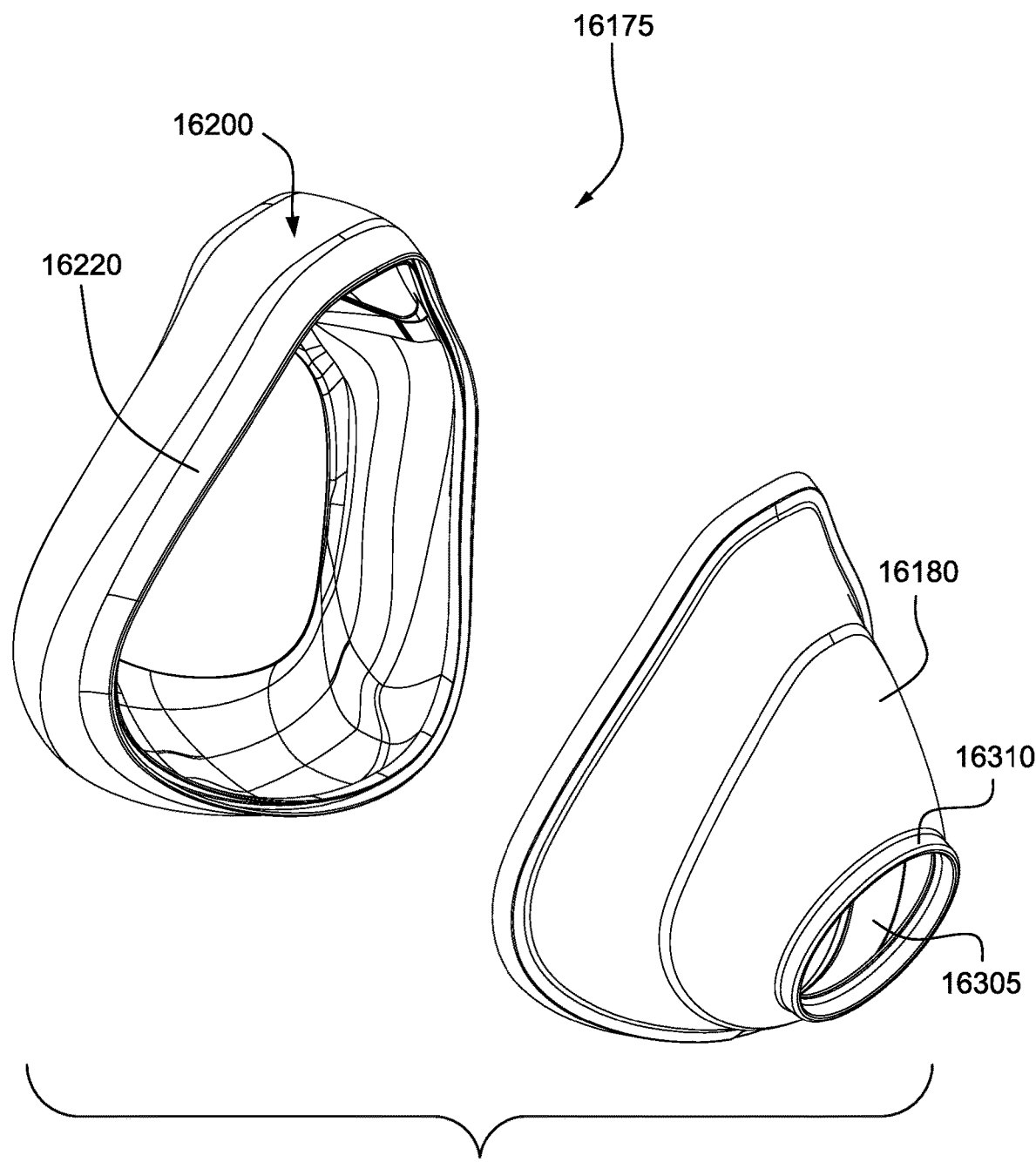

FIG. 69 is an exploded view of the patient interface shown in FIG. 67 showing the cushion assembly, frame assembly, arm covers, and elbow assembly;

FIG. 70 is a front exploded view of a cushion assembly according to an example of the present technology.

Figure 71:
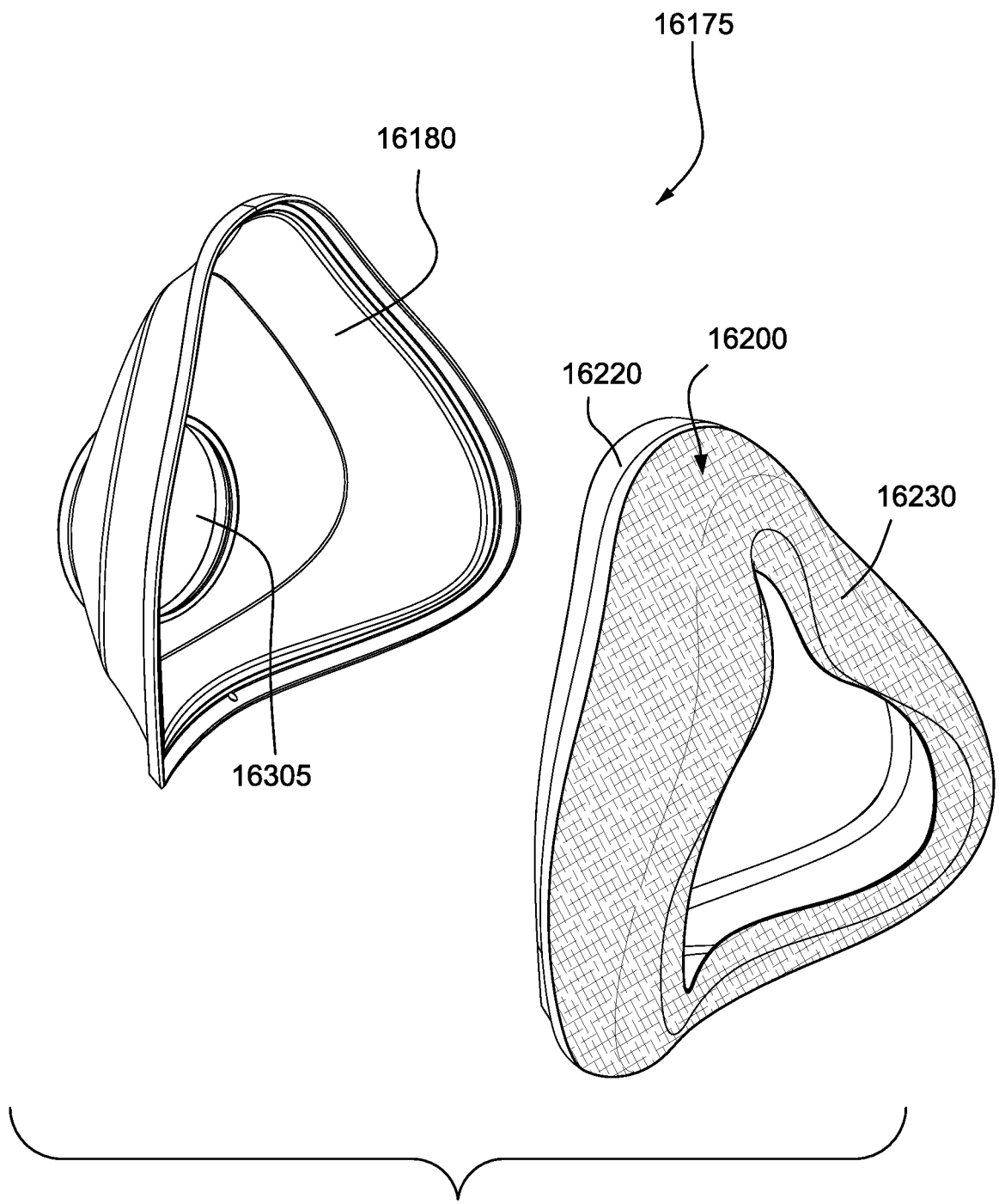

FIG. 71 is a rear exploded view of the cushion assembly of FIG. 70.

Figure 72:
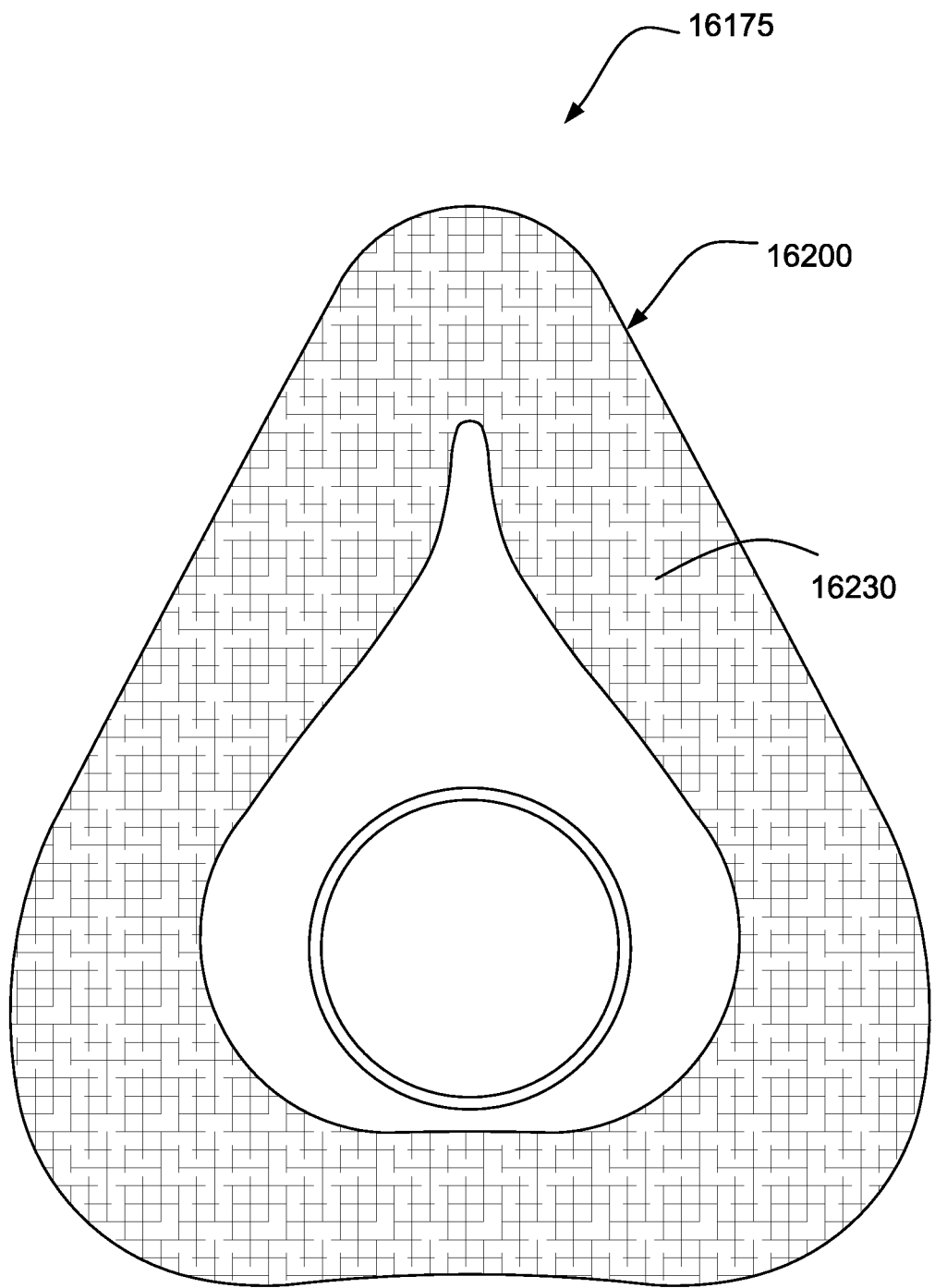

FIG. 72 is a front view of the cushion assembly of the patient interface of FIG. 67.

Figure 73:
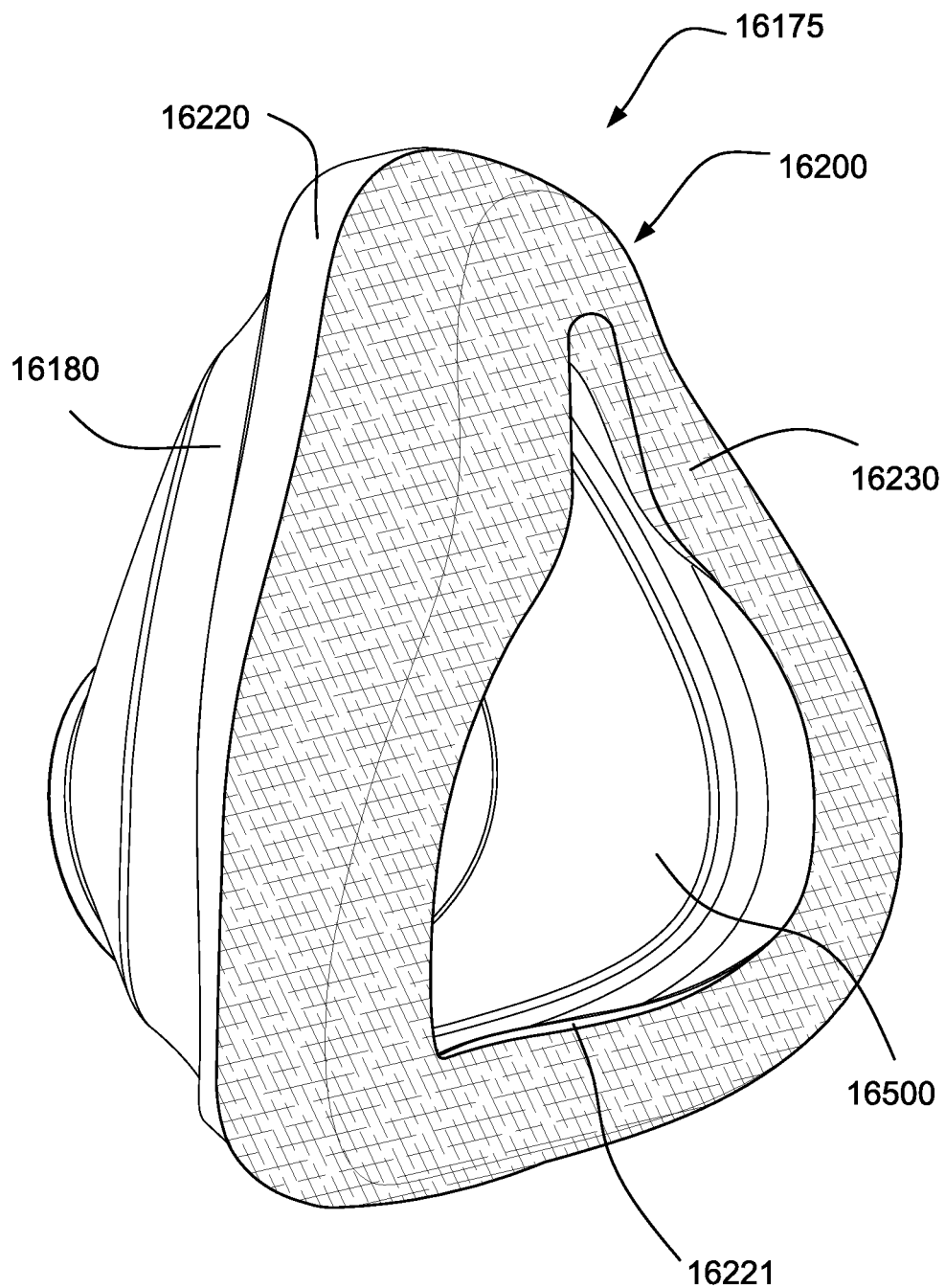

FIG. 73 is a front perspective view of the cushion assembly of FIG. 72.

Figure 74:
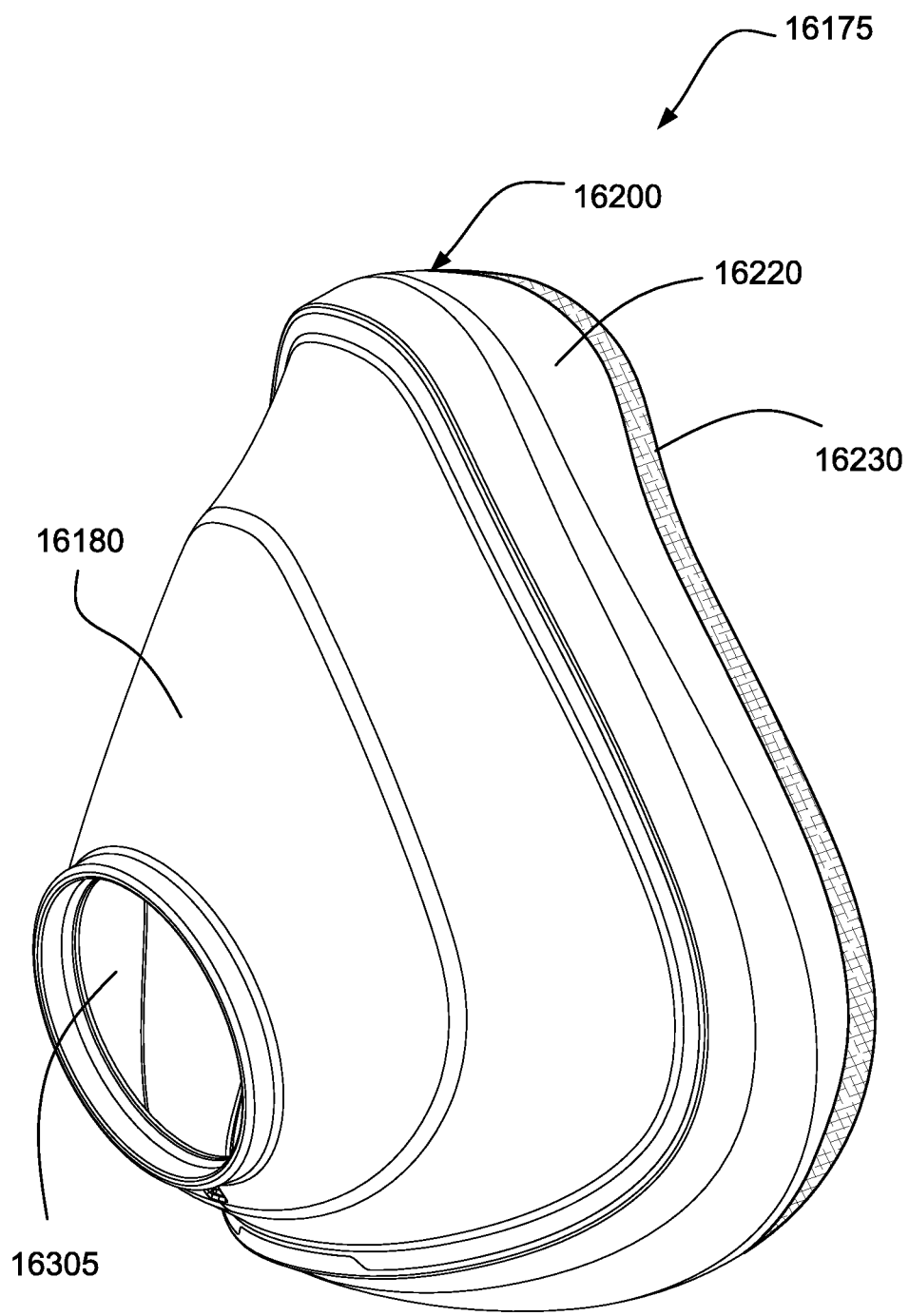

FIG. 74 is a rear perspective view of the cushion assembly of FIG. 72.

Figure 75:
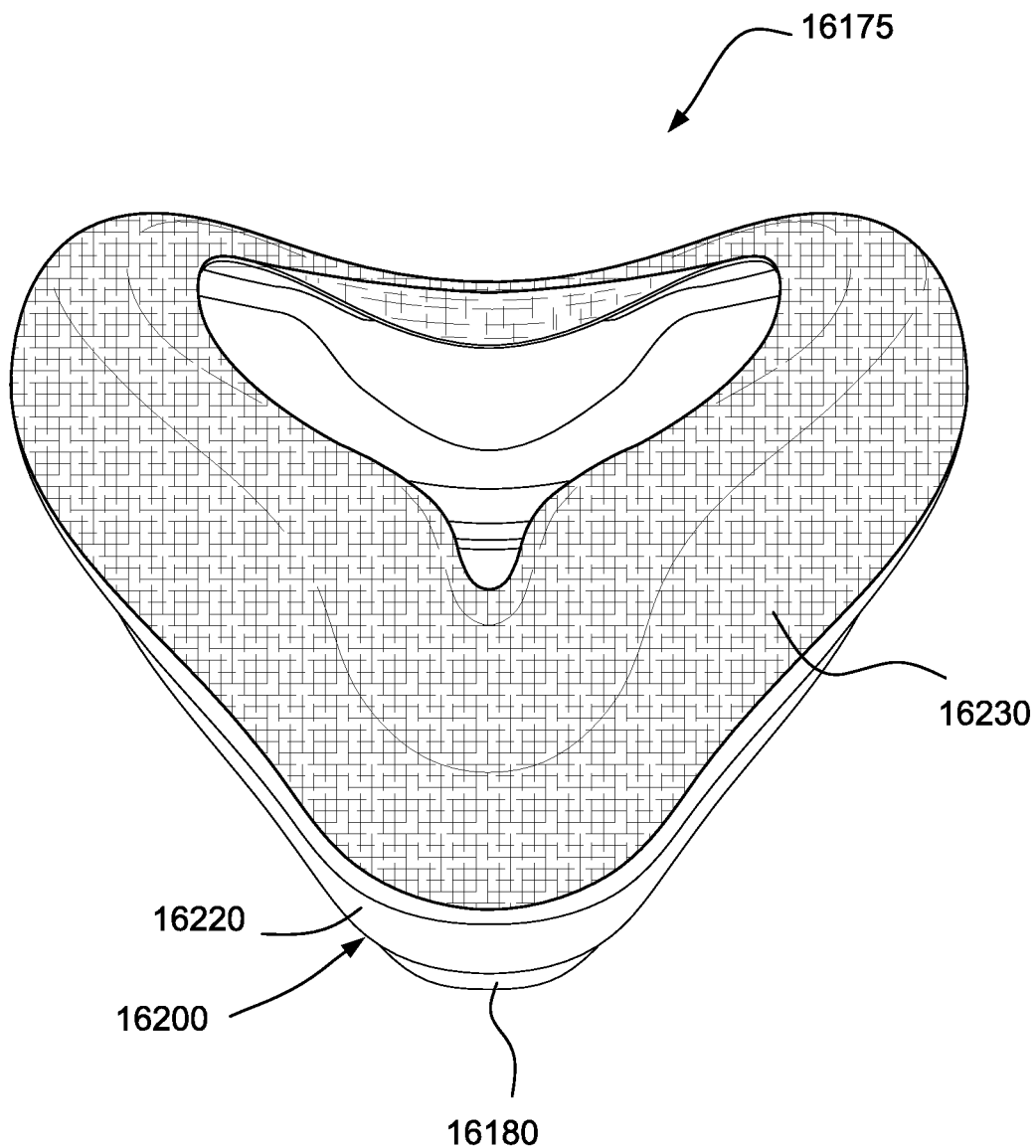

FIG. 75 is a top perspective view of the cushion assembly of FIG. 72.

Figure 76:
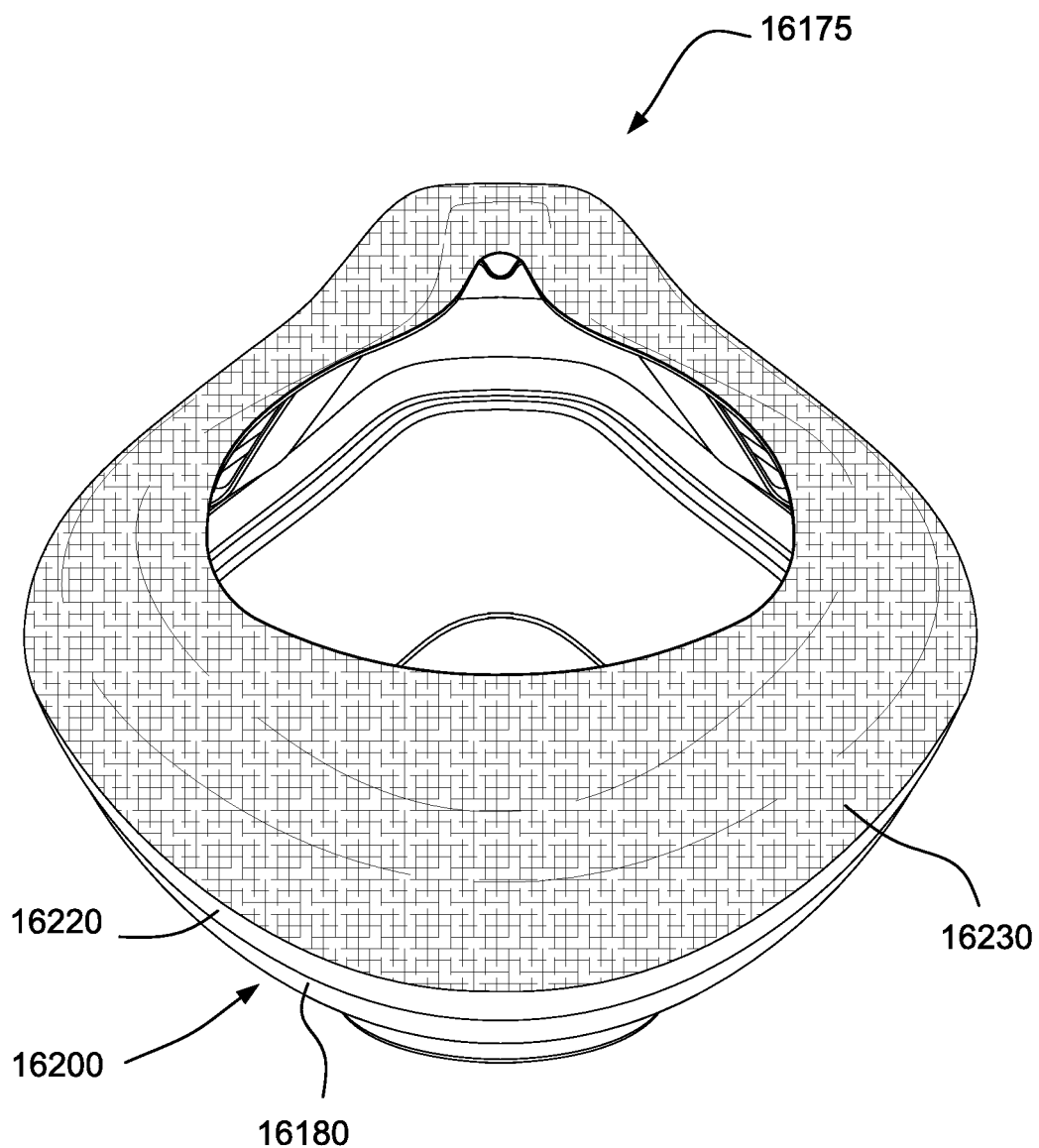

FIG. 76 is a bottom perspective view of the cushion assembly of FIG. 72.

Figure 77:
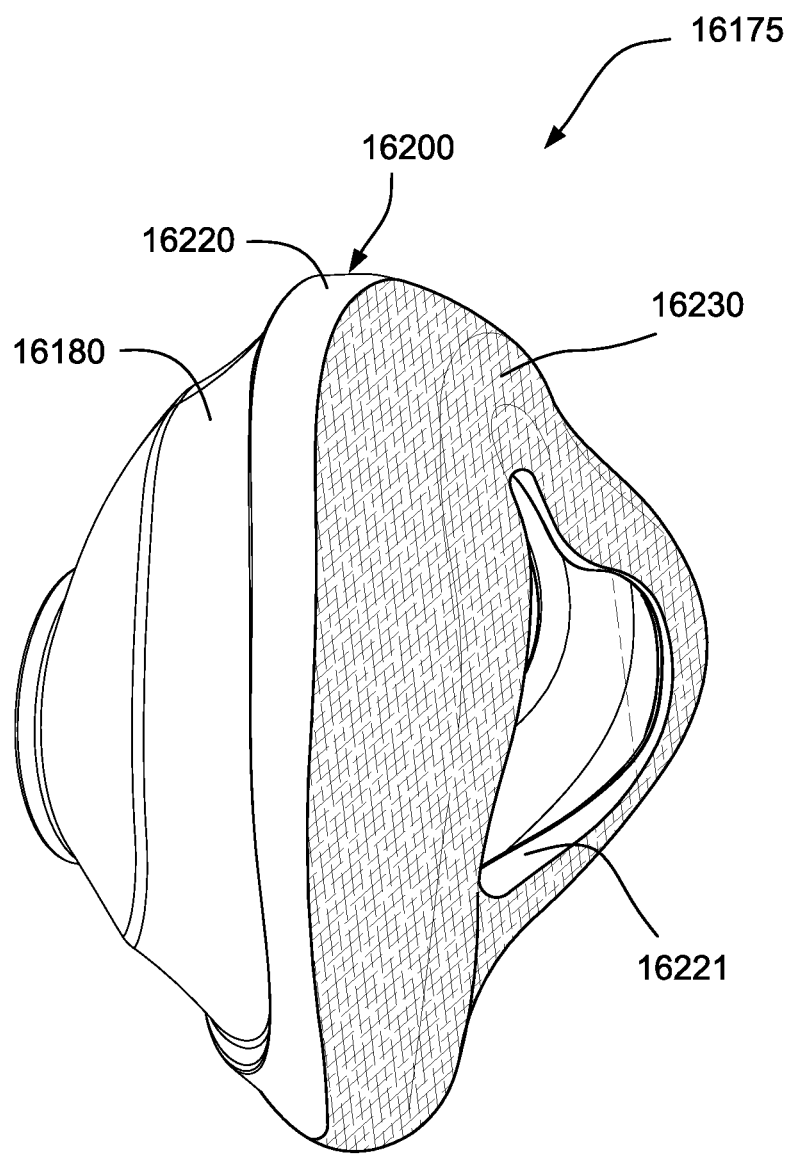

FIG. 77 is a side perspective view of the cushion assembly of FIG. 72.

Figure 78:
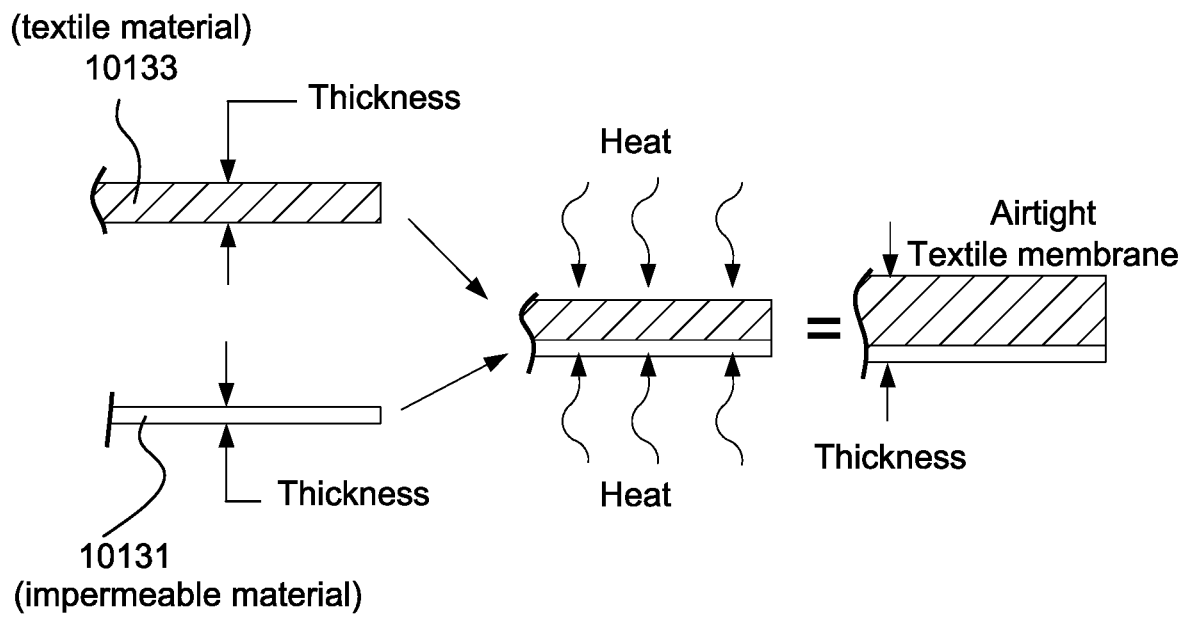

FIG. 78 is a schematic illustration of a process of providing an air impermeable layer to a textile material according to an example of the present technology.

Figure 79:
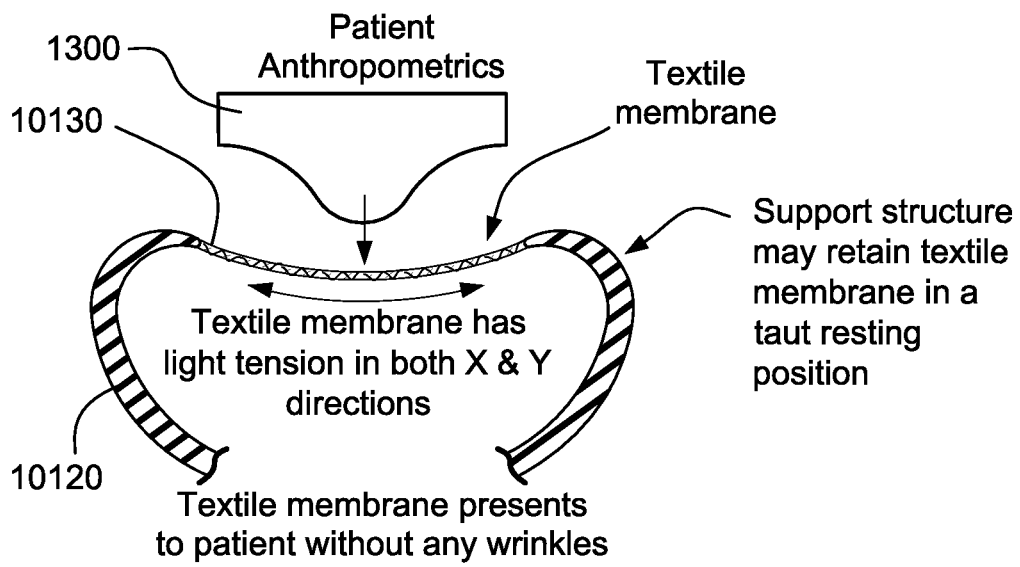

FIG. 79 is a schematic illustration depicting a patient's face being presented to a textile membrane in light tension prior to use.

Figure 80:
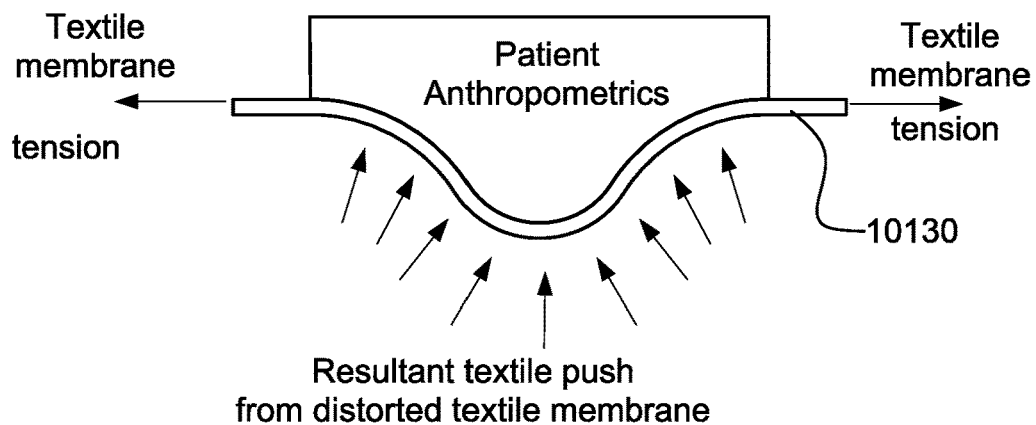

FIG. 80 is a schematic illustration showing a resulting force exerted by the textile membrane on the patient's face due to tensile stress in the textile membrane.

Figure 81:
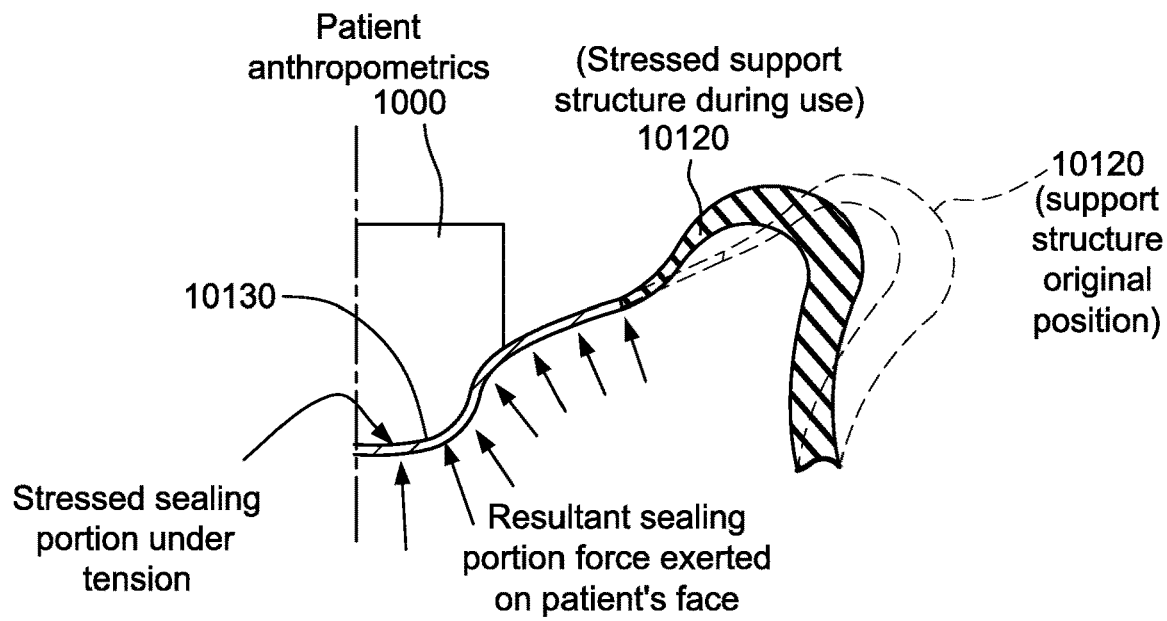

FIG. 81 is a schematic illustration of tension forces exerted on the sealing portion of a cushion assembly according to an example of the present technology.

Figure 82:
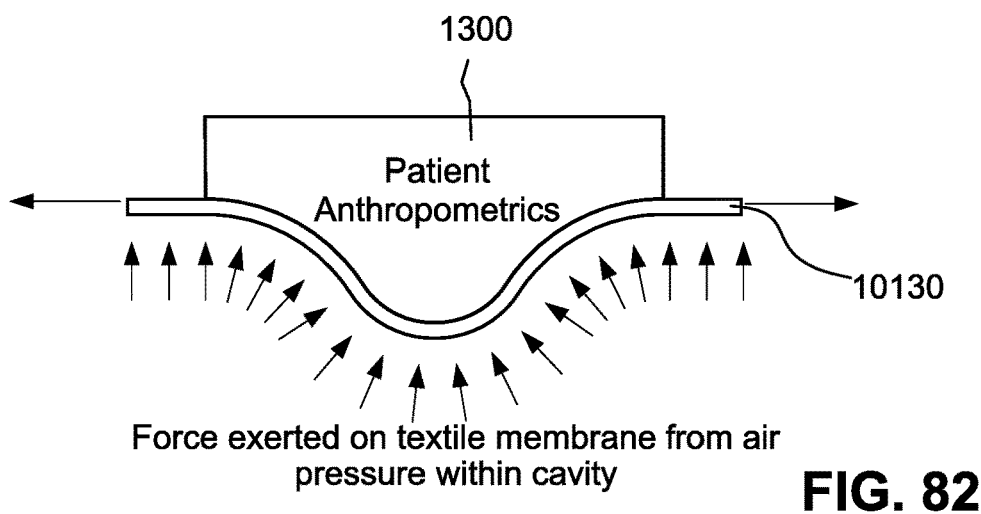

FIG. 82 is a schematic illustration of a force exerted by the textile membrane on the patient's face due to air pressure within the cavity formed by the cushion assembly.

Figure 83:
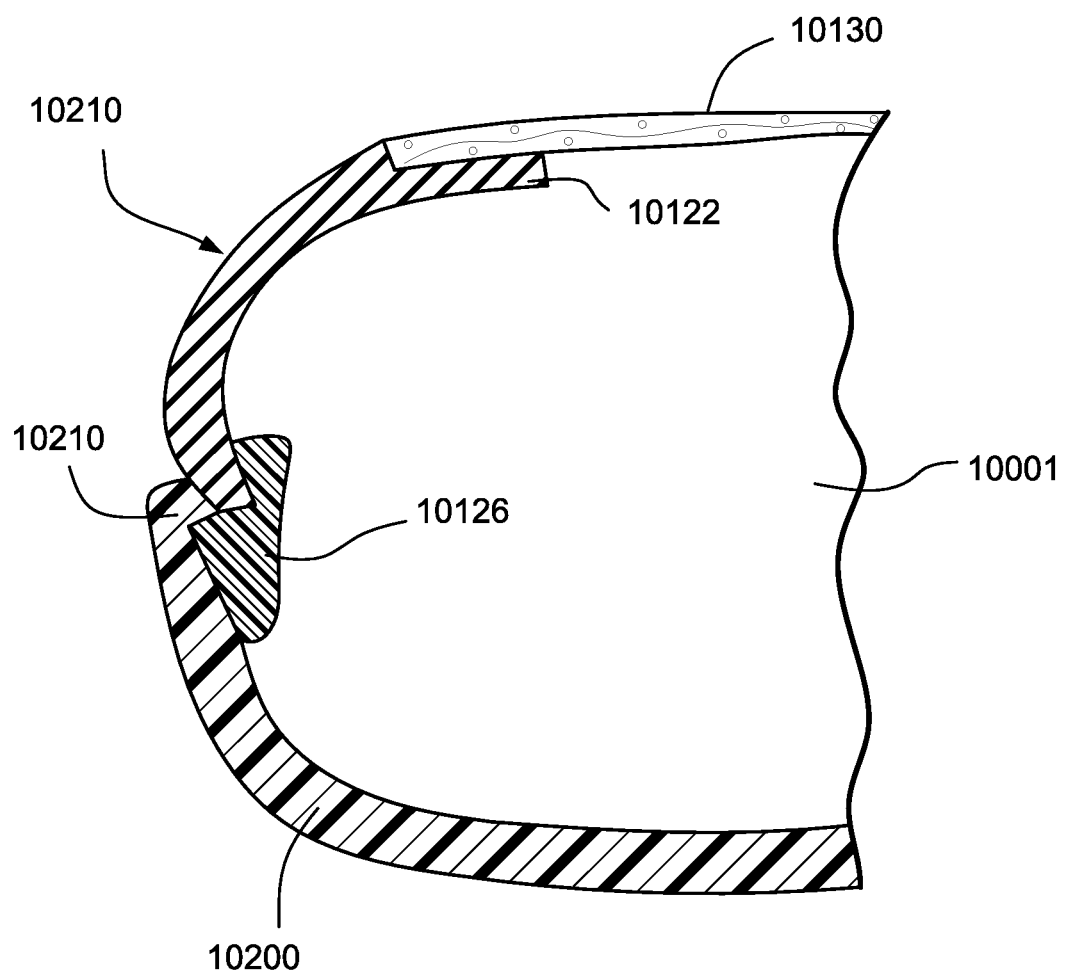

FIG. 83 is a cutaway cross-sectional view of a cushion assembly according to an example of the present technology.

Figure 84:
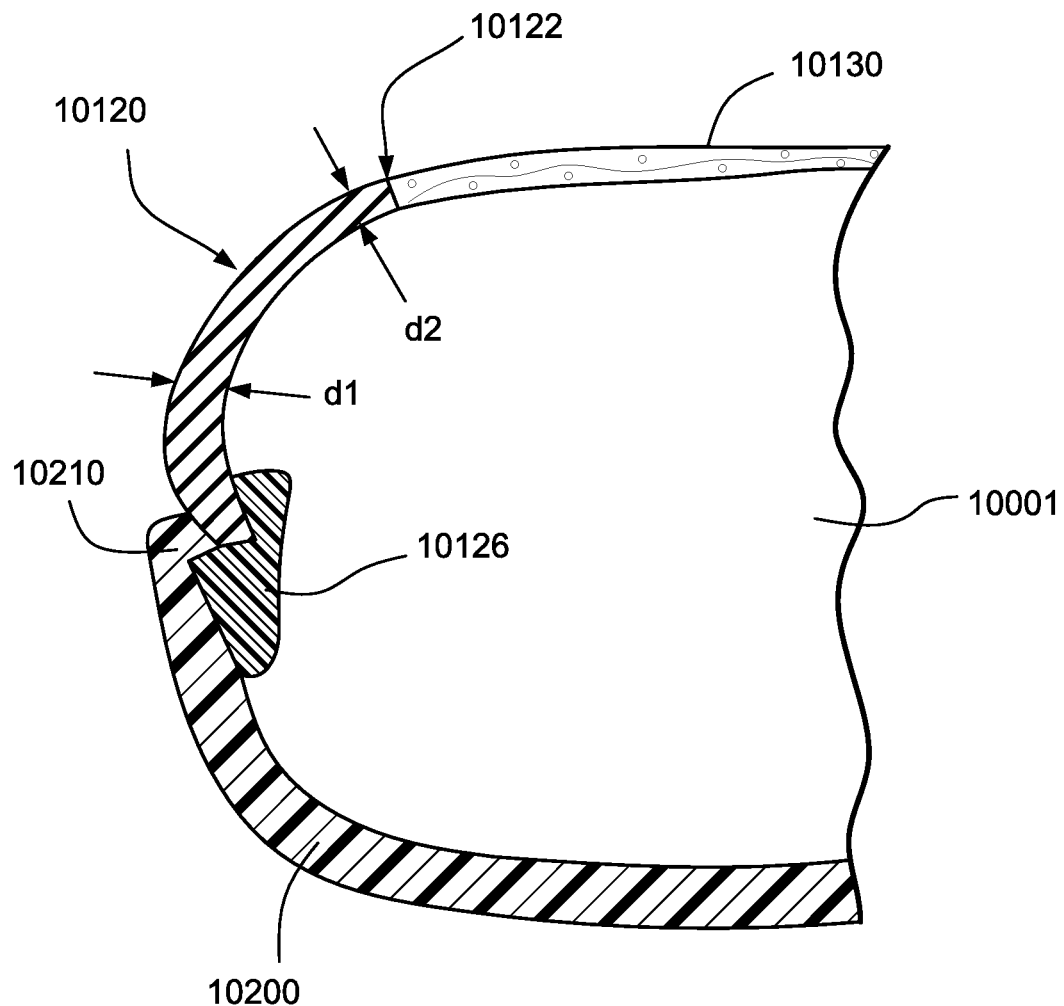

FIG. 84 is a cutaway cross-sectional view of a cushion assembly according to an example of the present technology.

Figure 85:
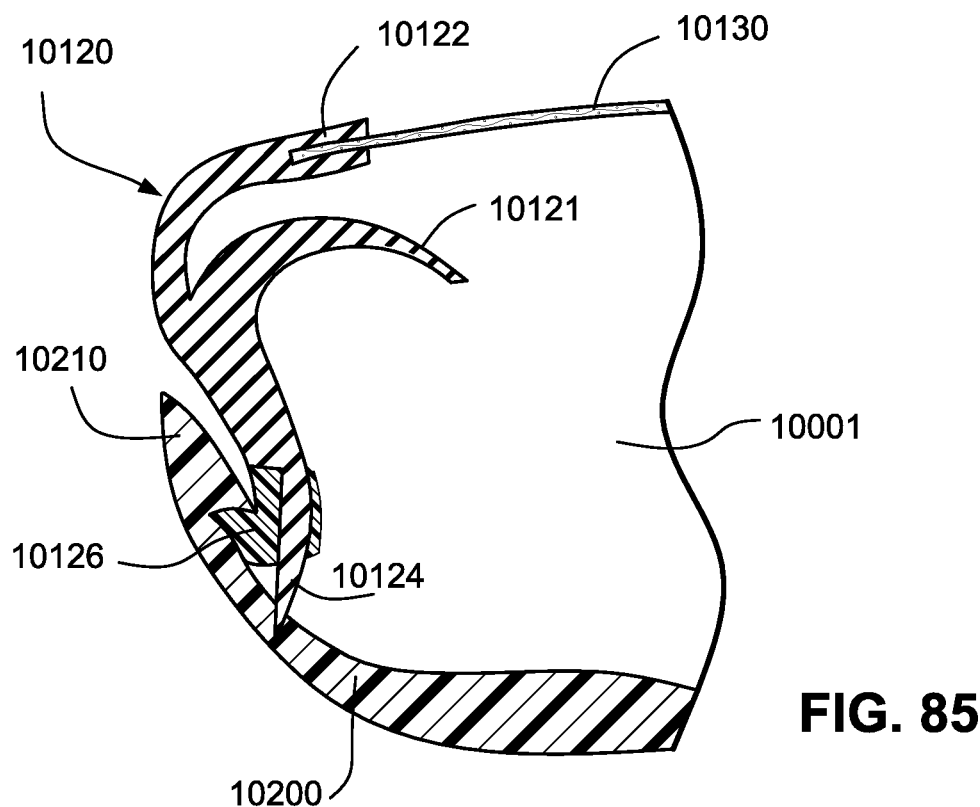

FIG. 85 is a cutaway cross-sectional view of a cushion assembly according to an example of the present technology.

Figure 86:
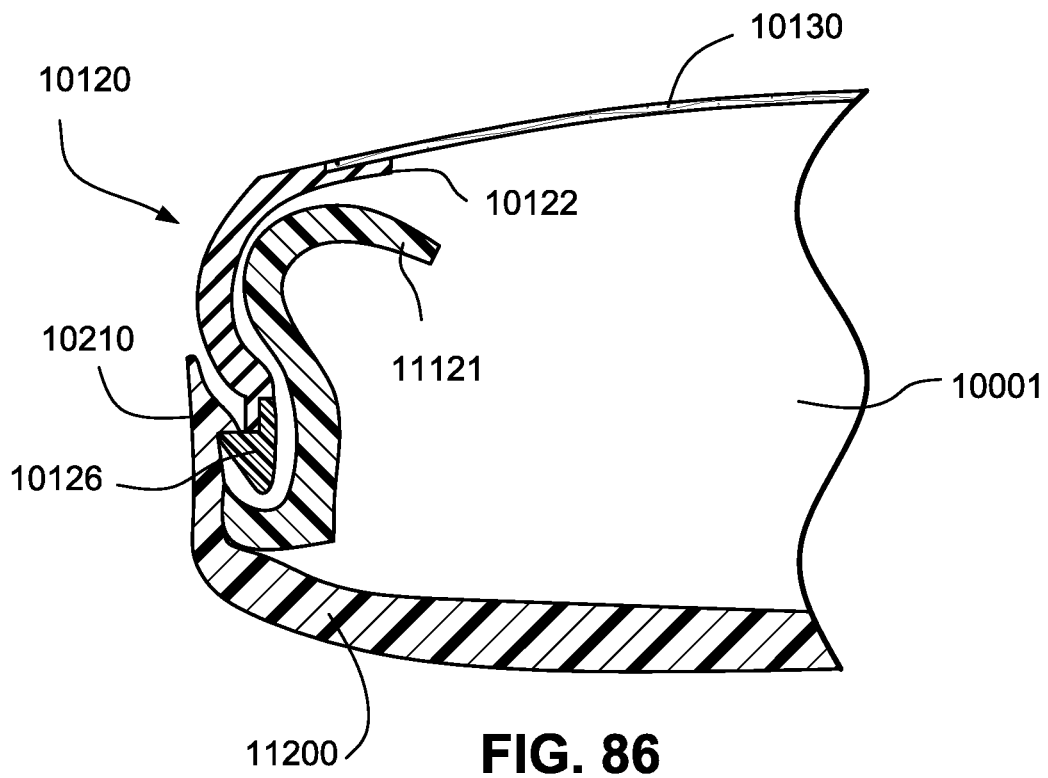

FIG. 86 is a cutaway cross-sectional view of a cushion assembly according to an example of the present technology.

Figure 87:
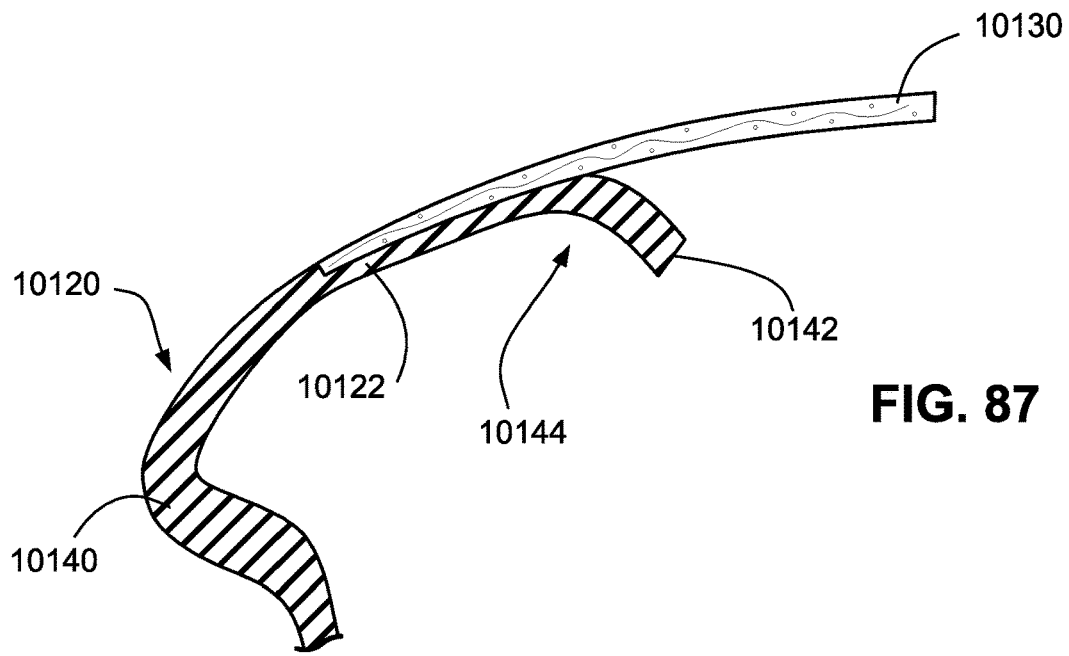

FIG. 87 is a partial cross-sectional view of a sealing portion and support structure of a cushion assembly with an external biasing portion according to an example of the present technology.

Figure 88:
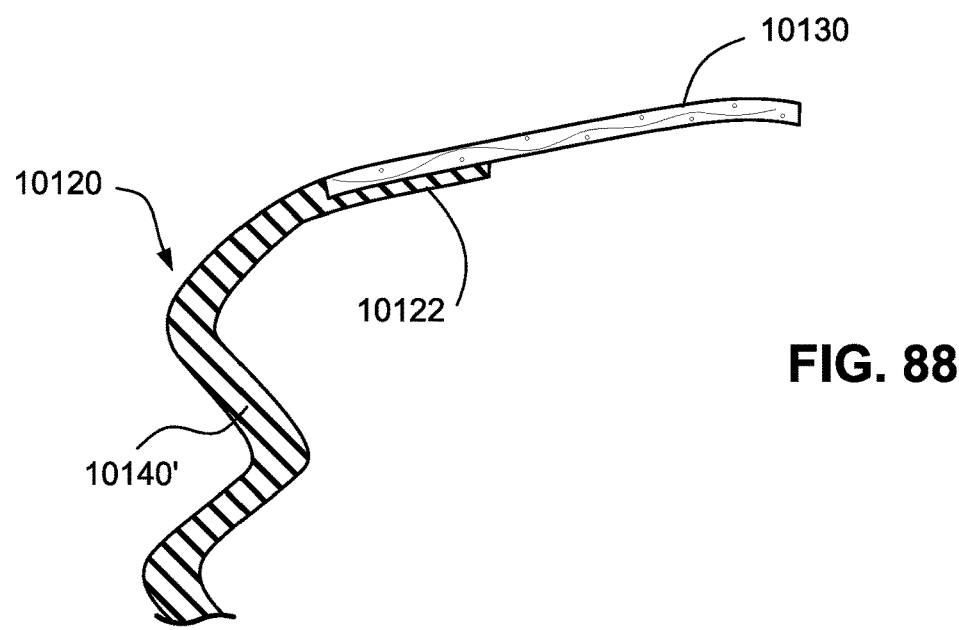

FIG. 88 is a partial cross-sectional view of a sealing portion and support structure of a cushion assembly with an internal biasing portion according to an example of the present technology.

Figure 89:
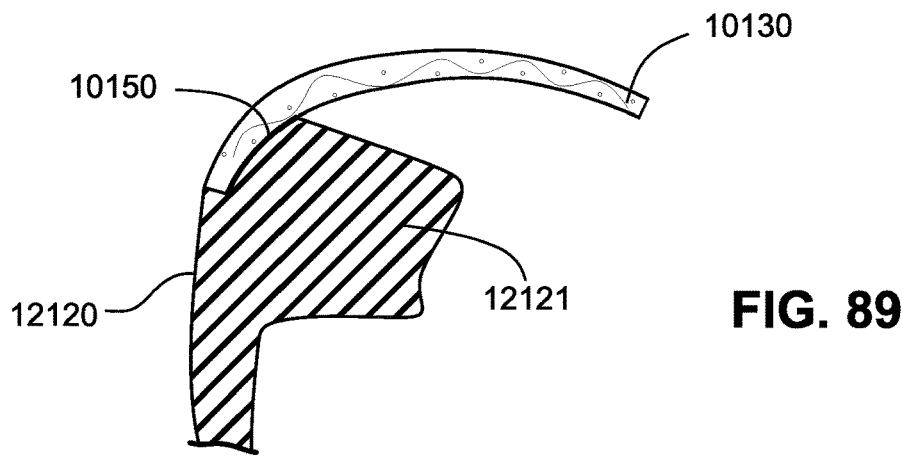

FIG. 89 is a partial cross-sectional view of a cushion assembly according to an example of the present technology.

Figure 90A:
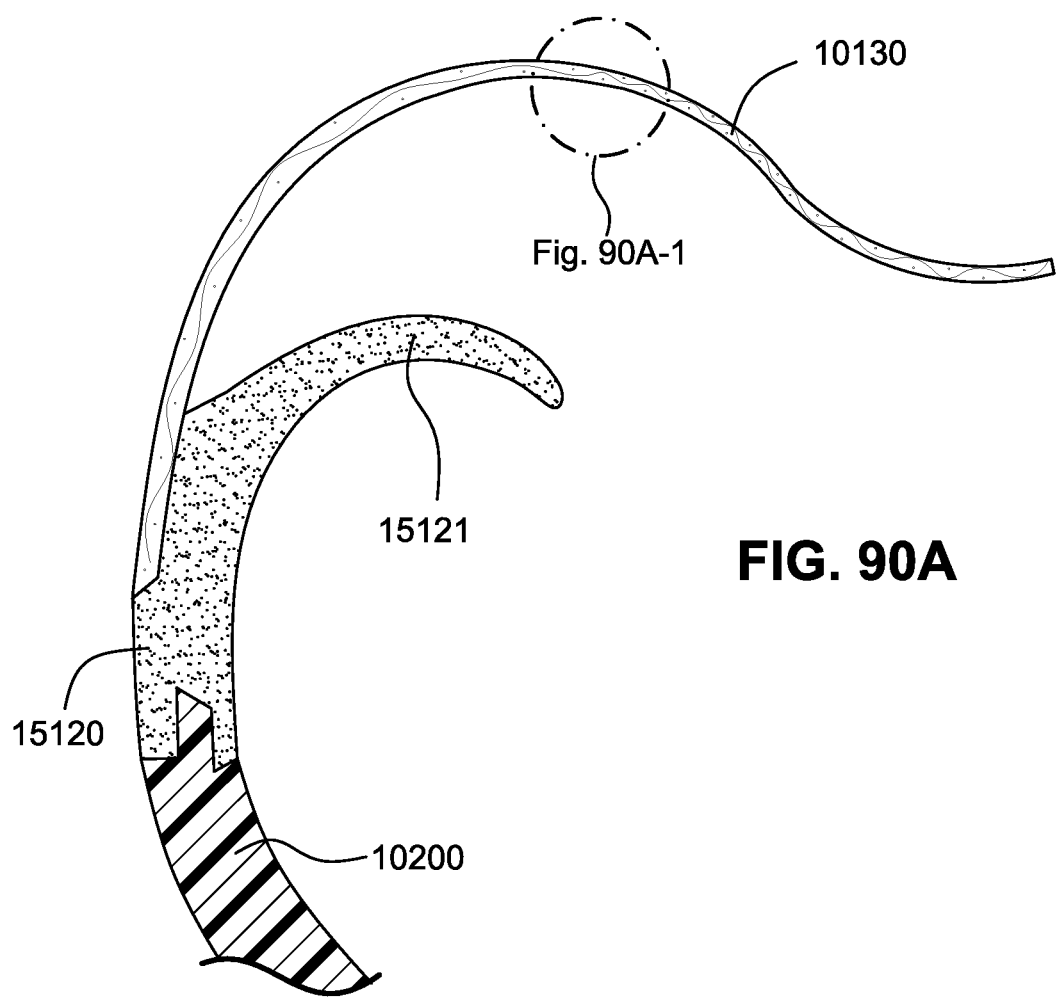
Figures 1, 90A:
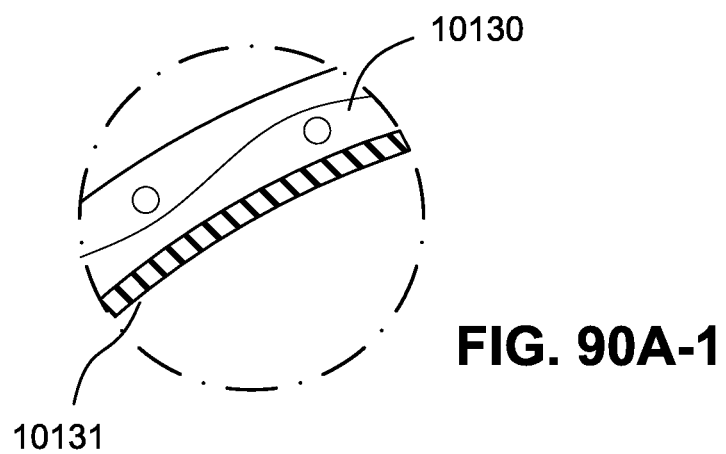

FIG. 90A is a partial cross-sectional view of a cushion assembly according to an example of the present technology.

FIG. 90A-1 is an enlarged view of a section of the sealing portion of the cushion assembly of FIG. 90A.

Figure 90B:
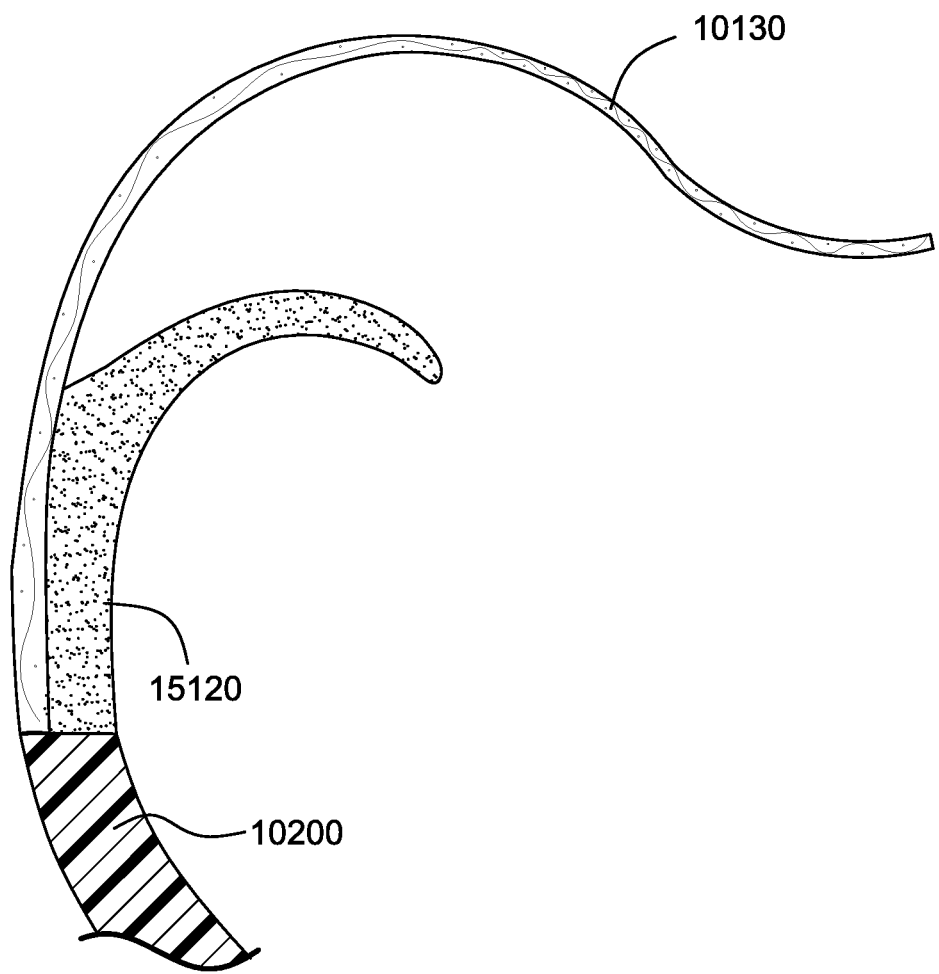

FIG. 90B is a partial cross-sectional view of a cushion assembly according to an example of the present technology.

Figure 91:
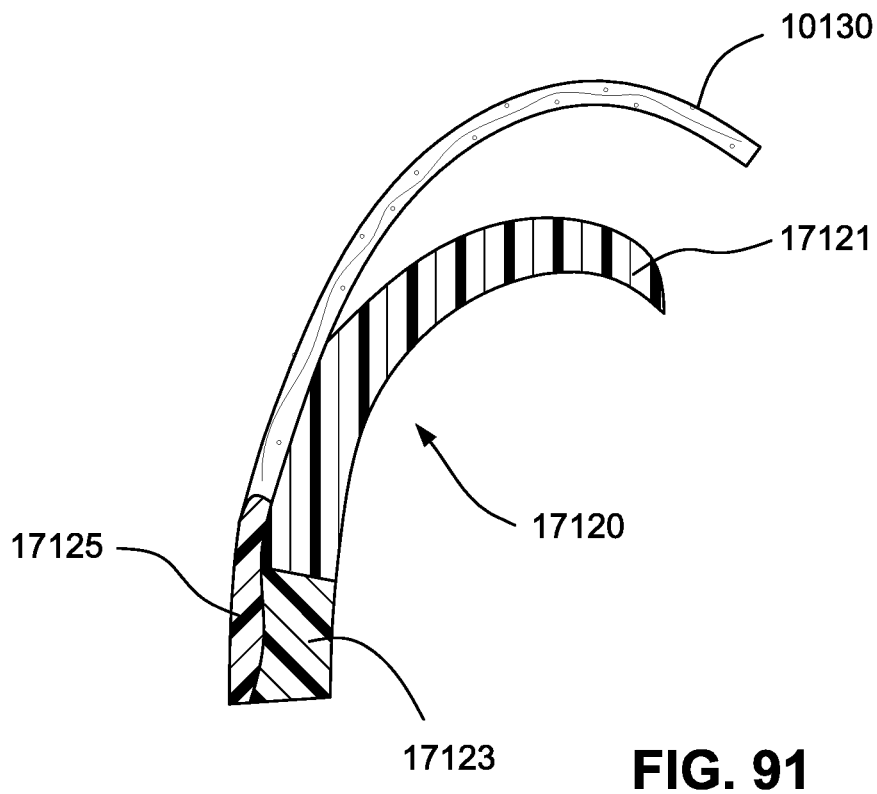

FIG. 91 is a partial cross-sectional view of a cushion assembly according to an example of the present technology.

Figure 92:
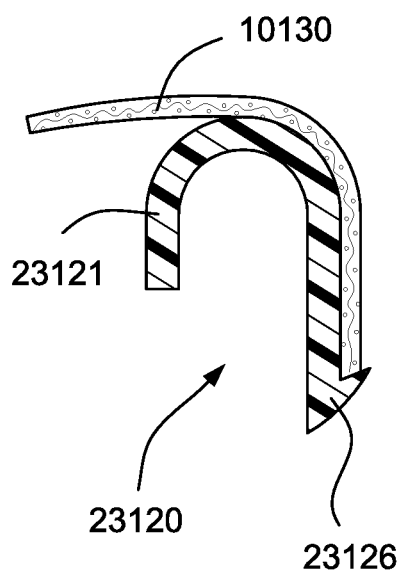

FIG. 92 is a partial cross-sectional view of a cushion assembly according to an example of the present technology.

Figure 93:
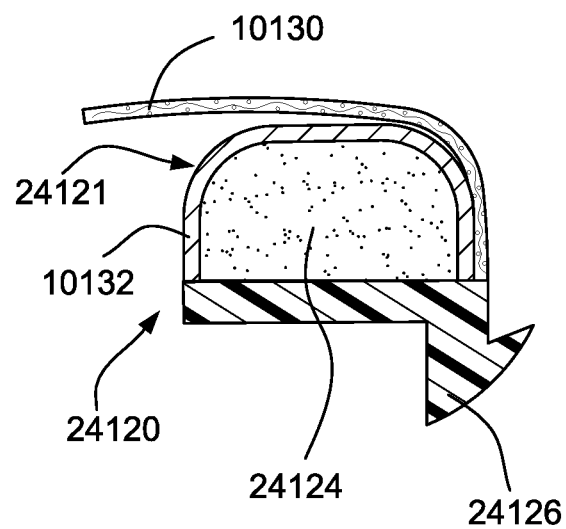

FIG. 93 is a partial cross-sectional view of a cushion assembly according to an example of the present technology.

Figure 94:
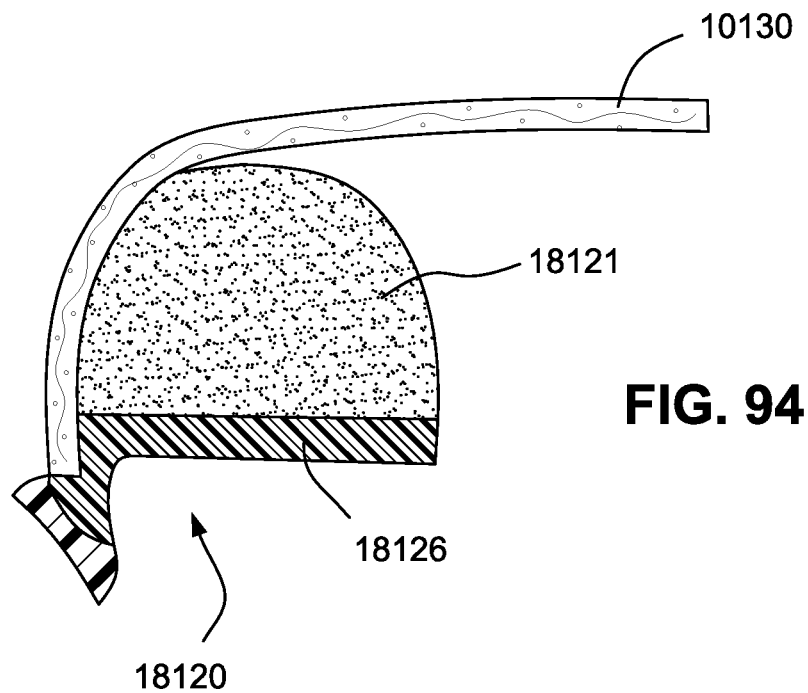

FIG. 94 is a partial cross-sectional view of a cushion assembly according to an example of the present technology.

Figure 95:
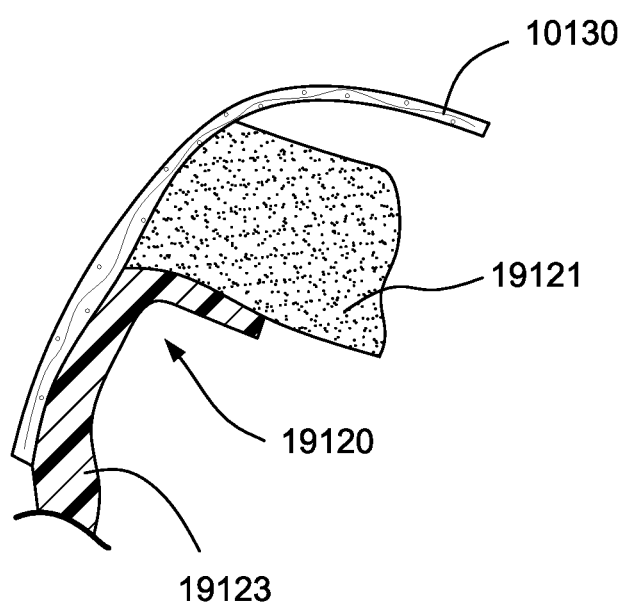

FIG. 95 is a partial cross-sectional view of a cushion assembly according to an example of the present technology.

Figure 96:
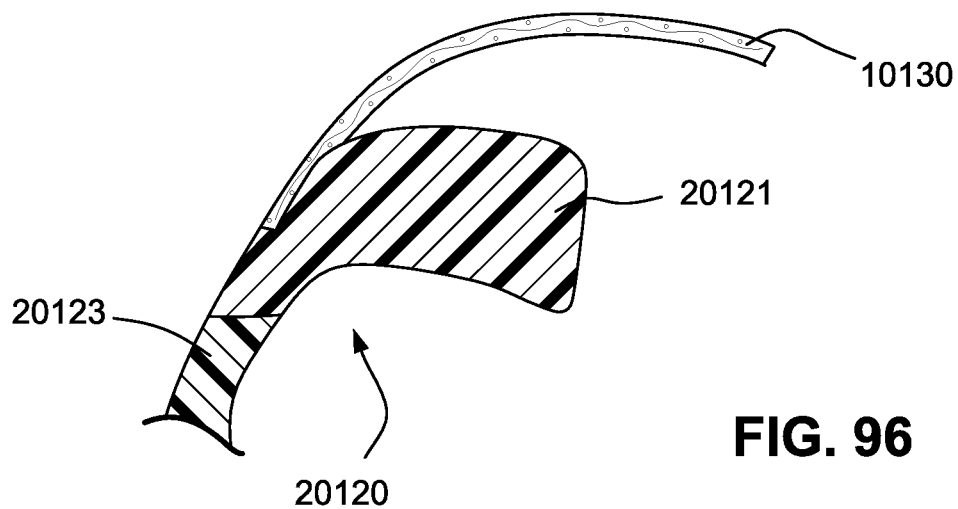

FIG. 96 is a partial cross-sectional view of a cushion assembly according to an example of the present technology.

Figure 97:
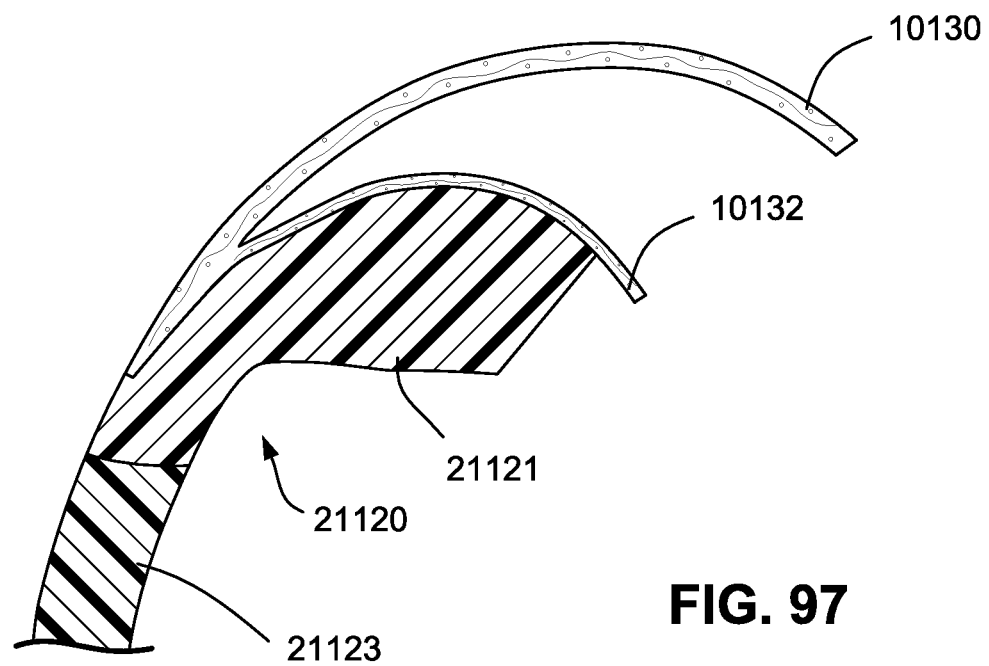

FIG. 97 is a partial cross-sectional view of a cushion assembly according to an example of the present technology.

Figure 98:
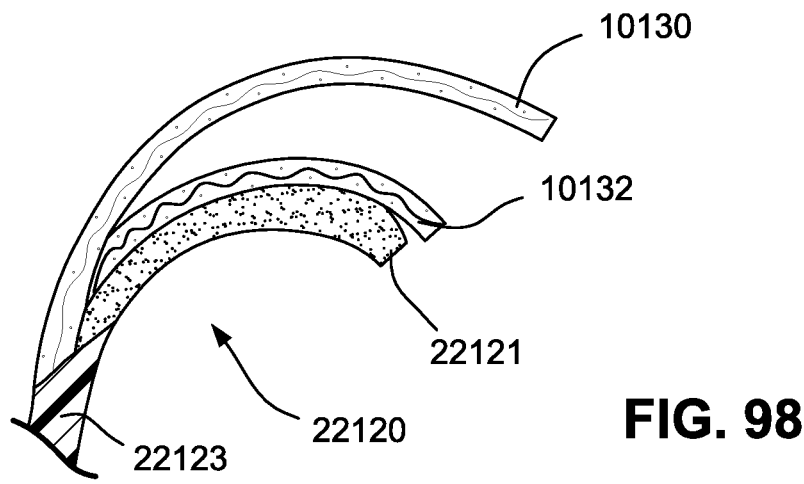

FIG. 98 is a partial cross-sectional view of a cushion assembly according to an example of the present technology.

Figure 99:
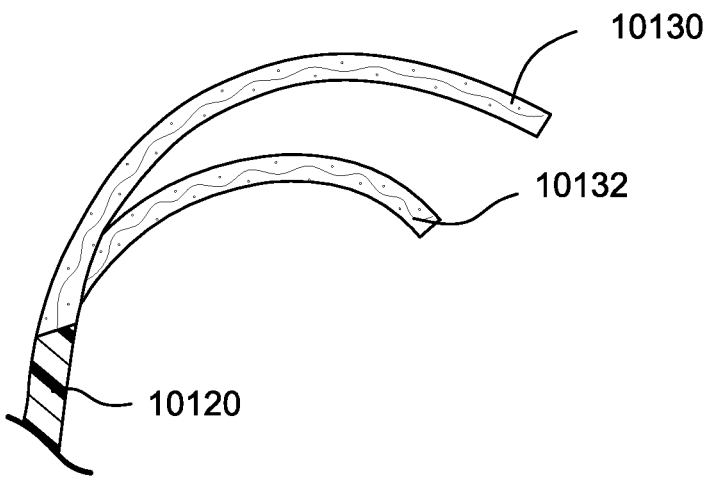

FIG. 99 is a partial cross-sectional view of a cushion assembly according to an example of the present technology.

Figure 100:
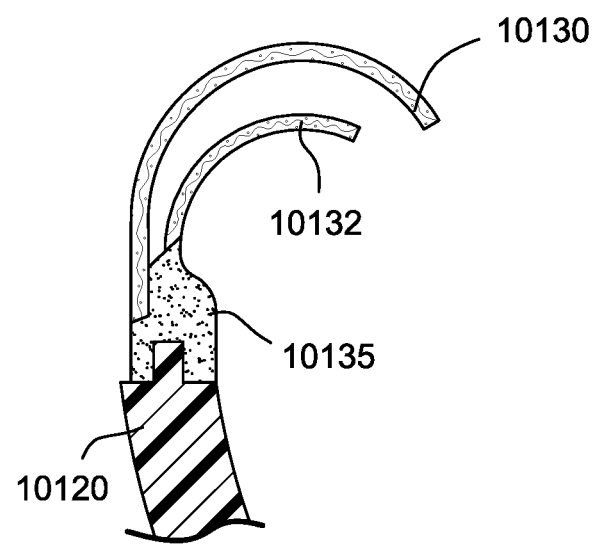

FIG. 100 is a partial cross-sectional view of a cushion assembly according to an example of the present technology.

Figure 101:
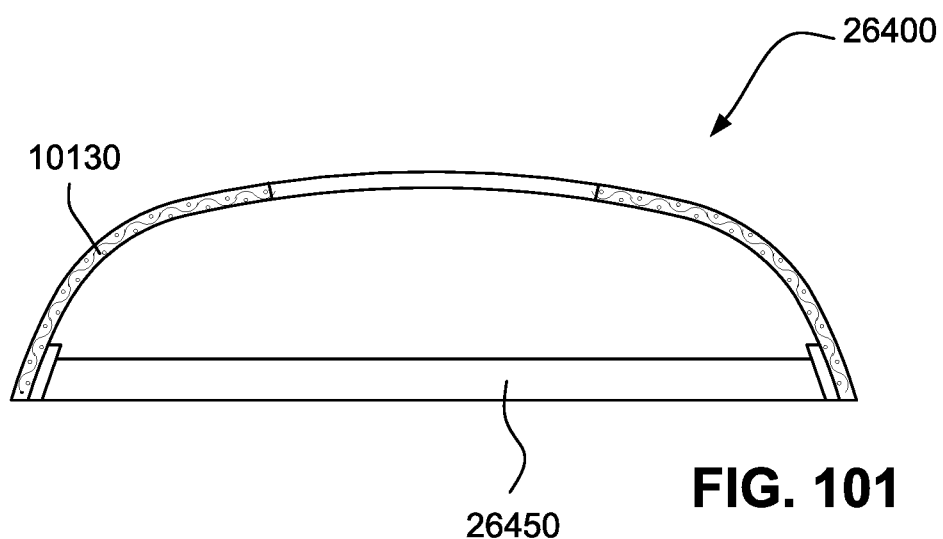

FIG. 101 is cross-sectional view of a sealing portion modular assembly according to an example of the present technology.

Figure 102:
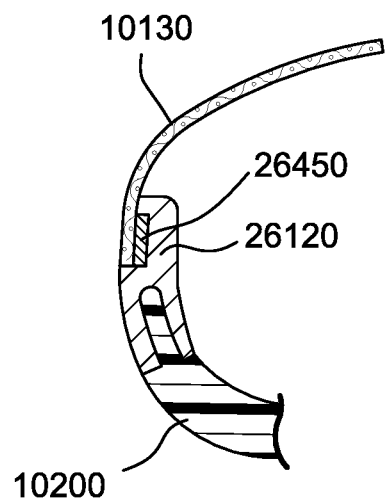

FIG. 102 is a partial cross-sectional view of a cushion assembly incorporating the sealing portion modular assembly of FIG. 101 according to an example of the present technology.

Figure 103:
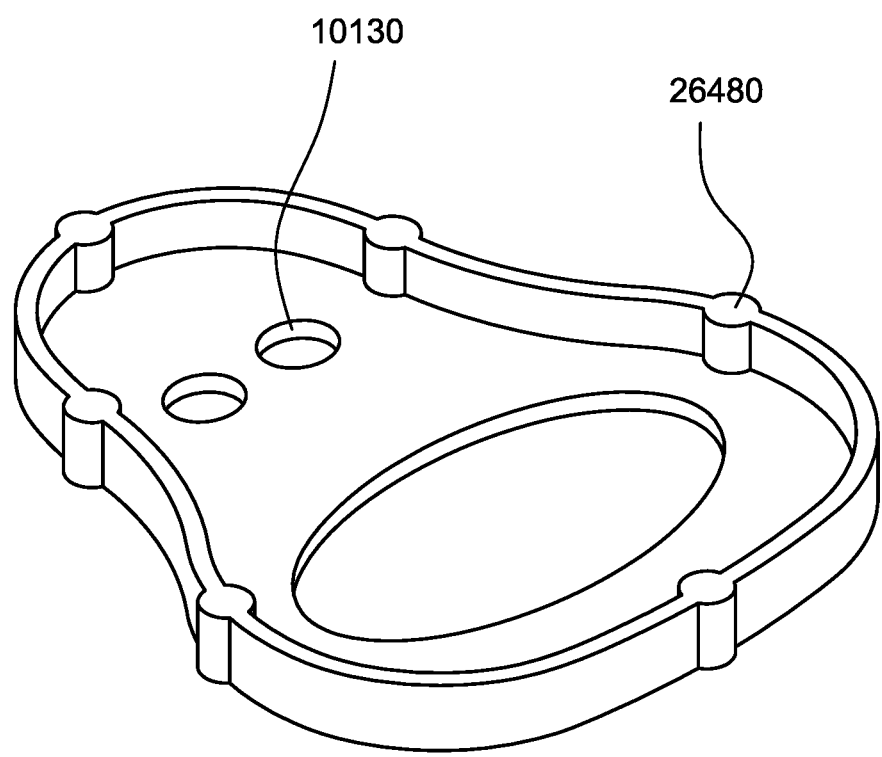

FIG. 103 is a perspective view of a modular support structure according to an example of the present technology.

FIGS. 104 and 105 show a process of molding a sealing portion to a supporting structure according to an example of the present technology.

FIG. 106 is a side view of a sealing portion modular assembly formed by the process illustrated in FIGS. 104 and 105.

Figure 107:
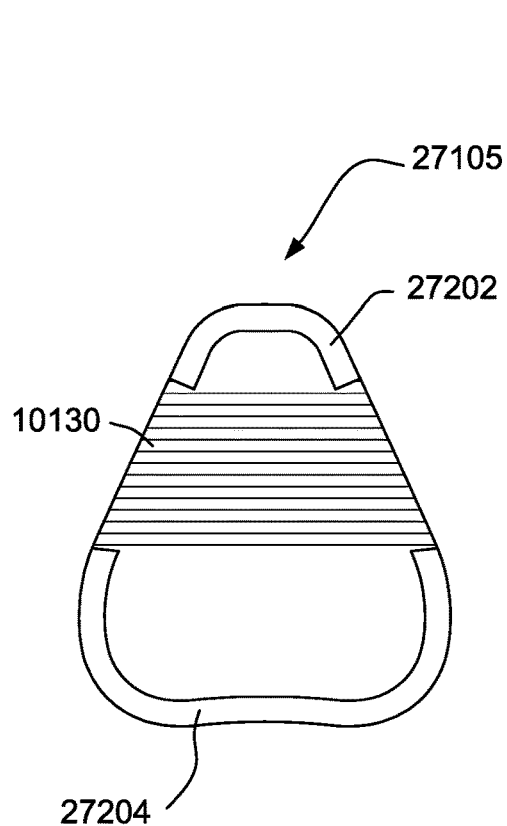
Figure 108:
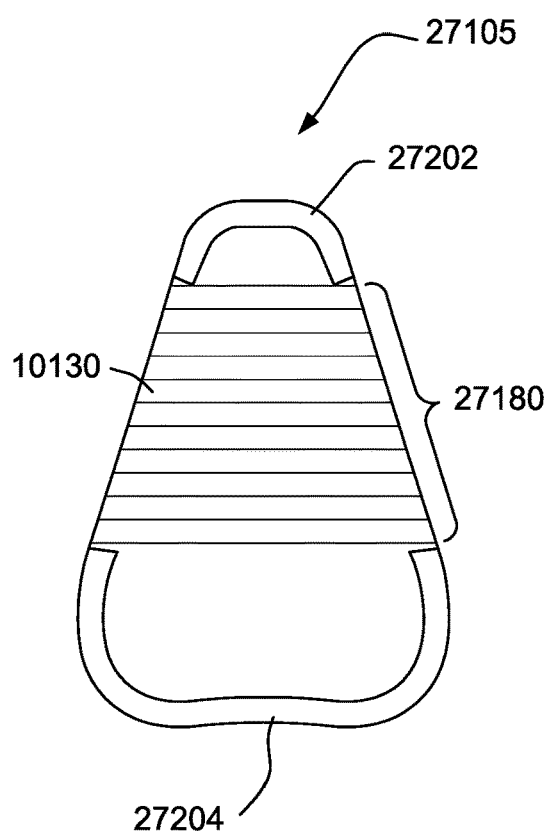

FIGS. 107 and 108 illustrate a one size fits all cushion assembly according to an example of the present technology.

Figure 109:
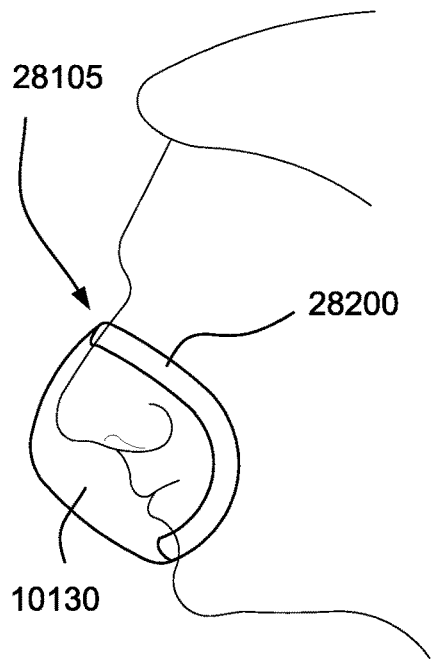
Figure 110:
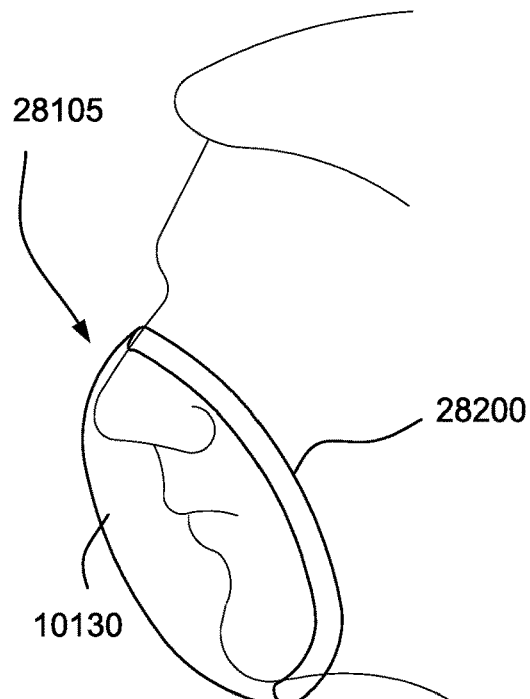

FIGS. 109 and 110 illustrate a custom made cushion assembly fabricated by utilizing a three-dimensional profile obtained by scanning a patient's face according to an example of the present technology.

Figure 111:
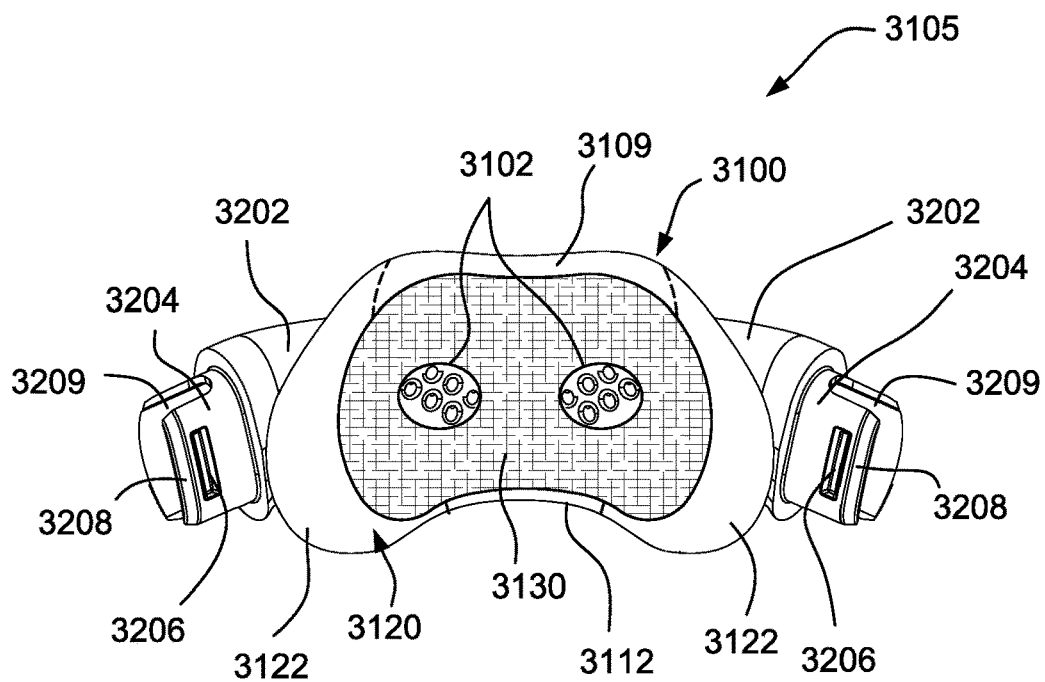

FIG. 111 is a front perspective view of a cushion assembly according to another example of the present technology.

Figure 112:
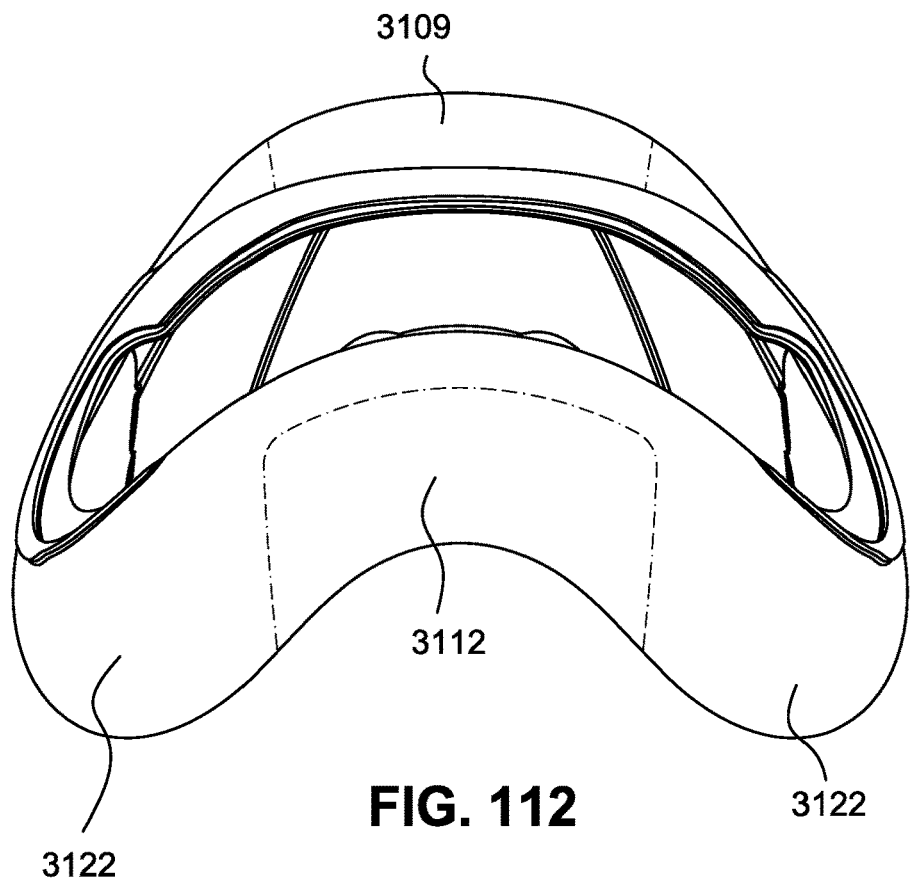

FIG. 112 is a rear perspective view of the seal-forming structure of the cushion assembly of FIG. 111.

Figure 113:
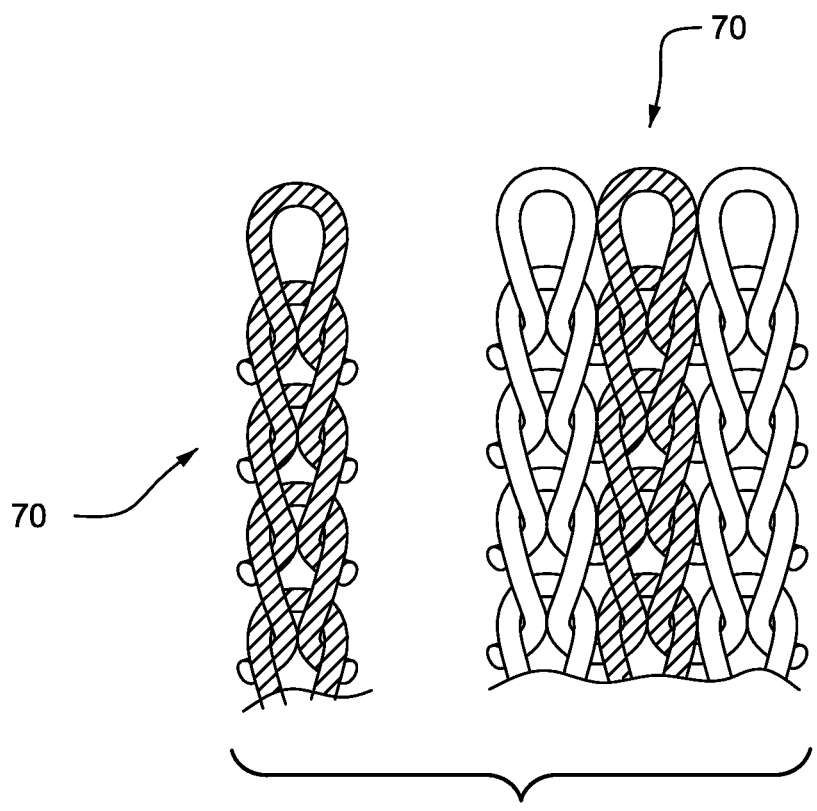
Figure 114:
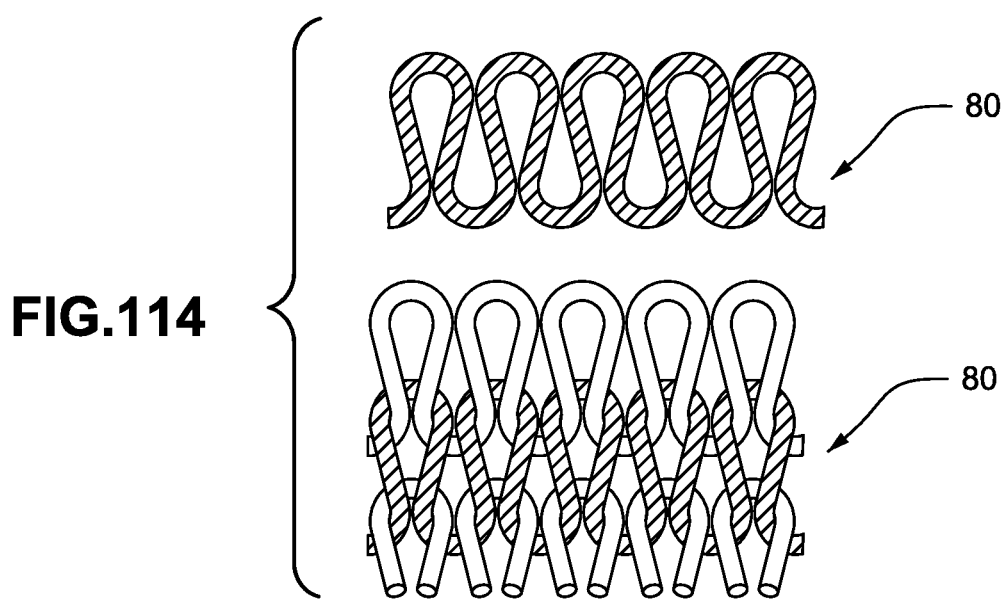

FIGS. 113 and 114 depict a knitting process.

Figure 115:
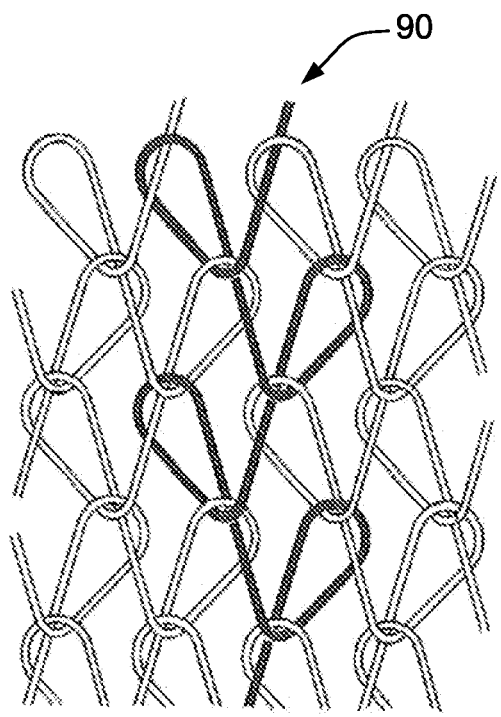

FIG. 115 illustrates a warp knitted textile according to an example of the present technology.

Figure 116:
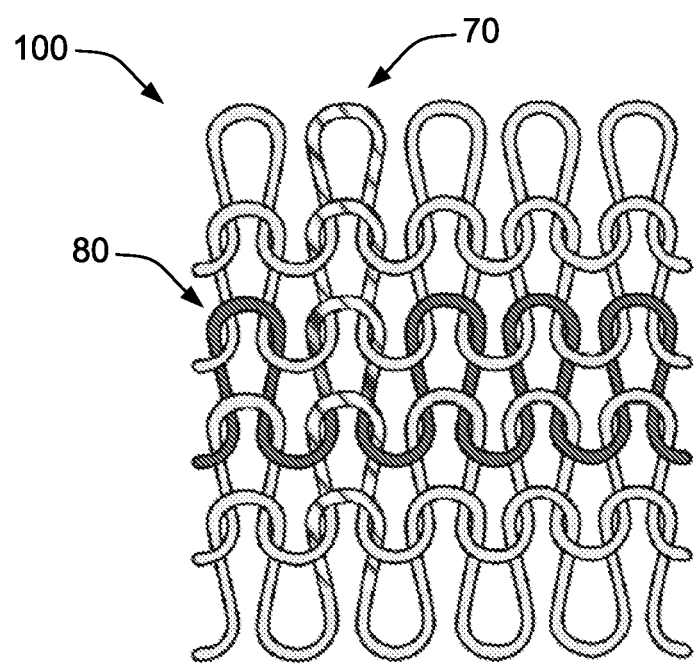

FIG. 116 illustrates a weft knitted textile according to an example of the present technology.

Figure 117:
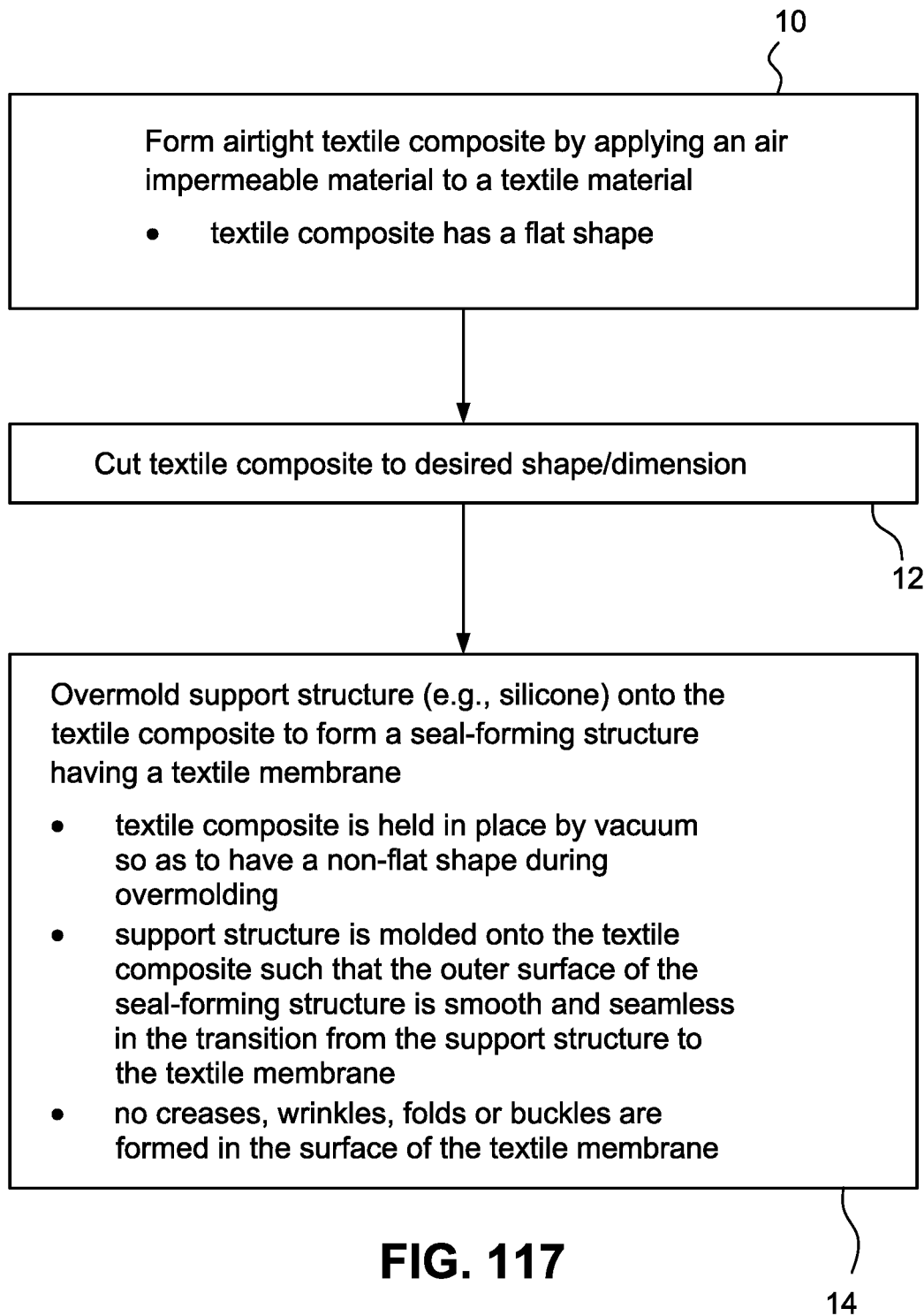

FIG. 117 is a functional block diagram illustrating a process of overmolding a support structure onto a textile composite to form a seal-forming structure with a textile membrane according to an example of the present technology.

Figure 118A:
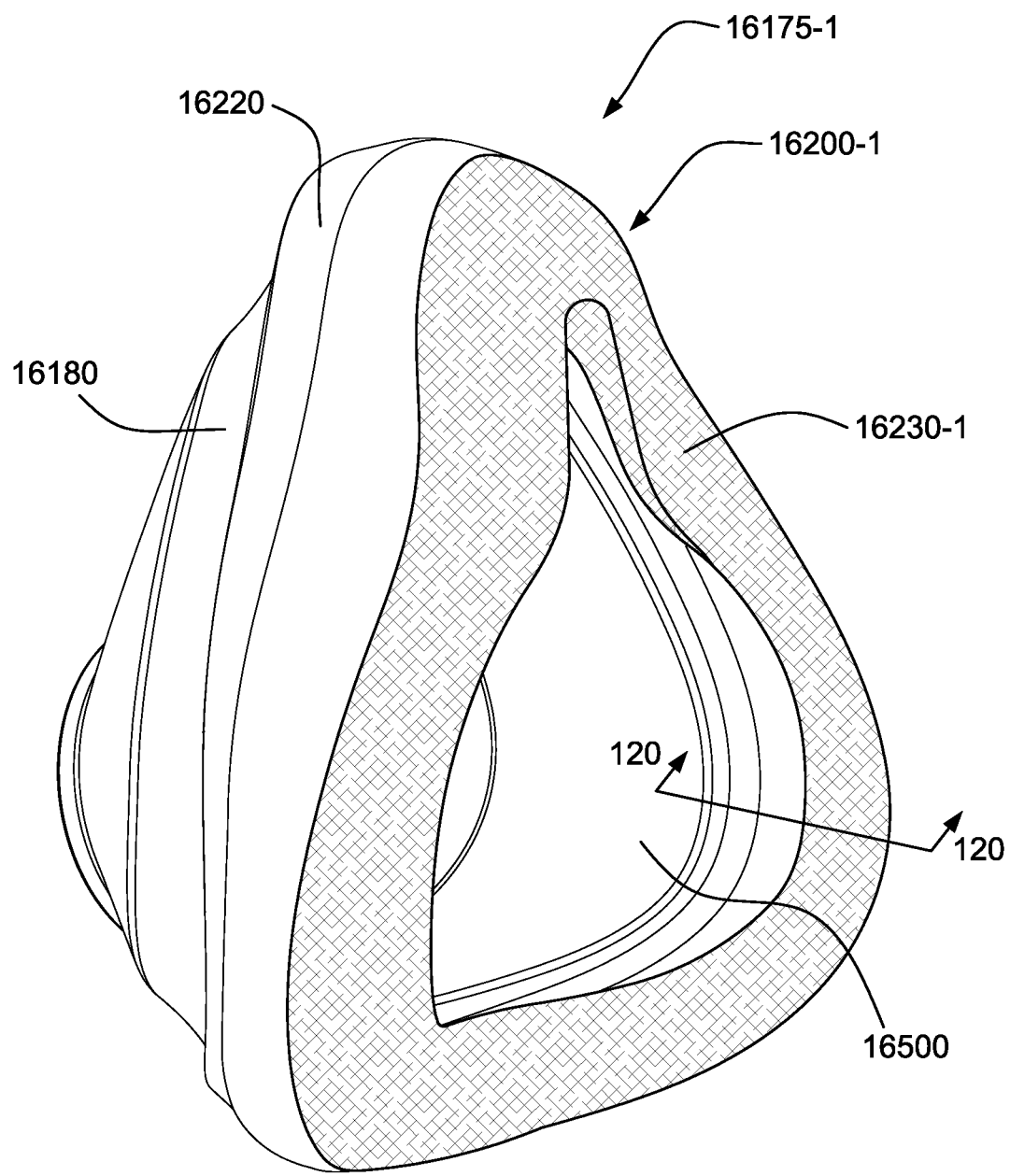

FIG. 118A is a front perspective view of a cushion assembly according to another example of the present technology.

Figure 118B:
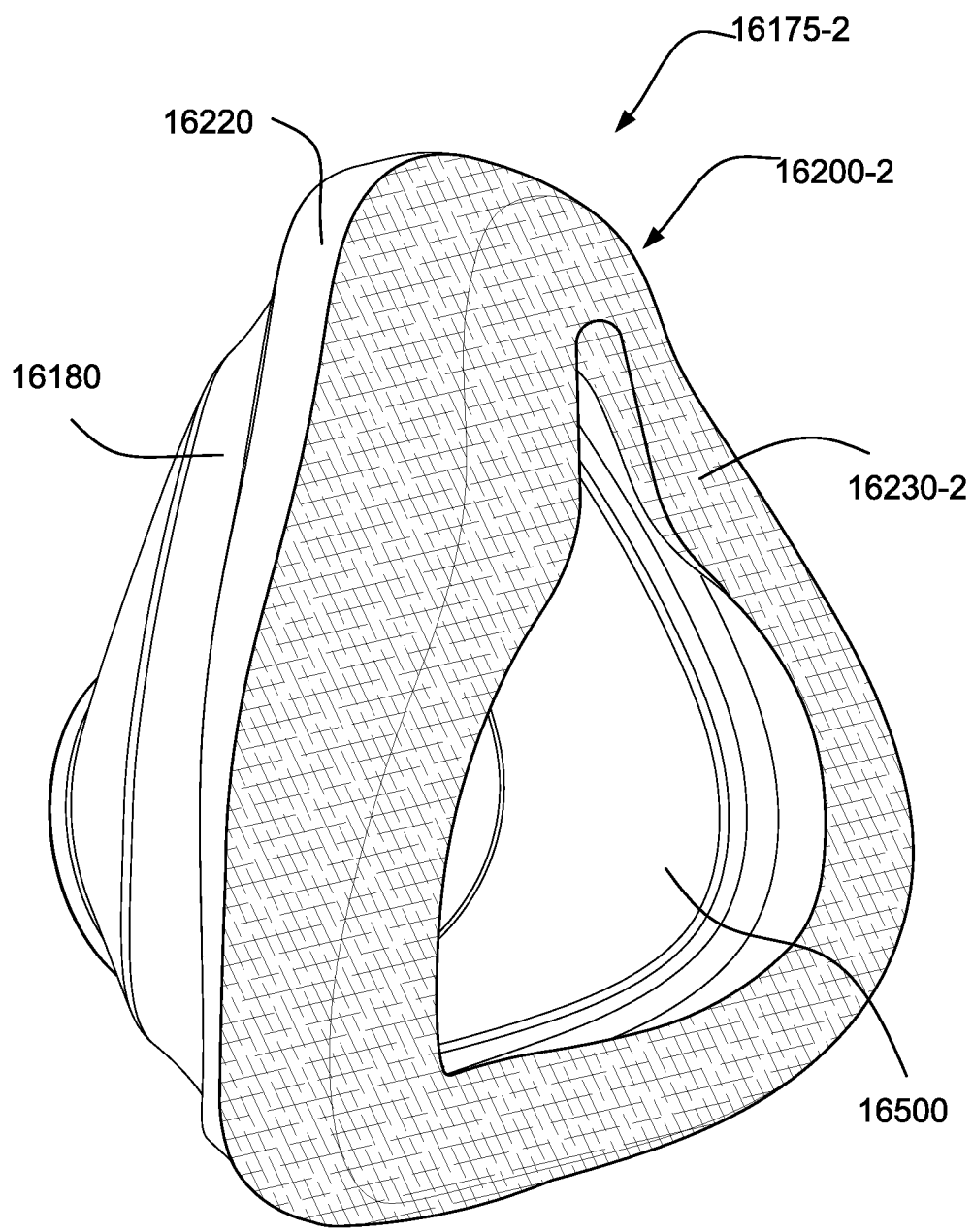

FIG. 118B is a front perspective view of a cushion assembly according to another example of the present technology.

Figure 119:
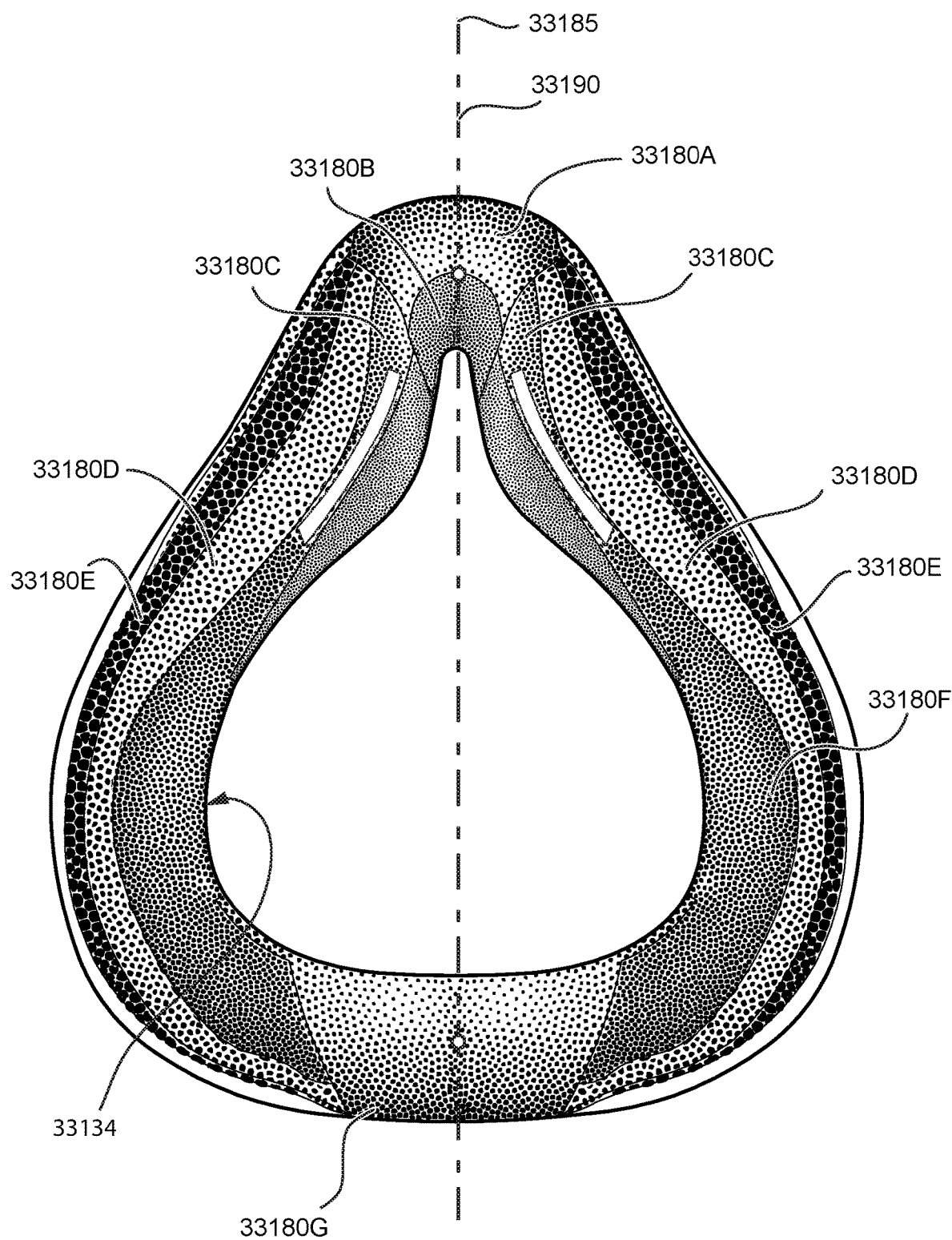

FIG. 119 depicts various regions of a seal forming structure according to an example of the present technology.

Figures 1, 120:
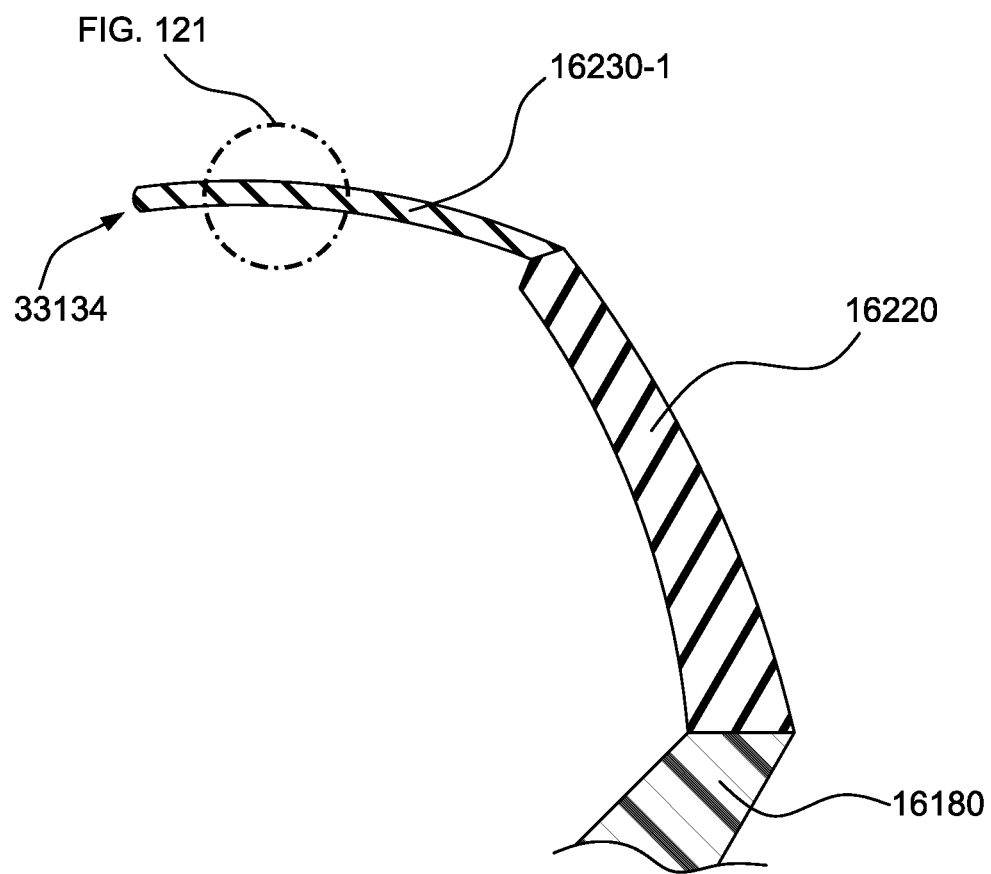
Figures 2, 120:
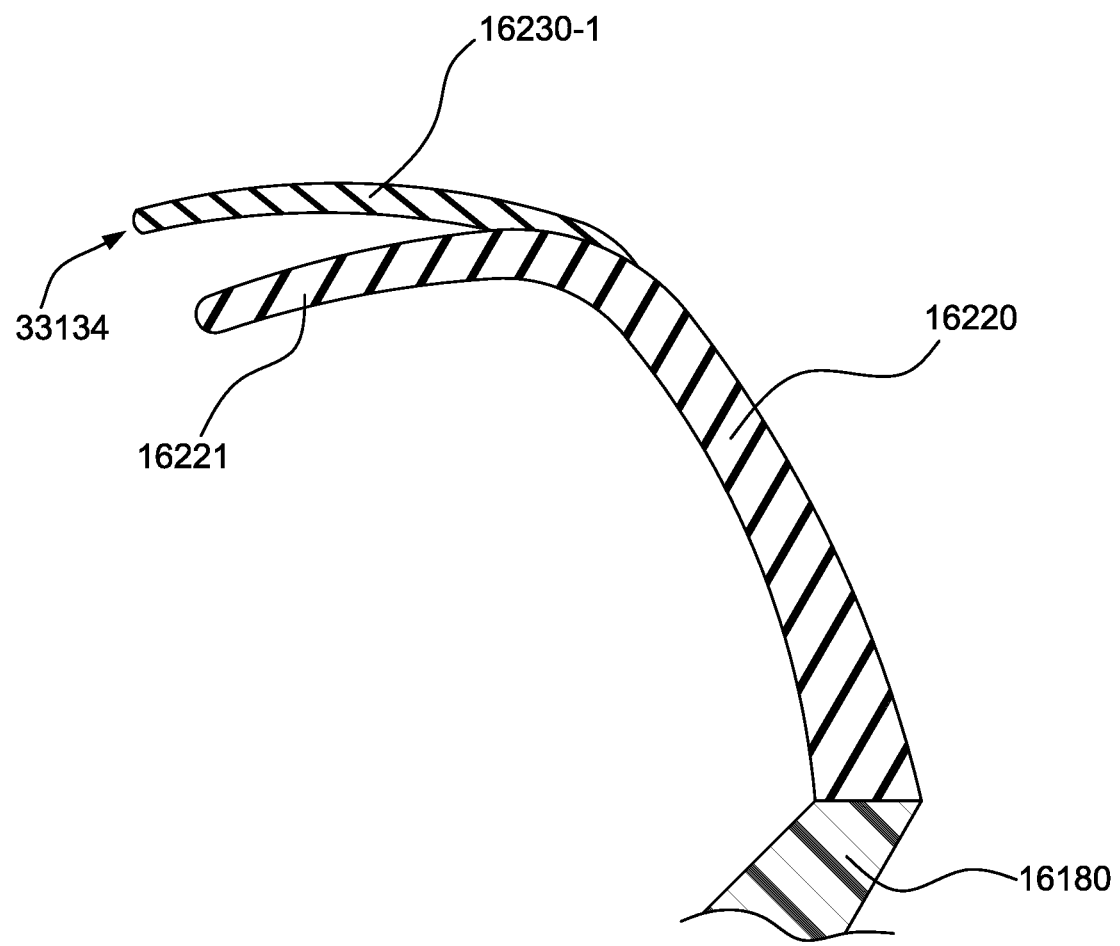
Figures 3, 120:
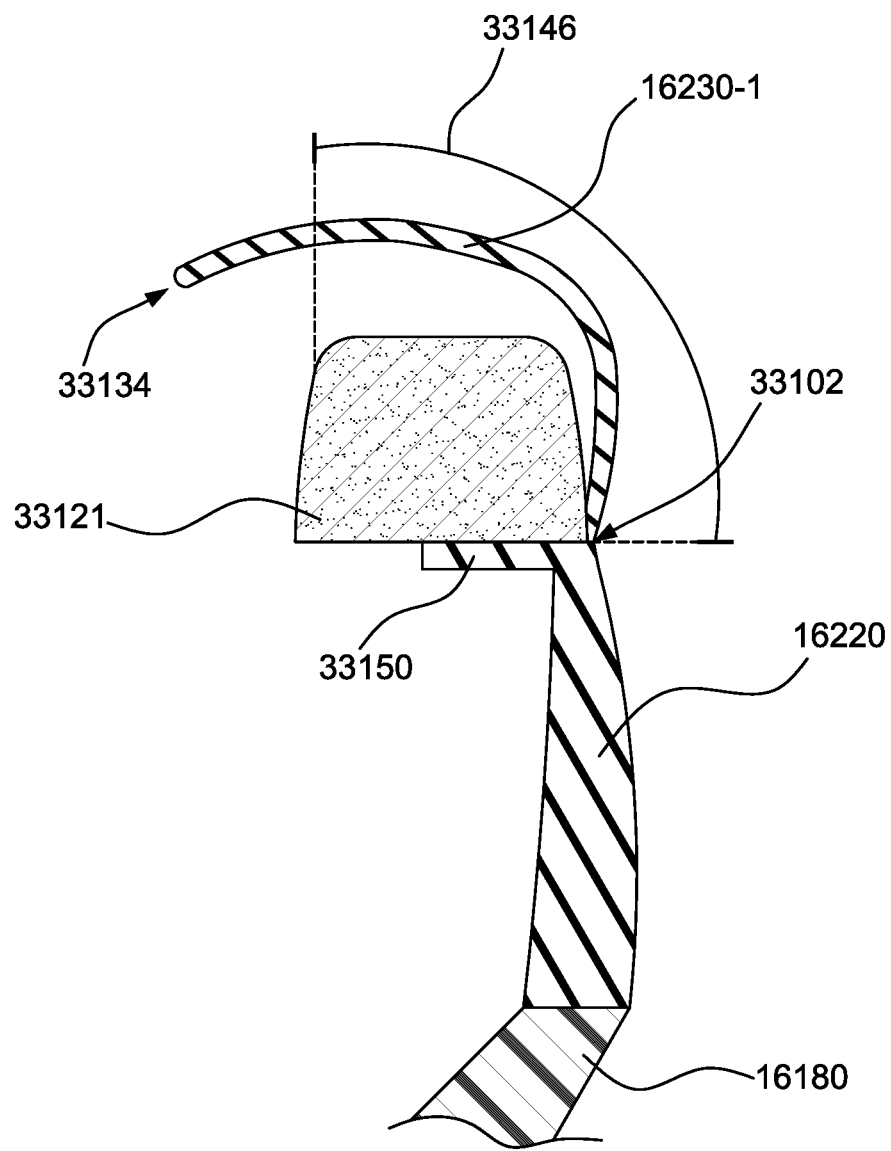
Figures 4, 120:
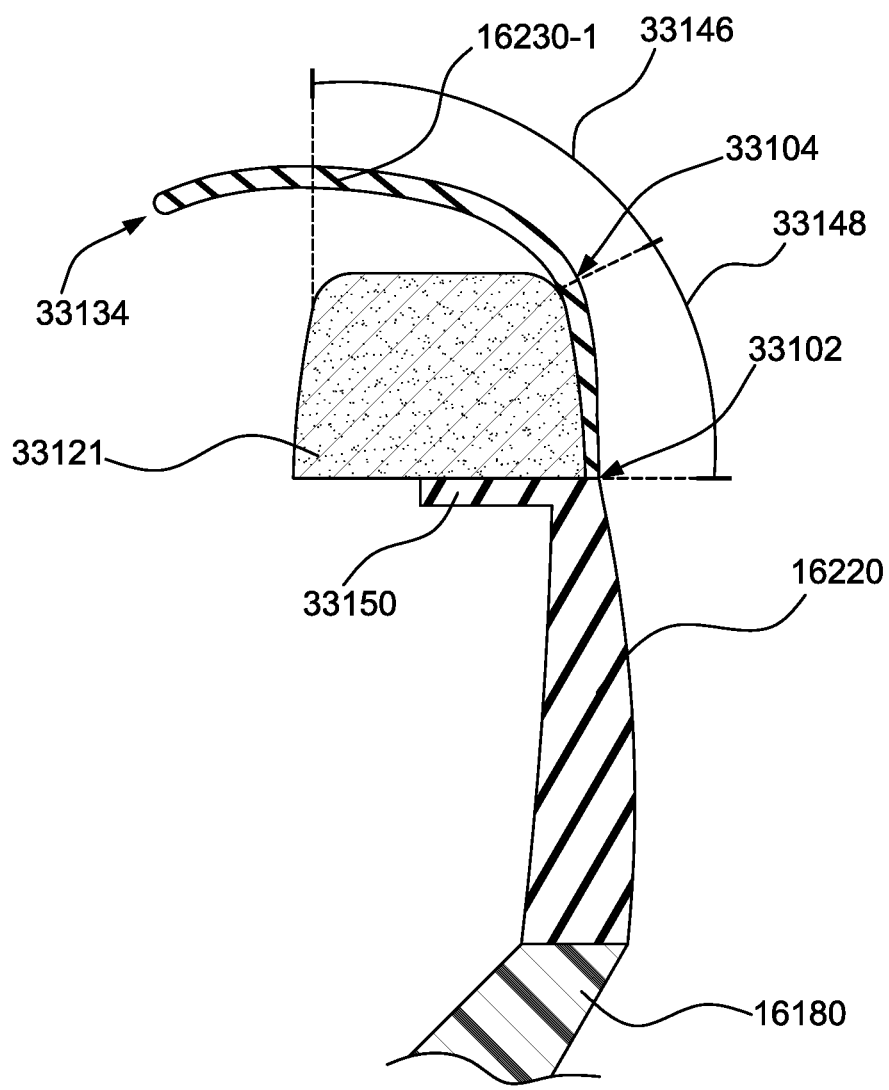
Figures 5, 120:
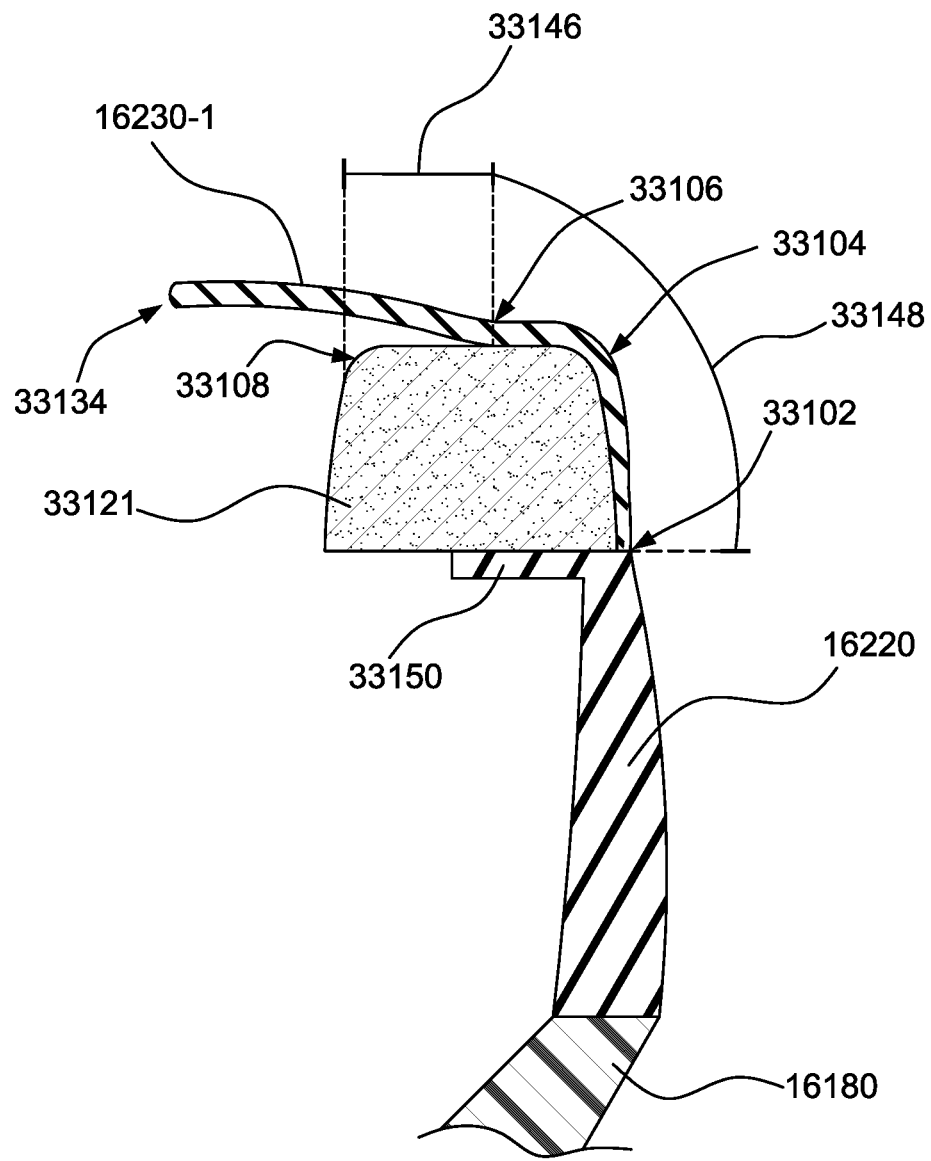
Figures 6, 120:
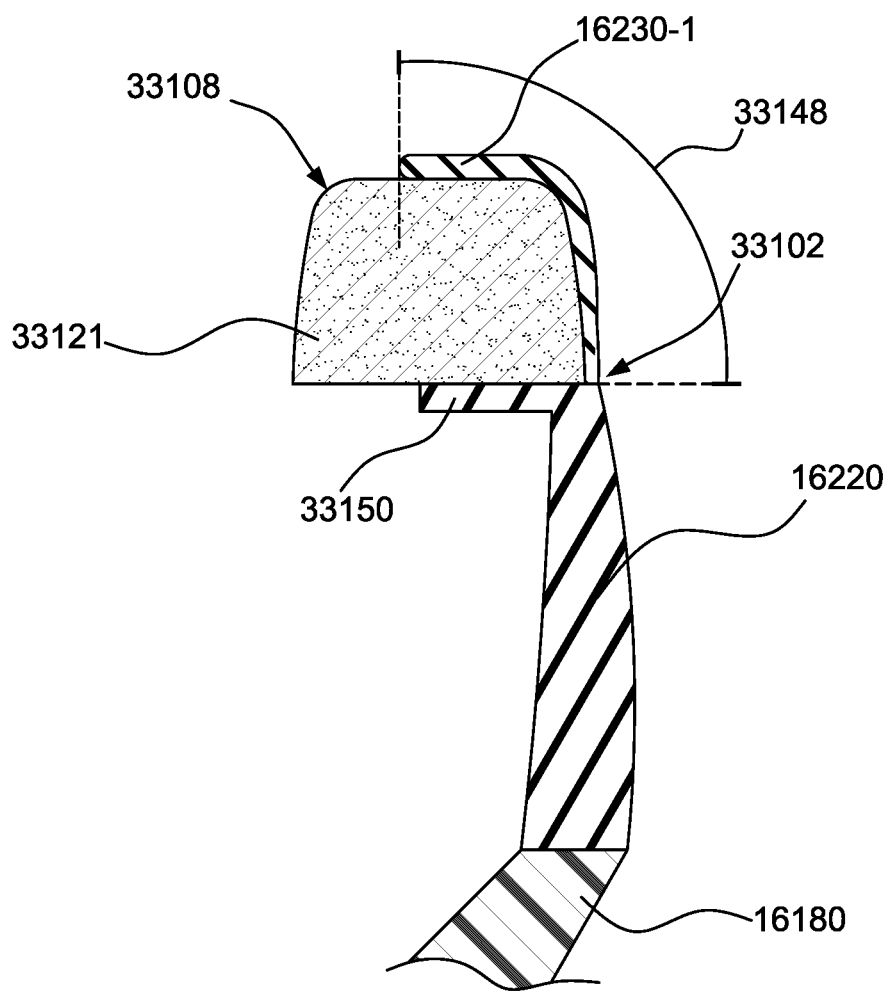

FIGS. 120-1 to 120-6 show cross-sectional views of the cushion assembly in FIG. 118A according to various examples of the present technology.

Figure 121:
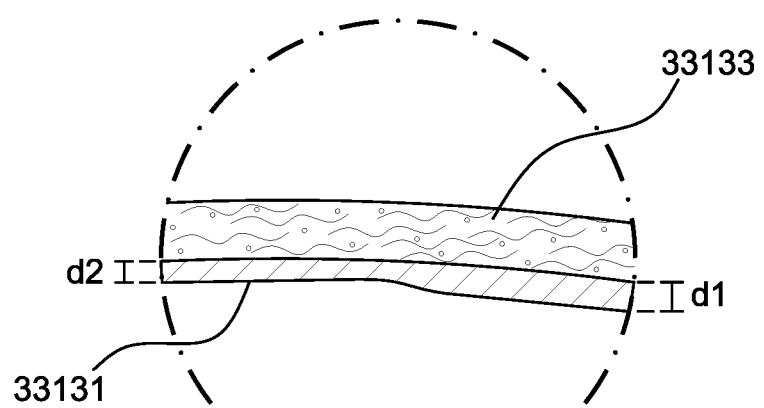

FIG. 121 is an enlarged detail of the textile membrane in FIG. 120-1.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1A:
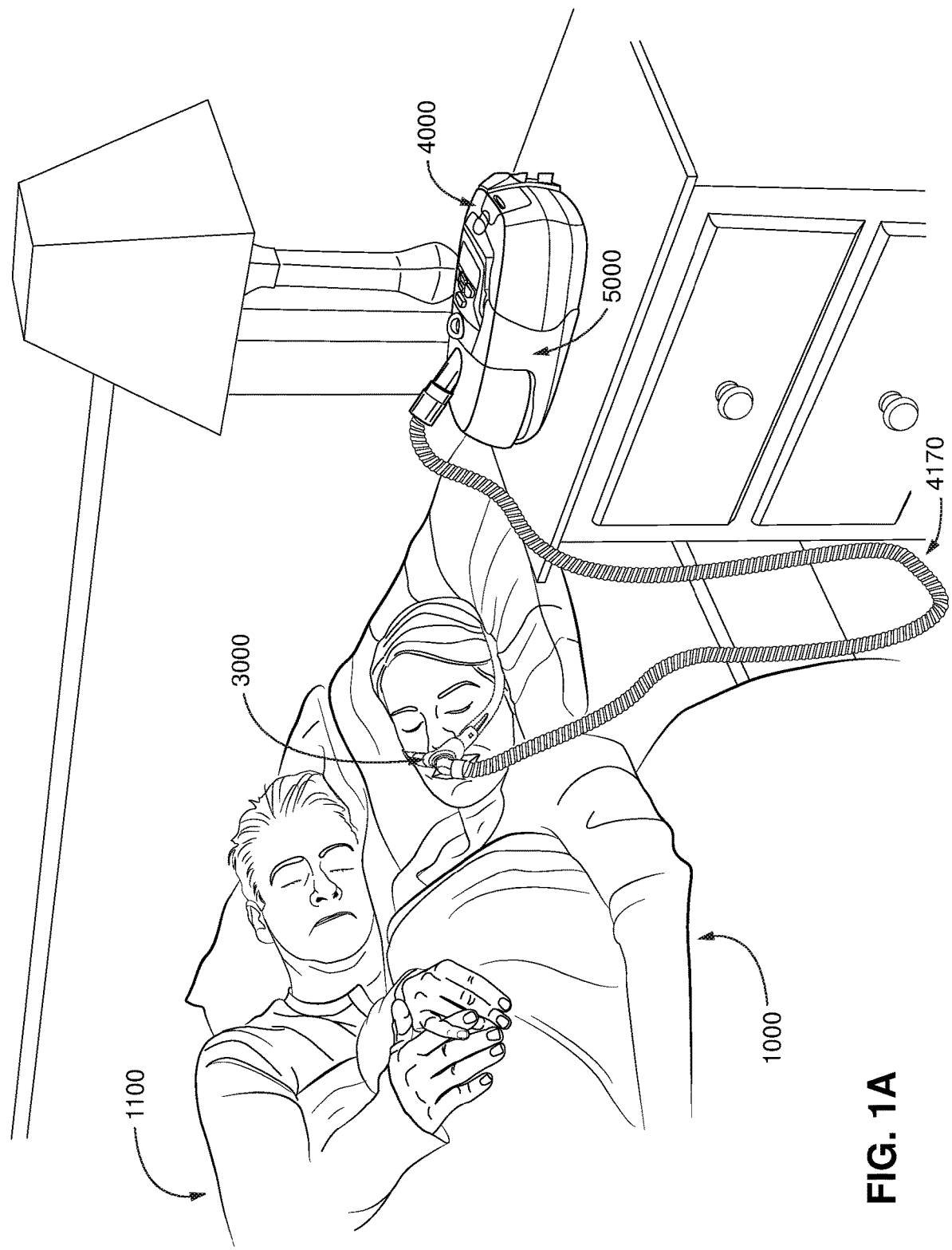
Figure 1B:
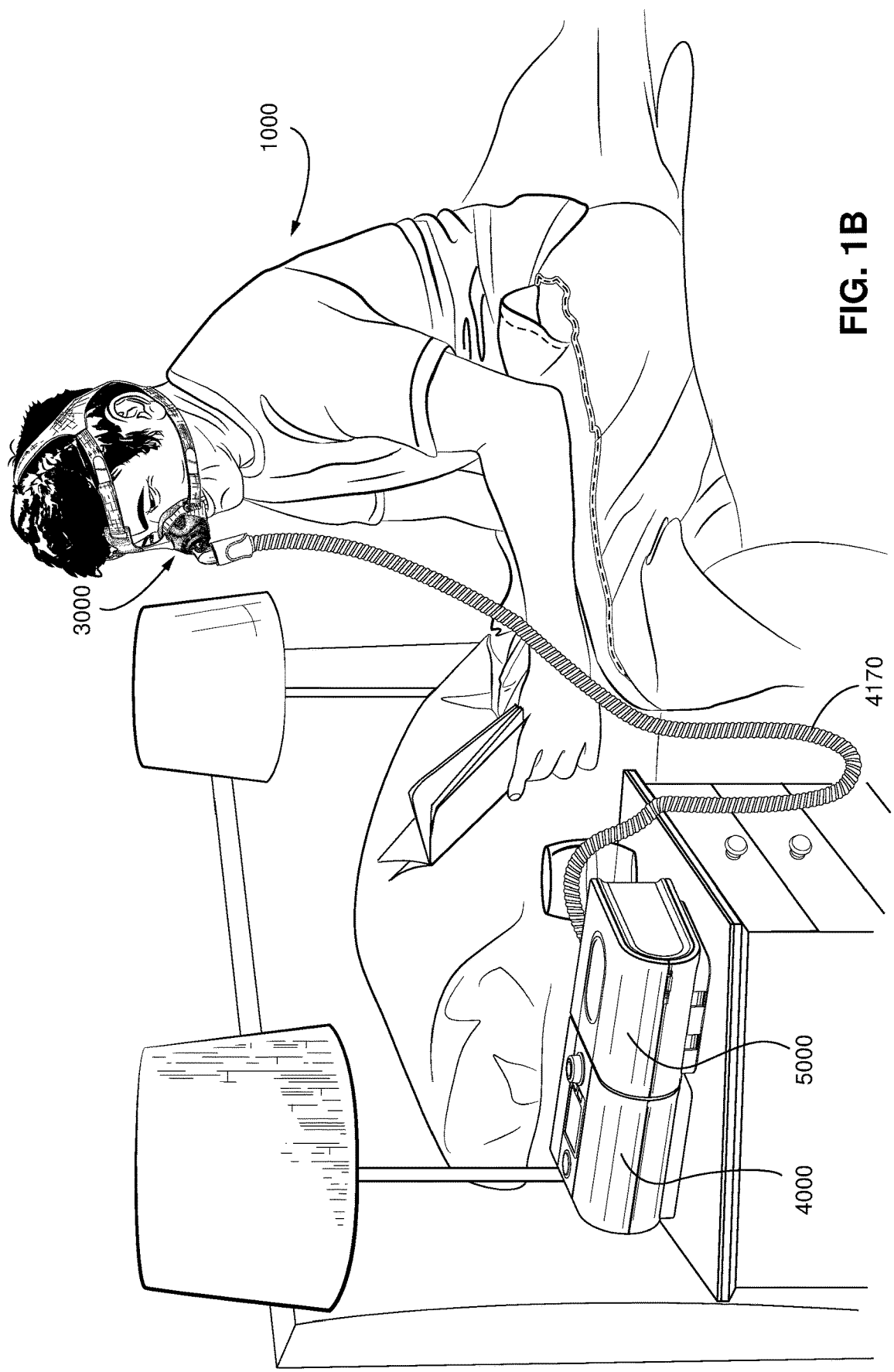
Figure 1C:

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Plenum Chamber

The plenum chamber has a perimeter that is shaped to be complementary to the surface contour of the face of an average person in the region where a seal will form in use. In use, a marginal edge of the plenum chamber is positioned in close proximity to an adjacent surface of the face. Actual contact with the face is provided by the seal-forming structure. The seal-forming structure may extend in use about the entire perimeter of the plenum chamber. In some forms, the plenum chamber and the seal-forming structure are formed from a single homogeneous piece of material. In an example, the plenum chamber may be constructed from a flexible material (e.g., silicone) and may be formed as a one-piece structure with the support structure (e.g., from any of the materials described herein as suitable for the support structure and/or plenum chamber). In an example, the seal-forming structure may be an extension of the plenum chamber or formed as a part of the plenum chamber such that the plenum chamber encompasses the seal-forming structure. In such an example, the support structure and textile membrane may be considered part of the plenum chamber.

5.3.2 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. liquid silicone rubber (LSR) (or "silicone").

A seal-forming structure 3100 in accordance with the present technology may be constructed from a soft, flexible, resilient material such as silicone.

In some forms, such as those illustrated in FIGS. 5 to 77, the seal-forming structure has a sealing portion that comprises a textile material, which may covered the entirety or a portion of the seal-forming structure. In some forms, the textile may comprise a material formed of a network of fibres and being adapted such that it is air impermeable. For example, the textile may have an air impermeable film on at least one surface thereof thereby forming a textile membrane or textile sealing portion.

In some forms, the textile membrane may be constructed so as to stretch elastically in at least one dimension. For example, when a textile membrane is constructed from a network of fibres, the textile membrane may be capable of elongating in a longitudinal warp direction and/or a lateral weft direction across the textile membrane. In some forms, a textile membrane is constructed so as to elongate elastically to an extent greater than that achievable by conventional silicone seal-forming structures.

In some forms, the textile membrane is constructed so as to be substantially inelastic in at least one dimension. For example, when a textile membrane is constructed from a woven textile material, the textile membrane may be capable of substantially resisting elongation in either, or both of, a longitudinal warp direction or a lateral weft direction across the textile membrane.

The textile membrane may comprise a single layer or a plurality of layers. In forms where a plurality of layers is utilised, the individual layers can be formed using the same material, or a variety of different materials each with unique material properties.

In some forms, the textile membrane may comprise at least one layer that exhibits substantially air-impermeable characteristics, while maintaining the material characteristics necessary for providing comfort and minimal pressure points to the patient. For example, as illustrated in FIG. 78, in some forms a textile membrane may comprise an air impermeable material 10131 formed on an inner surface of a textile material 10133. The air impermeable material can in some forms be laminated onto the textile material. The air impermeable material and textile material can in some forms be selected such that the resulting textile membrane can exhibit a predetermined overall elasticity, or a resistance to elasticity, as required. For example, the addition of the air impermeable material (or membrane layer) may add elasticity (or stretchiness) to the textile material such that the resulting textile membrane has increased stretchability.

In some forms, the membrane can exhibit a low spring constant (i.e. high compliance) in both warp and weft. In such forms, unlike conventional designs where a fixed cushion may cause the skin of a patient's face 1300 to distort to form an effective seal, the textile material and/or the resulting textile membrane may have a material spring constant and spring length such that the textile membrane is more compliant than the patient's skin that engages the textile membrane. This may advantageously improve the comfort of the mask, and reduce the formation of localized pressure "hot spots."

In some forms, the surface of the textile material that contacts the patient's face 1300 can have low friction characteristics. This may advantageously improve the comfort of the surface texture of the textile membrane and reduce friction relative to the patient's face 1300. The textile material may have a surface (e.g., herringbone) that may have a first coefficient of friction in a first direction that is different (e.g., greater or less) than a coefficient of friction in a second direction. In contrast, higher friction textiles may cause the textile membrane to grip or rub against contacted regions of the patient's face, in use. Such rubbing or gripping may cause the textile membrane to be distorted or deformed thereby reducing the effectiveness of the seal and allowing air to leak undesirably from the device.

In some forms, the textile material of the textile membrane can have an overall thickness of 0.275 mm or less.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

It is noted that although the specification may refer (e.g., by reference character) to a particular illustrated example or a feature of a particular illustrated example (e.g., seal-forming structure 3100), such discussion may be applicable to other examples and/or features (e.g., seal-forming structure 5100).

5.3.2.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, a textile membrane (e.g., comprising nylon, polyester, nylon and polyester mix, microfiber or polyurethane) is used as the face-contacting portion of the seal-forming structure 3100 for the CPAP mask. The textile membrane may have properties such that it is capable of elongating in at least one dimension. The textile membrane can be held under a tension force across the support structure prior to and/or during use. Prior to use, the textile membrane can be either permanently attached (e.g., molded) or attached as a removable module to the support structure in such a way that it is pre-tensioned and lightly stretched.

Alternatively, the textile can be formed as a complex three-dimensional pre-determined shape such that it is untensioned (e.g., loose, slack and/or unwrinkled) prior to and/or during use, but there are no substantial leak causing wrinkles. Due to manufacturing, the textile polymers can shrink such that the inherent pre-tension in the textile membrane is lost however the textile membrane may remain substantially wrinkle free.

FIG. 79 illustrates an example wherein the textile membrane has a light tension in both the X and Y directions through the textile surface. Before the patient's face 1300 (such as a nose) approaches and depresses the textile membrane 3130, the textile membrane is adapted to form a constant surface without interruptions such as creases, folds or wrinkles in the textile material prior to the contact between the patient's face 1300 and the seal-forming structure 3100. In some forms, this can be accomplished by the application of the light pre-tension, or by moulding the textile membrane such that it is substantially free of any leak causing wrinkles. This can be advantageous in ensuring that the textile membrane forms a smooth and continuous seal on and around the patient's face 1300. This may provide improved respiratory pressure therapy by reducing occurrences of folded or wrinkled sections of the seal-forming structure 3100 through which treatment air may leak. This can also be advantageous in ensuring the textile membrane remains under a minimum threshold of tension as it is forced against the patient's face 1300 (FIG. 80).

In some forms, regions of the textile membrane can be pre-tensioned and lightly stretched while other regions of the textile membrane can remain slack. For example, in some forms the subnasal region can be pre-tensioned whilst the region that cups the outer sides of the nostrils and/or the patient's mouth could remain tension-free (e.g., with excess material) so as to form a saddle region or valley shape prior to use. This may advantageously improve the seal efficiency while reducing pressure (i.e. "hot spots") on regions where the facial anthropometrics protrude a greater distance into or towards the cavity. In another example, the side of nose region and/or the nasal bridge region may remain untensioned and/or slack prior to use, in order to provide additional material to accommodate the facial contours of these sensitive facial areas. In another example a bridge portion (e.g., bridge portion 3104) extending between two naris openings may be untensioned, slack and/or buckled with excess material prior to use, as shown for example in FIG. 33-1. A bridge portion (e.g., 3104) with excess material may allow the textile membrane to expand (e.g., in the superior-inferior (height) direction to accommodate different size noses.

In some forms, instead of having a region that is pre-tensioned, the textile membrane may be formed to be substantially free of leak causing wrinkles. This may be advantageous as it may be difficult to form substantially leak free complex three-dimensional shapes from a slack textile membrane, or from a textile membrane that is provided with excess non-tensioned material. The untensioned textile membrane may be more comfortable is some arrangements as it may apply less pressure on the patient's face.

In some forms, the textile membrane may be in a substantially tension-free state and formed onto the support structure or directly onto the plenum chamber in such a manner so as to remain untensioned and/or slack. In an example, such a textile membrane may still maintain an unwrinkled state so as to avoid leaks in the seal with the patient's face. An untensioned and/or unwrinkled textile membrane may in some forms utilise a cushion support (e.g., underlying cushion, seal support region (e.g., support structure) and/or air pressure within the cavity to enable an effective seal to be formed with a patient's face.

In some forms, the tensioned and/or unwrinkled state (see FIGS. 80 and 81) in the textile membrane may be maintained so as to maintain sealing contact with the patient's face 1300 by one or a combination of the following:

a) the pre-applied tensile stress of the textile membrane and the additional applied tensile stress as the patient's face 1300 engages the textile membrane;

b) the pre-formed state of the textile membrane formed as a non-tensioned, yet substantially constant surface, without leak causing interruptions such as creases, folds, buckles or wrinkles in the textile membrane.

c) the rigidity of the support structure and/or plenum chamber, and the ability of the support structure and/or plenum chamber to accommodate and react to the applied tensile stress as the patient's face 1300 engages the textile membrane; and d) the additional applied loading of the air pressure from within the cavity against the inner surface of the textile membrane. The interior air pressure can apply additional tensile stress against the interior surface of the textile membrane so as to further stretch and stress the textile membrane against the patient's face 1300 (e.g., creating a pressure-assisted seal).

By retaining the textile membrane under tensile stress and/or in a unwrinkled state continuously prior to and during use, the textile membrane can conform to the patient's facial profile while minimizing wrinkles and/or blow-out of the seal-forming structure. In some forms, this may also improve seal performance by maximising the contact area of the textile membrane on the patient's face 1300. In some forms, this may also improve the performance of the CPAP device when it is impacted by external lateral or longitudinal forces (e.g., tube drag).

In some forms, when the plenum chamber is pulled a small distance away from the patient's face 1300, the applied loading of the air pressure from within the plenum chamber can assist the textile membrane in retaining an effective seal. The applied loading of the air pressure can be sufficient so as to elastically stretch the textile membrane in at least one dimension such that it forms a "hover-craft" like balloon effect over the anthropometric contours of a patient's face 1300 thus retaining an effective seal thereon.

In some forms, the textile membrane may be held under tension by a relatively stiffer support structure. In various forms, the support structure can be formed from for example, any of silicone, PU foam, PU solid material or another suitable materials. In some forms, the support structure may be relatively less stiff than a shell or frame of the plenum chamber.

In some forms, the magnitude of the tensile stress can vary across the textile membrane of the seal-forming structure as required. For example, there may be a region of stress concentration proximal to one or more holes in the textile membrane through which treatment is administered or in wider stretches of material.

In some forms, the seal-forming structure can utilize a number of different cushion configurations including a single air assisted textile membrane, a double air assisted textile membrane, a textile membrane with compression support, or a textile membrane with TPU/TPE/Si support. In some forms, the cushion configuration of the seal-forming structure may be formed such that it can advantageously provide a "one-size-fits-most" solution.

In examples, the seal-forming structure and plenum chamber can be applied to nasal cushions, nasal cradles, oronasal cushions, ultra-compact full-face masks, full-face masks and other suitable cushion arrangements.

In some forms, the textile membrane may be configured to generate an effective seal across the patient's pronasale, as shown for example in FIG. 58. In some forms, the textile membrane may be configured to generate an effective seal against the subnasale portion of the patients nose such that the textile membrane does not engage the pronasale, as shown for example in FIG. 40.

In some forms, the stretching and/or maintenance of an unwrinkled state of the textile membrane so as to conform to the patient's face 1300, in use, may apply stress on the walls of the support structure. This stress can pull the walls of the support structure inwardly towards one another in use. In some forms, the support structure may be adapted to resist the applied stress load so as to prevent an inward deformation. Thus, the rigidity of the support structure may apply further stress to the textile membrane which in turn may cause elastic stretching of the textile membrane, in use.

In some forms, such as illustrated in FIGS. 87 and 88, the support structure may include a pleat, fold or gusset (e.g., seal biasing portions 10140, 10140') that utilizes the internal air pressure to dynamically support the textile membrane. This may advantageously provide further support to the textile membrane when under dynamic loads (e.g. tube drags). In other forms, the pleat, fold or gusset may utilise internal air pressure to decouple dynamic loads (e.g. tube drags) from the seal forming structure. In some forms, the air pressure within the cavity may apply a load against the inside surface of the textile membrane to create further tensile stress such that the textile membrane substantially fills the depressed contours of a patient's face 1300 (e.g. around the sides of the nose). In some forms, the elasticity of the textile membrane, when combined with the applied load of the internal air pressure, can elastically stretch the textile membrane such that it forms a larger seal contact area on the patient's face. This may in some forms also be advantageous in providing a continuous seal, even when the mask is partially displaced from an optimal interface with the patient's face, as the textile membrane may partially inflate (i.e. a "hovercraft effect") due to the counter-force from the internal air pressure.

In some forms, such as illustrated in FIGS. 35-37 and 54-56, the textile membrane may have one or more grip pads 29150, 31150 arranged thereon. In an example, the grip pads 29150, 31150 may be configured to be either substantially flat along the patient facing surface of the textile membrane. In other examples, the grip pads 29150, 31150 may be embossed such that the grip pad may form a bead or rim that protrudes slightly above the surface of the textile membrane. In some forms, the grip pads 29150, 31150 may have a high coefficient of friction. In some forms, the grip pads may have a determined shape (e.g., ovular (see FIGS. 35, 37, 54, and 56), circular, square, etc.). In some forms, the grip pads may be elongate (see FIGS. 35 and 54). In some forms, the grip pads 29150, 31150 may be linear. In some forms, the grip pads may be arranged in a pattern across the surface of the seal-forming structure 3100. In some forms, the grip pads may be arranged sporadically across the surface of the seal-forming structure 3100 (see FIGS. 37 and 56). In some forms, the grip pads may be arranged to form a perimeter proximal to the peripheral edges of the textile membrane (see FIGS. 34, 35, 54 and 55). In some forms, the grip pads 29150, 31150 that form a perimeter can be in the form of a dotted line (see FIGS. 35 and 54). In some forms, the grip pads that form a perimeter can be in the form of a solid line (see FIGS. 36 and 55). In some forms, the grip pads that form a perimeter can be in the form of a plurality of lines, dotted or solid or a combination thereof. In some forms, the grip may assist a textile membrane in gripping a patient's face. In an example, the grip pads are formed as a relatively thin layer of silicone applied to the surface of the textile membrane.

In some forms, the textile membrane may be integrated to the support structure by attaching (e.g., molding) an outer edge (e.g., outer perimeter) of the textile membrane around a lip of the curved edges (i.e., inner edge) of the support structure. In an example, the textile membrane may be slightly angled "inwardly" toward the mask interior. In an example, the textile membrane is attached so as to provide a front face of the seal-forming structure. That is, the support structure forms the portion of the seal-forming structure that curves from an anterior side of the seal-forming structure to the posterior face-contacting side (see FIG. 11). In this way, the textile membrane can avoid having portions that curve around from the posterior side to the anterior side. By this arrangement, the textile membrane may be presented only along a front face of the seal-forming structure, as shown for example in FIGS. 11-17). This arrangement may be advantageous since the textile membrane may not need to be folded or cut to blend around the corners of the support structure. This may be beneficial in reducing the occurrence of protruding folds or wrinkles in the textile membrane (which may cause leakage) thereby improving the performance of the seal.

In some forms, the textile membrane may be attached to an outer edge of the textile membrane such that the textile membrane forms part of the portion of the seal-forming structure that curves from the anterior side of the seal-forming structure to the posterior face-contacting side (see FIGS. 33-1 to 33-4, 73 and 74 for example). This may present more of the textile membrane surface (as opposed to the support structure) for engagement with the patient's face, which may improve comfort. In an example, the textile membrane is attached to the support structure by a specific process (as will be described later) that may form the curved portions without creating folds, creases, wrinkles, or buckles in the textile membrane surface. As can be seen, in some examples, at a transition portion 36, the support structure and the textile membrane may both have a radius of curvature (e.g., the same or similar radius of curvature) along the curve 35 in a direction from the anterior side of the seal-forming structure to the posterior side of the seal-forming structure (see FIGS. 33-1 to 33-4). The textile membrane may have a predefined curvature imparted thereto such that a portion of the textile membrane not directly supported by the support structure extends along the curve 35 (FIGS. 33-2 to 33-4). This may help create a dome shape (e.g., convex dome) in certain regions (e.g., lateral side 3250 and/or corner regions 3252) of the textile membrane which may help the textile membrane seal against the contours of the patient's face (e.g., the subalare region of the patient's face (i.e., the corner of nose regions, i.e., the region where the ala terminate at the lip superior proximate the nasolabial sulcus)), as shown for example in FIG. 33-1. The dome shape may help prevent creases, wrinkles, folds, and buckles from forming in the textile membrane which may help avoid the creation of leak paths. Also, the dome shape may help the textile reach into hard to seal areas of the patient's face, such as the corner of nose regions. The textile membrane 29130 may have a saddle shape at a medial subnasale region 3260 configured to seal against the patient's subnasale thereby matching the saddle shape formed by the patient's nasolabial angle and lip superior, as shown in FIG. 33-1. Similarly, a pronasale region 3270 may also have a saddle shape configured to seal against the matching profile presented at or below the patient's pronasale. The curvature (e.g., magnitude of curvature and/or radius of curvature) of the textile membrane in the direction of the curve 35 may vary in different regions of the cushion assembly along an outer perimeter of the textile membrane. For example, as shown in FIG. 33-2, the textile membrane 29130 in the medial pronasale region 3270 may have different curvature in the direction of the curve 35 than the textile membrane in the medial subnasale region 3260. In the FIG. 33-2 example, the textile membrane in the medial pronasale region 3270 may a relatively larger (e.g., smaller radius) curvature (e.g., negative curvature in an inferior-superior direction along curve 35) than the curvature (e.g., negative curvature in an inferior-superior direction along curve 35) in the medial subnasale region 3260. In an example, the curvature (e.g., magnitude of curvature and/or radius of curvature) at a lateral side 3250 of the textile membrane may be different that the curvature at the medial pronasale region 3270 and/or medial subnasale region 3260. The nasal portion of the cushion assemblies 14105, 30105, 31105, as shown for example in FIGS. 43, 52 and 61, may have similar dome and saddle shape features.

In the FIG. 73 example, the curvature of the textile membrane 16230 from the connection with the support structure 16220 (e.g., at the transition portion) may continue to the inner edge of the textile membrane. For example, the textile membrane may have a dome shape or saddle shape at the inner edge of the textile membrane in certain regions of the cushion.

In some forms, the textile membrane may be slightly angled or curved inwardly toward the mask interior (e.g., positive curvature in a left-right direction), as shown for example in FIGS. 11-17, 23-26 and 3-37. In some forms, the textile membrane may form a dome shape over the support structure, as shown for example in FIGS. 19-22 and 43-50. It is noted that any of the cushion assemblies disclosed herein may have the textile membrane attached to an outer edge of the textile membrane such that the textile membrane forms part of the portion of the seal-forming structure that extends along the curve 35 from the anterior side of the seal-forming structure to the posterior face-contacting side as discussed above with reference to FIG. 33-1, such that, for example, the textile membrane 6130 of cushion assembly 6105 may have more of a dome shape by virtue of a more convex shape from one lateral side to the other lateral side.

In some forms where the textile membrane is not under continuous tension (prior to and/or during use) or is non-elastic, the textile membrane may form an improved air-assisted seal on a patient's face that conforms dynamically to alterations/movement (i.e. "hovercraft effect"), for example due to the textile membrane being thinner and having a lower structural stiffness than silicone membrane.

In some forms, the textile membrane may be supported by a secondary or tertiary support structure that may act as a cushion support. A cushion support can provide additional flexibility and may be suitable for use by most patient's faces (one-size-fits-most). The second or third support layer can be formed using a membrane of a textile, a textile with PU/Si membrane, laminated open cell foam, a laminated PU foam, PU molding, TPU/TPE or silicone. In some forms, additional support layers can themselves be supported by a structural/rigid plastic such as PP/PC/PA/PET or other suitable materials.

In some forms, 3D printing of the textile membrane and/or cushion support sections as a "skeleton" can reduce the thickness and as a consequence, may reduce the weight of the mask.

In some forms, multiple different layers of the mask layers could be printed with different rigidity, hardness, or thicknesses. For example, "skeleton" sections may be formed using Si, PU Foam, PU solid material or any suitable plastic material.

In some forms, a pleat or fold section can be formed along a cushion assembly (e.g., in the textile membrane and/or the support structure) that may provide a dynamic force/support or decoupling region.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.2.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.2.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.2.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.2.5 Forehead Region

In one form, the seal-forming structure forms a seal in use on a forehead region of the patient's face. In such a form, the plenum chamber may cover the eyes in use.

5.3.2.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.3 Nasal Cushion

Referring to FIGS. 5-14, a patient interface 3000, 6000 with a cushion assembly 3105 including a seal-forming structure 3100 and a plenum chamber 3200 is shown in accordance with a first example of the present technology. FIGS. 15-17 show a cushion assembly 5105 including a seal-forming structure 5100 and a plenum chamber 3200 in accordance with a second example of the present technology. FIGS. 18-22 show a cushion assembly 6105 including a seal-forming structure 6100 and a plenum chamber 3200 in accordance with a third example of the present technology. FIGS. 23-27 show a cushion assembly 7105 including a seal-forming structure 7100 and a plenum chamber 3200 in accordance with a fourth example of the present technology. Referring to FIGS. 28-32 a cushion assembly 8105 including a seal-forming structure 8100 and a plenum chamber 3200 is shown in accordance with a fifth example of the present technology. FIG. 3 shows a patient interface 9000 with a cushion assembly 9105 including a seal-forming structure 9100 and frame 9200 in accordance with a sixth example of the present technology.

FIGS. 11-14 include broken lines demarcating regions of different thickness, and it should be understood that these are only nominal boundaries, not actual structures.

The examples of seal-forming structures 3100, 5100, 6100, 7100, 8100, 9100 described in the preceding paragraphs may be considered nasal cradle cushions and are intended to provide a flow of pressurised gas to the patient's nares by sealing against at least the underside of the patient's nose. The exemplary seal-forming structures may engage the patient's face below the bridge of the nose and some examples, depending on the size and shape of the patient's nose, may engage the patient's nose below the pronasale. The exemplary seal-forming structures may also engage the patient's face at least above the upper vermillion Thus, the exemplary seal-forming structures may seal against the patient's lip superior in use. Furthermore, the patient's mouth may remain uncovered by the seal-forming structures of the depicted examples such that the patient may breathe freely, i.e., directly to atmosphere, without interference from the seal-forming structure. The under-the-nose nasal cradles may be configured such that they do not have an aperture sized to receive the patient's nose within the cavity. Further, a height of the cushion from an inferior edge of the textile membrane at a medial subnasale region to a superior edge of the textile membrane at a medial pronasale region may be less than a width of the cushion in a left-right direction from a lateral edge of the textile membrane to the other lateral edge of the textile membrane (see FIGS. 33 and 33-1 for example).

Examples of a nasal cradle cushion, e.g., the exemplary seal-forming structures disclosed herein, may include a superior saddle or concave region that has positive curvature across the cushion. Also, a nasal cradle cushion may be understood to have a single target seal forming region or surface, whereas a pillows cushion may have two target seal forming regions (one for each naris). Cradle cushions may also have a posterior wall that contacts the patient's lip superior and an upper, central, surface contacts the underside of the patient's nose. These two surfaces on the patient's face may form a nasolabial angle between them (see FIG. 2E). A cradle cushion may be shaped to have a nasolabial angle within the range of 90 degrees to 120 degrees.

Furthermore, the exemplary seal-forming structures may also be shaped and dimensioned such that no portion of the seal-forming structure enters into the patient's nares during use.

Plenum Chamber

Referring to FIGS. 5-17, the plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

In certain forms of the present technology, the plenum chamber 3200 is constructed from a relatively rigid material (e.g., polycarbonate) as compared to the seal-forming structure. Alternatively, the plenum chamber 3200 may be constructed from a flexible material (e.g., silicone) and may be formed as a one-piece structure with the support structure (e.g., from any of the materials described herein as suitable for the support structure and/or plenum chamber). In an example, the seal-forming structure may be an extension of the plenum chamber or formed as a part of the plenum chamber such that the plenum chamber encompasses the seal-forming structure. In such an example, the support structure and textile membrane may be considered part of the plenum chamber. In another example, the plenum chamber 3200 may be constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

FIGS. 5 and 10-17 show examples of the seal-forming structure 3100 with the plenum chamber 3200. The seal-forming structure 3100 may include a plenum chamber connection opening where the seal-forming structure 3100 is sealingly joined to the plenum chamber 3200. The seal-forming structure 3100 and the plenum chamber 3200 may at least partly form a cavity 3101 that is pressurized by the flow of air. In the illustrated example, the seal-forming structure 3100 and the plenum chamber 3200 together form the cavity 3101.

The connection between the seal-forming structure 3100 and the plenum chamber 3200 at the plenum chamber connection opening 3106 may be a permanent bond. The connection between the seal-forming structure 3100 and the plenum chamber 3200 at the plenum chamber connection opening 3106 may be a chemical bond. The seal-forming structure 3100 may be joined to the plenum chamber 3200 at the plenum chamber connection opening without a mechanical connection. Alternatively, the seal-forming structure 3100 may be joined to the plenum chamber 3200 at the plenum chamber connection opening by a mechanical removably detachable connection.

At each lateral side of the plenum chamber 3200 there may be a plenum chamber lateral end 3202 in the form of a hollow passageway forming a plenum chamber inlet port sized and structured to receive a flow of air. A plenum chamber connector 3204 may also be provided at each lateral side of the plenum chamber 3200 laterally outward of the plenum chamber lateral end 3202. The plenum chamber connectors 3204 may connect to respective ends 3314 of the positioning and stabilising structure 3300. The connection between the plenum chamber connectors 3204 and respective ends 3314 of the positioning and stabilising structure 3300 may be releasable at both sides. In other examples, one side may have a permanent connection while the other side has a releasable connection. In still further examples, both connections between the plenum chamber connectors 3204 and respective ends 3314 of the positioning and stabilising structure 3300 may be permanent.

The plenum chamber lateral ends 3202 may receive the flow of pressurised gas from the positioning and stabilising structure 3300. The flow of pressurised gas may then pass through the plenum chamber 3200, then through the seal-forming structure 3100, and into the patient's airways for inhalation.

The ends 3314 of the positioning and stabilising structure 3300 may be connected to the plenum chamber lateral ends 3202. Each plenum chamber connector 3204 in these examples may include a slot 3209, a chamfered edge 3208, and a notch 3206 that may be removably connected to a clip of the positioning and stabilizing structure with a snap-fit.

The plenum chambers 3200 shown in FIGS. 18-32 according to the third, fourth and fifth examples of the present technology may be similar or identical to the plenum chamber of FIGS. 10-17. It should also be appreciated that one or more aspects of the present technology may be combinable with one or more aspects of: U.S. Provisional Application No. 62/764,992, filed Aug. 20, 2018 and entitled "Patient Interface" or PCT/AU2019/050873, filed Aug. 20, 2019, each of which is hereby incorporated herein by reference in its entirety. For instance, the plenum chamber of the present technology may be identical to the plenum chamber in any of the embodiments of the '992 or '837 application. Additionally, the seal-forming structures disclosed herein may replace any of the seal-forming structures in any of the patient interfaces disclosed in the '992 or '873 application, and the seal-forming structures of the present technology may include any of the features of the seal-forming structures in any of the embodiments of the '992 or '873 application.

In the example of FIGS. 28-32, the plenum chamber 13200 has a plenum chamber lateral end 3202, plenum chamber connector 3204, notch 3206, chamfered edge 3208, and slot 3209 similar to the plenum chamber 3200 described above. However, the vent 3400 may be provided by a vent insert 13400 that attaches, removably or permanently, to the plenum chamber 13200 (e.g., by insertion into an opening in the plenum chamber). It is noted that any of the other examples may have a vent insert (e.g., the vent 3400 in plenum chamber 3200 of FIGS. 10-27 may be provided by a vent insert 13400 such as shown in FIGS. 28-32).

In the example of FIG. 38, the frame 9200 may include a centrally located connection for an air circuit 4170. The frame may also include headgear attachment portions 9210 at lateral sides thereof. The seal-forming structure 9100 may be connected to the frame 9200 by spaced-apart connectors 9122, which may include a clip on the seal-forming structure and a receiving connector on the frame.

Seal-Forming Structure of the Present Technology

The seal-forming structures 3100, 5100, 6100, 7100, 8100, 9100, 29100 may each include a support structure 3120, 6120, 7120, 8120, 9120, 29120 that provides support to a sealing portion 3130, 5130, 6130, 7130, 8130, 9130, 29130 (e.g., a textile membrane). The sealing portion is configured to sealingly engage the patient's face. Also, depending on the size and contours of the patient's nose, in the examples of FIGS. 5-27, the support structure may also sealingly engage the patient's face.

The exemplary seal-forming structures 3100, 5100, 6100, 7100, 8100, 9100, 29100 while different in various aspects to be described further below, may each include a support structure having at least two regions (e.g., two, three or four regions) of different thickness (e.g., seal-forming structure 3100 comprises support structure 3120 which has a wall structure having lateral support regions 3122 of an increased thickness with respect to other portions of the wall structure). For example, as shown in FIG. 59, portions (d1) of the support structure may be thicker than portions (d2) of the support structure. For example, portions (d1) may be adjacent to or connecting to the plenum chamber and portions (d2) may be adjacent to or connecting to the sealing portion so as to provide structural stability at the connection with the plenum chamber and flexibility at the interface with the patient. Alternatively, the thicker lateral support regions 3122 may be located, for example, at the corner of nose region of the seal-forming structure (and e.g., may connect directly to the textile membrane), to ensure adequate sealing in the subalare region of the patient's face.

Further, in the depicted examples, each sealing portion has two separate naris openings 3102 corresponding respectively to one of the patient's nares to provide the flow of air to both of the patient's nares. There may also be a bridge portion 3104 positioned between the naris openings 3102. The bridge portion 3104 may assist in providing a taut textile membrane prior to and/or during use. In an alternative example, a single hole may be used to provide the flow of air to both of the patient's nares.

The seal-forming structure 3100, as described above, may include a plenum chamber connection opening where the seal-forming structure 3100 is sealingly joined to the plenum chamber 3200. In the examples of FIGS. 5-38, the support structure 3120, 5120, 6120, 7120, 8120, 9120, 29120 is connected directly to the plenum chamber or frame. Thus, the support structure may include an opening where the support structure is sealingly joined to the plenum chamber 3200.

The support structure may be less rigid than the plenum chamber 3200 and may be constructed from silicone, foam (e.g., polyurethane foam) (see FIGS. 28-32), polyurethane solid material, thermoplastic elastomers (e.g., thermoplastic polyurethane), suitable plastics, or other suitable materials, as will be described later. Further, the sealing portion may be less rigid than the support structure and may be constructed from a textile material such as nylon, polyester, nylon and polyester mix, microfiber or polyurethane, for example, as will be described in more detail later. The sealing portion described in any of the examples of this disclosure may be referred to as a textile sealing portion or textile membrane and may comprise a textile material having an air impermeable material layered, coated or otherwise applied thereon.

The support structure may have an aperture formed therein providing an inner edge of the support structure along which the sealing portion (e.g., an outer perimeter of the sealing portion) may be attached to the support structure such that the sealing portion extends radially inwardly of the seal-forming structure beyond or to a further extent than the support structure, as shown for example in FIGS. 11-27 and 33-38. For example, the sealing portion may be molded around the inner edge of the support structure or connected to the support structure in other suitable ways, as will be described later. However, in the alternative example of FIGS. 28-32, the sealing portion 8130 may be layered onto the support structure 8120 (e.g., foam).

Referring to FIGS. 11-14, the seal-forming portion 3100 has a wall structure that may include lateral support regions 3122 having an increased thickness as compared to other portions of the wall structure of the support structure 3120. At each lateralmost side of the seal-forming structure 3100, a lateral support region 3122 may be provided. The seal-forming structure 3100 may include two lateral support regions 3122, each spaced distal from a plane bisecting the seal-forming structure 3100 that would be parallel to the patient's sagittal plane in use. The lateral support regions 3122 may be the thickest portions of the seal-forming structure 3100 to provide resistance to lateral displacement, e.g., caused by the patient sleeping on the side of their head such that the pillow pushes laterally against the seal-forming structure, and to provide robust engagement against the patient's ala. The lateral support regions 3122 may have a thickness of approximately 0.9 mm to approximately 1.5 mm, or approximately 1.3 mm to approximately 1.4 mm, or approximately 1.3 mm, or approximately 1 mm to approximately 1.5 mm Due to the lateral support regions 3122 being the thickest regions of the seal-forming structure 3100 in the depicted examples, the lateral support regions 3122 may also provide the greatest resistance to deformation.

Additionally, the lateral support regions 3122 may provide sufficient rigidity to ensure adequate sealing (e.g., by the lateral support regions 3122) in the subalare region of the patient's face (i.e., the region where the ala terminate at the lip superior proximate the nasolabial sulcus), which is a region of particularly complex geometry. The subalare region of a patient's face presents particularly complex geometry because at least three facial surfaces—the ala, the lip superior, and the cheek—converge at this region. Thus, sufficient stiffness in the lateral support regions 3122 may ensure that the seal-forming structure 3100 can be urged into the subalare region by tension forces from the positioning and stabilising structure 3300 without collapsing. The lateral support regions 3122 may lie on the patient's face in a region inferior to the ala of the patient's nose as well as inferior and laterally outwards of the patient's nose, for example, between the nasolabial sulcus and the regions of the lip superior located inferior to the ala.

The seal-forming structure 5100 in the example of FIGS. 15-17 may have a sealing portion 5130 that is expanded as compared to the sealing portion 3130 in FIGS. 11-14. That is, the support structure 5120 is reduced and the sealing portion 5130 is expanded in the seal-forming structure 5100 such that the sealing portion 5130 may be configured to engage the subalare region of the patient's face in use. As a result, the seal-forming structure 5100 may be more flexible and compliant so as to more readily conform to the patient's facial contours.

Turning to FIGS. 18-22, the seal-forming structure in this example is arranged to provide a larger cavity 3101 such that the sealing portion 6130 protrudes further from the plenum chamber in a direction towards the patient's face in use by creating more tension in the sealing portion thereby causing the sealing portion to balloon outwards. In use, the patient's nose is able to press against the sealing portion 6130 in the direction towards the cavity 3101 and the plenum chamber 3200 causing the sealing portion 6130 to stretch and invert such that space created by the cavity 3101 receives the patient's nose thereby allowing the sealing portion 6130 to seal above the patient's pronasale, as shown in FIG. 18. In contrast, the sealing portions 3130, 5130 seal below the patient's pronasale, as shown in FIG. 10.

The sealing portion 7130 in the example of FIGS. 23-27 is also configured to seal above the patient's pronasale due to the height of the cushion. The sealing portion 7130 is configured to seal further in the direction of the sellion along the ridge of the nose as compared to the sealing portion 6130.

In the example cushion assembly of FIGS. 28-32, the support structure 8120 may be provided by a foam material layered onto the plenum chamber 3200. The sealing portion 8130 may be layered directly onto the support structure. The support structure 8120 may extend across the plenum chamber connection opening except for a pair of holes formed therein corresponding to the naris opening 3102 in the sealing portion 8130. This arrangement may provide a compression type seal against the patient's face wherein the cushion assembly 8105 is pulled towards the patient's face by headgear causing the seal-forming structure 8100 to conform to the patient's facial contours through compression of the support structure 8120.

The cushion assembly 8105 is configured to seal against an underside of the patient' nose. The seal-forming structure 8100 includes an end portion 8122 that curves around a posterior portion of the plenum chamber 3200 and is configured to engage the patient's lip superior in use.

Referring to FIGS. 33-37, cushion assembly 29105 is similar to cushion assembly 3105, but may extend further in a lateral left-right direction. Cushion assembly 29105 includes seal-forming structure 29100, support structure 29120 and sealing portion 29130. Referring to FIG. 33-1, cushion assembly 29105-1 is similar to cushion assembly 29105, but may have a textile membrane 29105 formed such that the textile membrane forms part of the portion of the seal-forming structure that curves from the anterior side of the seal-forming structure to the posterior face-contacting side, as described earlier.

As described earlier, FIGS. 35-37 show grip pads 29150 on the surface of the textile membrane.

In the FIG. 38 example, the sealing portion 9130 is arranged to seal above the patient's pronasale.

5.3.3.1 Positioning and Stabilising Structure

The cushion assembly 3105, 5105, 6105, 7105, 8105, 29105 of the patient interface 3000, 6000 of the present technology may be held in sealing position in use by the positioning and stabilising structure 3300. The cushion assembly 9105 of the patient interface 9000 may be held in sealing position in use by the positioning and stabilising structure 9300.

In one form the positioning and stabilising structure 3300, 9300 provides a retention force at least sufficient to overcome the effect of the positive pressure in the cavity 3101 to lift off the face.

In one form the positioning and stabilising structure provides a retention force to overcome the effect of the gravitational force on the patient interface.

In one form the positioning and stabilising structure provides a retention force as a safety margin to overcome the potential effect of disrupting forces on the patient interface, such as from tube drag, or accidental interference with the patient interface.

In one form of the present technology, a positioning and stabilising structure 3300, 9300 is provided that is configured in a manner consistent with being worn by a patient while sleeping. In one example the positioning and stabilising structure has a low profile, or cross-sectional thickness, to reduce the perceived or actual bulk of the apparatus. In one example, the positioning and stabilising structure comprises at least one strap having a rectangular cross-section. In one example the positioning and stabilising structure comprises at least one flat strap.

In one form of the present technology, a positioning and stabilising structure is provided that is configured so as not to be too large and bulky to prevent the patient from lying in a supine sleeping position with a back region of the patient's head on a pillow.

In one form of the present technology, a positioning and stabilising structure is provided that is configured so as not to be too large and bulky to prevent the patient from lying in a side sleeping position with a side region of the patient's head on a pillow.

In one form of the present technology, a positioning and stabilising structure 3300, 9300 is provided with a decoupling portion located between an anterior portion of the positioning and stabilising structure, and a posterior portion of the positioning and stabilising structure. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure and disrupting the seal.

In one form of the present technology, a positioning and stabilising structure comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure comprises a strap that is bendable and e.g. non-rigid. An advantage of this aspect is that the strap is more comfortable for a patient to lie upon while the patient is sleeping.

In certain forms of the present technology, a positioning and stabilising structure comprises a strap constructed to be breathable to allow moisture vapour to be transmitted through the strap, In certain forms of the present technology, a system is provided comprising more than one positioning and stabilizing structure 3300, 9300, each being configured to provide a retaining force to correspond to a different size and/or shape range. For example the system may comprise one form of positioning and stabilizing structure suitable for a large sized head, but not a small sized head, and another suitable for a small sized head, but not a large sized head.

5.3.3.1.1 Positioning and Stabilising Structure of the Present Technology

FIG. 5 depicts an example of the present technology, including a positioning and stabilising structure 3300. In this example, the positioning and stabilising structure 3300 includes lateral portions 3302 and superior portions 3304 in the form of conduits that direct a flow pressurised gas from a hub 3306 to ends 3314. The positioning and stabilising structure 3300 may be arranged such that the hub 3306 and the decoupling structure 3500 are positioned superior to the patient's head in use. As described below, the decoupling structure 3500 may be rotatable within the hub 3306 and when the patient is wearing the patient interface 3000, e.g., during therapy, the location of the hub 3306 and the decoupling structure 3500 superior to the patient's head allows the patient to move more freely without becoming entangled with the air circuit 4170.

The positioning and stabilising structure 3300 may be constructed of silicone. For example, the lateral portions 3302, the superior portions 3304, the hub 3306, and the lateral ends 3314 may able constructed or molded from a single piece of silicone.

The superior portions 3304 of the positioning and stabilising structure 3300 have ridges and valleys (or concertina sections) that allow the superior portions 3304 to conform to the shape of the corresponding portion of the patient's head in use. The ridges and valleys of the superior portions 3304 allow the superior portions 3304 to be extended and contracted along the longitudinal axis to accommodate larger or smaller heads. The ridges and valleys of the superior portions 3304 allow the superior portions 3304 to be flexed to different radii of curvature to accommodate patient heads of different shapes and sizes.

The lateral portions 3302 of the positioning and stabilising structure 3300 may not be formed with the ridges and valleys of the superior portions 3304. Therefore, the lateral portions 3302 may be less extensible and flexible than the superior portions 3304, which may be advantageous because there is less variability in the shape and size of the lateral sides of a patient's head.

The ends 3314 may connect to respective plenum chamber lateral ends 3202. As described above, the plenum chamber lateral ends 3202 receive the flow of pressurised gas from the positioning and stabilising structure 3300, which passes through the plenum chamber 3200, through the seal-forming structure 3100, and on to the patient's airways.

As described above, the ends 3314 may connect to the plenum chamber connectors 3204 of a respective plenum chamber lateral end 3202.

The positioning and stabilising structure 3300 may be structured and arranged to direct a force/tension provided by the lateral portions 3302 into a partially superior and partially posterior force vector applied to the plenum chamber 3200. The partially superior and partially posterior force vector urges, in particular, the textile membrane of the seal forming structure 3100 into sealing contact with an underside of the patient's nose contacting, e.g., at or below the pronasale and at least above the upper vermillion.

The lateral portions 3302 may also each include a tab 3308 that receives a posterior strap end portion 3311 of a posterior strap 3310. The posterior strap 3310 may be length-adjustable, e.g., with a hook and loop material arrangement whereby one of the posterior strap end portion 3311 and the remainder of the posterior strap 3310 includes hook material on its exterior while the other includes loop material on its exterior. The length adjustability of the posterior strap 3310 allows tension on the lateral portions 3302 to be increased to pull the seal-forming structure 3100 into sealing engagement with the patient's face at a desired amount of pressure (i.e., sufficiently tight to avoid leaks while not so tight as to cause discomfort).

The lateral portions 3302 may also be provided with sleeves 3312 that cushion the patient's face against the lateral portions 3302. The sleeves 3312 may be constructed of a breathable textile material that has a soft feel.

In an alternative example shown in FIG. 6, patient interface 6000 includes a positioning and stabilizing structure 6300 having at least one tube 6350 that is formed of a textile material (e.g., one or more sheets or layers of textile material) and receives pressurized air from air delivery tube 6348 via connection port 6600. The tube 6350 includes left arm 6305 and right arm 6307.

In some forms, the textile tube 6350 may be formed with a first side that is configured to contact the patient. This may be referred to as the inner layer 6352. The textile conduit may also include a second side that is attached to the inner layer, but faces away from the patient that may be referred to as the outer layer 6354. The inner layer and the outer layer may each be secured to each other along the edges of the inner layer and the outer layer such that a channel or passageway is formed between the seams of the inner layer and the outer layer. That is, the space between the seams remains unattached and forms an air passage 6372. The inner layer and the outer layer may be joined using various techniques that impart particular properties to the seam or joint. For example, in some forms, the seams are formed using ultrasonic welding, radio frequency welding, as well as cut and weld techniques. Heat may be applied in particular areas that activates a thermoset or thermoplastic material used in tube 6350. This heat may not only be used to join the layers together, but may also be used to thermoform the layers, such as outer layer 6354. Further, in some forms stitching or an adhesive such as a glue may be utilized to join the layers together. In some forms, stitching is not used. In still further forms, material beyond what is located within the layers is not utilized to join the inner and outer layers of tube. For example, in some forms the inner and outer layers may be formed such that no additional material such as glue or stitching, is necessary to join the inner and outer layers together.

Each of the inner layer and the outer layer may include an interior surface and an exterior surface. The interior surface of the inner layer is the surface that faces the exterior layer.

The interior surface of the exterior layer is the surface that faces the interior layer. Likewise, the exterior surface of the outer layer faces away from the interior layer and the exterior surface of the inner layer faces away from the outer layer. Further, in forms that include a single sheet, the interior surface is the surface of the sheet that faces inwards and towards itself.

In some forms, the sheet or sheets of the tube may include an air impermeable layer or membrane. In some forms, the interior surface of both of the layers includes a membrane that is configured to restrict or restrain air from passing through the layer from the interior surface to the exterior surface. The impermeable layer may be a thin layer that is less than the thickness of the textile sheets of the inner layer or outer layer. In other forms, the impermeable layer may be greater than the thickness of the sheets of textiles of either of the layers. The impermeable layer or membrane or film may be completely impermeable to air transfer or may be formed to allow a predetermined rate or air transfer and particular pressures.

The membrane may be formed of thermoplastic or thermoset materials such that when exposed to a particular temperature membrane material may be able to be molded or shaped into a particular form and then cures or solidifies or sets upon cooling. In some forms the membrane may be formed of silicone or polyurethane. In some forms, outer layer 6354 may be pre-formed such that in an unpressurized or supported state, outer layer 6354 is pre-positioned and pre-formed to extend away from inner layer 6352 between the opposing joints 6312. That is, outer layer 6354 may support its own weight such that when not supported by pressurized air or other support mechanism, outer layer 6354 remains spaced from inner layer 6352 between joints 6312.

In contrast, inner layer 6352 may be a floppy component. Inner layer 6352 may be attached and secured to the edges of outer layer 6354 such that inner layer 6352 is a substantially planar layer.

As shown in FIG. 7, and in particular FIG. 8, inner layer 6352 comprises a textile sheet 6360 along with membrane 6362. Textile sheet 6360 may be formed of felt, foam, woven, knit, or non-woven material or other network of fibers.

Outer layer 6354 includes tube sheet 6364 and outer covering 6366. In some forms, both sides of tube sheet 6364 may be covered with a membrane. As shown in FIG. 9, tube sheet 6364 includes membrane 6368 exposed to the chamber of tube 6350 and membrane 6370 along an opposite surface of tube sheet 6364. Membrane 6368 may assist in providing a seal between inner layer 6352 and outer layer 6354 as well as forming an air tight tube. Membrane 6370 may assist in joining tube sheet 6364 to outer covering 6366.

It should also be appreciated that one or more aspects of the present technology may be combinable with one or more aspects of: U.S. Provisional Application No. 62/821,878, filed Mar. 21, 2019 and entitled "Textile Headgear Tubing for a Patient Interface" or PCT/AU2019/050655, filed Jun. 25, 2019, each of which is hereby incorporated herein by reference in its entirety. For instance, the positioning and stabilizing structure of the present technology may be identical to the positioning and stabilizing structure in any of the embodiments of the '968 or '655 application. Additionally, the cushion assemblies or seal-forming structures disclosed herein may replace any of the cushion assemblies or seal-forming structures in any of the patient interfaces disclosed in the '968 or '655 application.

In another example shown in FIG. 38, patient interface 9000 includes a positioning and stabilizing structure 9300 having a pair of side portions extending between the patient's eye and ear on respective sides of the patient's head. The side portions may include a hole or other connector for connecting with the headgear attachment portions 9210 of the frame 9200. The positioning and stabilizing structure 9300 also includes a rear strap 9310 extending around a rear portion of the patient's head, and a crown strap 9312 extending over a crown section of the patient's head.

5.3.3.2 Vent

In one form, the patient interface 3000, 6000, 9000 includes a vent 3400 constructed and arranged to allow for the washout of exhaled gases, e.g. carbon dioxide, as shown for example in FIG. 5.

In certain forms the vent 3400 is configured to allow a continuous vent flow from an interior of the cavity 3101 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. The vent 3400 may comprise a plurality of holes, as described above. The holes of the vent 3400 may be divided into two groups spaced apart laterally. The axis of the flow path through each of the holes of the vent 3400 may be parallel such that cross-flow is avoided to prevent generation of additional noise. The vent holes may be circular.

The holes of the vent 3400 may decrease in radius from the interior of the plenum chamber 3200 to the exterior. Each vent hole is provided with a draft angle. Each hole has a smaller diameter at its anterior end than at its posterior end. The draft angle means that the holes do not have a small cross section across the entire chassis thickness, which helps to provide effective carbon dioxide wash out at high levels of humidification. Additionally, a larger draft angle may result in a plenum chamber 3200 that is easier to manufacture, especially when the plenum chamber 3200 is formed from an injection moulded plastics material. The draft angle enables relatively thick vent pins to be used in the mould and easier ejection.

The holes of the vent 3400 may be provided in two sets towards the middle of the plenum chamber 3200 and the sets may be symmetrical across the centreline of the plenum chamber 3200. Providing a pattern of multiple vent holes may reduce noise and diffuse the flow concentration.

The holes of the vent 3400 may be placed at an optimum distance away from the centreline of the plenum chamber 3200. Placing the holes of the vent 3400 towards the centreline may advantageously reduce the chance that the vent holes are blocked when the patient is sleeping on their side. However, placing the vent holes too close to the middle of the plenum chamber 3200 may result in excessive weakening of the plenum chamber 3200 at the centre, especially since the cross-section of the plenum chamber 3200 in the depicted examples is smallest at the centre due to the overall shape of the plenum chamber 3200. The location of the holes of the vent 3400 may avoid hole blockage during side sleep while leaving the middle section of the chassis sufficiently strong.

The size of each vent hole and the number of vent holes may be optimised to achieve a balance between noise reduction while achieving the necessary carbon dioxide washout, even at extreme humidification. In the depicted examples, the vent holes of the vent 3400 may not provide the total amount of venting for the system. The decoupling structure 3500 may include a decoupling structure vent 3402. The decoupling structure vent 3402 may include one hole or a plurality of holes through the decoupling structure 3500. The decoupling structure vent 3402 may function to bleed off excess pressure generated by the RPT device 4000 before reaching the patient, while the vent 3400 may function to washout carbon dioxide exhaled by the patient during therapy.

FIGS. 31 and 32 show an alternative example of the vent 3400 in which holes are provided to a vent insert 13400 that attaches, removably or permanently, to the plenum chamber 3200 at a vent insert opening. The vent insert 13400 may be constructed from a material that is more flexible than the material of the plenum chamber 3200.

5.3.3.3 Decoupling Structure(s)

In one form the patient interface 3000, 6000, 9000 includes at least one decoupling structure, for example, a swivel or a ball and socket.

The hub 3306, described above, is connected to a decoupling structure 3500, which is a rotatable elbow in these examples. The decoupling structure 3500 may be rotatable 360° within the hub 3306 in use. The decoupling structure 3500 may be removable from the hub 3306 by manually depressing buttons 3504 to release catches (not shown) from within the hub 3306.

The decoupling structure 3500 may also include a swivel 3502 that allows for rotatable connection to an air circuit 4170.

The rotatability of the decoupling structure 3500, the decoupling structure 3500 being in the form of an elbow, and the rotatability of the swivel 3502 on the decoupling structure 3500 may all increased the degrees of freedom, which in turn reduce tube drag and torque on the patient interface 3000 caused by the connection to the air circuit 4170.

5.3.3.4 Connection Port

Connection port 3600 allows for connection to the air circuit 4170.

5.3.3.5 Forehead Support

In one form, the patient interface includes a forehead support 3700.

5.3.3.6 Anti-Asphyxia Valve

In one form, the patient interface includes an anti-asphyxia valve.

5.3.3.7 Ports

In one form of the present technology, a patient interface 3000, 6000, 9000 includes one or more ports that allow access to the volume within the cavity 3101. In one form this allows a clinician to supply supplemental oxygen. In one form, this allows for the direct measurement of a property of gases within the cavity 3101, such as the pressure.

5.3.4 Full Face Cushion 5.3.4.1 First Illustrated Example

Referring to FIGS. 39-50, patient interface 14000 includes cushion assembly 14105 having a seal-forming structure 14100 that is configured to seal separately around the patient's nares and mouth, i.e., an oro-nasal cushion assembly or ultra-compact full face mask. The cushion assembly 14105 is at least partially formed by a plenum chamber 14200 and a seal-forming structure 14100 that is attached to the plenum chamber in accordance with an example of the present technology.

Referring to FIGS. 51-56, a cushion assembly 31105 is shown. Cushion assembly 31105 is similar to cushion assembly 14105 and has a seal-forming structure 31100 that is configured to seal separately around the patient's nares and mouth, i.e., an oro-nasal cushion assembly or ultra-compact full face mask. The cushion assembly 31105 is at least partially formed by a plenum chamber 31200 and a seal-forming structure 31100 that is attached to the plenum chamber in accordance with an example of the present technology.

The cushion assembly 31105 includes nasal portion 31101, nasal portion holes 31103, oral portion 31102, oral portion hole 31104, cavity 31001, support structure 31120, sealing portion 31130, and vent 31400 which are similar to the features described in FIGS. 39-50 and are not discussed separately. A pair of plenum chamber holes are configured to receive a flow of air.

As described earlier, FIGS. 54-56 show grip pads 31150 on the surface of the textile membrane.

Plenum Chamber

The plenum chamber 14200 has a perimeter that is shaped to be complementary to the surface contour of the face of an average person in the region where a seal will form in use. In use, a marginal edge of the plenum chamber 14200 is positioned in close proximity to an adjacent surface of the face. Actual contact with the face is provided by the seal-forming structure 14100. The seal-forming structure 14100 may extend in use about the entire perimeter of the plenum chamber 14200.

In certain forms of the present technology, the plenum chamber 14200 is constructed from a relatively rigid material (e.g., polycarbonate) as compared to the seal-forming structure. In another example, the plenum chamber 14200 may be constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 14200 is constructed from a translucent material. The use of a translucent material can reduce the obtrusiveness of the patient interface, and help improve compliance with therapy.

The plenum chamber 14200 according to examples of the present technology may include a plenum chamber hole on each lateral side. The plenum chamber hole may provide pneumatic communication between the conduit connectors 14800, which are described in greater detail below, and the cavity 14001. A connection rim portion around each plenum chamber hole may facilitate a mechanical connection, e.g., snap-fit or friction fit, with the respective conduit connector. The plenum chamber 14200 may be constructed of a sufficiently rigid material to provide audible and/or tactile feedback to the patient when the conduit connectors 14800 are connected to or removed from the plenum chamber 14200.

The seal-forming structure 14100 may be sealingly connected to the plenum chamber 14200. The connection may be permanent or the seal-forming structure 14100 may be removable from the plenum chamber 14200. The seal-forming structure 14100 may be overmoulded to the plenum chamber 14200. The seal-forming structure 14100 and the plenum chamber 14200 may be joined by a mechanical connection in which no chemical bond is formed between the plenum chamber 14200 and the seal-forming structure 14100.

Seal-Forming Structure

Referring to FIGS. 39-50, the seal-forming structure 14100 may include a nasal portion 14101 having a pair of nasal portion holes 14103 to seal with the patient's nares.

The depicted examples provide two separate holes 14103 that each corresponds to one of the patient's nares to provide the flow of air to both of the patient's nares. There may also be a bridge portion 14106 positioned between the naris openings 14103. In an alternative example, a single hole may be used to provide the flow of air to both of the patient's nares.

The seal-forming structure 14100 may include an oral portion 14102 having an oral portion hole 14104 to seal with the patient's mouth.

The seal-forming structure 14100 may at least partly form a cavity 14001 that is pressurized by the flow of air. The plenum chamber 14200 may be joined to the seal-forming structure 14100 to further form the cavity 14001.

The seal-forming structure 14100 may include a support structure 14120 that provides support to a sealing portion 14130 (e.g., a textile membrane). The sealing portion is configured to sealingly engage the patient's face. Also, depending on the size and contours of the patient's nose, the support structure may also sealingly engage the patient's face.

The support structure 14120 may comprise a wall structure having at least two regions of different thicknesses (e.g., portions of the support structure adjacent to or connecting to the plenum chamber 14200 may be thicker than portions of the support structure adjacent to or connecting to the sealing portion 14130 so as to provide structural stability at the connection with the plenum chamber 14200 and flexibility at the interface with the patient). FIG. 84 illustrates an example where portions (d1) of the support structure may be thicker than portions (d2) of the support structure. For example, portions (d1) may be adjacent to or connection to the plenum chamber and portions (d2) may be adjacent to or connecting to the sealing portion so as to provide structural stability at the connection with the plenum chamber and flexibility at the interface with the patient. Alternatively, the thicker lateral support regions 3122 may be located, for example, at the corner of nose region and/or regions of the oral portion of the seal-forming structure (and e.g., may connect directly to the textile membrane), to ensure adequate sealing in the subalare region and/or mouth region of the patient's face.

As described above, the seal-forming structure 14100 may be sealingly connected to the plenum chamber 14200. The support structure 14120 may be less rigid than the plenum chamber 14200 and may be constructed from silicone, foam (e.g., polyurethane foam), polyurethane solid material, thermoplastic elastomers (e.g., thermoplastic polyurethane), suitable plastics, or other suitable materials, as will be described later. Further, the sealing portion 14130 may be less rigid than the support structure 14120 and may be constructed from a textile material such as nylon, polyester, nylon and polyester mix, microfiber or polyurethane, for example, as will be described in more detail later.

The support structure 14120 may have an aperture formed therein providing an inner edge of the support structure along which the sealing portion 14130 (e.g., an outer perimeter of the sealing portion) may be attached to the support structure such that the sealing portion extends radially inwardly of the seal-forming structure beyond or to a further extent than the support structure, as shown for example in FIGS. 43-46. For example, the sealing portion may be molded around the inner edge of the support structure or connected to the support structure in other suitable ways, as will be described later.

In the example of FIG. 49, the support structure 14120 may extend into the cavity 14001 forming an underlying cushion 14121 to provide support to the sealing portion 14130. The underlying cushion 14121 and the sealing portion 14130 may form a dual wall structure around the perimeter of sealing portion. In alternative examples, a second or third underlying cushion layer may be provided to form a triple or quadruple wall structure. In the example of FIG. 49, the underlying cushion is constructed of a foam material (e.g., polyurethane foam). In an alternative example, the underlying cushion 14122 may be constructed of silicone, as shown in FIG. 50. However, it will be recognized that the underlying cushion may be constructed from other suitable materials (e.g., textile).

It should also be appreciated that one or more aspects of the present technology may be combinable with one or more aspects of: U.S. Provisional Application No. 62/609,909, filed Dec. 22, 2017 or WO 2019/119058, filed Dec. 21, 2018, both entitled "Conduit Headgear Connector for Patient Interface," Each of which is hereby incorporated herein by reference in its entirety For instance, the conduits and positioning and stabilizing structures of the present technology may be identical to the conduits and positioning and stabilizing structures in any of the embodiments of the '909 or '058 application. Additionally, the cushion assemblies and seal-forming structures disclosed herein may replace any of the cushion assemblies (seal-forming structures and plenum chamber) and seal-forming structures in any of the patient interfaces disclosed in the '909 or '058 application.

5.3.4.1.1 Positioning and Stabilising Structure

The seal-forming structure 14100 of the patient interface 14000 of the present technology may be held in sealing position in use by the positioning and stabilising structure 14300.

In one form the positioning and stabilising structure 14300 provides a retention force at least sufficient to overcome the effect of the positive pressure in the cavity 14001 to lift off the face.

In one form the positioning and stabilising structure 14300 provides a retention force to overcome the effect of the gravitational force on the patient interface 14000.

In one form the positioning and stabilising structure 14300 provides a retention force as a safety margin to overcome the potential effect of disrupting forces on the patient interface 14000, such as from tube drag, or accidental interference with the patient interface.

In one form of the present technology, a positioning and stabilising structure 14300 is provided that is configured in a manner consistent with being worn by a patient while sleeping. In one example the positioning and stabilising structure 14300 has a low profile, or cross-sectional thickness, to reduce the perceived or actual bulk of the apparatus. In one example, the positioning and stabilising structure 14300 comprises at least one strap having a rectangular cross-section. In one example the positioning and stabilising structure 14300 comprises at least one flat strap.

In one form of the present technology, a positioning and stabilising structure 14300 is provided that is configured so as not to be too large and bulky to prevent the patient from lying in a supine sleeping position with a back region of the patient's head on a pillow.

In one form of the present technology, a positioning and stabilising structure 14300 is provided that is configured so as not to be too large and bulky to prevent the patient from lying in a side sleeping position with a side region of the patient's head on a pillow.

In one form of the present technology, a positioning and stabilising structure 14300 is provided with a decoupling portion located between an anterior portion of the positioning and stabilising structure 14300, and a posterior portion of the positioning and stabilising structure 14300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 14300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 14300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure may include a first tie (e.g., upper strap 14302 (FIG. 41)), the first tie being constructed and arranged so that in use at least a portion of an inferior edge thereof passes superior to an otobasion superior of the patient's head.

In one form of the present technology suitable for a full-face mask, the positioning and stabilising structure includes a second tie (e.g., lower strap 14303 (FIG. 41)), the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie (e.g., strap connector 14304 (FIG. 39)) that is constructed and arranged to interconnect the first tie and the second tie to reduce a tendency of the first tie and the second tie to move apart from one another.

In certain forms of the present technology, a positioning and stabilising structure 14300 comprises a strap that is bendable and e.g. non-rigid. An advantage of this aspect is that the strap is more comfortable for a patient to lie upon while the patient is sleeping.

In certain forms of the present technology, a positioning and stabilising structure 14300 comprises a strap constructed to be breathable to allow moisture vapour to be transmitted through the strap, In certain forms of the present technology, a system is provided comprising more than one positioning and stabilizing structure 14300, each being configured to provide a retaining force to correspond to a different size and/or shape range. For example, the system may comprise one form of positioning and stabilizing structure 14300 suitable for a large sized head, but not a small sized head, and another suitable for a small sized head, but not a large sized head.

The positioning and stabilising structure 14300 may include a clip 14301 to secure respective ties, e.g., to the conduit connectors 14800 as shown in FIG. 39. The clip 14301 and the conduit connector 14800 may each include a magnet arranged with opposing polarities to facilitate a connection therebetween.

5.3.4.1.2 Vent

In one form, the patient interface 14000 includes a vent 14400 constructed and arranged to allow for the washout of exhaled gases, e.g. carbon dioxide, as shown in FIG. 39.

In certain forms, the vent 14400 is configured to allow a continuous vent flow from an interior of the plenum chamber 14200 to ambient whilst the pressure within the plenum chamber is positive with respect to ambient. The vent 14400 is configured such that the vent flow rate has a magnitude sufficient to reduce rebreathing of exhaled $CO_2$ by the patient while maintaining the therapeutic pressure in the plenum chamber in use.

One form of vent 14400 in accordance with the present technology comprises a plurality of holes, for example, about 20 to about 80 holes, or about 40 to about 60 holes, or about 45 to about 55 holes.

A vent 3400 may be located in the plenum chamber 14200, as shown in FIG. 47. Alternatively, the vent 14400 is located in a decoupling structure, e.g., a swivel.

FIG. 39 shows an example of a vent 14400 provided on the connection port 14600 (e.g., a swivel elbow). Variations of these examples may exclude a vent 14400 from the connection port 14600.

The conduit connectors 14800, which are described in greater detail below, may also include vent features.

5.3.4.1.3 Decoupling Structure(s)

In one form, the patient interface 14000 includes at least one decoupling structure, for example, a swivel or a ball and socket.

5.3.4.1.4 Connection Port

Connection port 14600 allows for connection to the air circuit 4170. The connection port 14600 according to an example of the present technology may be connected to the connection port housing 14903. The connection port 14600 may be swivelable relative to the connection port housing 14903 and the connection to the air circuit 4170 may also be swivelable.

The connection port 14600 and the connection port housing 14903 may be positioned superior to the patient's head in use.

5.3.4.1.5 Forehead Support

Examples of the patient interface of the present technology shown in FIGS. 39-50 do not include a forehead support. Variations of the patient interface of the present technology may include a forehead support.

5.3.4.1.6 Conduits

The patient interface 14000 according to examples of the present technology may include conduits 14900 to provide the flow of pressurized air from the connection port 14600 to the cavity 14001 in the plenum chamber 14200. The conduits 14900 may be joined superior to the patient's head at the connection port housing 14903 and may pass along lateral sides of the patient's head between corresponding ones of the patient's eyes and ears. The conduits 14900 may be connected to the cushion assembly 14105 (e.g., plenum chamber 14200) via conduit connectors 14800, as described below, to provide the flow of pressurized air to the cavity 14001.

The conduits 14900 may also stabilize and position the seal-forming structure 14100 on the patient's face. Thus, the conduits 14900 may function similarly to the ties of the positioning and stabilising structure 14300. Accordingly, the mechanical connection of the conduits 14900 to the conduit connectors 14800 may be sufficient for tension forces in the conduits 3900 to be transmitted to the seal-forming structure 14100 through the conduit connectors 14800.

The conduits 14900 may include features of similar conduits disclosed in International Application Publication No. WO 2017/124155 A1, which is hereby incorporated by reference herein in its entirety. For example, the conduits 14900 of the present technology may include features of the headgear tubes 3350 depicted in FIGS. 3A-3L of this document, as well as the associated written description.

The conduits 14900 may also be provided with sleeves 14901 to cushion the patient's face against the conduits 14900. The sleeves 14901 may be removable. The sleeves 14901 may be made from a breathable material.

The conduits 14900 may also include tie connectors 14902 to facilitate connection with ties of the positioning and stabilising structure 14300.

5.3.4.1.7 Conduit Connectors

The patient interface 14000, according to examples of the present technology, may include conduit connectors 14800 to connect the conduits 14900 to the cushion assembly 14105 to provide the flow of pressurized air to the cavity 14001. The conduit connectors 14800 may each be formed with a conduit connector housing 14801. The conduit connectors 14800 may provide other functions, as described below, such as venting of the plenum chamber 14200, connection to the positioning and stabilising structure 14300, and asphyxia prevention by inclusion of an anti-asphyxia valve 14850.

FIG. 43-50 show several views of the conduit connectors 14800 of the patient interface 14000, according to examples of the present technology.

In FIGS. 39-50, the conduit connectors 14800 are shown attached to the plenum chamber 14200 at the plenum chamber holes (not shown). As can be seen, there is one conduit connector 14800 on each lateral side of the cushion assembly 14105, and each conduit connector 14800 is connected to a plenum chamber hole on each corresponding lateral side of the cushion assembly 14105. The conduit connectors 14800 may each include a conduit connector attachment structure to connect each of the conduit connectors 14800 to a respective plenum chamber hole at the connection rim (not shown). The connection may be mechanical, e.g., snap-fit or friction fit. The connection may also be removable. The material of the conduit connectors 14800 and the material of the plenum chamber 14200 may each be selected to facilitate the desired connection features. For example, the material of the conduit connectors 14800 and the material of the plenum chamber 14200 may each be relatively rigid to permit the audible and/or tactile feedback associated with a snap-fit. The material of the conduit connectors 14800 and the material of the plenum chamber 14200 may be different in at least one aspect or the materials may be the same. The conduit connectors 14800 may also be permanently connected to the plenum chamber at the plenum chamber holes. For example, the conduit connectors 14800 may be ultrasonically welded to the plenum chamber 14200. The connection between the conduit connectors 14800 and the plenum chamber 14200, whether removable or permanent, may also be designed to be sufficiently strong such that tension from the conduits 14900 can be transferred to the plenum chamber 14200 without disrupting the connection because, as explained above, the conduit connectors 14800 may facilitate positioning and stabilising of the seal-forming structure 14100 on the patient's head.

The conduit connectors 14800 may also be attached to lateral sides of the plenum chamber 14200 to improve aesthetics of the patient interface 14000. As explained above, the plenum chamber 14200 may be constructed of a transparent or translucent material, which may allow visibility of the patient's facial features. By locating the conduit connectors 14800 laterally on the plenum chamber, e.g., as shown in the depicted examples, more of the patient's face is visible, and that arrangement can improve aesthetics of the patient interface 14000. This contrasts with alternative designs where an elbow and air circuit may be joined to the center of the plenum chamber 14200, thereby obstructing the view of the patient's face.

The conduit connectors 14800 may also each include a conduit connection end 14802 that connects to a respective conduit 14900. The connection between the conduits 14900 and the conduit connectors 14800 at the conduit connection ends 14802 may be removable or permanent. A conduit connector inlet hole 14803 may be formed in the conduit connector housing 14801 at the conduit connection end 14802 to receive the flow of pressurized air. The conduit connectors 14800 may include structure, e.g., an undercut, to facilitate a removable, snap-fit connection with corresponding conduits 14900, and each conduit 14900 may include a relatively rigid structure at the end that connects to the conduit connectors 14800 to facilitate such a connection. The conduit connectors 14800 may also be joined to the conduits 14900 with a friction fit. Again, as explained above, the conduits 14900 may provide a positioning and stabilising function to locate the seal-forming structure in a therapeutically effective sealing position on the patient's face, and therefore the connection between the conduits 14900 and the conduit connectors 14800 at the conduit connection ends 14802 may be sufficiently secure to permit tension forces from the conduits 14900 to be transmitted to the conduit connectors 14800 without disrupting the connection between the conduits 14900 and the conduit connectors 14800 at the conduit connection ends 14802.

The conduit connectors 14800 may also provide a venting function for the patient interface 14000. The conduit connector housing 14801 may include a vent inlet that is in pneumatic communication with the cavity 14001 when the patient interface 14000 is assembled. The conduit connector housing 14801 may also include at least one conduit connector vent hole 14831. As can be seen in the depicted examples, each conduit connector housing 14801 includes a plurality of conduit connector vent holes 14831. This ensures adequate mixing of newly introduced air and air already present in the plenum chamber 14200, which can enhance carbon dioxide washout and increase the amount of fresh air provided to the patient for respiration.

As shown in FIG. 39-41, the conduit connectors 3800 may also provide a connection to ties of the positioning and stabilising structure 3300. The inferior ties may be joined to the conduit connectors 3800 with clips 14301. The clips 14301 and the conduit connectors 14800 may include magnets with opposing polarities to facilitate the connection. The connection between the ties of the positioning and stabilising structure 14300 and the conduit connectors 14800 may be releasable. The tension from the inferior ties of the positioning and stabilising structure 14300 may urge inferior portions of the seal-forming structure 14100 into sealing engagement with the patient's face, e.g., around the mouth. Alternatively, structure to connect to the clips 14301 may be formed directly on the conduit connector housing 14801.

5.3.4.1.8 Anti-Asphyxia Valve

In one form, the patient interface 14000 includes an anti-asphyxia valve. As best shown in FIGS. 47 and 48, each of the conduit connectors 14800 may include an anti-asphyxia valve assembly 14850. Accordingly, the patient interface 14000 may include two anti-asphyxia valve assemblies 14850. Each of the anti-asphyxia valve assemblies 14850 may operate independent of the other, i.e., in response to a cessation of the flow of pressurized air. For example, if the patient is sleeping on his or her side when there is a cessation of the flow of pressurized air and one of the anti-asphyxia valve assemblies 14850 is occluded, e.g., by a pillow, the other of the anti-asphyxia valve assemblies 14850 can function to prevent the patient from being asphyxiated.

5.3.4.1.9 Ports

In one form of the present technology, a patient interface 14000 includes one or more ports that allow access to the volume within the plenum chamber 4200. In one form this allows a clinician to supply supplemental oxygen. In one form, this allows for the direct measurement of a property of gases within the plenum chamber 14200, such as the pressure.

5.3.4.2 Second Illustrated Example

FIGS. 57 to 66 show a patient interface 30000 according to another example of the present technology. Patient interface 30000 includes cushion assembly 30105 having a seal-forming structure 30100 that is configured to seal separately around the patient's nares and mouth, i.e., an oro-nasal cushion assembly or ultra-compact full face mask. The cushion assembly 30105 is at least partially formed by a plenum chamber (or shell) 30200 and a seal-forming structure 30100 that is attached to the plenum chamber in accordance with an example of the present technology.

The cushion assembly 30105 includes nasal portion 30101, nasal portion holes 30103, oral portion 30102, oral portion hole 30104, cavity 30001, support structure 30120, and sealing portion 30130 which are similar to the features described in FIGS. 39-56 and are not discussed separately. An inlet port 30240 is formed in the plenum chamber and is configured to receive a flow of air for an air circuit.

5.3.4.2.1 Positioning and Stabilising Structure

FIGS. 57-66 show a patient interface 30000 according to one example of the present technology having a positioning and stabilising structure 30300 and a plenum chamber 30200 having a seal forming structure 30100. The positioning and stabilising structure 30300 in this example comprises a frame 30350 and a plurality of headgear straps connected to the frame 30350.

The plenum chamber 30200 of the patient interface 30000 is connected to the frame 30350. The plenum chamber 30200 may connect to the frame 30350 via a snap fit connection. In other examples, the plenum chamber may form a different type of removable connection to the frame, snap fit, removable press fit or otherwise, or may be permanently connected to the frame.

The positioning and stabilising structure 30300 may comprise a plurality of straps or strap portions connecting to the frame 30350 and passing around the patient's head in order to support the plenum chamber in sealing position against the patient's face. It will be understood that a single "strap" may be formed by multiple lengths of material(s) that have been cut or formed separately and then joined together at their ends to create a longer length or single "strap" may be a single length of material(s).

In the example illustrated in FIGS. 57-66, the positioning and stabilising structure 30300 comprises a pair of upper straps 30310. Each upper strap is configured to pass between a respective eye and ear of the patient. Additionally, the positioning and stabilising structure comprises a pair of lower straps 30320 configured to lie over the patient's cheeks below the patient's cheekbones. In this example, the plenum chamber is held in position via a four-point connection to headgear straps via the frame 30350.

The frame is shown in isolation in FIGS. 63-64. The frame comprises a frame inlet connection port 30354. The frame inlet connection port 30354 may be configured to connect to a source of pressurised breathable gas, such as air. In one example, the frame inlet connection port 30354 may be configured to enable connection to a swivel elbow assembly 30610 which provides a connection port 30600 for connection with an air circuit 4170. The frame inlet connection port in this example comprises a connection rim 30355. The connection rim 30355 may comprise a radially outwardly extending flange. The swivel elbow assembly 30610 may form a releasable snap-fit with the connection rim, creating a fluid connection between the swivel elbow assembly and the frame. The opposite side of the frame inlet connection port 30354 is configured to fluidly connect to the plenum chamber. The frame 30350 therefore enables a fluid connection between the swivel elbow assembly 30610 and the interior of the plenum chamber 30200.

The frame 30350 also comprises a pair of opposed upper strap connection points 30315 to which the upper straps 30310 connect. In this example, each upper strap connection point comprises an aperture formed in the frame. Each upper strap 30310 is able to connect to a respective upper strap connection point 30315 by passing through the aperture, looping back onto itself and securing to itself. Each upper strap may secured to itself via hook and loop materials configured to releasably bind to each other upon contact. In alternative examples, each upper strap 30310 may pass through a respective aperture, loop back onto itself and be secured onto itself with a band, clip or the like. In further alternative examples, the upper straps may connect to the frame via side release buckle connections.

The frame 30350 also comprises a pair of opposed lower strap connection points 30325 to which the lower straps 30320 connect. In this example, each lower strap connection point comprises a magnet. Each lower strap comprises a lower strap clip 30326 comprising a magnet or material that is attracted to the magnet at the lower strap connection point 30325. In this example, each lower strap clip 30326 comprises an aperture through which the end of a respective lower strap is able to pass and then loop back and be secured onto itself, for example with hook and loop material, a band, a clip or the like. In alternative examples, the lower straps may connect to the frame via side release buckle connections, onto hooks or via any other suitable connection.

In an example, the frame 30350 and upper strap connection points 30315 are structured and arranged to direct a force/tension provided by the upper straps 30310 into a partially superior and partially posterior force vector applied to the plenum chamber 30200. The partially superior and partially posterior force vector urges, in particular, the nasal portion 30101 of the seal forming structure 3100 into sealing contact with the lower periphery of the patient's nose and the patient's upper lip.

The upper straps 30310 may each be selectively adjustable. For example, the effective length of each of the upper straps may be varied by changing how much of the upper strap is passed through the aperture at the respective upper strap connection point 30315 and looped back on itself. Passing more of the upper strap through the aperture effectively reduces the length of the upper strap, allowing the force vectors to be modified and the fit of the patient interface to be adjusted.

In an example, the frame 30350 and the lower strap connection points 30325 are structured and arranged to direct a force/tension provided by the lower straps 30320 into a partially posterior and partially inferior force vector applied to the plenum chamber. The partially posterior and partially inferior force vector urges, in particular, the oral portion 30102 into sealing contact with the patient's face around the periphery of the patient's mouth. The partially inferior force applied to the frame by the lower straps may balances the partially superior force applied by the upper straps along with any inferiorly directed force that the patient's nose may apply onto the seal forming structure.

The lower straps 30320 may each by selectively adjustable. For example, the effective length of each of the lower straps may be varied by changing how much of each lower strap is passed through the aperture in the respective lower strap clip 30326 and looped back on itself. Passing more of each lower strap through the aperture effectively reduces the length of the lower strap, allowing the force vectors to be modified and the fit of the patient interface to be adjusted.

The positioning and stabilising structure 30300 may also comprise one or more of a top crown strap 30330, a pair of lateral crown straps 30332 and a neck strap 30334. In the example illustrated in FIGS. 57-66, the upper straps 30310 and lower straps 30320 are connected to ends of a top crown strap 30330. The top crown strap is configured to pass around the patient's head and lie against superiorly and posteriorly facing surfaces. The top crown strap 30330 may be configured to overlie the parietal bone of the patient's skull. Each end of the top crown strap connects to a respective one of the upper straps 30310 and also to a respective one of a pair of lateral crown straps 30332. Each one of the lateral crown straps connects between the upper strap and the lower strap on a respective side of the patient's head. The inferior ends of the lateral crown straps 30332 are connected to each other by a neck strap 30334. The neck strap may be configured to pass across the sagittal plane and lie against inferior and/or posterior facing surfaces of the patient's head or lie against the back of the patient's neck. The neck strap may overlie, or lie inferior to, the occipital bone of the patient's skull.

The length of the top crown strap 30330 may be selectively adjustable. The top crown strap 30330 is formed by two strap portions which are connected by a link having a pair of apertures. Each of the two strap portions forming the top crown strap is able to pass through a respective one of the apertures then loop back and secure to itself, for example via hook and loop material, a further clip, a band or the like. The amount of each top strap portion that passes through the link can be varied to adjust the length of the top crown strap 30330 and in turn adjust the fit of the positioning and stabilising structure.

Once all the headgear straps have been adjusted and the desired fit of the patient interface 30000 has been achieved, the magnetic clip connection provided by the lower strap clips 30326 enables the lower straps 30320 to be quickly disengaged from the lower strap connection points 30325 on the frame 30350, allowing the patient interface 30000 to be removed from the patient without adjustment of straps. Similarly, when the patient dons the patient interface again, the lower strap clips can be quickly engaged at the lower strap connection points to fit the patient interface without the need to adjust straps. Further advantages and features of a positioning and stabilising structure comprising magnetic clips are described in WO 2014/110622, the entire contents of which are incorporated herein by reference.

In certain forms of the present technology, a system is provided comprising more than one positioning and stabilizing structure, each being configured to provide a retaining force to correspond to a different size and/or shape range. For example the system may comprise one form of positioning and stabilizing structure suitable for a large sized head, but not a small sized head, and another. Suitable for a small sized head, but not a large sized head.

Also, it should be appreciated that one or more aspects of the present technology may be combinable with one or more aspects of: PCT/AU2019/050278, filed Mar. 28, 2019 and entitled "Patient Interface," the entire contents of which are hereby incorporated herein by reference in their entirety.

5.3.4.2.2 Vent

In one form, the patient interface 30000 includes a vent 30400 constructed and arranged to allow for the washout of exhaled gases, e.g. carbon dioxide.

In certain forms the vent 30400 is configured to allow a continuous vent flow from an interior of the plenum chamber 30200 to ambient whilst the pressure within the plenum chamber is positive with respect to ambient. The vent is configured such that the vent flow rate has a magnitude sufficient to reduce rebreathing of exhaled $CO_2$ by the patient while maintaining the therapeutic pressure in the plenum chamber in use.

One form of vent in accordance with the present technology comprises a plurality of holes, for example, about 20 to about 80 holes, or about 40 to about 60 holes, or about 45 to about 55 holes.

The vent 30400 may be located in the plenum chamber. Alternatively, the vent is located in a decoupling structure, e.g., a swivel.

In the example illustrated in FIGS. 57-66, the patient interface 30000 comprises a vent 30400. The vent in this example comprises passages within the frame and swivel elbow assembly through which air can flow from the interior of the plenum chamber to atmosphere. As shown in FIG. 59, air can flow into the swivel elbow assembly 30610 and then out to atmosphere through exterior holes of the swivel elbow assembly forming part of the vent 30400. The swivel elbow assembly 30610 may be substantially as described in International Publication No. WO 2017/049357 A1, the entire contents of which are incorporated herein by reference.

5.3.4.2.3 Decoupling Structure(s)

In one form the patient interface 30000 includes at least one decoupling structure, for example, a swivel or a ball and socket.

5.3.4.2.4 Connection Port

Connection port 30600 allows for connection to the air circuit 4170.

5.3.4.2.5 Forehead Support

In one form, the patient interface 30000 includes a forehead support 3700 such as that shown in FIG. 3A. In other examples, the patient interface may exclude a forehead support. Furthermore, the patient interface 30000 may be configured not to contact the patient's forehead at all.

5.3.4.2.6 Anti-Asphyxia Valve

In one form, the patient interface 30000 includes an anti-asphyxia valve.

5.3.4.2.7 Ports

In one form of the present technology, a patient interface 30000 includes one or more ports that allow access to the volume within the plenum chamber. In one form this allows a clinician to supply supplemental oxygen. In one form, this allows for the direct measurement of a property of gases within the plenum chamber 302000, such as the pressure.

5.3.4.3 Third Illustrated Example

FIGS. 67 to 77 show a patient interface 16000 according to another example of the present technology. The patient interface includes a frame assembly 16100, a cushion assembly 16175 including a seal-forming structure 16200, an air delivery connector (e.g., elbow assembly 16600), and a positioning and stabilising structure (e.g., headgear 16800 including upper side straps 16802, lower side straps 16804, and crown strap 16806). In use, one form of the seal-forming structure 16200 is arranged to surround an entrance to the airways of the patient 1000 so as to facilitate the supply of air at positive pressure to the airways. In the example shown in FIGS. 46-56, the patient interface is a full-face/oro-nasal interface type including a seal-forming structure 16200 structured to form a seal around the patient's nose and mouth. However, aspects of the present technology may be adapted for use with other suitable interface types, e.g., nasal interface, nasal prongs, pillows, etc.

The seal-forming structure 16200 may also be commonly referred to as a cushion. FIGS. 67 and 68 are exemplary views of the patient interface 16000 with arm covers 16750 for upper arms 16134 of the frame assembly 16100 attached, and FIG. 69 is an exemplary view of the patient interface 16000 with the headgear 16800 and the arm covers 16750 removed.

In this example, the cushion assembly 16175 connects to the frame assembly 16100 (via a first retention feature on the frame assembly) independently of the elbow assembly 16600, and the elbow assembly 16600 connects to the frame assembly 16100 (via a second retention feature on the frame assembly) independently of the cushion assembly 16175. That is, the retention connections of the cushion assembly 16175 and the elbow assembly 16600 to the frame assembly 16100 are separate and distinct from one another and allow independent engagement/disengagement.

In the example of patient interface 16000, a first seal for the air flow path is formed between the elbow assembly 16600 and the frame assembly 16100, and a separate second seal is formed between the frame assembly 16100 and the cushion assembly 16175. In this example, the frame assembly 16100 is provided in the air flow path. That is, the elbow assembly 16600 is structured to establish a hard-to-hard connection and dynamic seal with the frame assembly 16100, and the cushion assembly 16175 is structured to establish a separate hard-to-hard connection and static seal with the frame assembly 16100.

Also, in the example of patient interface 16000, the frame assembly 16100 includes a lockout feature along the opening 16105 that is structured and arranged to prevent direct connection or insertion of the air circuit 4170, e.g., air delivery tube. This arrangement requires use of the elbow assembly 16600 to interconnect the frame assembly 16100 and the air circuit 4170, thereby ensuring that the elbow assembly 16600 (and its vent and anti-asphyxia valve (AAV)) are present in the system.

Frame Assembly

Still referring to FIGS. 67-77, the frame assembly 16100 includes a shroud or wall member 16110, a pair (i.e., right and left) of upper headgear connector arms 16134 (each comprising two flexible portions 16140, 16145) extending from respective sides of an upper portion of the shroud 16110, and a pair (i.e., right and left) of lower headgear connector arms 16154 extending from respective sides of a lower portion of the shroud 16110. Each lower headgear connector arm 16154 comprises the magnetic connector 16155 (including encased magnet) structured to locate and connect to the headgear clip 16160 (including encased magnet) provided to the respective lower headgear strap 16804 of the headgear.

In the illustrated example, the opening 16105 of the shroud 16110 (e.g., constructed of a relatively hard plastic material such as polycarbonate) is bounded by an outer annular flange and an inner annular flange.

Cushion Assembly & Elbow Assembly

Referring to FIGS. 67-77, the cushion assembly 16175 includes a main body, chassis, plenum chamber or shell 16180 that is connected or otherwise provided to the seal-forming structure or cushion 16200 (see FIGS. 70 and 71). The shell 16180 may be permanently (e.g., co-molded, overmolded) or removably (e.g., mechanical connection) connected to the cushion 16200. In an example, the cushion 16200 is constructed of a relatively flexible or pliable material and the shell 16180 is constructed of a relatively rigid material (e.g., polycarbonate). The shell 16180 and the cushion 16200 cooperate to form the cavity 16500 (e.g., see FIGS. 70, 71 and 73). The shell 16180 includes an opening 16305 by which breathable gas is delivered to the cavity 16500. The opening 16305 is bounded by an annular flange 16310 which is adapted to connect to the frame assembly 16100.

The shell 6180 has multiple functions. For example, it at least partially forms the cavity for delivery of pressurised gases to the entrance of a patient's airways. The shell 6180 is a rigid structure that directs a force onto the seal-forming structure for sealing to a patients face. The force is provided by tension forces from tightening the headgear straps. These forces are translated from a pair of upper and lower headgear straps to the corresponding upper and lower arms. In an example, the upper and lower arms are provided with the frame assembly, which provides the headgear tension forces to the shell 16180.

The shell 16180 of the cushion assembly 16175 is repeatedly engageable with and removably disengage able from the shroud 16110 of the frame assembly 16100 via a mechanical connection, e.g., snap-fit connection. The inner annular flange of the shroud 16110 extends through the opening 16305 of the shell 16180, and the tabs or catches of the flange engage or interlock on a posterior side of the annular flange 16310 of the shell 16180 so as to releasably connect the frame assembly 16100 to the cushion assembly 16175. Such connection maintains ease of use, provides a sealed hard to hard connection, minimizes rattling and rocking movement between components, and reduces impact on stability. Also, such connection stably holds the cushion assembly 16175 in position, while allowing the appropriate force vectors to be imparted onto the cushion assembly 16175 for seal.

In the example shown in FIG. 67, the elbow assembly 16600 includes a first end portion 16610 with pinch arms 16650 to releasably engage with the frame assembly 16100 (and form a swivel connection therewith) and a second end portion 16620 adapted to connect to the air circuit 4170, e.g., via a swivel connector 16625. The elbow assembly 16600 is structured to establish a hard-to-hard connection and seal with the frame assembly 16100.

In this example, the first end portion 16610 includes inner and outer radial walls defining a radial channel leading to a plurality of vent holes 16700 to permit the exit of exhausted gases from the patient interface.

Also, it should be appreciated that one or more aspects of the present technology may be combinable with one or more aspects of: U.S. Application Publication No. 2018/0250486, filed Mar. 12, 2018 and entitled "Patient Interface," the entire contents of which are hereby incorporated herein by reference in their entirety. For instance, the cushion assembly 16175 disclosed herein may replace the cushion assembly in any of the patient interface embodiments disclosed in the '486 publication. Furthermore, the seal-forming structure 16200 disclosed herein made replace the seal-forming structure in any of the patient interface embodiments disclosed in the '486 publication.

Seal-Forming Structure

As described above, the shell 16180 is sealingly connected or otherwise provided to the seal-forming structure or cushion 16200, and the shell 16180 and the cushion 16200 cooperate to form the cavity 16500.

The cushion 16200 may include a support structure 16220 that provides support to a sealing portion 16230 (e.g., a textile membrane). The sealing portion is configured to sealingly engage the patient's face.

The support structure 16220 may comprise a wall structure having at least two regions of different thickness (e.g., portions of the support structure adjacent to or connecting to the shell 16180 may be thicker than portions of the support structure adjacent to or connecting to the sealing portion 16230 so as to provide structural stability at the connection with the shell 16180 and flexibility at the interface with the patient). FIG. 84 illustrates an example where portions (d1) of the support structure may be thicker than portions (d2) of the support structure. For example, portions (d1) may be adjacent to or connection to the plenum chamber and portions (d2) may be adjacent to or connecting to the sealing portion so as to provide structural stability at the connection with the frame and flexibility at the interface with the patient. Alternatively, the thicker lateral support regions 3122 may be located, for example, at the lower cheek region of the seal-forming structure (and e.g., may connect directly to the textile membrane), to ensure adequate sealing in the lower cheek region of the patient's face.

The support structure 16220 may be less rigid than the shell 16180 and may be constructed from silicone, foam (e.g., polyurethane foam), polyurethane solid material, thermoplastic elastomers (e.g., thermoplastic polyurethane), suitable plastics, or other suitable materials, as will be described later. Further, the sealing portion 16230 may be less rigid than the support structure 16220 and may be constructed from a textile material such as nylon, polyester, nylon and polyester mix, microfiber or polyurethane, for example, as will be described in more detail later.

The support structure 16220 may have an aperture formed therein providing an inner edge of the support structure along which the sealing portion 16230 (e.g., an outer perimeter of the sealing portion) may be attached to the support structure such that the sealing portion extends radially inwardly of the seal-forming structure beyond or to a further extent than the support structure, as shown for example in FIGS. 71 and 73-77. For example, the sealing portion may be molded around the inner edge of the support structure or connected to the support structure in other suitable ways, as will be described later.

The support structure 16220 may extend into the cavity 16500 forming an underlying cushion or support flange 16221 to provide support to the sealing portion 16230, as shown in FIGS. 73 and 77. The underlying cushion 16221 and the sealing portion 16230 may form a dual wall structure around the perimeter of sealing portion. In alternative examples, a second or third underlying cushion layer may be provided to form a triple or quadruple wall structure. The underlying cushion may be constructed of the same materials as the support structure and may also be constructed of other suitable materials (e.g., textile).

5.3.4.3.1 Positioning and Stabilising Structure

The seal-forming structure of the patient interface of the present technology may be held in sealing position in use by the positioning and stabilising structure.

In one form of the present technology, a positioning and stabilising structure is provided that is configured in a manner consistent with being worn by a patient while sleeping. In one example the positioning and stabilising structure has a low profile, or cross-sectional thickness, to reduce the perceived or actual bulk of the apparatus. In one example, the positioning and stabilising structure comprises at least one strap having a rectangular cross-section. In one example the positioning and stabilising structure comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure comprises a strap that is bendable and e.g. non-rigid. An advantage of this aspect is that the strap is more comfortable for a patient to lie upon while the patient is sleeping.

In certain forms of the present technology, a positioning and stabilizing structure provides a retaining force configured to correspond to a particular size of head and/or shape of face. For example one form of positioning and stabilizing structure provides a retaining force suitable for a large sized head, but not a small sized head. In another example, a form of positioning and stabilizing structure provides a retaining force suitable for a small sized head, but not a large sized head.

5.3.4.3.2 Vent

In one form, the patient interface includes a vent constructed and arranged to allow for the washout of exhaled gases, e.g. carbon dioxide.

One form of vent in accordance with the present technology comprises a plurality of holes, for example, about 20 to about 80 holes, or about 40 to about 60 holes, or about 45 to about 55 holes.

The vent may be located in the plenum chamber or shell. Alternatively, the vent is located in a decoupling structure, e.g., a swivel.

5.3.4.3.3 Decoupling Structure(s)

In one form the patient interface includes at least one decoupling structure, for example, a swivel or a ball and socket.

5.3.4.3.4 Connection Port

Connection port allows for connection to the air circuit.

5.3.4.3.5 Forehead Support

In the illustrated example, the frame assembly 6100 is provided without a forehead support.

In another form, the patient interface may include a forehead support, e.g., the frame assembly may include a forehead support.

5.3.4.3.6 Anti-Asphyxia Valve

In one form, the patient interface includes an anti-asphyxia valve.

5.3.4.3.7 Ports

In one form of the present technology, a patient interface includes one or more ports that allow access to the volume within the cavity. In one form this allows a clinician to supply supplemental oxygen. In one form, this allows for the direct measurement of a property of gases within the cavity, such as the pressure.

5.3.5 Support Structure and Sealing Portion Arrangements

The support structures and sealing portions in the examples described above may have a number of different configurations and arrangements.

In use, the sealing portion (e.g., textile membrane) may be maintained in sealing contact with the patient's face by 1) tension (e.g., a light tension) in the textile membrane and/or a resilient stretch characteristic (e.g., elasticity) of the material (e.g., the textile material, the air impermeable layer material and/or the composite material of the textile membrane) of the sealing portion; 2) a reactive stress of the support structure; 3) a pre-formed state of the textile membrane formed as a non-tensioned, yet substantially constant surface, without leak causing interruptions such as creases, folds, buckles or wrinkles in the textile membrane; and/or 4) air pressure within the cavity against an inside surface of the sealing portion. Each of these factors may contribute to the sealing portion being under constant tension such that the sealing portion complies to the anthropometric contours of the patient's face, thereby minimizing wrinkles or blow-out and maximizing the contact area of the sealing portion.

In some examples, the sealing portion may comprise a relatively thin, compliant, stretchable, elastic material, such as a textile membrane comprising a suitable textile material (e.g., nylon, polyester, nylon and polyester mix, microfiber or polyurethane). The sealing portion may be held taut and in tension by the support structure prior to and during use. The sealing portion may be molded or otherwise attached (e.g., adhered, glued) to the support structure so that the sealing portion is pre-tensioned (slightly stretched) so that there are no wrinkles in the material of the sealing portion. This may be advantageous in ensuring that the sealing portion forms a smooth and continuous seal on the patient's face without any folded sections through which air may leak. Further, the sealing portion may be shaped or have curvature imparted thereto, e.g., by thermoforming, so that the sealing portion holds its own shape. The support structure may also impart curvature to the sealing portion.

For example, as shown in FIGS. 11-17 and 23-37 the sealing portion may have a concave curved profile from one lateral side (right) to an opposing lateral side (left) (e.g., positive curvature in a left-right direction) to cradle the patient's nose.

In some forms, as shown for example in FIGS. 10-66, the patient's nose is not intended to be received in the cavity formed by the plenum chamber and the seal-forming structure. Instead, unlike conventional masks, the patient's nose is intended to press against the textile membrane which in turn accommodates the contours of the patient's face to comfortably form a reliable seal with the patient's airways. In the way, the textile membrane may stretch to accommodate the patient's face. The bridge portion 3104, 1406 extending between the naris openings may assist maintaining the textile membrane in a taut manner prior to and/or during use. The bridge portion may also function to help provide, by eliminating a central opening in the textile membrane, a sealing portion that presses against the patient's nose rather than receives the patient's nose in the cavity. This creates a different sealing experience as compared to conventional masks. This sealing experience may provide enhanced comfort due to contact with a compliant textile membrane rather than the more rigid materials of conventional masks or conventional sealing arrangements where the sealing portion has a smaller contact area around a perimeter of the nose and/or mouth.

The sealing portion may be constructed from a single or a plurality of layers of material (e.g., textile material). The textile membrane (and/or the textile material of the textile membrane) may exhibit a low spring constant (i.e., highly compliant) in both warp and weft. Unlike conventional masks (e.g., silicone sealing membrane), where a fixed cushion may cause a patient's skin to distort to form an effective seal, the textile membrane may have a material spring constant and spring length (i.e., the amount of material available to stretch) such that the textile membrane is more compliant than the patient's skin so as to more readily conform to the patient's facial features. This may improve comfort of the mask and reduce formation of localized pressure "hot spots."

Compared to conventional silicone membranes and compression foam seals, the sealing portion of the present technology has a more flexible structural stiffness and therefore has a dynamic spring back characteristic that enables the sealing portion to recover more quickly when disturbed by an external force. Further, due to the lower structural stiffness a smaller seal force is required allowing the sealing portion to be more comfortable and create less facial marks during use.

The textile membrane may exhibit variable tension forces across the material (e.g., less tension forces proximal to holes or in wider stretches of material). In some forms, the surface of the material of the sealing portion that contacts the patient's face may have low friction characteristics (e.g., a low friction finish), which may advantageously improve compliance of the material with the patient's face while also improving patient comfort.

The textile membrane may also comprise at least one layer that exhibits substantially air-impermeable characteristics, while maintaining the resilient stretch characteristics necessary for comfort and minimal pressure points. That is, a membrane layer or laminate film layer (e.g., a polymer such as silicone, polyurethane, thermoplastic polyurethane (TPU), polyester, nylon, etc.) may be applied to the textile material to provide a substantially air-tight material. In an alternative example, the fibers of a textile may be tightly weaved to create a substantially air impermeable material.

In some forms, the textile material of the sealing portion may have a thickness in the range of 0.275 or less (e.g., 0.275 to 0.075 mm, 0.275 to 0.175 mm, 0.25 mm or less, 0.225 mm or less, 0.225 to 0.09 mm, 0.225 to 0.095 mm, 0.225 mm, or 0.25 mm). The membrane layer may have a thickness in the range of 0.03 to 0.01 mm (e.g., 0.015, 0.02 mm, or 0.025 mm). The textile material of the sealing portion with the membrane layer may have an overall composite material thickness in the range of 0.305 mm or less (e.g., 0.305 to 0.085 mm, 0.305 to 0.185 mm, 0.28 mm or less, 0.255 mm or less, 0.255 to 0.10 mm, 0.255 to 0.105 mm, 0.25 mm, or 0.275 mm). In an example, a textile composite including a microfiber textile and a polyurethane film layer may have these dimensions.

In another example, the textile material of the sealing portion may have a thickness in the range of 0.15 mm to 0.5 mm (e.g., 0.2 mm to 0.4 mm, or 0.3 mm to 0.4 mm, or 0.25 mm, or 0.3 mm, or 0.4 mm). The membrane layer may have a thickness in the range of 0.03 mm to 0.125 mm (e.g., 0.05 mm to 0.1 mm, or 0.075 mm to 0.1 mm, or 0.05 mm to 0.075 mm, or 0.05 mm, or 0.075 mm, or 0.1 mm). The textile material of the sealing portion with the membrane layer may have an overall composite material thickness in the range of 0.18 mm to 0.625 mm (e.g., 0.25 mm to 0.6 mm, or 0.25 mm to 0.5 mm, or 0.3 mm to 0.5 mm, or 0.35 mm to 0.45 mm, or 0.3 mm, or 0.35 mm, or 0.4 mm, or 0.45 mm, or 0.5 mm). In an example, a textile composite including a nylon or nylon and polyester mix textile and a silicone film layer may have these dimensions.

Tensile forces may also be transferred to the sealing portion as a result of the stiffness and resilient properties of the support structure. The support structure may be formed from a variety of materials, including silicone, foam (e.g., polyurethane foam), polyurethane solid material, thermoplastic elastomers (TPE) (e.g., thermoplastic polyurethane (TPU)), and suitable plastic materials. The support structure may be configured so as to create a number of different cushion configurations, including a single air assisted sealing portion (e.g., textile membrane) and a sealing portion with underlying cushion support layer(s) such as a double air assisted sealing portion (e.g., dual textile membranes), a sealing portion with compression support (e.g., open cell foam, polyurethane foam, gel), a sealing portion with TPU, TPE or silicone support, or a double air assisted sealing portion with additional support (e.g., dual textile membranes wherein the inner membrane has a foam laminate layer (e.g., open cell, polyurethane) or a TPU, TPE, polyurethane or silicone molded layer thereon).

The underlying cushion layer(s) may assist in optimizing the sealing portion contact surface area with the patient's face. Further, in examples where the sealing portion is constructed from a breathable material (e.g., a breathable textile), the underlying cushion layer(s) may provide sufficient contact area behind the sealing portion to adequately seal the sealing portion against the patient's face and prevent leakage.

In use, engagement of the patient's face 1000 with the sealing portion 10130 will create a temporary strain force that attempts to pull the walls of the support structure 10120 toward one another, as shown in FIG. 81. The support structure 10120 will respond to the strain force with an outwardly pulling reaction force. The reaction force transfers more tension to the sealing portion 10130 by preferentially stretching the more compliant sealing portion which creates a resultant spring force in the sealing portion that is exerted on the patient's face.

In some examples, the support structure may comprise a biasing portion that utilizes the internal air pressure to dynamically support the support structure and sealing portion. This may advantageously provide further support of the sealing portion when under dynamic loads (e.g., tube drag).

The air pressure within the cavity and acting against the inside surface of the sealing portion may also ensure that a surface of the textile membrane without wrinkles, creases, buckles or folds (e.g., by creating tension in the sealing portion) in presented to the patient's face such that the sealing portion may substantially fill depressed contours of a patient's face (e.g., around the sides of the nose). This may enable the compliant sealing portion to form a larger seal contact area on the patient's face. The tension in the sealing portion created by the air pressure within the cavity may also be advantageous in providing a continuous seal even when the mask is partially displaced with an optimal positioning on the patient's face, as the sealing portion may partially inflate (i.e., a "hovercraft effect") due to the counter-force from the internal air pressure.

In examples where the textile membrane is not under constant tension (and e.g., also non-elastic), the sealing portion may still be maintained in sealing contact with the patient's face by the air pressure within the cavity and form an improved air assisted seal with the patient's face that conforms dynamically to alterations/movements (i.e., "hovercraft effect") due to the sealing portion being thinner and having a lower structural stiffness than the support structure.

The sealing portion may be integrated with the support structure by molding or otherwise attaching the sealing portion to the inner edge of the support structure. Thus, for example, an outer perimeter of the sealing portion may be attached to the inner edge of the support structure such that the sealing portion extends radially inwardly of the seal-forming structure beyond or to a further extent than the support structure. The inner edge of the support structure may be curved such that the sealing portion may be slightly angled inwardly toward the mask interior. By attaching the sealing portion along the inner edge of the support structure, the sealing portion does not need to be folded or cut to blend around the corners of the support structure. This may advantageously reduce the occurrence of protruding folds or wrinkles in the sealing portion, which may cause leakage, thereby improving the performance of the seal.

As described earlier, the seal-forming structure may be removably connected or fixedly attached to the plenum chamber. In some forms, the sealing portion may have a removable or modular structure. For example, the sealing portion may be attached to a supporting frame structure along its perimeter. The supporting frame may be removably attached as a module to the support structure. The sealing portion may be attached to the supporting frame so as to reduce the occurrence of protruding folds or wrinkles in the textile surface. The modular arrangement may also substantially simplify the manufacturing of the sealing portion (e.g., textile sealing portion) as all the complex bonding can be done in a simple unstressed state. While the sealing portion may be treated to have substantially self-cleaning properties, the use of a modular sealing portion may also provide a cheaper and more hygienic alternative.

The supporting frame may be pre-formed to have a flat or three-dimensional shape such as an arc so as to impart a curved shape to the sealing portion. The supporting frame may form an air-tight seal with the support structure. In some examples, the supporting frame may engage the support structure by connectors (e.g., male/female location pins/holes, tongue and groove).

The sealing portion may have underlying cushion support layer(s) (e.g., second, third or more cushion layers) incorporated therein. The underlying cushion layer(s) may provide additional flexibility and allow the cushion to be suitable for use by most patient faces (e.g., one size fits most). For example, the sealing portion may be structured as a double air assisted sealing portion (e.g., dual textile membranes), a sealing portion with compression support layer(s) (e.g., open cell foam, polyurethane foam, gel), a sealing portion with TPU, TPE or silicone support layer(s), or a double air assisted sealing portion with additional support layer(s) (e.g., dual textile membranes wherein the inner membrane has a foam laminate layer (e.g., open cell, polyurethane) or a TPU, TPE, polyurethane or silicone molded layer thereon).

In some examples, the support layers may be supported by a rigid structure such as plastic, e.g., polypropylene (PP), polycarbonate (PC), polyamide (PA), or polyethylene terephthalate (PET).

In some examples, 3D printing of the sealing portion, support layers and/or support structure as a "skeleton" may reduce the thickness of the structure and thus the weight of the mask. Also, different layers of the mask could be printed with different rigidity, hardness, or thickness. For example, "skeleton" sections may be formed using silicone, foam (e.g., polyurethane foam), polyurethane (e.g., polyurethane solid material), or any suitable plastic material. In some examples, a biasing portion may be formed that may provide dynamic support in use.

5.3.5.1 Textile Membrane

In accordance with an example of the disclosed technology, the sealing-forming structure may include a textile membrane comprising a textile material. The textile material may have an airtight membrane/film or layer coated or otherwise applied thereto to create an air-holding textile composite. The textile composite may be cut (e.g., die cut, ultrasonic, laser, or RF) to a desired shape and then attached to the support structure. The resulting textile sealing portion (or textile membrane) may be attached to the support structure (e.g., silicone, TPE), for example, by overmolding or injection molding. In another example, the textile sealing portion may be thermo-welded at its edges (outer perimeter) onto the support structure material (e.g., silicone, TPE).

A textile is a material including at least one natural or artificial fiber (e.g., yarn or thread). The fiber may be a filament (mono or poly), a strand, a thread or twine. The fiber(s) may include animal-based material such as wool or silk, plant-based material such as linen and cotton, and synthetic material such as polyester and rayon. Textiles may be formed by various techniques, such as weaving, knitting, crocheting, knotting, tatting, bonding, felting, tufting, or braiding, and may include, for example, woven and nonwoven materials, e.g., by intertwining or interlacing one or more of the fibers.

In an example, the textile material is a knitted material. A knitted material may be preferable as it provides the textile with elasticity (e.g., stretchiness), particularly in comparison with woven materials. This may be advantageous in providing comfort to the patient, as described below. The elasticity may be in all directions (e.g., four-way stretch/elasticity, e.g., substantially equal elasticity in all directions), and at least in the lateral left-right direction of the textile membrane. The textile material may have a weft knit structure or a warp knit structure, for example. A weft knit structure may be more desirable as the elasticity of weft knit textiles is higher than the elasticity of warp knit textiles.

FIG. 113 illustrates the wale 70 of a weft knit fabric, or the direction that the loops of one thread join to a loop of another thread. The course 80, or the direction of the loops from a single thread is shown in FIG. 114. FIG. 115 illustrates a basic closed loop warp knit 90 in which the wales and courses running parallel to one another. FIG. 116 illustrates a weft knit 100 in which the wales 70 run perpendicular to the course 80.

5.3.5.1.1 Manufacturing

In an example, an overmolding process may be used to construct a seal-forming structure having a, e.g., flexible, support structure (e.g., silicone) attached to a textile membrane.

As shown in FIG. 117, in step 10, an airtight textile composite may be formed by combining a textile material with an impermeable material. A heat process may be used to attach the impermeable layer to the textile material, as shown in FIG. 78 for example. The textile composite may have a flat shape (e.g., sheet-shaped).

In step 12, the textile composite may be cut to a desired shape according to a particular cushion assembly to be used.

In step 14, the support structure (e.g., silicone) may be overmolded onto the textile composite to form a seal-forming structure with a textile membrane. The textile composite may be held in place by a vacuum so as to have a non-flat predefined shape during the overmolding process.

That is, the flat textile composite may be overmolded with the support structure so as to impart curvature to the textile composite thereby forming a textile membrane that may have curvature without wrinkles, folds, creases and/or buckles being formed in the textile membrane. As can be seen in FIG. 33-1, the textile membrane may extend along the curve 35 from the anterior side of the seal-forming structure to the posterior side of the seal-forming structure. In an example, as shown in FIG. 33-1, the support structure and textile membrane may both have a radius of curvature (e.g., the same or similar radius of curvature) along the curve 35. The textile membrane may have a predefined curvature imparted thereto such that a portion of the textile membrane not directly supported by the support structure extends along the curve 35 (FIGS. 33-2 to 33-4). As discussed earlier, the textile membrane may also have, for example, curvature in the way of dome and saddle shapes in other regions of the textile membrane. The textile membrane may have a concave curved profile from one lateral side (right) to an opposing lateral side (left) (e.g., positive curvature in a left-right direction) that may be imparted during the overmolding process and maintained by connection to the support structure (see FIGS. 11-17, 23-27, and 33-37 for example). In another example, the textile membrane may have negative curvature in an inferior-superior direction that may be imparted during the overmolding process and maintained by connection to the support structure (see FIGS. 18-22 for example).

The support structure may be molded onto the textile composite such that the outer surface of the seal-forming structure is smooth and seamless in the transition from the support structure to the textile membrane (see FIG. 33-4). The support structure may bond to the impermeable material of the textile membrane. While the outer surface of the seal-forming structure may be smooth and seamless, a step may be present on the inner surface of the seal-forming structure where the thickness of the support structure is different (e.g., greater) than the thickness of the impermeable layer.

The overmolding process forms the seal-forming structure without creating any wrinkles, folds, creases and/or buckles in the textile membrane while also imparting curvature to the textile membrane.

5.3.5.1.2 Textile Membrane Examples

Below are example properties and structural arrangements of the textile composite used as the material for the textile membrane.

5.3.5.1.2.1 Textile Composite Structure

Various combinations of textile materials and membrane/film layers may be used. In an example, a three-layer arrangement including a thermoplastic polyurethane (TPU) film disposed between two textile layers (e.g., nylon, nylon and polyester mix, nylon and spandex mix, polyester and spandex mix, or nylon/polyester/spandex mix) is used. The additional textile layer is needed to protect the TPU film from breaking (e.g., during cleaning).

In another example, a two-layer arrangement including a textile (e.g., nylon, nylon and polyester mix, nylon and spandex mix, polyester and spandex mix, or nylon/polyester/spandex mix) having a silicone layer (e.g., coated thereon) is used. This composite material may be less expensive than the three-layer arrangement discussed above, since only one layer of textile is needed.

In another example, a textile material (e.g., a microfiber or polyurethane material) may be coated with a polyurethane film to form a two-layer arrangement.

5.3.5.1.2.2 Textile Material

As described above, a number of textile materials maybe used to form the sealing portion, such as nylon, polyester, spandex, nylon and polyester mix, nylon and spandex mix, polyester and spandex mix, nylon/polyester/spandex mix, microfiber or polyurethane.

In an example, a nylon material is used. Nylon may provide comfort benefits to the patient as it is softer than polyester. Nylon is also more durable than polyester and therefore provides enhancements in life span and durability. Further, as compared to polyester, nylon has a higher melt temperature and therefore is able to withstand higher temperature manufacturing conditions.

In another example, a nylon and polyester mix material is used. This material may be more desirable as it absorbs moisture less readily due to the addition of polyester and therefore reduces irritation to the patient. The nylon and polyester mix is also less expensive than nylon.

5.3.5.1.2.3 Textile Material Thickness

In an example, the textile material of the sealing portion may have a thickness in the range of 0.15 mm to 0.5 mm (e.g., 0.2 mm to 0.4 mm, or 0.3 mm to 0.4 mm, or 0.25 mm, or 0.3 mm, or 0.4 mm). Such a thickness may be suitable for a nylon material or nylon and polyester mix material.

In another example, the textile material of the sealing portion may have a thickness in the range of 0.275 or less (e.g., 0.275 to 0.075 mm, 0.275 to 0.175 mm, 0.25 mm or less, 0.225 mm or less, 0.225 to 0.09 mm, 0.225 to 0.095 mm, 0.225 mm, or 0.25 mm). Such a thickness may be suitable for a microfiber textile material or a polyurethane textile material.

5.3.5.1.2.4 Air Impermeable Layer Thickness

In examples where silicone is used as the membrane/film layer, the silicone may have a thickness in the range of 0.03 mm to 0.125 mm (e.g., 0.05 mm, 0.05 mm to 0.1 mm, or 0.05 mm to 0.075 mm, or 0.075 mm to 0.1 mm, or 0.1 mm). A thinner silicone layer (e.g., 0.05 mm) may be more desirable as it provides a lighter weight product and also provides more stretch than thicker silicone layers (e.g., 0.1 mm). Thicker silicone layers (e.g., 0.1 mm), however, are more durable than thinner layers (e.g., 0.05 mm).

In another example, where a polyurethane film is used as the membrane layer, the polyurethane film may have a thickness in the range of 0.03 to 0.01 mm (e.g., 0.015, 0.02 mm, or 0.025 mm).

5.3.5.1.2.5 Textile Composite Total Thickness

In examples where a textile material is coated with a silicone membrane/film layer, the overall composite material may have a thickness in the range of 0.18 mm to 0.625 mm (e.g., 0.25 mm to 0.6 mm, or 0.25 mm to 0.5 mm, or 0.3 mm to 0.5 mm, or 0.35 mm to 0.45 mm, or 0.3 mm, or 0.35 mm, or 0.4 mm, or 0.45 mm, or 0.5 mm).

Thicker textile membrane thicknesses (e.g., 0.5 mm) may be sturdier and provide a less flimsy impress. These textile membranes may be easier to handle during manufacturing as they are less likely to flop around.

A middle range thickness (e.g., 0.35 mm to 0.45 mm) may provide a flexible, lightweight structure that is relatively easy to handle during manufacturing and may provide more comfort to the patient than a thicker textile membranes.

A thinner textile membrane may provide a very lightweight structure that provides a soft comfortable touch to the patient, but may provide less durability than thicker textile membranes.

In examples where a textile material is coated with polyurethane film, the overall composite material may have a thickness in the range of 0.305 mm or less (e.g., 0.305 to 0.085 mm, 0.305 to 0.185 mm, 0.28 mm or less, 0.255 mm or less, 0.255 to 0.10 mm, 0.255 to 0.105 mm, 0.25 mm, or 0.275 mm).

5.3.5.1.2.6 Knit Structure

The textile material of the textile membrane may have a weft knit structure or, alternatively, a warp knit structure, for example A weft knit textile may be more desirable as this may provide the material with higher elasticity as compared to a warp knit textiles. This may be advantageous as it may provide more comfort to the patient by stretching as the patient's face engages the textile membrane thereby reducing the force applied to the patient's face by the textile membrane.

In an example, the weft direction (direction of the course 80) may extend in the nose width direction of the textile membrane, since the weft direction may have greater elasticity or stretch. Alternatively, the weft direction may extend in the nose length direction (superior-inferior direction).

Additionally, weft knitting is more suitable for producing relatively thin materials, such as discloses herein. Also, weft knitting is generally less cost prohibitive than warp knitting.

However, in some examples, warp knitting may be desirable as it provides less shrinkage than weft knit materials.

5.3.5.1.2.7 Knitting Machine

A weft knit textile material may have a single jersey knit structure which provides a technical face and a technical back that have different appearances. A single jersey knit may be formed by one set of needles and may provide knit stitches on the technical face (front) and purl stitches on the technical back. In an example, the technical face may form the outer surface of the textile membrane and the air impermeable membrane may be attached to the technical back. Alternatively, the technical face could be oriented towards an inner surface of the textile membrane and have the membrane attached thereto.

In an example where the textile membrane includes an air impermeable membrane sandwiched between two textile layers, the technical face of each textile material may form the exposed surfaces of the textile membrane.

5.3.5.1.2.8 Textile Weight

The textile material may have a weight in the range of 95 grams per square meter (gsm) to 130 gsm (e.g., 105 gsm to 120 gsm, or 110 gsm to 115 gsm, or 105 gsm, or 110 gsm, or 120 gsm). A heavier weight textile (e.g., 120 gsm) may provide a desirable comfortable textile feel even after being coated with a laminate layer due to the weightiness/thickness of the textile. A lighter weight textile (e.g., 105 gsm) may be desirable as it provides a lighter product.

5.3.5.1.2.9 Machine Gauge

The machine gauge (i.e., the number of stitches per inch) of the textile material may vary. For example, the machine gauge may be in the range of 35GG to 70GG (e.g., 44GG to 60GG, or 50GG to 55GG, or 55GG to 60GG, or 44GG, or 50GG, or 55GG, or 60GG).

Using relatively larger gauge materials (e.g., 44GG) may be desirable as this provides greater options for melange materials. However, a finer gauge materials (e.g., 60GG) may be desirable as this softer materials which may enhance patient comfort.

5.3.5.1.2.10 Aesthetic

The textile material may have a solid color aesthetic or a melange aesthetic. A melange material may be considered a material that has been made with more than one color of fabric/textile/yarn, either by using different color fabrics/textiles/yarns or made with different fabrics/textiles/yarns which are then individually dyed. A melange material may be desirable as it may have a greater ability to hide dirt or grime thereby more easily improving the sense of cleanliness of the product. A melange material may also provide benefits during manufacturing as it is easier to visually align the textile knit structure correctly during cutting and/or overmolding.

However, a solid color material may be desirable as it provides greater options for finer gauge materials (e.g., 55GG+) which are softer and therefore more comfortable to the patient.

5.3.5.2 Seal-Forming Structure with Varying Construction

Referring to FIG. 118A, a cushion assembly 16175-1 according to another example of the present technology is shown. The cushion assembly 16175-1 is similar to the cushion assembly 16175 described above with reference to FIGS. 67-77 and may be used with the frame assembly 16100, positioning and stabilising structure (e.g., headgear 16800), etc. described in FIGS. 67-77. Referring to FIG. 118B, a cushion assembly 16175-2 is similar to cushion assembly 16175-1 but has a larger textile section that extends further toward an anterior side of the cushion assembly, as will be described in more detail later.

Cushion assembly 16175-1 may include a seal-forming structure 16200-1 having a textile sealing portion (or textile membrane 16230-1) connected to the support structure 16220. The textile membrane 16230-1 may be configured to form a seal around a periphery of a patient's airways. The seal may be formed around the patient's nose (e.g., nasal cushion) or the patient's nose and mouth (e.g., full face cushion, wherein the patient's nose is received in the cavity). The textile membrane 16230-1 may be structured to avoid sealing against the alar, e.g., by being spaced sufficiently far radially outward with respect to the alar to avoid or minimize contact with the alar.

Textiles may have greater compliance and/or less resilience as compared to an elastomeric material (e.g., silicone). Thus, in order for the textile membrane to retain its shape and/or provide air impermeability, the textile membrane may comprise a substrate support layer (e.g., an elastomeric material such as silicone), an air impermeable laminate layer, or other such layering. The additional layer may increase the rigidity (while reducing compliance) of the textile material. It is noted, however, that in some examples, the textile membrane is air permeable and does not comprises an air impermeable layer.

The textile membrane 16230-1 may have a total thickness in the range of less than 1.25 mm, (e.g., 0.15 mm to 1.0 mm, 0.15 mm to 0.8 mm, 0.2 mm to 0.7 mm, 0.2 mm to 0.5 mm, 0.25 mm to 0.45 mm, 0.3 mm to 0.4 mm, 0.25 mm, 0.3 mm, 0.35 mm, or 0.45 mm). However, it is noted that the textile membrane may have a thickness in accordance with other examples described in other sections of this disclosure.

In use, the textile membrane 16230-1 may be inflated towards the patient's face, as described in other sections of this disclosure, by forces exerted on the textile membrane due to pressurization in the cavity of the cushion assembly, to create a pressure-assisted seal with the patient's face. In some examples, the textile membrane may be configured to stretch when inflated, which may improve conformance of the textile membrane to the patient's facial contours, and thus may improve the efficiency of the seal created with the patient's face.

The seal-forming structure may have a varying construction in order to accommodate different regions and the varying contours of the patient's face to ensure a robust and comfortable seal. For example, an air impermeable material of the textile membrane may have a thickness that varies in different portions of the textile membrane and/or different regions of the cushion assembly, while the thickness of the textile material remains constant. In another example, the textile membrane may be provided with an underlying cushion (e.g., a compressible underlying cushion, e.g., a foam material). The arrangement of the textile membrane and the underlying cushion and/or the configuration of the underlying cushion may vary in different regions of the cushion assembly to optimize patient comfort and the effectiveness of the seal in different regions of the patient's face.

As those skilled in the art will understand, the varying construction of the seal-forming structure may also be employed in other cushion types, such as the other cushion types described in this disclosure (e.g., nasal (e.g., under-the-nose type), oro-nasal, etc.).

FIGS. 120-1 to 120-6 illustrate cross-sections of the cushion assembly 16175-1 of FIG. 118A, according to various examples of the present technology. It is noted that the point on the cushion assembly 16175-1 in FIG. 118A at which the cross-sections are taken is exemplary and the cross-sectional views could represent any point around the cushion assembly.

5.3.5.2.1 Air Impermeable Material with Varying Thickness

Referring to FIGS. 120-1 and 121, the textile membrane 16230-1 may include a plurality of layers, including a textile material 33133 to contact the patient's face and an air impermeable material (forming an air impermeable layer 33131) to provide air impermeability to the textile material, as described in other sections of the disclosure. As mentioned above, the air impermeable layer may provide rigidity to the textile membrane.

In an example, as illustrated in FIG. 121, the thickness of the air impermeable layer 33131 may vary across the textile membrane in order to vary compliance of the textile membrane in different areas of the textile membrane and/or different regions of the cushion assembly. As shown in FIG. 121, a thickness d1 of the impermeable layer 33131 at a first location on the textile membrane 16230-1 may be different than a thickness d2 of the impermeable layer 33131 at a second location on the textile membrane. By varying the thickness of the impermeable layer 33131, several properties of the textile membrane may be varied, such as stretchability, resilience, and/or rigidity, which may affect the ability of the textile membrane to conform to the patient's facial features as well as comfort to the patient. Thus a portion of the textile membrane having a thinner impermeable layer 33131 may have increased flexibility, stretchability and compliance as compared to a portion of the textile membrane having a thicker impermeable layer. Similarly, the thicker portion of the textile membrane may have increased rigidity, stiffness and resilience as compared to the thinner portion of the textile membrane.

For example, the thickness of the air impermeable layer 33131 may vary in different regions of the cushion assembly, e.g., around the perimeter of the cushion assembly. In examples, the air impermeable layer 33131 may be thinner in sensitive regions (e.g., nasal bridge region) than in other regions (e.g., cheek region) in order to increase compliance and reduce rigidity of the textile membrane so as to accommodate patient comfort. Also, the air impermeable layer 33131 may be thinner in regions (e.g., thinner in nasal bridge, side of nose and/or chin region than in cheek region) where increased stretchability of the textile membrane is desired in order to conform to (or stretch around) facial contours without creating discomfort.

In addition, as shown in FIG. 121, the thickness of the air impermeable layer 33131 may vary, in a cross-sectional view, toward an inner edge 33134 of the textile membrane 16230-1. That is, more radially outer portions (e.g., portions more toward the anterior side of the cushion assembly) of the textile membrane may have an air impermeable layer 33131 that is thicker than the air impermeable layer of more radially inner portions of the textile membrane. In this way, the more radially outer portions of the textile membrane may provide structural support, by virtue of their increased rigidity, to the more radially inner portions of the textile membrane.

In an example, the air impermeable layer 33131 comprises silicone. However, as discussed elsewhere in this disclosure, the air impermeable layer 33131 may comprise other materials. The air impermeable layer 33131 may have a Shore A hardness in the range of 15 to 45 (e.g., 20 to 40, 25 to 35, 20, 25, 30, or 35). Additionally, the air impermeable layer 33131 may have a thickness that ranges from 0.015 mm to 0.085 mm across the textile membrane in order to vary compliance of the textile membrane (e.g., 0.02 mm to 0.07 mm, 0.03 mm to 0.04 mm, 0.02 mm to 0.04 mm, 0.025 mm to 0.035 mm, 0.04 mm to 0.07 mm, 0.02 mm, 0.025 mm, 0.03 mm, 0.035 mm, 0.04 mm, or 0.06 mm). However, due to penetration of the air impermeable layer 33131 into the textile material during curing, the thickness of the air impermeable layer 33131 may not be completely uniform in any particular area. The air impermeable layer 33131 may have a weight in the range of 90 gsm to 215 gsm (e.g., 100 gsm to 200 gsm, 120 gsm to 180 gsm, 135 gsm to 165 gsm, 110 gsm, 120 gsm, 150 gsm, or 180 gsm).

The thickness of the textile material 33133 may be in the range of 0.135 mm to 0.985 mm (e.g., 0.18 mm to 0.73 mm, 0.2 mm to 0.535 mm, 0.28 mm to 0.485 mm, 0.4 mm to 0.7 mm, 0.22 mm, 0.25 mm, 0.3 mm, 0.5 mm, or 0.7 mm).

FIG. 119 shows various regions of the seal-forming structure 16200-1 with patterns designating regions of similar wall thickness of the seal-forming structure. Since the thickness of the textile material 33133 is constant, the patterns illustrate regions of similar thickness of the air impermeable layer 33131 and/or the support structure 16220.

In an example, regions delimiting the aperture in the seal-forming structure 16200-1, such as regions 33180B, 33180F and 33180G may generally correspond to the textile membrane 16175-1, whereas regions 33180A, 33180C, 33180D, 33180E may generally correspond to the support structure.

Region 33180A (e.g., support structure 16220) may be a relatively thin region of the seal-forming structure 16200-1, for example, about 0.3 mm wall thickness. This region may be thin for comfort and compliance at the nasal bridge.

A region 33180B may be a very thin region of the seal-forming structure 16200-1. This reduction in thickness relative to region 33180A may reduce tension significantly, which may result in minimal to no facial marking at the nasal bridge. The nasal bridge is quite bony for most patients and thus sensitive and prone to discomfort. In addition, the region 3180A may extend from the region 33180B to a mask shell 16180 attached to the anterior side of the seal forming structure 16200-1.

Regions 33180A and 33180B may both straddle a sagittal plane 33185 that may bisect the seal forming structure 16200-1 into left and right sides.

A portion of the region 33180B may also be configured to seal against the sides of the nose over the nasal bones and/or lateral cartilage and may also seal against a portion of the upper cheek region. This portion of the region 33180B may be configured to, in use, contact the sides of the nose and/or the lateral cartilage prior to the textile membrane contacting other parts of the face to form a seal. This portion of the region 33180B may also be very thin to prevent excessive force and pinching at the sides of the nose to avoid occlusion of the airways.

A region 33180C may be a semi-thin region of the seal-forming structure 16200-1, for example, about 0.85 mm. This region may be semi-thin to prevent pinching at the sides of the nose. In addition, the region 33180C may border on both the region 33180A and the region 33180B.

A region 33180D may be a transition region in which the wall thickness varies. In particular, the wall thickness of the seal forming structure 16200-1 (e.g., support structure 16220) in the region 33180D may decrease in the direction toward the inner edge 33134. For example, the wall thickness may decrease from about 2.0 mm to 1.3 mm. The change in wall thickness may be gradual or abrupt. In addition, the region 33180D may border on the regions 33180A and 33180C.

A region 33180E (e.g., support structure 16220) may be a thick region, for example, about 2.0 mm wall thickness. This thicker peripheral region may provide a more rigid outer wall to provide support for the more inner portion of the cushion. The region 33180E may act like an undercushion of prior dual layer cushion designs, e.g., the region 33180E may support the portion(s) of the seal forming structure 16200-1 that contact the patient's face. In addition, the region 33180E may border on the regions 33180D and 33180A.

Region 33180F may be a semi-thick region of the seal-forming structure 16200-1 (e.g., thicker than region 33180B). This region may seal on the cheeks alongside the mouth (e.g., lower cheek region). This area on the face is typically fattier than the sides of the nose or nasal bridge, which allows for a relatively greater seal force to be applied without discomfort. The semi-thick region may also provide for more structural rigidity than thinner regions.

The region 33180G may be a thin region of the seal-forming structure 16200-1 (e.g., thinner than region 33180F). The portion that seals below the lower lip (e.g., chin region) may be thin to allow for movement of the lower jaw. Such a thin region may also provide a lighter load against the patient's gums for comfort. The region 33180G may maintain a seal with micro variations of the facial profile and movement during sleep. In addition, the region 33180G may extend from the inner edge 33134 to the mask shell 16180 attached to the anterior side of the seal forming structure 16200-1. The region 33180G may also border on the region 33180D, the region 33180E and the region 33180F.

Although distinct lines are illustrated between the regions 33180, the regions may smoothly transition in relative thickness from region to region and thus the borders between regions are approximations. However, distinct transitions may also be provided.

Also, it is noted that the thickness of the air impermeable layer 33131 and/or the support structure 16200-1 may vary within each region.

In reference to FIG. 118A, regions 33180B, 33180F and 33180G generally are positioned to contact the patient's face, and as mentioned above, may correspond to the textile membrane 16230-1, whereas regions 33180A, 33180C, 33180D, 33180E may correspond to the support structure 16200-1.

However, in other examples such as the cushion assembly 16175-2 in FIG. 118B, one or more of regions 33180A, 33180C, 33180D, 33180E may also comprise a textile material. Even if all or portions of such regions do not contact the patient's face, the presence of the textile material may be aesthetically pleasing to the patient. For instance, one or more of regions 33180A, 33180C, 33180D, 33180E may comprise the textile membrane 16230-2, thereby reducing the extent of the support structure 16200-2. In such examples, the thickness of the air impermeable layer 33131 in those regions may correspond to the thickness of the support structure as described above in reference to the cushion assembly 16175-1.

That is, in examples, the support structure 16200-2 may extend to a lesser extent toward the posterior side of the cushion assembly thereby providing a larger textile section. However, sections (e.g., regions 33180A, 33180C, 33180D, and/or 33180E) of the textile membrane 16230-2 toward the anterior side of the cushion assembly may have an air impermeable layer with a greater thickness than more posterior sections in order to provide sufficient structural support to the textile membrane. The thickness of the air impermeable layer in such anterior sections may be similar to the thickness of the support structure in the same sections in the FIG. 118A example described above. In fact, in regions 33180A, 33180C, 33180D, and/or 33180E, the textile material 33133 may simply be provided over the support structure which would then function as an air impermeable layer to the textile material.

It is noted that the connection between the textile membrane 16230-1 and the support structure 16200-1 may form a lap joint where an edge portion of the textile membrane overlaps with an edge portion of the support structure, thereby possibly creating an area of increased elastomeric material (air impermeable layer 33131 and/or support structure 16200-1) thickness. It is noted that the varying thickness of the air impermeable layer 33131 across the textile membrane, described herein, is outside of any such connection or overlap area.

It is noted that regions 33180A through 33180G have various curvatures. For example, at least a portion of the region 33180A may be a dome-shaped region, while the region 33180B may have a saddle shape. In addition, various portions of the regions 33180C, 33180D, 33180E, and 33180F may be saddle-shaped, dome-shaped or cylinder-shaped. In addition, the region 33180G may be saddle-shaped.

The textile membrane may be resiliently retained in the desired shape, with minimal undesirable folds and creases, by the structure of the textile membrane and/or the support structure.

In another example, the support structure 16220 may also include an underlying cushion 16221, as shown in FIG. 120-2. The underlying cushion 16221 may be provided in at least one region of the cushion assembly, and in some examples, may extend around the entire perimeter of the cushion assembly. In examples, the underlying cushion 16221 may be thicker than the textile membrane.

The underlying cushion 16221 may provide a spring-like element that functions to support the textile membrane 16230-1 and may prevent the textile membrane from buckling in use. In examples, the textile membrane 16230-1 may loosely overlay the underlying cushion 16221 such that the textile membrane and the underlying cushion may respond independently to the forces exerted on their respective undersides due to the pressurized cavity within the cushion assembly. In some examples, the textile membrane 16230-1 may be bonded to the underlying cushion 16221 such that the textile membrane and the underlying cushion respond to the forces of the pressurized cavity in unison.

It should also be appreciated that one or more aspects of the present technology may be combinable with one or more aspects of: WO 2017/049361, filed Sep. 23, 2016, entitled "Patient Interface with a Seal-Forming Structure having Varying Thickness," which is hereby incorporated herein by reference in its entirety For instance, the thickness profiles of the air impermeable layer and/or the support structure may be identical to the thickness profiles of the seal-forming structures in any of the embodiments of the '361 application. For example, the thickness profile of the air impermeable layer may correspond to the thickness profiles of the seal-forming structures in any of the embodiments in the '361 application. Additionally, the cushion assemblies and seal-forming structures disclosed herein may replace any of the cushion assemblies (seal-forming structures and plenum chamber) and seal-forming structures in any of the patient interfaces disclosed in the '361 application.

5.3.5.2.2 Textile Membrane with Underlying Cushion

Referring to FIGS. 120-3 to 120-6, the support structure 16220 may be provided with an underlying cushion (e.g., a compressible underlying cushion, e.g., a foam underlying cushion 33121) to provide support to the textile membrane 16230-1. The underlying cushion may be formed of a foamed silicone material, a foamed textile material, polyurethane foam, spacer fabric, TPU, TPE, or any of the materials described elsewhere in the disclosure as suitable for an underlying cushion layer. In the illustrated examples, the underlying cushion 33121 is formed of a polymer-based foam, such as polyurethane foam.

The foam underlying cushion 33121 may be supported at least partially by a cushion coupling portion 33150 that extends underneath the foam underlying cushion attaching to an underside surface of the foam underlying cushion. The cushion coupling portion 33150 may be part of the support structure 16220, and may be formed in one piece with the support structure. The cushion coupling portion 33150 may be in the form of a peripheral lip that connects to the foam underlying cushion to form an effective cantilever over-hang portion.

The foam underlying cushion 33121 may be attached to the cushion coupling portion 33150, e.g., by adhesive (e.g., glue and/or tape); by flame lamination; by moulding (e.g., moulding of foam onto the cushion coupling portion, or vice versa); by welding; mechanical connection between foam and cushion coupling portion; and/or by sewing; etc.

The cushion coupling portion 33150 may assist the foam underlying cushion 33121 in facilitating a tight sealing engagement with the patient's face in use by responding to forces created within the pressurized cavity in the cushion assembly so as to urge the foam underlying cushion 33121 (and thereby the textile membrane) towards the patient's face.

In some examples, the cushion coupling portion 33150 provides a cantilever spring force that can be soft enough to allow the nose to press into the textile membrane and foam underlying cushion at set-up without occluding the nares. Conversely, the spring force of the cushion coupling portion 33150 can provide enough reaction force to press the foam underlying cushion 33121 into all the sealing zones of the mask. This may be significant for areas such as at the sides of nose.

The arrangement of the textile membrane 16230-1 and foam underlying cushion 33121 and/or the configuration of the foam underlying cushion may vary in different regions of the cushion assembly to optimize patient comfort and the effectiveness of the seal in different regions of the patient's face.

Referring to FIG. 120-3, in an example, the textile membrane 16230-1 may loosely overlay the foam underlying cushion 33121 without being bonded to the foam underlying cushion. The textile membrane may be attached to and may project from a marginal edge 33102 of the support structure 16220. Reference character 33146 represents a length of the textile membrane 16230-1 (e.g., from the marginal edge 33102 (or a lower exterior edge of the foam underlying cushion) toward the inner edge 33134 of the textile membrane) that loosely overlays the foam underlying cushion 33121 without being bonded to the foam underlying cushion. In use, the textile membrane may be inflated by forces created in the pressurized cavity, thereby urging the textile membrane towards the patients face so as to facilitate the textile membrane at least partially conforming to the patient's facial contours. In some forms, the textile membrane may also resiliently stretch when inflated by the forces within the pressurized cavity.

It is noted that the length of the textile membrane 16230-1 that loosely overlays the foam underlying cushion 33121 refers to a portion of the textile membrane that extends over the foam underlying cushion up to an interior edge 33108 of the foam underlying cushion, and does not refer to any portion of the textile membrane that extends radially inwardly beyond the interior edge 33108 of the foam underlying cushion.

Referring to FIG. 120-4, in an example, the textile membrane 16230-1 may loosely overlay a portion of the foam underlying cushion 33121 while also being bonded to a portion of the foam underlying cushion. For example, as shown in FIG. 120-4, the textile membrane may be bonded to an exterior facing side wall of the foam underlying cushion 33121 from the marginal edge 33102 of the support structure 16220 (or lower exterior edge of the foam underlying cushion) to an upper exterior edge 33104 of the foam underlying cushion. The remaining length 33146 of the textile membrane may loosely overlay the foam underlying cushion 33121.

Reference character 33148 represents a length of the textile membrane 16230-1 (e.g., from the marginal edge 33102 (or a lower exterior edge of the foam underlying cushion) toward the inner edge 33134 of the textile membrane) that is bonded to the foam underlying cushion. It is noted that the textile membrane may be bonded to any desired length of the foam underlying cushion. The capacity of the textile membrane 16230-1 to inflate may be inversely proportional to the length of the textile membrane that is bonded to the foam underlying cushion 33121 (considering the length of the textile membrane that loosely overlays the foam underlying cushion). As such, the textile membrane 16230-1 in FIG. 120-3 may have a greater capacity to inflate towards the patient's face than the textile membrane in FIG. 120-4.

Referring to FIG. 120-5, in an example, the textile membrane 16230-1 may be bonded to the exterior facing side wall of the foam underlying cushion 33121 as well as a portion of a patient-facing surface of the foam underlying cushion 33121. The textile membrane may be bonded to the foam underlying cushion up to an intermediate point 33106 along the patient-facing surface of the foam underlying cushion. It is noted that the intermediate point 33106 may be anywhere along the patient-facing surface of the foam underlying cushion up to and including the interior edge 33108 of the foam underlying cushion, such that the bonding length 33148 may terminate at any point along the patient-facing surface of the foam underlying cushion.

Since the length 33146 of the textile membrane loosely overlaying the foam underlying cushion in FIG. 120-5 is shorter than the length 33146 of the textile membrane loosely overlaying the foam underlying cushion in FIG. 120-4, the textile membrane 16230-1 in FIG. 120-4 may have a greater capacity to inflate towards the patient's face than the textile membrane in FIG. 120-5.

Referring to FIG. 120-6, in an example, the textile membrane 16230-1 is bonded to the patient-facing surface of the foam underlying cushion 33121 with substantially no portion of the textile membrane loosely extending over or projecting loosely away from the foam underlying cushion. It is noted that the bonding length 33148 may terminate at any point along the patient-facing surface of the foam underlying cushion, up to and including the interior edge 33108 of the foam underlying cushion.

Since the length 33146 of the textile membrane loosely overlaying the foam underlying cushion in FIG. 120-6 is shorter than the length 33146 of the textile membrane loosely overlaying the foam underlying cushion in FIG. 120-5, the textile membrane 16230-1 in FIG. 120-5 may have a greater capacity to inflate towards the patient's face than the textile membrane in FIG. 120-6.

In examples, it may be desirable to vary how much the textile membrane 16230-1 is able to move (e.g., by inflation due to forces in the pressurized cavity) relative to the foam underlying cushion 33121 in different regions around the perimeter of the cushion assembly. For example, it may be desirable to have more relative movement in the nasal bridge region than in the cheek region (e.g., lower cheek region). As described above, the relative movement between the textile membrane and the foam underlying cushion may be altered by adjusting the length of the textile membrane that is bonded to the foam underlying cushion versus the length of the textile membrane that loosely overlays the foam underlying cushion.

In some examples, the degree (e.g., length) of bonding between the overlaid textile membrane and the foam underlying cushion 33121 can be configured to vary in different regions along the perimeter of the cushion assembly. For example, there may be some regions (e.g., nasal bridge) of the seal forming structure 16200-1 where there is a greater need for an air-assisted inflated sealing portion formed by the textile membrane that is compliant and able to conform to the facial curvatures at the nasal bridge, whereas in other regions (e.g., cheek regions, e.g., lower cheek region) a compression type seal formed simply of the foam cushion, with or without the textile membrane bonded thereto may be desired. Thus, in an example, the textile membrane may be configured to have a relatively longer length of the textile membrane loosely overlaying the foam underlying cushion in the nasal bridge region than in the cheek regions. That is, in an example, both the nasal bridge region and the cheek region (e.g., lower cheek region) may have portions of the textile membrane that loosely overlay the foam underlying cushion and portions of the textile membrane that are bonded to the foam underlying cushion; however, in the nasal bridge region, the textile membrane may have a relatively longer length of the textile membrane loosely overlaying the foam underlying cushion than in the cheek region.

In another example, the textile membrane 16230-1 in the nasal bridge region may have substantially no portion of the textile membrane bonded to the foam underlying cushion 33121 such that substantially the entire portion of the textile membrane that overlays the foam underlying cushion would be able to move relative to the foam underlying cushion.

This may allow the textile membrane to bend (and/or stretch) to conform to the curvature of the patient's nasal bridge. The relative movement between the textile membrane and the foam underlying cushion may allow the textile membrane to bend (and/or stretch) around the patient's nasal bridge before engaging the foam underlying cushion beneath the textile membrane.

In some examples, the textile membrane in the cheek region (e.g., lower cheek region) may be completely bonded to the foam underlying cushion such that substantially no portion of the textile membrane loosely overlays the foam underlying cushion. This arrangement may allow the foam underlying cushion to immediately exert a force against the patient's face upon engage of the patient's face with the textile membrane. This arrangement may create a compression type seal against the patient's face in which the foam underlying cushion compresses as the seal-forming structure engages the patient's face. The cheek region, particularly the lower cheek region, is typically fattier than the sides of the nose or nasal bridge, which allows for a relatively greater seal force to be applied without discomfort. Such seal force in this region may form a stabilizing point for the cushion against the patient's face.

In a side of nose region of the cushion assembly, the textile membrane may have substantially no portion of the textile membrane bonded to the foam underlying cushion, similar to the nasal bridge region in an example discussed above. It is noted that the nasal bridge region and side of nose region could also have similar arrangements where in both regions portions of the textile membrane are bonded to the foam underlying cushion and other portions of the textile membrane loosely overlay the foam underlying cushion. This may allow the textile membrane to inflate while also allowing the foam underlying cushion to press into the patient's face to better conform to the contours of these regions.

However, in the side of nose region, it may be desirable to have less of the textile membrane loosely overlay the foam underlying cushion as compared to the nasal bridge region such that the textile membrane would still be able to inflate while also increasing the ability of the foam underlying cushion to press into the sides of nose area to better conform to the contours of this region. In another example, the textile membrane in the sides of nose region could have substantially no loosely overlaying portion of the textile membrane, in order to allow for a compression type seal only.

In the chin region of the cushion assembly, it may be desirable to have more of the textile membrane loosely overlay the foam underlying cushion as compared to the cheek region (e.g., lower cheek region), such that the textile membrane in the chin region would be able to move relative to the foam underlying cushion so as to inflate towards the patient's face in use. In an example, the textile membrane may have substantially no portion of the textile membrane bonded to the foam underlying cushion, similar to the nasal bridge region in an example discussed above.

In another example, portions of the textile membrane in the chin region may be bonded to the foam underlying cushion while other portions of the textile membrane may loosely overlay the foam underlying cushion. This may allow the textile membrane to inflate and bend (and/or stretch) around the curvature across the chin region while also allowing the foam underlying cushion to press into the patient's face to exert a stabilizing force against the patient's face.

In examples, the textile membrane 16230-1 may not extend over the patient-facing surface of the foam underlying cushion in some regions around the perimeter of the cushion assembly, such that the textile membrane is configured to engage the patient's face in some regions and the foam cushion is configured to engage the patient's face in other regions. For example, it may be desirable to have the foam cushion directly contact the patient's face in cheek regions of the cushion assembly where a compression type seal may be desired.

It is further noted that a cross-sectional configuration of the foam underlying cushion may vary around the perimeter of the cushion assembly. That is, the cross-sectional configuration of the foam underlying cushion in the sides of nose region of the cushion assembly may be different than a cross-sectional configuration of the foam underlying cushion in a cheek region (e.g., lower cheek region), nasal bridge region, or chin region of the cushion assembly.

In an example, the height of the foam underlying cushion may be about 8 mm-16 mm. The width of the foam underlying cushion may be about 12 mm to 30 mm, preferably about 15-20 mm.

It is noted that the textile membrane 16230-1 having an air impermeable layer 33131 with a thickness that varies, as described above, may be employed with the underlying cushion described in FIGS. 120-3 to 120-6.

In some forms of the present technology, the foam underlying cushion 33121 may include a radially flat region having a three-dimensional surface contour that is arranged so that the radially flat region in at least a portion of the cushion assembly is inwardly inclined, with respect to a mid-contact plane of the cushion assembly, for embracing and conforming to a shape of the patient's face in use. In some forms, the radially flat region may be in one or both of a side of mouth region (e.g., lower cheek region) and a side of nose region, or may extend about the entire perimeter of the cushion assembly.

In some forms, at least a portion of the foam underlying cushion 33121 may include a planar surface region that is inwardly inclined, with respect to a mid-planar plane of the patient interface, in at least one region of the cushion assembly, for embracing and conforming to a shape of the patient's face in use.

It should also be appreciated that one or more aspects of the present technology may be combinable with one or more aspects of: US 2017/0128689, filed Nov. 16, 2016, entitled "Respiratory Apparatus," which is hereby incorporated herein by reference in its entirety. For instance, the cushion coupling portion and foam underlying cushion of the present technology may be identical to the cushion coupling portion and foam cushion in any of the embodiments of the '689 application. Additionally, the cushion assemblies and seal-forming structures disclosed herein may replace any of the cushion assemblies (seal-forming structures and plenum chamber) and seal-forming structures in any of the patient interfaces disclosed in the '689 application. Further, the foam underlying cushion may have identical physical properties and/or identical physical configurations as the foam cushion in any of the embodiments in the '689 application. For example, foam properties such as permeability, hardness, compression stress strain, apparent density, dynamic coefficient of friction, compression set, tensile strength, elongation at break, and/or tear strength may be identical to the foam cushion in any of the embodiment in the '689 application. Also, the cross-sectional configurations of the foam cushion in different regions of the cushion assembly may be identical to the cross-sectional configurations in any of the embodiments in the '689 application.

5.3.5.3 Illustrated Examples of Support Structure and Sealing Portion Arrangements FIGS. 81-112 show a number of different cushion assembly configurations including various support structure and sealing portion arrangements and/or processes. It is noted that these examples can be applied to any of the patient interfaces and/or cushion assemblies described in the disclosure. Further, any feature of any example may be applied to a different example and/or used with different features. The plenum chambers, support structures and sealing portions shown in these figures may be constructed from any of the suitable materials described earlier. It should also be noted that components, for example the support structure, may comprise more than one material. For example, an underlying cushion of a support structure may comprise a different material than other portions of the support structure.

Referring to FIG. 83, support structure 10120 is removably connected to plenum chamber 10200 via clip 10126 on the support structure and connector 10210 on the plenum chamber to form cavity 10001. In some examples, the clip 10126 may be formed from polyurethane, polypropylene (PP) or polyethylene terephthalate (PET). Plenum chamber 10200 may be constructed from a material that is more rigid than the clip, such as polycarbonate or polyurethane having a higher Shore A hardness than the clip. The support structure 10120 and sealing portion 10130 are configured into a cushion arrangement having a single air assisted sealing portion 10130 (e.g., textile membrane).

The connection between the outer perimeter (or outer edge) of the textile membrane and the inner edge of the support structure may be formed in a number of different ways. As shown in FIGS. 83 and 85, the connection may form a lap joint where an edge portion of the textile membrane overlaps with an edge portion of the support structure. In an example, an attachment portion 10122 of the support structure may form a recessed portion to receive the sealing portion 10130 so that the support structure and sealing portion form a smooth outer surface, as shown in FIG. 83. The overlap may be minimal and provided only for manufacturing purposes (i.e., necessary in order to attach the sealing portion and the support structure) by for example, overmolding and/or injection molding. This is in contrast to conventional arrangements in which the overlapping region may be arranged to provide additional support (e.g., stiffness) to the sealing portion due to the presence of the support structure (in such arrangements, the overlap may vary around the perimeter of the seal-forming structure to vary the level of support or stiffness (e.g., less overlap, less support, more flexibility, less tension in sensitive nasal bridge region).

In contrast to the above described lap joint, the connection between the textile membrane and the support structure may form an end-to-end joint (e.g., butt joint), as shown in FIG. 84. Due to manufacturing techniques (e.g., overmolding, injection molding), the end-to-end joint may have some overlap, however such overlap is negligible and constant around the perimeter of the sealing portion at the connection with the support structure. In other words, as described above, any overlap of the support structure and the textile membrane is not designed to adjust the stiffness, tension, flexibility or support in different regions of the face (e.g., less overlap, less support, more flexible, less tension in sensitive nasal bridge region).

Instead, whether a lap joint or end-to-end joint is provided, the present arrangement allows the compliant textile membrane to appropriately accommodate the patient's facial features. That is, the seal-forming structure is designed to allow the patient's facial features (e.g., nose) to sink into the textile membrane which compliantly receives the patient's face.

The sealing portion may be glued, molded (e.g., overmolded or injection molded) or otherwise attached to the support structure. In an alternative example, the recessed portion may be removed and the attachment portion 10122 may be used to attach the sealing portion 10130 and the support structure 10120 end to end, as shown in FIG. 84. Further, FIG. 84 also illustrates that portions (d1) of the support structure 10120 adjacent to or connecting to the plenum chamber 10200 may be thicker than portions (d2) of the support structure 10120 adjacent to or connecting to the sealing portion 10130 so as to provide structural stability at the connection with the plenum chamber and flexibility at the interface with the patient.

In FIG. 85, the support structure 10120 includes an underlying cushion 10121. The support structure also includes a sealing lip 10124 to seal the interface between the plenum chamber 10200 and the support structure 10120. The attachment portion 10122 of the support structure may be configured so as sandwich an end portion of the sealing portion between opposing sections of the attachment portion 10122.

In another example, plenum chamber 11200 may have an underlying cushion 11121 attached to an inner portion thereof, as shown in FIG. 86. As such, the underlying cushion 11121 may be permanently attached to the plenum chamber 11200, whereas the support structure 10120 and sealing portion 10130 may be removably connected to the plenum chamber via clip 10126 and connector 10210.

Referring to FIGS. 87 and 88, support structure 10120 may have an external biasing portion 10140 or an internal biasing portion 10140' which may utilize the internal air pressure in the cavity to dynamically support the support structure and sealing portion 10130. The support structure 10120 may include an inwardly curved end portion 10142 thus forming an air-assisted support region 10144 which may optimize the force, due to air pressure within the cavity, acting on the support structure and sealing portion to urge the sealing portion into sealing contact with the patient's face.

Turning to FIG. 89, support structure 12120 includes an underlying cushion 12121. The support structure and/or underlying cushion may be formed, for example, of molded polyurethane. In this example, the sealing portion 10130 is adhered to the support structure with an adhesive 10150 (e.g., heat-activated polyurethane, tape, glue).

In FIG. 90A, support structure 15120 is removably connected to plenum chamber 10200. The support structure includes an underlying cushion 15121. In this example, the support structure is formed of foam (e.g., polyurethane foam molding), but may also be formed of TPE, TPU or any other suitable material. The sealing portion 10130 may have a membrane layer or film laminate layer 10131 to provide a substantially air-tight material, as shown in FIG. 90A-1. Alternatively, the support structure 15120 may be glued, bonded, or otherwise attached to the plenum chamber 10200.

FIG. 90B shows an example similar to that of FIG. 90A, however the sealing portion 10130 in FIG. 90B is connected directly to the plenum chamber 10200 and may form a seamless cover over the underlying cushion 15121. The sealing portion 10130 and underlying cushion 15121 may be glued or otherwise bonded to the plenum chamber 10200. Alternatively, the sealing portion 10130 and/or the underlying cushion 15121 may be removably connected to the plenum chamber.

Referring to FIG. 91, support structure 17120 includes a first portion 17123 and an underlying cushion 17121. The first portion 17123, which may connect to the plenum chamber, may be constructed from a material that is more rigid than a material of the underlying cushion 17121. For example, the first portion 17123 and the underlying cushion may both be constructed of polyurethane, but the polyurethane material of the first portion may have a higher hardness than the material of the underlying cushion. A reinforcing member 17125 may extend along an outer perimeter of the cushion bridging the intersection between the first portion 17123 and the underlying cushion 17121 to provide structural support.

As shown in FIG. 92, support structure 23120 may include an underlying cushion 23121 (e.g., constructed of TPU) having a U-shape or hook shape. The underlying cushion may include a clip 23126 for removable connection to the cushion (e.g., the frame, plenum chamber, or other portion of the support structure). Alternatively, the sealing portion 10130 may be attached to the support structure 23120 as a removable module that as a unit may be removably connected to the cushion (e.g., the frame, plenum chamber, or other portion of the support structure). The sealing portion 10130 may be attached to the underlying cushion 23121, for example, by thermoforming. The underlying cushion also may be shaped by thermoforming.

Support structure 24120 may include a rigid clip 24126 that supports an underlying cushion 24121, as shown in FIG. 93. The underlying cushion 24121 may include an outer textile layer 10132 and an inner layer (e.g., constructed of foam) enclosed by the textile layer and the clip. The support structure 24120 may be removably connectable to the cushion (e.g., the frame, plenum chamber, or other portion of the support structure). Alternatively, the sealing portion 10130 may be attached to the support structure 24120 as a removable module that as a unit may be removably connected to the cushion (e.g., the frame, plenum chamber, or other portion of the support structure). The sealing portion 10130 may be attached to the underlying cushion 24121, for example, by thermoforming. The underlying cushion also may be shaped by thermoforming.

Referring to FIG. 94, support structure 18120 may include a rigid clip 18126 that supports an underlying cushion 18121 (e.g., constructed of foam). The support structure 18120 may be removably connectable to the cushion (e.g., the frame, plenum chamber, or other portion of the support structure). Alternatively, the sealing portion 10130 may be attached to the support structure 18120 as a removable module that as a unit may be removably connected to the cushion (e.g., the frame, plenum chamber, or other portion of the support structure). The sealing portion 10130 may be attached to the underlying cushion 18121, for example, by thermoforming. The underlying cushion also may be shaped by thermoforming.

Turning to FIG. 95, support structure 19120 includes a first portion 19123 and an underlying cushion 19121. The first portion 19123, which may connect to the plenum chamber, may be constructed of a material that is more rigid than a material of the underlying cushion 19121. For example, the first portion may be constructed from polyurethane and the underlying cushion may be constructed from foam.

Referring to FIG. 96, support structure 20120 includes a first portion 20123 and an underlying cushion 20121. The first portion 20123, which may connect to the plenum chamber, may be constructed from a material that has different rigidity or Shore A hardness than a material of the underlying cushion. For example, the first portion 20123 and the underlying cushion 20121 may both be constructed of polyurethane, whereas the first portion 20123 may be less or more rigid or have higher or lower Shore A hardness than the underlying cushion 20121. In an alternative example, the first portion 20123 and the underlying cushion 20121 may be constructed of the same material and may have the same rigidity or Shore A hardness.

The support structure 21120 of FIG. 97 includes a first portion 21123 and an underlying cushion 21121 and is similar to support structure 20120 discussed above, except that the cushion includes a second sealing portion layer (e.g., textile layer 10132) forming dual textile membranes. The underlying cushion 21121 may be molded or otherwise attached to an underside of the textile layer 10132.

Referring to FIG. 98, support structure 22120 includes a first portion 22123 and an underlying cushion 22121 and is similar to support structure 21120 discussed above, except that the underlying cushion 22121 is a foam layer laminated or otherwise attached to the underside of the textile layer 10132.

Turning to FIG. 99, the illustrated cushion assembly includes a dual sealing portion structure without underlying cushion support. The cushion assembly includes a first textile layer 10130 and second textile layer 10132 connected to support structure 10120.

The cushion assembly in FIG. 100 is similar to the cushion assembly in FIG. 99, except that the sealing portion includes a support section 10135 from which the first textile layer 10130 and the second textile layer 10132 extend. Support section 10135 may be constructed of TPU or foam (e.g., polyurethane foam molding), for example. The support section 10135 may add resilience to the sealing portion and allow the textile layers to spring back more quickly from external forces. The support section 10135 may be removably connected, as a modular unit with the textile layers, to support structure 10120. In an alternative example, the support section 10135 is removably connected to the plenum chamber.

Turning to FIGS. 101 and 102, sealing portion modular assembly 26400 may be permanently or removably connected (e.g., with a mechanical clip) to support structure 26120 (or alternatively to plenum chamber 10200). The sealing portion modular assembly may include a skeleton supporting frame 26450 having the sealing portion 10130 attached thereto. The sealing portion 10130 may be thermoformed or insert molded, for example, to attach the sealing portion to the supporting frame 26450. The thermoforming or molding process and/or the supporting frame itself may form and hold the sealing portion in a curved or three-dimensional shape. Support structure 26120 may be constructed from insert molded polyurethane, for example.

In the example of FIG. 103, the textile membrane 10130 and/or support structure may be configured to be removable or modular. As illustrated in FIG. 103, the textile membrane 10130 may be attached to a modular support structure 26480 around its perimeter. The modular support structure 26480 may then be removably engaged as a module to the plenum chamber. A modular form may advantageously reduce the occurrence of protruding folds or wrinkles in the textile membrane surface.

In some forms, the textile membrane may be a sleeve or sock that is adapted to cover and be retained above the plenum chamber or support structure.

A modular textile membrane seal may also substantially simplify the manufacturing as all the complex bonding may be done in a simple unstressed state. While some textiles may be treated to have substantially self-cleaning properties, the use of a modular textile membrane may also advantageously provide a cheaper and more hygienic alternative. In some forms, the textile membrane or support structure can be a removable and/or replaceable sub-assembly that attaches to the plenum chamber, support structure or frame assembly.

In forms where the textile membrane is attached to a supporting frame of the modular supporting structure 26480, the supporting frame can be pre-formed to be either flat (as shown in FIG. 103) or as a 3-D structure such as an arc.

In some forms, the modular supporting structure 26480 can engage the plenum chamber through corresponding male/female location pins/holes. In some forms, the modular supporting structure may utilize a tongue and groove arrangement around the peripheral sides of the structure to form an effective air-tight seal with the plenum chamber. The modular supporting structure 26480 may be formed, for example, from a plastic material, polyurethane, or similar materials.

Turning to FIGS. 104-106, a process of insert molding the sealing portion (e.g., a textile material) as an In Mold Decoration (IMD) is illustrated. As shown in FIGS. 104 and 105, a first mold 26500 may be brought into contact with a second mold 26550 to attach the sealing portion 10130 to the supporting frame 26450 while also imparting curvature to the sealing portion. The molding process may also stretch the sealing portion 10130 so that attachment of the sealing portion to the supporting frame 26450 maintains the sealing portion in tension prior to use.

Referring to FIGS. 107 and 108, a one size fits all cushion assembly 27105 is shown. Cushion assembly 27105 may include a sealing portion 10130 attached to an upper supporting frame portion 27202 and a lower supporting frame portion 27204. The upper supporting frame portion 27202 may be spaced from the lower supporting frame portion 27204 thereby forming an elastic region 27108 in which the sealing portion may stretch to distance the upper supporting frame portion 27202 and the lower supporting frame portion 27204 to accommodate a range of patient face sizes.

A patient's face may be scanned to create a custom mask, as shown in FIGS. 109 and 110. A three-dimensional profile may be obtained by facial scan to create a cushion assembly 28105 including a sealing portion 10130 attached to a supporting frame 28200. Supporting frame 28200 may include a relatively rigid support element (e.g., a polyurethane molded piece) and a cushioning element (e.g., foam) between the support element and the sealing portion. As shown in FIG. 84, the cushion assembly may be arranged to stretch to accommodate different patient face sizes.

In some examples of the nasal cushion, such as shown for example in FIGS. 111 and 112, the support structure 3120 may actually be configured to deform inwardly at certain fold or pivot points. For example, thinner regions of the support structure may be designed to created fold or pivot points. In an example, a bottom central portion (e.g., nose base region 3112) of the support structure 3120 may have a relatively reduced thickness such that when stress is applied to the walls of the support structure due to engagement by the patient's face, the bottom central portion of the support structure may create a pivot point thus allowing the left and right lateral sides of the support structure to deform inwardly to cradle the patient's face (e.g., nose) thereby accommodating engagement of the patient'. An upper anterior region 3109 may also have a reduced thickness as compared to lateral support regions 3122 so as to create a fold or pivot point.

Thus, in the example of FIGS. 111 and 112, the support structure 3120 may have three regions of different stiffness (e.g., by having different thicknesses). The upper anterior region 3109 may have a thickness that is the same as or greater than the thickness of the nose base region 3112. The lateral support regions 3122 may have a thickness that is greater than the thickness of the upper anterior region 3109 and the nose base region 3112. Thus, the lateral support region may be stiffer than the upper anterior region 3109 which may be stiffer than the nose base region 3112. It is noted that the plenum chamber and the support structure may both be formed of a flexible material (e.g., silicone) and may form a one-piece structure (e.g., molded together). This may assist the bending/folding/pivoting of the cushion assembly to accommodate the patient's facial features. In an example, the seal-forming structure may be an extension of the plenum chamber or formed as a part of the plenum chamber such that the plenum chamber encompasses the seal-forming structure. In such an example, the support structure and textile membrane may be considered part of the plenum chamber.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller, a therapy device controller, a pressure generator, one or more protection circuits, memory, transducers, data communication interface and one or more output devices.

Electrical components 4200 may be mounted on a single Printed Circuit Board Assembly (PCBA) 4202. In an alternative form, the RPT device 4000 may include more than one PCBA 4202.

5.5 Glossary

For the purposes of the present technology disclosure, in certain forms of the present technology, one or more of the following definitions may apply. In other forms of the present technology, alternative definitions may apply.

5.5.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.5.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.5.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or 143hermos-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.5.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(ii) Flattened: Having a rise followed by a relatively flat portion, followed by a fall.
(ii) M-shaped: Having two local peaks, one at the leading edge, and one at the trailing edge, and a relatively flat portion between the two peaks.
(ii) Chair-shaped: Having a single local peak, the peak being at the leading edge, followed by a relatively flat portion.
(ii) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(ii) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.5.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.5.4 Anatomy
5.5.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion

5.5.4.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.5.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.5.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a thin structural element that has:
resistance to being stretched; and
substantially no resistance to bending.
A membrane may be curved.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structural element having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.5.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.5.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.5.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.5.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.5.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.6 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.7 Reference Signs List

Step 10
Step 12
Step 14
Curve 35
Transition portion 36
Wale 70
Course 80
Warp knit 90
Weft knit 100
Patient 1000
Bed partner 1100
Patient interface 3000
Seal-forming structure 3100
Cavity 3101
Naris opening 3102
Bridge portion 3104
Cushion assembly 3105
Frame connection opening 3106
Upper anterior region 3109
Nose base region 3112
Support structure 3120
Lateral support region 3122
Sealing portion 3130
Plenum chamber 3200
Plenum chamber lateral end 3202
Plenum chamber connector 3204
Notch 3206
Chamfered edge 3208
Slot 3209
Chord 3210
Superior point 3220
Inferior point 3230
Lateral sides 3250
Corner region 3252
Medial subnasale region 3260
Medial pronasale region 3270
Positioning and stabilising structure 3300
Lateral portion 3302
Superior portion 3304
Hub 3306
Tab 3308
Posterior strap 3310
Posterior strap end portion 3311
Sleeve 3312
End 3314
Vent 3400
Decoupling structure vent 3402
Decoupling structure 3500
Swivel connector 3502
Button 3504
Connection port 3600
Forehead support 3700
RPT device 4000
External housing 4010
Upper portion 4012
Lower portion 4014
Panel 4015
Chassis 4016
Handle 4018
Pneumatic block 4020
Inlet air filter 4112
Inlet muffler 4122
Outlet muffler 4124
Blower 4142
Air circuit 4170
Electrical components 4200
Printed Circuit Board Assembly (PCBA) 4202
Power supply 4210
Input device 4220
Pressure sensor 4272
Flow rate sensor 4274
Algorithms 4300
Humidifier 5000
Seal-forming structure 5100
Cushion assembly 5105
Support structure 5120
Sealing portion 5130
Patient interface 6000
Seal-forming structure 6100
Cushion assembly 6105
Support structure 6120
Sealing portion 6130
Positioning and stabilizing structure 6300
Left arm 6305
Right arm 6307
Joint 6312
Air delivery tube 6348
Tube 6350
Inner layer 6352
Outer layer 6354
Textile sheet 6360
membrane 6362
Tube sheet 6364
Outer covering 6366
membrane 6368
membrane 6370
Air passage 6372
Connection port 6600
Seal-forming structure 7100
Cushion assembly 7105
Support structure 7120
Sealing portion 7130

Seal-forming structure 8100
Cushion assembly 8105
Support structure 8120
End portion 8122
Sealing portion 8130
Sealing portion 8130
Patient interface 9000
Seal-forming structure 9100
Cushion assembly 9105
Support structure 9120
Connector 9122
Sealing portion 9130
Frame 9200
Headgear attachment portions 9210
Positioning and stabilising structure 9300
Rear strap 9310
Crown strap 9312
Cavity 10001
Support structure 10120
Underlying cushion 10121
Attachment portion 10122
Sealing lip 10124
Clip 10126
Sealing portion 10130
Membrane layer 10131
Sealing portion 10132
Textile material 10133
Support section 10135
Biasing portion 10140
Biasing portion 10140'
Inwardly curved end portion 10142
Air-assisted support region 10144
Adhesive 10150
Plenum chamber 10200
Connector 10210
Underlying cushion 11121
Plenum chamber 11200
Support structure 12120
Underlying cushion 12121
Plenum chamber 13200
Patient interface 14000
Cavity 14001
Seal-forming structure 14100
Nasal portion 14101
Oral portion 14102
Nasal portion holes 14103
Oral portion hole 14104
Cushion assembly 14105
Bridge portion 14106
Support structure 14120
Underlying cushion 14121
Underlying cushion 14122
Sealing portion 14130
Plenum chamber 14200
Positioning and stabilising structure 14300
Clip 14301
Upper strap 14302
Lower strap 14303
Strap connector 14304
Vent 14400
Connection port 14600
Conduit connector 14800
Conduit connector housing 14801
Conduit connection end 14802
Conduit connector inlet hole 14803
Conduit connector vent hole 14831
Anti-asphyxia valve assembly 14850
Conduit 14900
Sleeve 14901
Tie connector 14902
Connection port housing 14903
Support structure 15120
Underlying cushion 15121
Patient interface 16000
Frame assembly 16100
Opening 16105
Shroud 16110
Upper headgear connector arm 16134
Central flexible portion 16140
Peripheral flexible portion 16145
Lower headgear connector arm 16154
Magnetic connector 16155
Headgear clip 16160
Cushion assembly 16175
Cushion assembly 16175-1
Cushion assembly 16175-2
Shell 16180
Seal-forming structure 16200
Seal-forming structure 16200-1
Seal-forming structure 16200-2
Support structure 16220
Underlying cushion 16221
Sealing portion 16230
Textile membrane 16230-1
Textile membrane 16230-2
Opening 16305
Flange 16310
Cavity 16500
Elbow assembly 16600
First end portion 16610
Second end portion 16620
Swivel connector 16625
Channel 16645
Pinch arm 16650
Vent holes 16700
Arm cover 16750
Headgear 16800
Upper side strap 16802
Lower side strap 16804
Crown strap 16806
Support structure 17120
Underlying cushion 17121
First portion 17123
Reinforcing member 17125
Support structure 18120
Underlying cushion 18121
Clip 18126
Support structure 19120
Underlying cushion 19121
First portion 19123
Support structure 20120
Underlying cushion 20121
First portion 20123
Support structure 21120
Underlying cushion 21121
First portion 21123
Support structure 22120
Underlying cushion 22121
First portion 22123
Support structure 23120
Underlying cushion 23121
Clip 23126
Support structure 24120
Underlying cushion 24121

Inner layer 24124
Clip 24126
Support structure 26120
Sealing portion modular assembly 26400
Supporting frame 26450
Modular supporting structure 26480
First mold 26500
Second mold 26550
Cushion assembly 27105
Upper supporting frame portion 27202
Lower supporting frame portion 27204
Elastic region 27108
Cushion assembly 28105
Supporting frame 28200
Seal-forming structure 29100
Cushion assembly 29105
Support structure 29120
Sealing portion 29130
Grip pad 29150
Patient interface 30000
Cavity 30001
Seal-forming structure 30100
Nasal portion 30101
Oral portion 30102
Nasal portion holes 30103
Oral portion hole 30104
Cushion assembly 30105
Support structure 30120
Sealing portion 30130
Plenum chamber or shell 30200
Inlet port 30240
Positioning and stabilising structure 30300
Upper straps 30310
Upper strap connection points 30315
Lower straps 30320
Lower strap connection point 30325
Lower strap clip 30326
Top crown strap 30330
Lateral crown straps 30332
Neck strap 30334
Frame 30350
Frame inlet connection port 30354
Connection rim 30355
Vent 30400
Swivel elbow assembly 30610
Connection port 30600
Cavity 31001
Seal-forming structure 31100
Nasal portion 31101
Oral portion 31102
Nasal portion holes 31103
Oral portion hole 31104
Cushion assembly 31105
Support structure 31120
Sealing portion 31130
Grip pad 31150
Plenum chamber 31200
Plenum chamber holes 31210
Vent 31400
Marginal edge 33102
Exterior edge 33104
Face-engaging portion 33106
Interior edge 33108
Underlying cushion 33121
Air impermeable layer 33131
Textile material 33133
Inner edge 33134
Length of textile membrane 33146
Length of textile membrane 33148
Cushion coupling portion 33150
Region 33180A
Region 33180B
Region 33180C
Region 33180D
Region 33180E
Region 33180F
Region 33180G
Sagittal plane 33185
Line 33190
Thickness d1
Thickness d2

The invention claimed is:

1. A patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; said patient interface comprising:
 a plenum chamber at least partially forming a cavity pressurisable to a therapeutic pressure of at least 6 cmH2O above ambient air pressure, said plenum chamber including a plenum chamber inlet port sized and structured to receive a flow of air at the therapeutic pressure for breathing by a patient; and
 a seal-forming structure having a textile membrane constructed and arranged to form a pressure-assisted seal with a region of the patient's face surrounding an entrance to the patient's airways inferior to a nasal bridge region of the patient's face, said textile membrane having a hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use,
 wherein the seal-forming structure includes a flexible support structure attached to and supporting the textile membrane, and
 wherein the textile membrane comprises a textile material and an air impermeable layer applied directly to the textile material to make the textile material air impermeable, the air impermeable layer having a first thickness at a first location on the textile membrane and a second thickness at a second location on the textile membrane that is different than the first thickness.

2. The patient interface of claim 1, wherein the first thickness of the air impermeable layer is less than the second thickness.

3. The patient interface of claim 1, wherein stretchability of the textile membrane at the first location is greater than stretchability of the textile membrane at the second location.

4. The patient interface of claim 1, wherein a rigidity of the textile membrane at the first location is less than a rigidity of the textile membrane at the second location.

5. The patient interface of claim 1, wherein the first location on the textile membrane is in a nasal bridge region of the seal-forming structure, and the second location on the textile membrane is in a cheek region of the seal-forming structure.

6. The patient interface of claim 1, wherein the first location on the textile membrane is in a chin region of the seal-forming structure, and the second location on the textile membrane is in a cheek region of the seal-forming structure.

7. The patient interface of claim 1, wherein a thickness of the air impermeable layer varies in different regions around a perimeter of the seal-forming structure to vary compliance of the textile membrane in the different regions.

8. The patient interface of claim 7, wherein the thickness of the air impermeable layer in a nasal bridge region of the seal-forming structure is less than a thickness of the air impermeable layer in a cheek region of the seal-forming structure.

9. The patient interface of claim 7, wherein the thickness of the air impermeable layer in a chin region of the seal-forming structure is less than a thickness of the air impermeable layer in a cheek region of the seal-forming structure.

10. The patient interface of claim 7, wherein a thickness of the textile material is constant in the different regions around the perimeter of the seal-forming structure.

11. The patient interface of claim 1, wherein, in cross-sectional view, a thickness of the air impermeable layer decreases toward an inner edge of the textile membrane, such that the first location on the textile membrane is more radially inner as compared to the second location on the textile membrane.

12. The patient interface of claim 1, wherein the support structure comprises an underlying cushion to support the textile membrane in use.

13. The patient interface of claim 1, wherein the support structure comprises silicone and the textile membrane is molded to an inner edge of the support structure.

14. The patient interface of claim 1, further comprising:
a cushion assembly, the cushion assembly including the plenum chamber and the seal-forming structure,
wherein the textile membrane has a saddle shape nasal bridge region of the cushion assembly.

15. The patient interface of claim 1, wherein the textile material is weft knit.

16. The patient interface of claim 1, wherein the textile material comprises nylon, spandex, or polyester.

17. The patient interface of claim 1, wherein the air impermeable layer comprises silicone.

18. The patient interface of claim 1, wherein in use the therapeutic pressure in the cavity urges the textile membrane towards the patient's face.

19. The patient interface of claim 1, further comprising a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use.

20. The patient interface of claim 1, further comprising a vent structure to allow a continuous flow of gases exhaled by the patient from an interior of the cavity to ambient, said vent structure being sized and shaped to maintain the therapeutic pressure in the cavity in use.

21. The patient interface of claim 1, wherein the plenum chamber and seal-forming structure form a full-face cushion assembly.

22. The patient interface of claim 1, wherein, in use, the patient's nose is configured to be received in the cavity.

23. A treatment system used for treatment of sleep disordered breathing, comprising:
the patient interface according to claim 1;
a respiratory pressure therapy (RPT) device to supply breathable gas at positive pressure; and
an air delivery tube to pass the breathable gas from the RPT device to the patient interface.

* * * * *